United States Patent
Alexander et al.

(10) Patent No.: US 9,932,343 B2
(45) Date of Patent: Apr. 3, 2018

(54) FUSED TRICYCLIC BENZIMIDAZOLES DERIVATIVES AS MODULATORS OF TNF ACTIVITY

(71) Applicant: UCB BIOPHARMA SPRL, Brussels (BE)

(72) Inventors: Rikki Peter Alexander, Slough (GB); Mark Daniel Calmiano, Slough (GB); Sabine Defays, Brussels (BE); Veronique Durieu, Brussels (BE); Michael Deligny, Brussels (BE); Jag Paul Heer, Brussels (BE); Victoria Elizabeth Jackson, Slough (GB); Jean Keyaerts, Brussels (BE); Boris Kroeplien, Slough (GB); Malcolm Mac Coss, Seabrook Island, SC (US); Yogesh Anil Sabnis, Brussels (BE); Matthew Duncan Selby, Slough (GB); Dominique Louis Leon Swinnen, Brussels (BE); Nathalie Van Houtvin, Brussels (BE); Zhaoning Zhu, Slough (GB); Uwe Heinelt, Frankfurt am Main (DE); Volkmar Wehner, Frankfurt am Main (DE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/102,003

(22) PCT Filed: Dec. 8, 2014

(86) PCT No.: PCT/EP2014/076880
§ 371 (c)(1),
(2) Date: Jun. 6, 2016

(87) PCT Pub. No.: WO2015/086525
PCT Pub. Date: Jun. 18, 2015

(65) Prior Publication Data
US 2016/0304523 A1  Oct. 20, 2016

(30) Foreign Application Priority Data

Dec. 9, 2013  (GB) .................................. 1321728.6

(51) Int. Cl.
| | | |
|---|---|---|
| A61K 31/415 | (2006.01) |
| A61K 31/495 | (2006.01) |
| A61K 31/44 | (2006.01) |
| A61K 31/425 | (2006.01) |
| C07D 403/02 | (2006.01) |
| C07D 487/00 | (2006.01) |
| C07D 513/00 | (2006.01) |
| C07D 491/00 | (2006.01) |
| C07D 498/02 | (2006.01) |
| C07D 487/04 | (2006.01) |
| A61K 31/4188 | (2006.01) |
| C07D 471/04 | (2006.01) |
| C07D 498/04 | (2006.01) |
| C07D 519/00 | (2006.01) |
| C07D 513/04 | (2006.01) |

(52) U.S. Cl.
CPC ........ C07D 487/04 (2013.01); A61K 31/4188 (2013.01); C07D 471/04 (2013.01); C07D 498/04 (2013.01); C07D 513/04 (2013.01); C07D 519/00 (2013.01)

(58) Field of Classification Search
CPC .. C07D 478/04; C07D 513/04; C07D 471/04; C07D 489/04; A61K 31/4188; A61K 31/429; A61K 31/437; A61K 31/4985; A61K 31/538
USPC ..... 548/302.4, 302.1, 151; 546/85; 544/101, 544/346; 514/230.2, 250, 292, 366, 394
See application file for complete search history.

(56) References Cited

FOREIGN PATENT DOCUMENTS

| WO | 2007/112093 | 10/2007 |
|---|---|---|
| WO | 2013/186229 | 12/2013 |
| WO | 2014/009295 | 1/2014 |
| WO | 2014/009296 | 1/2014 |

OTHER PUBLICATIONS

Hardman et al. "Goodman & Gilman's The pharmaceutical Basis of Therapeutics," 9th ed. 1996, pp. 51 and 57-58.*
Matera et al. "TNF-alpha inhibitors in the asthma and COPD: we must not throw the baby out with the bath water," Pulmonary Pharmacology & Therapeutics, 2010, vol. 23, pp. 121-128.*

(Continued)

Primary Examiner — Shengjun Wang
(74) Attorney, Agent, or Firm — McDonnell Boehnen Hulbert & Berghoff LLP

(57) ABSTRACT

A series of tricyclic benzimidazole derivatives, in particular dihydro-1H-imidazo [1,2-a]benzimidazole, dihydro-1H-pyrrolo [1,2-a]benzimidazole, dihydro-1H-pyrazino[1,2-a]benzimidazole, dihydro-1H-[1,4]oxazino[4,3-a]benzimidazole and dihydrothiazolo[3,4-a]benzimidazolem, and analogs thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

16 Claims, No Drawings

(56) References Cited

OTHER PUBLICATIONS

Chrimirri et al., Archly Der Pharmazie, 2001, 334(6), 203-208.
Palma et al., Biochemical and Biophysical Research Communications, 2007, 353(3) pp. 628-632.
Tansey et al., Drug discovery Today, 2009, 1082-1088.
Carneiro et al., J. Sexual Medicine, 2010, vol. 7, pp. 3823-3834.
Wu et al., JAMA, 2013, vol. 309, pp. 2043-2044.
Hauwermeiren et al., J. Clin. Invest, 2013, vol. 123, pp. 2590-2603.
International Search Report and Written Opinion of International Searching Authority dated Mar. 23, 2015 of International Application No. PCT/EP2014/076880 filed Dec. 8, 2014.

* cited by examiner

FUSED TRICYCLIC BENZIMIDAZOLES DERIVATIVES AS MODULATORS OF TNF ACTIVITY

This application is the US national phase under 35 U.S.C. §371 of international application PCT/EP2014/076880, filed Dec. 8, 2014, which claims priority to GB application 1321728.6, filed Dec. 9, 2013.

The present invention relates to a class of fused tricyclic benzimidazole derivatives, and to their use in therapy. More particularly, this invention is concerned with pharmacologically active substituted fused benzimidazole derivatives. In particular the present invention is concerned with dihydro-1H-imidazo[1,2-a]benzimidazole, dihydro-1H-pyrrolo[1,2-a]benzimidazole, dihydro-1H-pyrazino[1,2-a]benzimidazole, dihydro-1H-[1,4]oxazino[4,3-a]benzimidazole and dihydrothiazolo[3,4-a]benzimidazole.

These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

Co-pending international patent applications WO 2013/186229 (published 19 Dec. 2013), WO 2014/009295 (published 16 Jan. 2014) and WO 2014/009296 (also published 16 Jan. 2014) describe fused imidazole derivatives which are modulators of human TNFα activity.

None of the prior art available to date, however, discloses or suggests the precise structural class of fused benzimidazole derivatives as provided by the present invention. The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ value of 50 µM or less, generally of 20 µM or less, usually of 5 µM or less, typically of 1 µM or less, suitably of 500 nM or less, ideally of 100 nM or less, and preferably of 20 nM or less (the skilled person will appreciate that a lower $IC_{50}$ figure denotes a more active compound).

Certain compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, certain compounds of the present invention exhibit an $IC_{50}$ value of 50 µM or less, generally of 20 µM or less, usually of 5 µM or less, typically of 1 µM or less, suitably of 500 nM or less, ideally of 100 nM or less, and preferably of 20 nM or less (as before, the skilled person will appreciate that a lower $IC_{50}$ figure denotes a more active compound).

The present invention provides a compound of formula (I) or an N-oxide thereof, or a pharmaceutically acceptable salt or solvate thereof, or a glucuronide derivative thereof, or a co-crystal thereof:

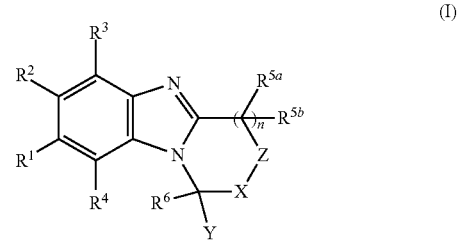

wherein n represents an integer equal to 0 or 1;

X and Z independently represent a covalent bond; or an heteroatom; or carbonyl, or $S(O)-$, $-S(O)_2-$, $-S(O)(N-R^d)$, $-NC(O)-R^d$, $-N(CO)-OR^d$, $-NS(O)_2R^d$, or $-N(R^d)$; or an optionally substituted straight or branched $C_{1-4}$ alkylene chain;

Y represents $C_{3-7}$ cycloalkyl, aryl, $C_{3-7}$ heterocycloalkyl or heteroaryl, any of which groups may be optionally substituted by one or more substituents;

$R^1$ and $R^2$ independently represent hydrogen, halogen, cyano, nitro, hydroxy, trifluoromethyl, trifluoromethoxy, $-OR^a$, $-SR^a$, $-SOR^a$, $-SO_2R^a$, $-SF_5$, $-NR^bR^c$, $-NR^cCOR^d$, $-NR^cCO_2R^d$, $-NHCONR^bR^c$, $-NR^cSO_2R^e$, $-N(SO_2R^e)_2$, $-NHSO_2NR^bR^c$, $-COR^d$, $-CO_2R^d$, $-CONR^bR^c$, $-CON(OR^a)R^b$, $-SO_2NR^bR^c$, or $-S(O)(N-R^d)R^a$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^3$ and $R^4$ independently represents hydrogen, halogen, cyano, nitro, hydroxy, trifluoromethyl, trifluoromethoxy; or $-OR^a$, $-SR^a$, $-SOR^a$, or $-SO_2R^a$; or $C_{1-6}$ alkyl optionally substituted by one or more substituents.

$R^{5a}$ and $R^{5b}$ independently represent hydrogen, hydroxy, halogen, trifluoromethyl, or cyano; or $-NR^bR^c$, $-NR^cC(O)R^d$, $-(CO)NR^cR^d$, $-NHS(O)_2R^e$, $-S-R^a$, $-(SO)-R^a$, $-S(O)_2R^a$, $-S(O)(N-R^d)R^a$, $-S(O)_2(N-R^d)$, $-OR^d$, $-C(O)-OR^d$, or $-O(CO)-R^d$; or $C_{1-6}$ alkyl, $C_{2-6}$ alkenyl, $C_{2-6}$ alkynyl, aryl, or heteroaryl, any of which groups may be optionally substituted by one or more substituents; or $R^{5a}$ and $R^{5b}$ when taken together with the carbon to which they are attached represent a carbonyl, thiocarbonyl or $-C=N-OH$; and $R^6$ represents hydrogen, hydroxy, halogen, trifluoromethyl or cyano; or $-NR^bR^c$, $-NR^cC(O)R^d$, $-(CO)NR^cR^d$, $-NHS(O)_2R^e$, $-S-R^a$, $-(SO)-R^a$, $-S(O)_2R^a$, $-S(O)(N-R^d)R^a$, $-S(O)_2(N-R^d)$, $-OR^d$, $-C(O)-OR^d$, or $-O(CO)-R^d$; or $C_{1-6}$ alkyl, $C_{2-6}$ alkenyl, $C_{2-6}$ alkynyl, aryl, or heteroaryl, any of which groups may be optionally substituted by one or more substituents; or $R^6$ and Y together with the carbon to which they are attached form a $C_{3-7}$ cycloalkyl or $C_{3-7}$ heterocycloalkyl, optionally substituted with one or more substituents; and $R^a$ represents $C_{1-6}$ alkyl, $C_{3-7}$ cycloalkyl, $C_{3-7}$ heterocycloalkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo) thiazinan-4-yl or (dioxo)thiazinan-4-yl any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as defined above or an N-oxide thereof, or a pharmaceutically acceptable salt or solvate thereof, or a glucuronide derivative thereof, or a co-crystal thereof, for use in therapy.

The present invention also provides a compound of formula (I) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides for the use of a compound of formula (I) as defined above, or an N-oxide thereof, or a pharmaceutically acceptable salt thereof, for the manufacture of a medicament useful for the treatment of an inflammatory or autoimmune disorder, a neurological or neurodegenerative disorder, pain or a nociceptive disorder, a cardiovascular disorder, a metabolic disorder, an ocular disorder, or an oncological disorder.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharma-* ceutical Salts: Properties, Selection and Use, ed. P. H. Stahl & C. G. Wermuth, Wiley-VCH, 2002. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups, which may comprise benzo-fused analogues thereof, include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl, bicyclo[2.2.2]octanyl and bicyclo[3.2.2]-nonanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, dihydroisoindolinyl, isoindolinyl, oxazolidinyl, thiazolidinyl, isothiazolidinyl, imidazolidinyl, tetrahydropyranyl, chromanyl, tetrahydrothiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl, azocanyl, (imino)(oxo)thiazinanyl, (oxo)thiazinanyl and (dioxo)thiazinanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable $C_{3-7}$ heterocycloalkenyl groups include thiazolinyl, imidazolinyl, dihydropyranyl, dihydrothiopyranyl, 1,2,3,6-tetrahydropyridinyl, and 1-H-pyridin-2-one.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3-azabicyclo[3.2.1]octanyl, 3,6-diazabicyclo[3.2.2]nonanyl, 3-oxa-7-azabicyclo [3.3.1]nonanyl, 3,9-diazabicyclo[4.2.1]nonanyl and 3,7-dioxa-9-azabicyclo [3.3.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro-[2.4]heptanyl, 2-azaspiro[3.3]heptanyl, 2-oxa-6-azaspiro[3.3]heptanyl, 2-oxa-6-azaspiro-[3.4]octanyl, 2-oxa-6-azaspiro[3.5]

nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, 2,3-dihydro-1H-isoindolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "amino" as used herein represents a group of formula —$NR^bR^c$ wherein $R^b$ and $R^c$ are as defined herein.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)⇌enol (CH=CHOH) tautomers or amide (NHC=O)⇌hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a first embodiment, n represent an integer equal to 0.
In a second embodiment, n represents an integer equal to 1.

In one embodiment, X represents a covalent bond; or an heteroatom; or —S(O), —S(O)$_2$, —S(O)(N—$R^d$), —NC(O)$R^d$, —N(CO)—$OR^d$, —NS(O)$_2R^d$, or —N($R^d$); or an optionally substituted straight or branched $C_{1-4}$ alkylene chain; and
Z represents an optionally substituted straight or branched $C_{1-4}$ alkylene chain.

In another embodiment, X represents an optionally substituted straight or branched $C_{1-4}$ alkylene chain; and
Z represents a covalent bond; or an heteroatom; or —S(O), —S(O)$_2$, —S(O)(N—$R^d$), —NC(O)$R^d$, —N(CO)—$OR^d$, —NS(O)$_2R^d$, or —N($R^d$); or an optionally substituted straight or branched $C_{1-4}$ alkylene chain.

Typically X represents an heteroatom-S(O), or —N—$R^d$; or an optionally substituted straight or branched $C_{1-4}$ alkylene chain;

In a first embodiment, X represents a covalent bond.
In a second embodiment, X represents an heteroatom. In one aspect of that embodiment X is oxygen. In a second aspect of that embodiment X is sulphur.
In a third embodiment, X represents —S(O).
In a fourth embodiment, X represents —S(O)$_2$.
In a fifth embodiment, X represents —S(O)(N—$R^d$).
In a sixth embodiment, X represents —NC(O)$R^d$.
In a seventh embodiment, X represents —N(CO)—$OR^d$.
In an eighth embodiment, X represents —NS(O)$_2R^d$.
In a ninth embodiment, X represents —N($R^d$). In a particular aspect of this embodiment, X represents —NH.
In a tenth embodiment, X represents an optionally substituted straight or branched $C_{1-4}$ alkylene chain. Typical values of X according to this embodiment include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. In one aspect of this embodiment X represents an unsubstituted straight or branched $C_{1-4}$ alkylene chain. In a second aspect of this embodiment, X represents a monosubstituted straight or branched $C_{1-4}$ alkylene chain. In a third aspect of this embodiment, X represents a disubstituted straight or branched $C_{1-4}$ alkylene chain.

In an eleventh embodiment, X represents a carbonyl.
Specific values of X include methylene, —S(O), oxygen or sulphur.

Generally, Z represents a covalent bond; or an heteroatom; or —S(O), —S(O)$_2$, —S(O)(N—$R^d$), —NC(O)$R^d$, —N(CO)—$OR^d$, —NS(O)$_2R^d$, or —N($R^d$); or an optionally substituted straight or branched $C_{1-4}$ alkylene chain.

Typically, Z represents a covalent bond; or an heteroatom; or —NC(O)$R^d$, —N(CO)—$OR^d$, —NS(O)$_2R^d$, or —N($R^d$); or an optionally substituted straight or branched $C_{1-4}$ alkylene chain.

In a first embodiment, Z represents a covalent bond. In a second embodiment, Z represents an heteroatom. In one aspect of that embodiment Z is an oxygen. In a second aspect Z is sulphur. In a third embodiment, Z represents —S(O). In a fourth embodiment, Z represents —S(O)$_2$. In a fifth embodiment, Z represents —S(O)(N—$R^d$). In a sixth embodiment, Z represents —NC(O)$R^d$. In a seventh embodiment, Z represents —N(CO)—$OR^d$ In an eighth embodiment, Z represents —NS(O)$_2R^d$. In a ninth embodiment, Z represents —N($R^d$). In a particular aspect of that embodiment, Z represents —NH.

In tenth embodiment, Z represents an optionally substituted straight or branched $C_{1-4}$ alkylene chain. Typical values of Z according to this embodiment include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. In one aspect of this embodiment Z represents an unsubstituted straight or branched $C_{1-4}$ alkylene chain. In a second aspect of this embodiment, Z represents a monosubstituted straight or branched $C_{1-4}$ alkylene chain. In a third aspect of this embodiment, Z represents a disubstituted straight or branched $C_{1-4}$ alkylene chain.

In an eleventh embodiment, Z represents a carbonyl.

Examples of typical substituents on the alkylene chain which may be present in a compound in accordance with the invention include halogen, hydroxy, oxo, $C_{1-6}$ alkoxy, aryl, —C(O)R$^d$, —CO$_2$R$^d$, —CONR$^b$R$^c$—S(O)(N—R$^d$)R$^a$, and —SO$_2$NR$^b$R$^c$.

Specific values of Z include a covalent bond, oxygen, sulphur, —NH, —NCH$_3$, —N—(SO$_2$)—CH$_3$, —N—(CO)—CH$_3$ and —N—(CO)—O—CH$_3$.

In a particular embodiment, X represents an optionally substituted straight or branched $C_{1-4}$ alkylene chain; and Z represents a covalent bond; or an heteroatom; or —NC(O)R$^d$, —N(CO)—OR$^d$, —NS(O)$_2$R$^d$, or —N(R$^d$); or an optionally substituted straight or branched $C_{1-4}$ alkylene chain.

In another particular embodiment, Z represents a covalent bond; or an optionally substituted straight or branched $C_{1-4}$ alkylene chain; and X represents an heteroatom; —S(O), or —N—R$^d$.

Generally, Y represents $C_{3-7}$cycloalkyl, aryl or heteroaryl, any of which groups may be optionally substituted by one or more substituents.

Typically, Y represents aryl or heteroaryl, either of which groups may be optionally substituted by one or more substituents.

In a first embodiment, Y represents optionally substituted $C_{3-7}$ cycloalkyl. In one aspect of that embodiment, Y represents unsubstituted $C_{3-7}$cycloalkyl. In another aspect of that embodiment, Y represents monosubstituted $C_{3-7}$cycloalkyl. In a further aspect of that embodiment, Y represents disubstituted $C_{3-7}$cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted $C_{3-7}$ heterocycloalkyl. In one aspect of that embodiment, Y represents unsubstituted $C_{3-7}$ heterocycloalkyl. In another aspect of that embodiment, Y represents monosubstituted $C_{3-7}$ heterocycloalkyl. In a further aspect of that embodiment, Y represents disubstituted $C_{3-7}$ heterocycloalkyl.

In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thienyl, thiazolyl, pyridinyl, pyrimidinyl or pyrazolyl any of which groups may be optionally substituted by one or more substituents.

Appropriately, Y represents phenyl, thienyl or thiazolyl, any of which groups may be optionally substituted by one or more substituents.

Appositely, Y represents phenyl, which may be optionally substituted by one or more substituents.

Examples of optional substituents which may be present on the moiety Y include one, two or three substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, ($C_{1-6}$)alkylsulfonyloxy, amino, $C_{1-6}$ alkyl-amino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, methylsulfonyloxy, amino, methylamino, tert-butylamino, dimethylamino, phenylamino, acetylamino, methylsulfonylamino, formyl, acetyl, cyclopropylcarbonyl, azetidinylcarbonyl, pyrrolidinyl-carbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl. Additional example of particular substituent on Y include butoxycarbonyl.

Suitable examples of particular substituents on the moiety Y include chloro, fluoro, cyano, methoxy, methylsulphonyl, trifluoromethoxy difluoromethoxy and butoxycarbonyl.

Typical examples of particular substituents on the moiety Y include chloro, fluoro, cyano, methoxy, methylsulphonyl, trifluoromethoxy and difluoromethoxy.

Typical values of Y include benzocyclobutenyl, phenyl, (methysulphonyl)phenyl (including 4-methylsulphonyl-phenyl), benzonitrile (including 2-benzonitrile, 3-benzonitrile and 4-benzonitrile), fluorophenyl (including 2-fluorophenyl, 3-fluorophenyl and 4-fluorophenyl), chlorophenyl (including 2-chloro-phenyl, 3-chlorophenyl and 4-chlorophenyl), difluorophenyl (including 2,6-difluoro-phenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5-dimethylphenyl and 2,6-dimethylphenyl), (trifluoromethyl)phenyl [including 2-(trifluoromethyl)phenyl], (chloro)(trifluoromethyl)phenyl [including 5-chloro-2-(trifluoromethyl)phenyl], (methyl)-(trifluoromethyl)phenyl [including 2-methyl-5-(trifluoromethyl)phenyl], bis(trifluoro-methyl)phenyl [including 2,5-bis(trifluoromethyl)phenyl], methoxyphenyl (including 2-methoxyphenyl), (difluoromethoxy)phenyl [including 2-(difluoromethoxy)phenyl, 3-(difluoromethoxy)phenyl and 4-(difluoromethoxy)phenyl], (bis-(difluoromethoxy))phenyl [including 2,5-(bis-(difluoromethoxy))-phenyl and including 2,6-(bis-(difluoromethoxy))-phenyl], (difluoromethoxy)(fluoro)phenyl [including 2-(difluoromethoxy)-5-fluorophenyl, 2-(difluoromethoxy)-3-fluorophenyl, 2-(difluoromethoxy)-6-fluorophenyl and 5-(difluoromethoxy)-2-fluorophenyl], (difluoromethoxy)(difluoro)phenyl (including 2-difluoromethoxy-3,5-difluoro-phenyl), (chloro)(difluoromethoxy)phenyl [including 2-chloro-5-(difluoromethoxy) phenyl, 5-chloro-2-(difluoromethoxy) phenyl, 5-chloro-3-(difluoromethoxy) phenyl, and 6-chloro-2-(difluoromethoxy) phenyl], (cyano)(difluoromethoxy) [including 6-cyano-2-(difluoromethoxy)-phenyl (trifluoromethoxy)phenyl [including 2-(trifluoromethoxy)-phenyl], methylsulfonyloxyphenyl, (chloro)(trifluoromethoxy)phenyl, [including 3-chloro-6-trifluoromethoxy-phenyl], (amino)(chloro)phenyl [including 5-amino-2-chloro-phenyl], methylthienyl [including 3-methylthien-2-yl], methylthiazolyl [including 2-methyl-1,3-thiazol-4-yl and 4-methyl-1,3-thiazol-4-yl], (chloro)thiazolyl [including 4-chloro-1,3-thiazolyl], (chloro)(methyl)thiazolyl [including 5-chloro-2-methyl-1,3-thiazol-4-yl], dimethylthiazolyl [including 2,4-dimethyl-1,3-thiazol-5-yl], pyridinyl [including pyridin-3-yl and pyridin-4-yl], (methyl)(trifluoromethyl)thiazolyl [including 2-methyl-4-trifluoromethyl-1,3-thiazolyl], (dimethoxy)pyrimidinyl [including 4,6-dimethoxy-pyridin-5-yl] and (methoxy)pyrazinyl [including 5-methoxypyrazinyl]. Additional particular values of Y include (difluoromethoxy)(butoxycarbonyl)phenyl [including 2-difluoromethoxy-6-butyloxycarbonyl-phenyl].

Definitive values of Y include phenyl, (methysulphonyl)phenyl, benzonitrile chlorophenyl, (chloro)(fluoro)phenyl, dichlorophenyl, dimethylphenyl, (trifluoromethyl)phenyl, (difluoromethoxy)phenyl, (bis-(difluoromethoxy))phenyl (difluoromethoxy)(fluoro)phenyl, (difluoromethoxy)(cyano)phenyl, (difluoromethoxy)(difluoro)phenyl, (chloro)(difluoromethoxy)phenyl, (chloro)(trifluoromethoxy)phenyl, (chloro)(methyl)thiazolyl, (chloro)thiazolyl, (methyl)(trifluoromethyl)thiazolyl, (dimethoxy)pyrimidinyl, (methoxy)pyrazinyl and (butoxycarbonyl)-(difluoromethoxy)phenyl. Selected values of Y include phenyl, (methysulphonyl)phenyl, benzonitrile chlorophenyl, (chloro)(fluoro)phenyl, dichlorophenyl, dimethylphenyl, (trifluoromethyl)phenyl, (difluoromethoxy)phenyl, (bis-(difluoromethoxy))phenyl (difluoromethoxy)(fluoro)phenyl, (difluoromethoxy)(cyano)phenyl, (difluoromethoxy)(difluoro)phenyl, (chloro)(difluoromethoxy)phenyl, (chloro)(trifluoromethoxy)phenyl, (chloro)(methyl)thiazolyl, (chloro)thiazolyl, (methyl)(trifluoromethyl)thiazolyl, (dimethoxy)pyrimidinyl and (methoxy)pyrazinyl. Additional selected value include (butoxycarbonyl)(difluromethoxy)phenyl.

Appropriate values of Y include (difluoromethoxy)phenyl, (difluoromethoxy)(fluoro)phenyl, (chloro)(difluoromethoxy)phenyl (difluoromethoxy)(cyano)phenyl and (butoxycarbonyl)(difluromethoxy)phenyl.

Particular values of Y include (difluoromethoxy)phenyl, (difluoromethoxy)(fluoro)phenyl, (chloro)(difluoromethoxy)phenyl and (difluoromethoxy)(cyano)phenyl.

Specific values of Y include 2-difluoromethoxy-phenyl, 2-difluoromethoxy-5-chloro-phenyl, 2-difluoromethoxy-6-chloro-phenyl, 2-difluoromethoxy-6-fluoro-phenyl, and 2-difluoromethoxy-6-cyano-phenyl. Additional specific values of Y include 2-difluoromethoxy-6-butyloxyarbonyl-phenyl.

In a particular embodiment, Y represents 2-(difluoromethoxy)phenyl.

Suitably, $R^1$ and $R^2$ independently represent hydrogen, halogen, cyano, trifluoromethyl; —S(O)$_2$(N—$R^d$), or —CO$_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl($C_{1-6}$)alkyl-aryl-, heteroaryl-$(C_{3-7})$heterocycloalkyl-, $(C_{3-7})$cycloalkyl-heteroaryl-, $(C_{3-7})$cycloalkyl($C_{1-6}$)alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl($C_{1-6}$)alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Typically, $R^2$ represents hydrogen, halogen, cyano, nitro, hydroxy, trifluoromethyl, trifluoromethoxy or —OR$^a$; or $C_{1-6}$ alkyl optionally substituted by one or more substituents.

Generally, $R^3$ represents hydrogen, halogen, cyano, nitro, hydroxy, trifluoromethyl, trifluoromethoxy; or —OR$^a$, —SR$^a$, —SOR$^a$, —SO$_2R^a$; or $C_{1-6}$ alkyl optionally substituted by one or more substituents.

Typically, $R^3$ represents hydrogen, halogen, cyano, nitro, hydroxy, trifluoromethyl, trifluoromethoxy or —OR$^a$; or $C_{1-6}$ alkyl optionally substituted by one or more substituents.

Generally, $R^4$ represents hydrogen, halogen, cyano, nitro, hydroxy, trifluoromethyl, trifluoromethoxy; or —OR$^a$, —SR$^a$, —SOR$^a$, —SO$_2R^a$; or $C_{1-6}$ alkyl optionally substituted by one or more substituents.

Typically, $R^4$ represents hydrogen, halogen, cyano, nitro, hydroxy, trifluoromethyl, trifluoromethoxy or —OR$^a$; or $C_{1-6}$ alkyl optionally substituted by one or more substituents.

Generally, $R^{5a}$ represents hydrogen, hydroxy, halogen, cyano, trifluoromethyl; or —NR$^bR^c$, —NR$^cC(O)R^d$, —(CO)NR$^cR^d$, —NHS(O)$_2R^e$, —S—$R^a$, —(SO)—$R^a$, —S(O)$_2R^a$, —S(O)(N—$R^d$), —S(O)$_2$(N—$R^d$), —OR$^a$, —C(O)$_2R^d$, or —O(CO)—$R^d$—; or $C_{1-6}$ alkyl, $C_{2-6}$ alkenyl, $C_{2-6}$ alkynyl, aryl, or heteroaryl, any of which groups may be optionally substituted by one or more substituents.

Generally, $R^{5b}$ represents hydrogen, hydroxy, halogen, cyano, trifluoromethyl; or —NR$^bR^c$, —NR$^cC(O)R^d$, —(CO)NR$^cR^d$, —NHS(O)$_2R^e$, —S—$R^a$, —(SO)—$R^a$, —S(O)$_2R^a$, —S(O)(N—$R^d$), —S(O)$_2$(N—$R^d$), —OR$^a$, —C(O)$_2R^d$, or —O(CO)—$R^d$—; or $C_{1-6}$ alkyl, $C_{2-6}$ alkenyl, $C_{2-6}$ alkynyl, aryl, heteroaryl, any of which groups may be optionally substituted by one or more substituents.

Suitably, $R^{5a}$ represents hydrogen, hydroxy, halogen, cyano, trifluoromethyl; or —NR$^bR^c$, —NR$^cC(O)R^d$, —(CO)NR$^cR^d$, —NHS(O)$_2R^e$, —S—$R^a$, —(SO)—$R^a$, —S(O)$_2R^a$, —S(O)(N—$R^d$), —S(O)$_2$(N—$R^d$), —OR$^a$, —C(O)$_2R^d$, or —O(CO)—$R^d$—; or $C_{1-6}$ alkyl, $C_{2-6}$ alkenyl, $C_{2-6}$ alkynyl, aryl, heteroaryl, any of which groups may be optionally substituted by one or more substituents; and $R^{5b}$ represents hydrogen, hydroxy, halogen, cyano, or trifluoromethyl; or $C_{1-6}$ alkyl, any of which groups may be optionally substituted by one or more substituents.

Alternatively, $R^{5a}$ and $R^{5b}$ when taken together with the carbon to which they are attached represent a carbonyl, thiocarbonyl, or —C═N—OH.

Generally, $R^6$ represents hydrogen, hydroxy, halogen, cyano, or trifluoromethyl; or —NR$^bR^c$, —NR$^cC(O)R^d$, —(CO)NR$^cR^d$, —NHS(O)$_2R^e$, —S—$R^a$, —(SO)—$R^a$, —S(O)$_2R^a$, —S(O)(N—$R^d$), —S(O)$_2$(N—$R^d$), —OR$^a$, —C(O)$_2R^d$, or —O(CO)—$R^d$—; or $C_{1-6}$ alkyl, $C_{2-6}$ alkenyl, $C_{2-6}$ alkynyl, aryl, or heteroaryl, any of which groups may be optionally substituted by one or more substituents.

Examples of optional substituents which may be present on $R^1$, $R^2$, $R^3$, $R^4$ $R^{5a}$, $R^{5b}$ and $R^6$ include one, two or three substituents independently selected from halogen, halo-$(C_{1-6})$alkyl, cyano, cyano$(C_{1-6})$alkyl, nitro, nitro$(C_{1-6})$alkyl, $C_{1-6}$ alkyl, $(C_{3-7})$cycloalkyl, difluoromethyl, trifluoromethyl, difluoroethyl, trifluoroethyl, $C_{2-6}$ alkenyl, hydroxy, hydroxy$(C_{1-6})$alkyl, $C_{1-6}$ alkoxy, difluoromethoxy, trifluoromethoxy, trifluoroethoxy, carboxy$(C_{3-7})$cycloalkyl-oxy, $C_{1-3}$ alkylenedioxy, $C_{1-6}$ alkoxy$(C_{1-6})$alkyl, $C_{1-6}$ alkylthio, $C_{1-6}$ alkylsulphinyl, $C_{1-6}$ alkylsulphonyl, $(C_{1-6})$alkylsulphonyl$(C_{1-6})$alkyl, oxo, amino, amino$(C_{1-6})$alkyl, $C_{1-6}$ alkyl-amino, di$(C_{1-6})$alkylamino, hydroxy$(C_{1-6})$alkylamino, $C_{1-6}$ alkoxyamino, $(C_{1-6})$alkoxy-$(C_{1-6})$alkylamino, [$(C_{1-6})$alkoxy](hydroxy)$(C_{1-6})$alkylamino, [$(C_{1-6})$alkylthio](hydroxy)-$(C_{1-6})$alkylamino, N—[$(C_{1-6})$alkyl]-N-[hydroxy$(C_{1-6})$alkyl]amino, di$(C_{1-6})$alkylamino-$(C_{1-6})$alkylamino, N-[di$(C_{1-6})$alkylamino$(C_{1-6})$alkyl]-N-[hydroxy$(C_{1-6})$alkyl]amino, hydroxy$(C_{1-6})$alkyl$(C_{3-7})$cycloalkylamino, (hydroxy)[$(C_{3-7})$cycloalkyl$(C_{1-6})$alkyl]amino, $(C_{3-7})$heterocycloalkyl$(C_{1-6})$alkylamino, oxo$(C_{3-7})$heterocycloalkyl$(C_{1-6})$alkylamino, $(C_{1-6})$alkylheteroarylamino, heteroaryl$(C_{1-6})$alkylamino, $(C_{1-6})$alkylheteroaryl$(C_{1-6})$alkyl-amino, $C_{2-6}$ alkylcarbonylamino, N—[$(C_{1-6})$alkyl]-N—[$(C_{2-6})$alkylcarbonyl]amino, $(C_{2-6})$alkyl-carbonylamino$(C_{1-6})$alkyl, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]amino, $C_{2-6}$ alkoxycarbonylamino, $C_{2-6}$ alkoxycarbonyl$(C_{1-6})$alkylamino, $C_{1-6}$ alkylaminocarbonylamino, $C_{1-6}$ alkylsulphonyl-amino, N—[$(C_{1-6})$alkyl]-N—[$(C_{1-6})$alkylsulphonyl]amino, bis[$(C_{1-6})$alkylsulphonyl]amino, N—[$(C_{1-6})$alkyl]-N-[carboxy$(C_{1-6})$alkyl]amino, carboxy$(C_{3-7})$cycloalkylamino, carboxy-$(C_{3-7})$cycloalkyl$(C_{1-6})$alkylamino, formyl, $C_{2-6}$ alkylcarbonyl, $(C_{3-7})$cycloalkylcarbonyl, phenylcarbonyl, $(C_{2-6})$alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonylmethylidenyl, a carboxylic acid isostere or prodrug moiety $\Omega$, —$(C_{1-6})$alkyl-$\Omega$, aminocarbonyl, $C_{1-6}$ alkylaminocarbonyl, hydroxy$(C_{1-6})$alkylaminocarbonyl, di$(C_{1-6})$alkylaminocarbonyl, aminocarbonyl$(C_{1-6})$alkyl, aminosulphonyl, di$(C_{1-6})$alkylaminosulphonyl, $(C_{1-6})$alkylsulphoximinyl, [$(C_{1-6})$alkyl][N—$(C_{1-6})$alkyl]-sulphoximinyl and heteroaryl. Additional examples of optional substituents on $R^1$, $R^2$, $R^3$, $R^4$ $R^{5a}$, $R^{5b}$ and $R^6$ include $(C_{3-7})$cycloalkyl-sulphonyl and hydroxy$(C_{1-6})$alkylamino sulphonyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). An alternative carboxylic acid isostere is described by N Pemberton et al. in *ACS Med. Chem. Lett.*, 2012, 3, 574-578. Typical examples of suitable carboxylic acid isostere or prodrug moieties represented by $\Omega$ include the functional groups of formula (i) to (xliii):

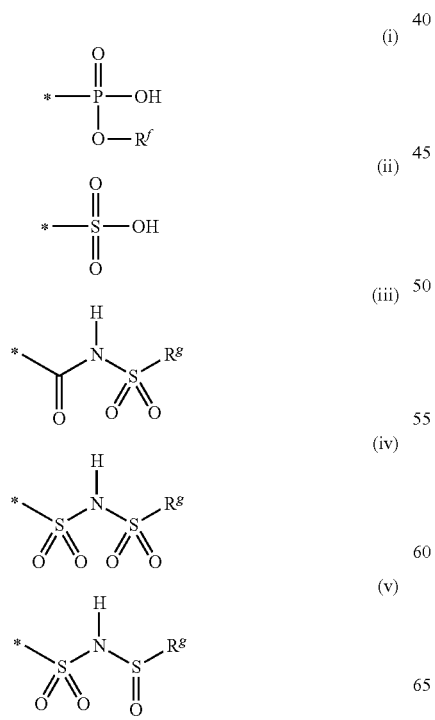

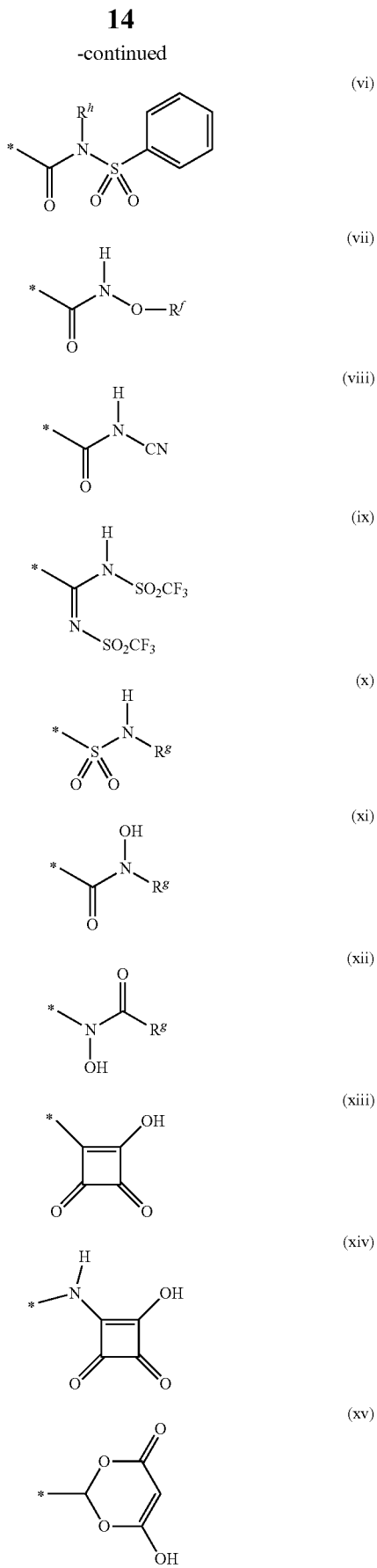

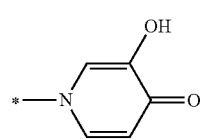
(xvi)
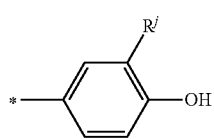
(xvii)
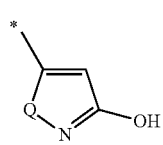
(xviii)
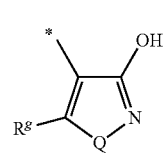
(xix)
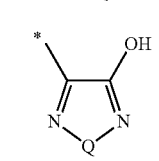
(xx)
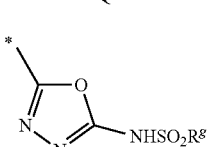
(xxi)
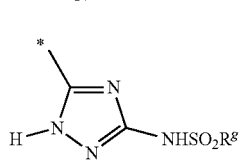
(xxii)
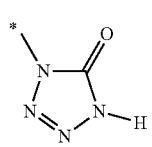
(xxiii)
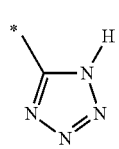
(xxiv)
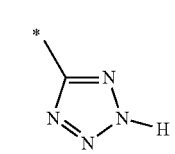
(xxv)
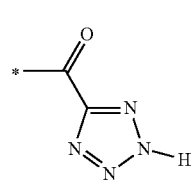
(xxvi)
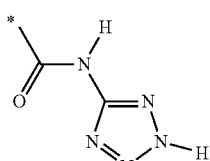
(xxvii)
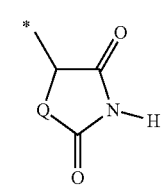
(xxviii)
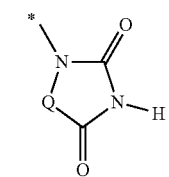
(xxix)
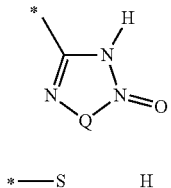
(xxx)
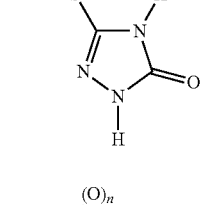
(xxxi)
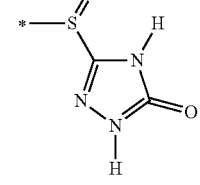
(xxxii)
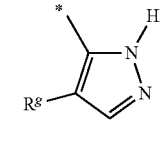
(xxxiii)
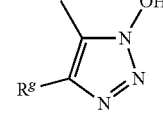
(xxxiv)
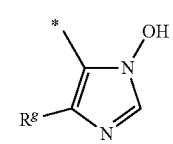
(xxxv)

-continued

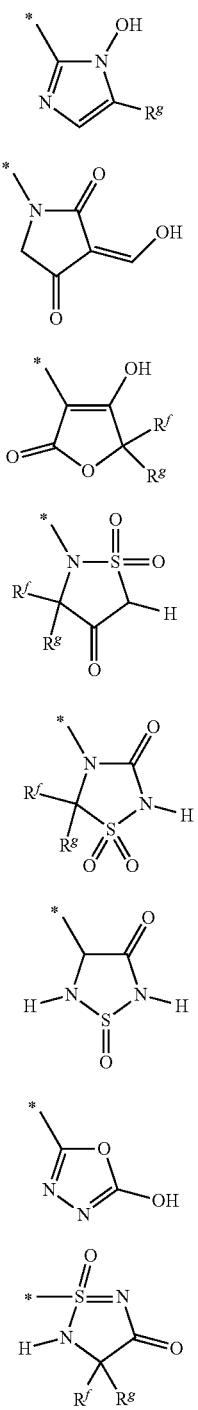

(xxxvi)
(xxxvii)
(xxxviii)
(xxxix)
(xl)
(xli)
(xlii)
(xliii)

wherein the asterisk (*) represents the site of attachment to the remainder of the molecule;

n is zero, 1 or 2;

Q represents oxygen or sulphur;

$R^f$ represents hydrogen, $C_{1-6}$ alkyl or —$CH_2CH(OH)CH_2OH$;

$R^g$ represents $C_{1-6}$ alkyl, trifluoromethyl, —$CH_2CH_2F$, —$CH_2CHF_2$, —$CH_2CF_3$ or —$CF_2CF_3$;

$R^h$ represents hydrogen, cyano or —$CO_2R^d$, in which $R^d$ is as defined above; and $R^j$ represents hydrogen or halogen.

In one embodiment, n is zero. In another embodiment, n is 1. In a further embodiment, n is 2.

In one embodiment, Q represents oxygen. In another embodiment, Q represents sulphur.

In one embodiment, $R^f$ represents hydrogen. In another embodiment, $R^f$ represents $C_{1-6}$ alkyl, especially methyl. In a further embodiment, $R^f$ is —$CH_2CH(OH)CH_2OH$.

In one embodiment, $R^g$ represents $C_{1-6}$ alkyl, especially methyl. In another embodiment, $R^g$ represents trifluoromethyl, —$CH_2CH_2F$, —$CH_2CHF_2$, —$CH_2CF_3$ or —$CF_2CF_3$. In a first aspect of that embodiment, $R^g$ represents trifluoromethyl. In a second aspect of that embodiment, $R^g$ represents —$CH_2CH_2F$. In a third aspect of that embodiment, $R^g$ represents —$CH_2CHF_2$. In a fourth aspect of that embodiment, $R^g$ represents —$CH_2CF_3$. In a fifth aspect of that embodiment, $R^g$ represents —$CF_2CF_3$.

In one embodiment, $R^h$ is hydrogen. In another embodiment, $R^h$ represents cyano. In a further embodiment, $R^h$ represents —$CO_2R^d$, especially methoxycarbonyl.

In one embodiment, $R^j$ represents hydrogen. In another embodiment, $R^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents $C_{1-6}$ alkylsulphonylaminocarbonyl, i.e. a moiety of formula (iii) as depicted above wherein $R^g$ represents $C_{1-6}$ alkyl.

In another embodiment, Ω represents $C_{1-6}$ alkylaminosulphonyl, i.e. a moiety of formula (x) as depicted above wherein $R^g$ represents $C_{1-6}$ alkyl.

In a further embodiment, Ω represents $(C_{1-6})$alkylcarbonylaminosulphonyl, i.e. a moiety of formula (v) as depicted above wherein $R^g$ represents $C_{1-6}$ alkyl.

Examples of particular substituents on $R^1$, $R^2$, $R^3$, $R^4$ $R^{5a}$, $R^{5b}$ and $R^6$ include fluoro, chloro, bromo, fluoromethyl, fluoroisopropyl, cyano, cyanoethyl, nitro, nitromethyl, methyl, ethyl, isopropyl, isobutyl, tert-butyl, cyclopropyl, difluoromethyl, trifluoromethyl, difluoroethyl, trifluoroethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethylamino, oxopyrrolidinylmethylamino, ethyloxadiazolylamino, methylthiadiazolylamino, thiazolylmethylamino, thiazolylethylamino, pyrimidinylmethylamino, methylpyrazolyl-methylamino, acetylamino, N-acetyl-N-methylamino, N-isopropylcarbonyl-N-methyl-amino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl) amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylaminocarbonyl, hydroxyethylaminocarbonyl, dimethylaminocarbonyl, aminocarbonylmethyl, aminosulphonyl, methylaminosulphonyl, dimethylaminosulphonyl, methylsulphoximinyl, (methyl)(N-methyl)sulphoximinyl and triazolyl. Additional examples of particular substituents on $R^1$, $R^2$, $R^3$, $R^4$ $R^{5a}$, $R^{5b}$ and $R^6$ include cyanosisopropyl, cyclopropyl-sulphonyl, isopropylsulphonyl and (hydroxy)ethylaminosulphonyl.

Suitable examples of particular substituents on $R^1$, $R^2$, $R^3$, $R^4$ $R^{5a}$, $R^{5b}$ and $R^6$ include fluoro, hydroxy, methyl-sulphonyl, methyl, isopropyl, methoxy, ethoxycarbonyl, cyclpropyl, cyclobutyl, carboxy, methylsulphoximinyl, acetyl, cyanosiopropyl, cyclopropyl-sulphonyl, isopropylsulphonyl and (hydroxy)ethylaminosulphonyl.

Typical examples of particular substituents on $R^1$, $R^2$, $R^3$, $R^4$ $R^{5a}$, $R^{5b}$ and $R^6$ include fluoro, hydroxy, methyl-sulphonyl, methyl, isopropyl, methoxy, ethoxycarbonyl, cyclpropyl, cyclobutyl, carboxy, methylsulphoximinyl and acetyl.

Typically, $R^1$ represents hydrogen, halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Suitably, $R^1$ represents halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Generally, $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Appropriately, $R^1$ represents aryl, $(C_{3-7})$heterocycloalkenyl-, heteroaryl, $(C_{3-7})$heterocycloalkyl-heteroaryl-, $(C_{4-9})$heterobicycloalkyl-heteroaryl- or $(C_{4-9})$spiroheterocycloalkyl-heteroaryl, any of which groups may be optionally substituted by one or more substituents.

More generally, $R^1$ represents aryl, heteroaryl, or $(C_{3-7})$ heterocycloalkyl-heteroaryl-, either of which groups may be optionally substituted by one or more substituents.

In a first embodiment, $R^1$ represents hydrogen.

In a second embodiment, $R^1$ represents halogen. In one aspect of that embodiment, $R^1$ represents bromo.

In a third embodiment, $R^1$ represents cyano.

In a fourth embodiment, $R^1$ represents —$CO_2R^d$.

In a fifth embodiment, $R^1$ represents optionally substituted $C_{1-6}$ alkyl. In one aspect of that embodiment, $R^1$ represents optionally substituted ethyl.

In a sixth embodiment, $R^1$ represents optionally substituted $C_{2-6}$ alkynyl. In one aspect of that embodiment, $R^1$ represents optionally substituted butynyl.

In a seventh embodiment, $R^1$ represents optionally substituted aryl. In one aspect of that embodiment, $R^1$ represents optionally substituted phenyl.

In an eighth embodiment, $R^1$ represents optionally substituted $C_{3-7}$ heterocycloalkyl.

In a ninth embodiment, $R^1$ represents optionally substituted $C_{3-7}$ heterocycloalkenyl. In one aspect of this embodiment $R^1$ represents optionally substituted 1H-pyridin-2-one.

In a tenth embodiment, $R^1$ represents optionally substituted heteroaryl. In selected aspects of that embodiment, $R^1$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In an eleventh embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexylpyrazinyl-. In an eighth aspect of that embodiment, $R^1$ represents optionally substituted cyclopropylpyridinyl.

In a fourteenth embodiment, $R^1$ represents optionally substituted $(C_{4-7})$-cycloalkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinylpyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanylpyrimidinyl-. In a twenty-first aspect of that embodiment, $R^1$ represents optionally substituted oxetanylpyrazinyl-. In a twenty-second aspect of that embodiment, R represents optionally substituted piperidinylpyrazinyl-. In a twenty-third aspect of that embodiment, $R^1$ represents optionally substituted tetrahydropyranylpyridinyl. In twenty-third aspect of that embodiment, $R^1$ represents (imino)(oxo)thiazinanyl-pyrimidinyl. In twenty-fourth aspect of that embodiment, $R^1$ represents (oxo)thiazinanyl-pyrimidinyl. In twenty-fifth aspect of that embodiment, $R^1$ represents and (dioxo)thiazinanyl-pyrimidinyl.

In a sixteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-. In one aspect of that embodiment, $R^1$ represents optionally substituted 3,7-dioxa-9-azabicyclo [3.3.1]nonanyl-pyrimidinyl. In another aspect of this embodiment, $R^1$ represents optionally substituted 3-azabicyclo [3.2.1]octanyl-pyrimidinyl.

In a nineteenth embodiment, $R^1$ represents optionally substituted $(C_{4-9})$-spiroheterocycloalkyl-heteroaryl-. In one aspect of that embodiment, $R^1$ represents optionally substituted 2-oxa-7-aza-spiro[3,5]nonanyl-pyrimidinyl.

In a twentieth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a twenty-first embodiment, $R^1$ represents optionally substituted $(C_{4-9})$-bicycloalkyl-heteroaryl-.

Appositely, $R^1$ represents hydrogen, bromo, cyano or —$CO_2R^d$; or ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexyl-pyrimidinyl, cyclohexylpyrazinyl, cyclohexylmethylpyrimidinyl, cyclohexenylpyridinyl, cyclopropylpyridinyl, cyclohexenylpyrimidinyl, bicyclo[3.1.0]hexanylpyridinyl, bicyclo[3.1.0]hexanyl-pyrimidinyl, bicyclo[4.1.0]heptanylpyrimidinyl, bicyclo[2.2.2]octanylpyrimidinyl, pyrrolidinylpyridinyl, tetrahydropyranylpyridinyl, piperidinylpyridinyl, piperazinyl-pyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinyl-pyrimidinyl, tetrahydropyranylpyrimidinyl, piperidinylpyrimidinyl, piperazinyl-pyrimidinyl, hexahydro-[1,2,5]thiadiazolo[2,3-a]pyrazinylpyrimidinyl, morpholinylpyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinylpyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 3-azabicyclo[4.1.0]heptanylpyridinyl, 3-azabicyclo[4.1.0]heptanyl-pyrimidinyl, 2-oxabicyclo[2.2.2]octanylpyrimidinyl, 3-azabicyclo[3.2.1]octanyl-pyrimidinyl, 8-azabicyclo[3.2.1]octanylpyrimidinyl, 3-oxa-8-azabicyclo[3.2.1]octanyl-pyrimidinyl, 3,6-diazabicyclo[3.2.2]nonanylpyrimidinyl, 3-oxa-7-azabicyclo[3.3.1]-nonanylpyrimidinyl, 5-azaspiro[2.3]hexanylpyrimidinyl, 5-azaspiro[2.4]heptanyl-pyrimidinyl, 2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, 2,4,8-triazaspiro[4.5]decanyl-pyrimidinyl, (imino)(oxo)thiazinanyl-pyrimidinyl, (oxo)thiazinanyl-pyrimidinyl or (dioxo)thiazinanyl-pyrimidinyl, any of which groups may be optionally substituted by one or more substituents. Additionally, $R^1$ represents 1H-pyridin-2-one optionally substituted by one or more substituents.

Appropriately, $R^1$ represents phenyl, tetrahydropyranylpyrimidinyl, oxetanylpyrimidinyl, tetrahydropyranylpyridinyl, pyrimidinyl, pyrazolyl, pyridinyl, pyrimidinyl, morpholinylpyrimidinyl, piperazinylpyridinyl, diazepanylpyrimidinyl, 3-azabicyclo[3.2.1]octanylpyrimidinyl, piperidinylpyrimidinyl, cyclobutypyrimidinyl, (imino)(oxo)thiazinanyl-pyrimidinyl, (oxo)thiazinanyl-pyrimidinyl, (dioxo)thiazinanyl-pyrimidinyl, 2-oxa-7-azaspiro[3.5]nonanyl-pyrimidinyl, 3,7-dioxa-9-azabicyclo[3.3.1]nonanyl-pyrimidinyl, 3-azabicyclo [3.2.1]octanyl-pyrimidinyl, or 1H-pyridin-2-one, any of which groups may be optionally substituted by one or more substituents.

Illustratively, $R^1$ represents phenyl, tetrahydropyranylpyrimidinyl, oxetanylpyrimidinyl, tetrahydropyranylpyridinyl, pyrimidinyl, pyrazolyl, pyridinyl, pyrimidinyl, morpholinylpyrimidinyl, piperazinylpyridinyl, diazepanylpyrimidinyl, 3-azabicyclo[3.2.1]octanylpyrimidinyl, piperidinylpyrimidinyl, cyclobutypyrimidinyl, (imino)(oxo)thiazinanyl-pyrimidinyl, (oxo)thiazinanyl-pyrimidinyl or (dioxo) thiazinanyl-pyrimidinyl, any of which groups may be optionally substituted by one or more substituents.

Typical examples of optional substituents on $R^1$ include one, two or three substituents independently selected from halogen, halo($C_{1-6}$)alkyl, cyano, cyano($C_{1-6}$)alkyl, nitro ($C_{1-6}$)alkyl, $C_{1-6}$ alkyl, ($C_{3-7}$)cycloalkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, N—[($C_{1-6}$)alkyl]-N-[carboxy($C_{1-6}$)alkyl]amino, carboxy($C_{3-7}$)cycloalkyl-amino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, aminocarbonyl, aminosulphonyl, ($C_{1-6}$)alkylsulphoximinyl and [($C_{1-6}$)alkyl][N—($C_{1-6}$)alkyl]sulphoximinyl. Additional examples of optional substituents on $R^1$ include ($C_{3-7}$)cycloalkyl-sulphonyl and hydroxy($C_{1-6}$)alkylaminosulphonyl.

Appropriate examples of optional substituents on $R^1$ include one, two or three substituents independently selected from halogen, hydroxy, $C_{1-6}$ alkyl, $C_{1-6}$ alkoxy, $C_{1-6}$ alkylcarbonyl, (hydroxy)$C_{1-6}$alkyl, ($C_{3-7}$)cycloalkyl, $C_{1-6}$ alkylsulphonyl, ($C_{1-6}$)alkylsulphonyl($C_{1-6}$)alkyl, ($C_{1-6}$)alkylsulphoximinyl, heteroaryl, oxo, carboxy, (cyano)$C_{1-6}$alkyl, (halo)$C_{1-6}$ alkyl, aminosulphonyl, ($C_{3-7}$)cycloalkyl-sulphonyl and hydroxy($C_{1-6}$)alkylaminosulphonyl.

Suitable examples of optional substituents on $R^1$ include one, two or three substituents independently selected from halogen, hydroxy, $C_{1-6}$ alkyl, $C_{1-6}$ alkoxy, $C_{1-6}$ alkylcarbonyl, (hydroxy)$C_{1-6}$alkyl, ($C_{3-7}$)cycloalkyl, $C_{1-6}$ alkylsulphonyl, ($C_{1-6}$)alkylsulphonyl($C_{1-6}$)alkyl, ($C_{1-6}$)alkylsulphoximinyl, heteroaryl, oxo and carboxy.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, isopropylmethyl, cyclopropyl, cyclobutyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl) amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyamino-carbonyl, tetrazolyl, tetrazolylmethyl, hydroxyoxadiazolyl, aminocarbonyl, amino-sulphonyl, methylsulphoximinyl and (methyl)(N-methyl)sulphoximinyl. Additional examples of particular substituents on $R^1$ include cyanoisopropyl, cyclopropylsulphonyl, isopropylsulphonyl and (hydroxy)ethylaminosulphonyl Particular examples of substituents on $R^1$ include one, two or three substituents independently selected from fluoro, methyl, isopropyl, isopropylmethyl, methylsulphonylmethyl, hydroxyisopropyl, cyclopropyl, cyclobutyl, methylsulphonyl, carboxy, hydroxymethyl, acetyl, methylsulphoximinyl, oxo, methoxy amino-sulphonyl, cyanoisopropyl, cyclopropyl-sulphonyl, isopropylsulphonyl and (hydroxy) ethylaminosulphonyl In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

In second particular embodiment, $R^1$ is substituted by $C_{1-6}$ alkylsulphonyl. In one aspect of this embodiment, $R^1$ is substituted by methylsulphonyl.

In a third particular embodiment $R^1$ is substituted by a halogen. In one aspect of this embodiment, $R^1$ is substituted by a fluoro.

In a fourth particular embodiment, $R^1$ is substituted by an ($C_{1-6}$)alkylsulphoximinyl. In one aspect of this embodiment, $R^1$ is substituted by methylsulphoximinyl.

Selected values of $R^1$ include hydrogen, bromo, chloro, cyano, —$CO_2R^d$, methoxycarbonyl-ethyl, ethoxycarbonyl-ethyl, hydroxybutynyl, chlorophenyl, hydroxyphenyl, methyl-sulphonylphenyl, (methylsulphonyl)methylphenyl, (methylsulphonyl)ethylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (di-((trifluoromethyl)(hydroxy)phenyl, methoxyazetidinyl, methoxypyrrolidinyl, (methoxycarbonyl)(methyl)pyrrolidinyl, (methoxymethyl)pyrrolidinyl, chloropyridinyl, (chloromethyl)pyridinyl, oxopiperidinyl, (carboxy)piperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, methylsulphonylpyrazolyl, methylsulphonylethylpyrazolyl, dimethylpyrazolyl, (methyl) [N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, tetrahydropyranylpyridinyl, fluoro-pyridinyl, cyanopyridinyl, methylpyridinyl, (cyano)(methyl)pyridinyl, dimethylpyridinyl, cyclopropylpyridinyl, trifluoromethylpyridinyl, ethenylpyridinyl, hydroxyisopropylpyridinyl, hydroxymethylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, methylsulphonylmethylpyridinyl, oxopyridinyl, (methyl)(oxo)-pyridinyl, (dimethyl)(oxo)pyridinyl, aminopyridinyl, methylaminopyridinyl, dimethyl-aminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, isopropylpyrimidinyl, fluoroisopropyl-pyrimidinyl, hydroxyisopropylpyrimidinyl, methoxypyrimidinyl, carboxycyclobutyloxy-pyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxy-cyclohexylpyrazolyl, carboxycyclohexylpyridinyl, cyclopropylpyrimidinyl, fluoromethylcyclopropylpyrimidinyl, acetylaminomethylcyclopropylpyrimidinyl, hydroxymethylpyrimidinyl, hydroxycyclobutylpyrimidinyl, (methyl)cyclobutyldiol-pyrimidinyl, carboxy-cyclopentylpyrimidinyl, carboxycyclohexylpyrimidinyl, (carboxy)(methyl)cyclohexyl-pyrimidinyl, (carboxy)(hydroxy)cyclohexylpyrimidinyl, carboxymethylcyclohexyl-pyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxycyclohexylpyrazinyl, carboxycyclohexylmethylpyrimidinyl, carboxycyclohexenyl-pyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexenylpyridinyl carboxybicyclo[3.1.0]hexanylpyrimidinyl, ethoxycarbonylbicyclo[3.1.0]hexanylpyrimidinyl, carboxybicyclo[4.1.0]heptanyl-pyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methyl-sulphonylethylpiperazinylpyridinyl, oxopiperazinylpyridinyl, acetylpiperazinylpyridinyl, (tert-butoxycarbonylpiperazinyl)pyridinyl, (tert-butoxycarbonylpiperazinyl)(methyl)pyridinyl, methylpiperazinylpyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinyl-pyridinyl, (tert-butoxycarbonyl)-3,6-dihydropyridine, oxothiomorpholinylpyridinyl, dioxothiomorpholinylpyridinyl, oxodiazepanyl-pyridinyl, tetrahydropyranylpyrimidinyl, fluorooxetanylpyrimidinyl, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxy-pyrrolidinylpyrimidinyl, (carboxy)(methyl)pyrrolidinylpyrimidinyl, carboxymethyl-pyrrolidinylpyrimidinyl, ethoxycarbonylpyrrolidinylpyrimidinyl, fluoro-tetrahydropyranylpyrimidinyl, hydroxytetrahydropyranylpyrimidinyl, (hydroxy)dioxidotetrahydrothiopyranyl)pyrimidinyl, piperidinylpyrimidinyl, difluoropiperidinylpyrimidinyl, (cyano)(methyl)piperidinylpyrimidinyl, (hydroxy)(nitromethyl)piperidinyl-pyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methyl-sulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinyl-pyrimidinyl, (carboxy)(methyl)piperidinylpyrimidinyl, (carboxy)(ethyl)piperidinyl-pyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxy-carbonyl)(methyl)piperidinylpyrimidinyl, (ethyl)(methoxycarbonyl)piperidinylpyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylpiperidinylpyrimidinyl, acetylamino-sulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethyl-piperazinylpyrimidinyl, tert-butoxycarbonylpiperazinylpyrimidinyl, tetrazolylmethylpiperazinylpyrimidinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, oxothiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinyl-pyrazinyl, (ethoxycarbonyl)(methyl)piperidinylpyrazinyl, morpholinylmethylthienyl, morpholinylethylpyrazolyl, isopropylmethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanyl-pyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, 3-carboxy-8-azabicyclo-[3.2.1]-octanylpyrimidinyl, 3-(dimethylamino carbonyl)-8-azabicyclo-[3.2.1]octanylpyrimidinyl, oxo-3,6-diazabicyclo[3.2.2]nonanylpyrimidinyl, 3,7-dioxa-9-azabicyclo[3.3.1]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanylpyrimidinyl, carboxy-2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, (dioxo)(methyl)-2,4,8-triazaspiro[4.5]decanylpyrimidinyl, 3,6-epiminofuro[3.2-b]furanylpyrimidinyl, 5-(methyl-1H-1,2,4-triazol-3yl)phenyl, dihydroisoindolyl, (methylsulphonyl)dihydroisoindolyl (tetrahydrothiopenyl)pyrazolyl, methylsulphoximinylphenyl, (imino)(oxo)thiazinanyl, (oxo)thiazinanyl and (dioxo)thiazinanyl. Additional values of $R^1$ include cyanoisopropylpyrimidinyl, 3-azabicyclo [3.2.1]octanylpyrimidinyl, 1H-pyridin-2-one, (methyl)-1H-pyridin-2-one, (cyclopropyl)-1H-pyridine-2-one, (cyclopropyl)sulphonyl-phenyl, aminosulphonyl-phenyl, (isopropyl)sulphonylphenyl and (hydroxy)ethylaminosulphonyl-phenyl. Appropriate values of $R^1$ include bromo, fluoro-tetrahydropyranylpyrimidinyl, fluoro-oxetanylpyrimidinyl, tetrahydropyranylpyridinyl, isopropylpyrimidinyl, isopropylmethylpyrazolyl, methylsulphonylmethylpyridinyl, morpholinylpyrimidinyl, hydroxyisopropylpyrimidinyl, cyclopropylpyridinyl, (methyl)cyclobutyldiol-pyrimidinyl, hydroxyisopropylpyridinyl, carboxy-3-azabicyclo[3.2.1]octanyl, methyl-sulphonylphenyl, hydroxymethylpyridinyl, methylsulphonylpyridinyl, methylsulphonylpiperazinylpyridinyl, methylpiperazinylpyridinyl, acetylpiperazinylpyridinyl, dimethylpyridinyl, methylpyrazolyl, oxodiazepanylpyrimidinyl, piperazinylpyridinyl, pyridinyl, (carboxy)(methyl)piperidinylpyrimidinyl, methoxypyridinyl, oxopyridinyl, (methylsulphonyl)methylphenyl, methylsulphoximinylphenyl, (imino)(oxo)thiazinanyl, (oxo)thiazinanyl, (dioxo)thiazinanyl, tetrahydropyranyl-pyrimidinyl; 2-oxa-7-azaspiro[3.5]nonanylpyrimidinyl, cyanoisopropyl-pyrimidinyl, (hydroxy)oxetanyl-pyridmidinyl, fluoroisopropylpyrimidinyl, 3,7-dioxa-9-azabicyclo [3.3.1]nonanyl-pyrimidinyl, 3-azabicyclo [3.2.1]octanylpyrimidinyl, 1H-pyridin-2-one, (methyl)-1H-pyridin-2-one, (cyclopropyl)-1H-pyridine-2-one, (cyclopropyl)sulphonyl-phenyl, (isopropyl)sulphonylphenyl, amino sulphonyl-phenyl, and (hydroxy)ethylaminosulphonyl-phenyl.

Illustrative values of $R^1$ include bromo, fluoro-tetrahydropyranylpyrimidinyl, fluoro-oxetanylpyrimidinyl, tetrahydropyranylpyridinyl, isopropylpyrimidinyl, isopropylmethylpyrazolyl, methylsulphonylmethylpyridinyl, morpholinylpyrimidinyl, hydroxyisopropylpyrimidinyl, cyclopropylpyridinyl, (methyl)cyclobutyldiol-pyrimidinyl, hydroxyisopropylpyridinyl, carboxy-3-azabicyclo[3.2.1]octanyl, methyl-sulphonylphenyl, hydroxymethylpyridinyl, methylsulphonylpyridinyl, methylsulphonylpiperazinylpyridinyl, methylpiperazinylpyridinyl, acetylpiperazinylpyridinyl, dimethylpyridinyl, methylpyrazolyl, oxodiazepanylpyrimidinyl, piperazinylpyridinyl, pyridinyl, (carboxy)(methyl)piperidinylpyrimidinyl, methoxypyridinyl, oxopyridinyl, (methylsulphonyl)methylphenyl, methylsulphoximinylphenyl, (imino)(oxo)thiazinanyl, (oxo)thiazinanyl and (dioxo)thiazinanyl.

Typically, $R^2$ represents hydrogen, halogen, cyano, nitro, hydroxy, trifluoromethyl, or trifluoromethoxy; or —OR$^a$; or an optionally substituted $C_{1-6}$ alkyl.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —OR$^a$. In a ninth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl.

Typical values of $R^2$ include hydrogen, fluoro, chloro, trifluoromethyl, trifluoromethoxy, —OR$^a$, methyl and ethoxycarbonylethyl.

Particular values of $R^2$ include hydrogen and fluoro.

Typically, $R^3$ represents hydrogen, halogen or $C_{1-6}$ alkyl.

In a first embodiment, $R^3$ represents hydrogen.

In a second embodiment, $R^3$ represents halogen. In one aspect of that embodiment, $R^3$ represents fluoro.

In a third embodiment, $R^3$ represents $C_{1-6}$ alkyl. In one aspect of that embodiment, $R^3$ represents unsubstituted $C_{1-6}$ alkyl. In a second aspect of that embodiment, $R^3$ represents substituted $C_{1-6}$ alkyl. In a particular aspect of this embodiment, $R^3$ represents methyl. In another particular aspect of that embodiment, $R^3$ represents ethyl.

In a particular embodiment, $R^3$ represents hydrogen.

Typically, $R^4$ represents hydrogen, halogen or $C_{1-6}$ alkyl.

In a first embodiment, $R^4$ represents hydrogen.

In a second embodiment, $R^4$ represents halogen. In one aspect of that embodiment, $R^4$ represents fluoro.

In a third embodiment, $R^4$ represents $C_{1-6}$ alkyl. In one aspect of that embodiment, $R^4$ represents unsubstituted $C_{1-6}$ alkyl. In a second aspect of that embodiment, $R^4$ represents substituted $C_{1-6}$ alkyl. In a particular aspect of this embodiment, $R^4$ represents methyl. In another particular aspect of that embodiment, $R^4$ represents ethyl.

In a particular embodiment, $R^4$ represents hydrogen. In another particular embodiment, $R^4$ represents fluoro.

Generally, $R^{5a}$ represents hydrogen, hydroxy, halogen, cyano, trifluoromethyl; or —NR$^b$R$^c$, —NR$^c$C(O)R$^d$, —(CO)NR$^c$R$^d$, —NHS(O)$_2$R$^e$, —S—R$^a$, —(SO)—R$^a$, —S(O)$_2$R$^a$, —S(O)(N—R$^d$), —S(O)$_2$(N—R$^d$), —OR$^a$, —C(O)$_2$R$^d$, or —O(CO)—R$^d$—; or $C_{1-6}$ alkyl, $C_{2-6}$ alkenyl, $C_{2-6}$ alkynyl, aryl, or heteroaryl, any of which groups may be optionally substituted by one or more substituents.

Typically, $R^{5a}$ represents hydrogen, hydroxy, halogen, or trifluoromethyl; or —NR$^b$R$^c$, S(O)$_2$R$^a$, —OR$^a$, or O—(CO)—R$^d$; or $C_{1-6}$ alkyl, any of which groups may be optionally substituted.

Suitable examples of optional substituents on $R^{5a}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, di$(C_{1-6})$alkylaminocarbonyl, oxo, and carboxy.

Typical examples of particular substituents on $R^{5a}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5a}$ represents hydrogen. In a second embodiment, $R^{5a}$ represents hydroxy. In a third embodiment, $R^{5a}$ represents halogen. In one aspect of this embodiment, $R^{5a}$ represents fluoro. In a fourth embodiment, $R^{5a}$ represents trifluoromethyl. In a fifth embodiment, $R^{5a}$ represents —$NR^bR^c$. In one aspect of that embodiment, $R^{5a}$ represents —$NH_2$. In a sixth embodiment, $R^{5a}$ represents —$NR^cC(O)R^d$. In a seventh embodiment, $R^{5a}$ represents —$C(O)$—$NR^cR^d$. In an eighth embodiment, $R^{5a}$ represents —$NHS(O)_2R^e$. In a ninth embodiment, $R^{5a}$ represents —S—$R^a$. In a tenth embodiment, $R^{5a}$ represents —S(O)—Ra. In an eleventh embodiment, $R^{5a}$ represents —$S(O)_2R^a$. In a particular aspect of this embodiment, $R^{5a}$ represents —$S(O)_2$—CH3. In a twelfth embodiment, $R^{5a}$ represents —$S(O)(N$—$R^d)R^a$. In a thirteenth embodiment, $R^{5a}$ represents —$S(O)_2(N$—$R^d)$. In a fourteenth embodiment, $R^{5a}$ represents —$OR^a$. In one aspect of this embodiment, $R^a$ is an optionally substituted $C_{1-6}$ alkyl. In second aspect of this embodiment $R^a$ is an optionally substituted aryl. In a third aspect of this embodiment, $R^a$ is an optionally substituted heteroaryl. In a fifteenth embodiment, $R^{5a}$ represents —O—(CO)—$R^d$. In a particular aspect of this embodiment, $R^{5a}$ represents —O—(CO)—$CH_3$. In a sixteenth embodiment, $R^{5a}$ represents —C(O)—$OR^d$. In a seventeenth embodiment, $R^{5a}$ represents optionally substituted $C_{1-6}$ alkyl. In one aspect of that embodiment, $R^{5a}$ represents substituted $C_{1-6}$ alkyl. In a second aspect of this embodiment, $R^{5a}$ represents unsubstituted $C_{1-6}$ alkyl. In a particular aspect of this embodiment, $R^{5a}$ represents methyl. In an eighteenth embodiment, $R^{5a}$ represents an optionally substituted $C_{2-6}$ alkynyl. In a nineteenth embodiment, $R^{5a}$ represents an optionally substituted heteroaryl.

In a twentieth embodiment $R^{5a}$ represents an optionally substituted aryl. In a twenty-first embodiment, $R^a$ represents an optionally substituted $C_{2-6}$ alkenyl.

In a twenty-second embodiment, $R^{5a}$ represents cyano.

Generally, $R^{5b}$ represents hydrogen, hydroxy, halogen, cyano, trifluoromethyl; or —$NR^bR^c$, —$NR^cC(O)R^d$, —(CO)$NR^cR^d$, —$NHS(O)_2R^e$, —S—$R^a$, —(SO)—$R^a$, —$S(O)_2R^a$, —$S(O)(N$—$R^d)$, —$S(O)_2(N$—$R^d)$, —$OR^a$, —$C(O)_2R^d$, or —$O(CO)$—$R^d$—; or $C_{1-6}$ alkyl, $C_{2-6}$ alkenyl, $C_{2-6}$ alkynyl, aryl, heteroaryl, any of which groups may be optionally substituted by one or more substituents.

Typically, $R^{5b}$ represents hydrogen, hydroxy, halogen, or trifluoromethyl; or —$NR^bR^c$, $S(O)_2R^a$, —$OR^a$, or O—(CO)—$R^d$; or $C_{1-6}$ alkyl any of which groups may be optionally substituted.

Suitable examples of optional substituents on $R^{5b}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$alkyl, $(C_{3-7})$cycloalkyl, $C_{1-6}$ alkylsulphonyl, $(C_{1-6})$alkylsulphonyl$(C_{1-6})$alkyl, di$(C_{1-6})$alkylaminocarbonyl, oxo, and carboxy.

Typical examples of particular substituents on $R^{5b}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl In a first embodiment, $R^{5b}$ represents hydrogen. In a second embodiment, $R^{5b}$ represents hydroxy. In a third embodiment, $R^{5b}$ represents halogen. In one aspect of this embodiment, $R^{5b}$ represents fluoro. In a fourth embodiment, $R^{5b}$ represents trifluoromethyl. In a fifth embodiment, $R^{5b}$ represents —$NR^bR^c$. In one aspect of that embodiment, $R^{5b}$ represents —$NH_2$. In a sixth embodiment, $R^{5b}$ represents —$NR^cC(O)R^d$. In a seventh embodiment, $R^{5b}$ represents —$C(O)$—$NR^cR^d$. In an eighth embodiment, $R^{5b}$ represents —$NHS(O)_2R^e$. In a ninth embodiment, $R^{5a}$ represents —S—$R^a$. In a tenth embodiment, $R^{5b}$ represents —S(O)—Ra. In an eleventh embodiment, $R^{5b}$ represents —$S(O)_2R^a$. In a particular aspect of this embodiment, $R^{5b}$ represents —$S(O)_2$—CH3. In a twelfth embodiment, $R^{5b}$ represents —$S(O)(N$—$R^d)R^a$. In a thirteenth embodiment, $R^{5b}$ represents —$S(O)_2(N$—$R^d)$. In a fourteenth embodiment, $R^{5b}$ represents —$OR^a$. In one aspect of this embodiment, $R^a$ is a $C_{1-6}$ alkyl. In second aspect of this embodiment $R^a$ is an aryl. In a third aspect of this embodiment, $R^a$ is an heteroaryl. In a fifteenth embodiment, $R^{5b}$ represents —O—(CO)—$R^d$. In a particular aspect of this embodiment, $R^{5b}$ represents —O—(CO)—$CH_3$. In a sixteenth embodiment, —C(O)—$OR^d$. In a seventeenth embodiment $R^{5b}$ represents optionally substituted $C_{1-6}$ alkyl. In one aspect of that embodiment, $R^{5b}$ represents substituted $C_{1-6}$ alkyl. In a second aspect of this embodiment, $R^{5b}$ represents unsubstituted $C_{1-6}$ alkyl. In a particular aspect of this embodiment, $R^{5b}$ represents methyl. In an eighteenth embodiment, $R^{5b}$ represents an optionally substituted $C_{2-6}$ alkynyl. In a nineteenth embodiment, $R^{5b}$ represents an optionally substituted heteroaryl. In a twentieth embodiment $R^{5b}$ represents an optionally substituted aryl. In a twenty-first embodiment, $R^{5b}$ represents an optionally substituted $C_{2-6}$ alkenyl. In a twenty-second embodiment, $R^{5b}$ represents cyano.

Particularly, $R^{5b}$ represents hydrogen or methyl.

In an alternative embodiment, $R^{5a}$ and $R^{5b}$ when taken together with the carbon to which they are attached represent a carbonyl, thiocarbonyl or —C=N—OH.

In one aspect of that alternative embodiment, $R^{5a}$ and $R^{5b}$ when taken together with the carbon to which they are attached represent a carbonyl.

On a second aspect of that alternative embodiment, $R^{5a}$ and $R^{5b}$ when taken together with the carbon to which they are attached represent a thiocarbonyl.

In another aspect of that alternative embodiment, $R^{5a}$ and $R^{5b}$ when taken together with the carbon to which they are attached represent-C=N—OH.

Particular values of $R^{5a}$ include hydrogen, hydroxy, fluoro, trifluoromethyl, —$N(CH_3)_2$, —$NH(CO)CH_3$, —$SO_2$—$CH_3$, —O—(CO)—$CH_3$, methyl, methoxy, (hydroxy) ethoxy, (hydroxy)propoxy and 2-oxo-1-pyrrolidinyl-.

Selected values of $R^{5a}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl and methoxy.

Selected values of $R^{5b}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl and methoxy.

In a particular embodiment, $R^{5a}$ is as defined above and $R^{5b}$ represents hydrogen. In a particular aspect of this embodiment, $R^{5a}$ is hydroxy.

In another particular embodiment $R^{5a}$ is as defined above and $R^{5b}$ represents $C_{1-4}$ alkyl, preferably methyl. In a particular aspect of this embodiment, $R^{5a}$ is hydroxy.

Generally, $R^6$ represents hydrogen, hydroxy, halogen, cyano, trifluoromethyl; or —NR$^b$R$^c$, —NR$^c$C(O)R$^d$, —NHS(O)$_2$R$^e$, —S(O)$_2$R$^a$, —S(O)(N—R$^d$)R$^a$ or —O—(CO)—R$^d$; or $C_{1-6}$ alkyl, $C_{2-6}$ alkenyl, $C_{2-6}$ alkynyl, aryl, or heteroaryl, any of which groups may be optionally substituted by one or more substituents.

Typically, $R^6$ represents hydrogen, hydroxy, halogen, or trifluoromethyl.

In a particular embodiment, $R^6$ represents hydrogen.

In an alternative embodiment, $R^6$ and Y together with the carbon to which they are attached form a $C_{3-7}$ cycloalkyl.

In another alternative embodiment, $R^6$ and Y together with the carbon to which they are attached form a $C_{3-7}$ heterocycloalkyl. In one particular aspect according to this embodiment, $R^6$ and Y together with the carbon to which they are attached form a dihydrobenzofuran. In a second particular aspect according to this embodiment, $R^6$ and Y together with the carbon to which they are attached form a 3H-benzofuranone. In a third particular aspect according to this embodiment, $R^6$ and Y together with the carbon to which they are attached form a dihydroisoindole. In a fourth particular aspect according to this embodiment, $R^6$ and Y together with the carbon to which they are attached form a dihydroisoindolone.

Typical examples of suitable substituents on $R^a$, $R^b$, $R^c$, $R^d$ or $R^e$, or on the heterocyclic moiety —NR$^b$R$^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl. Additional examples of optional substituents on $R^a$ include 2-oxo-1-pyrrolidinyl.

Typical examples of specific substituents on $R^a$, $R^b$, $R^c$, $R^d$ or $R^e$, or on the heterocyclic moiety —NR$^b$R$^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents. Additional values of $R^a$ include propyl.

Selected examples of suitable substituents on $R^a$ include $C_{1-6}$ alkoxy and oxo. Additional examples of suitable substituents on $R^a$ include 2-oxo-1-pyrrolidinyl.

Appropriate examples of specific substituents on $R^a$ include methoxy, oxo, hydroxy and 2-oxo-1-pyrrolidinyl.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl. In a further embodiment, $R^a$ represents $C_{3-7}$ cycloalkyl. In a further embodiment, $R^a$ represents $C_{3-7}$ heterocycloalkyl.

Specific values of $R^a$ include methyl, methoxyethyl, benzyl and dioxoisoindolylpropyl. Additional specific values of $R^a$ include (hydroxy)ethyl, (hydroxy)propyl and 2-oxo-1-pyrrolidinyl-ethyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-$(C_{1-6})$ alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, (imino)(oxo)thiazinan-4-yl, (oxo)thiazinan-4-yl or (dioxo)thiazinan-4-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy$(C_{1-6})$alkyl, amino$(C_{1-6})$alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino$(C_{1-6})$alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the heterocyclic moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, amino carbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl, oxohomopiperazin-1-yl, (imino)(oxo)thiazinan-4-yl, (oxo)thiazinan-4-yl, and (dioxo)thiazinan-4-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di$(C_{1-6})$alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl.

In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl.

In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl.

In a further embodiment, $R^d$ represents optionally substituted $C_{3-7}$ heterocycloalkyl, e.g. thiazolidinyl or oxo-thiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Particular examples of selected values for $R^d$ include hydrogen and methyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA) and N-oxides thereof, and pharmaceutically acceptable salts and solvates thereof, and glucuronide derivatives thereof, and co-crystals thereof:

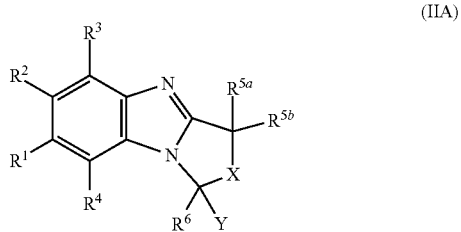

(IIA)

Wherein

X, Y, $R^1$, $R^2$, $R^3$, $R^4$ $R^{5a}$, $R^{5b}$ and $R^6$ are as defined above.

A particular sub-group of the compounds of formula (IIA) above is represented by the compounds of formula (IIB) and N-oxides thereof, and pharmaceutically acceptable salts and solvates thereof, and glucuronide derivatives thereof, and co-crystals thereof:

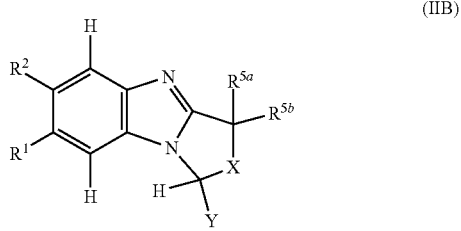

(IIB)

wherein $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl $(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents;

$R^2$ represents hydrogen, halogen, cyano, trifluoromethyl; or an optionally substituted $C_{1-6}$ alkyl;

X represents an oxygen atom or a sulphur atom; or —S(O), —N—$R^d$; or an optionally substituted straight or branched $C_{1-4}$ alkylene chain;

$R^{5a}$ represents hydrogen, hydroxy, halogen, cyano, or trifluoromethyl; or —$NR^bR^c$, —$NR^cC(O)R^d$, —(CO)$NR^cR^d$, —$NHS(O)_2R^e$, —S—$R^a$, —(SO)—$R^a$, —$S(O)_2R^a$, —$S(O)(N-R^d)$, —$S(O)_2(N-R^d)$, —$OR^a$, —$C(O)_2R^d$, or —$O(CO)-R^d$—; or $C_{1-6}$ alkyl, $C_{2-6}$ alkenyl, $C_{2-6}$ alkynyl, aryl, heteroaryl, any of which groups may be optionally substituted by one or more substituents; and $R^{5b}$ represents hydrogen, hydroxy, halogen, cyano, or trifluoromethyl; or $C_{1-6}$ alkyl, any of which groups may be optionally substituted by one or more substituents; or $R^{5a}$ and $R^{5b}$ when taken together with the carbon to which they are attached represent a carbonyl, thiocarbonyl, or —C=N—OH; and Y, $R^a$, $R^b$, $R^c$ and $R^d$ are as defined above for compounds of formula (I).

Examples of optional substituents which may be present on $R^1$, $R^2$, $R^{5a}$ and $R^{5b}$ include one, two or three substituents independently selected from halogen, halo-$(C_{1-6})$alkyl, cyano, cyano$(C_{1-6})$alkyl, nitro, nitro$(C_{1-6})$alkyl, $C_{1-6}$ alkyl, $(C_{3-7})$cycloalkyl, difluoromethyl, trifluoromethyl, difluoroethyl, trifluoroethyl, $C_{2-6}$ alkenyl, hydroxy, hydroxy$(C_{1-6})$alkyl, $C_{1-6}$ alkoxy, difluoromethoxy, trifluoromethoxy, trifluoroethoxy, carboxy$(C_{3-7})$cycloalkyl-oxy, $C_{1-3}$ alkylenedioxy, $C_{1-6}$ alkoxy$(C_{1-6})$alkyl, $C_{1-6}$ alkylthio, $C_{1-6}$ alkylsulphinyl, $C_{1-6}$ alkylsulphonyl, $(C_{1-6})$alkylsulphonyl $(C_{1-6})$alkyl, oxo, amino, amino$(C_{1-6})$alkyl, $C_{1-6}$ alkyl-amino, di$(C_{1-6})$alkylamino, hydroxy$(C_{1-6})$alkylamino, $C_{1-6}$ alkoxyamino, $(C_{1-6})$alkoxy-$(C_{1-6})$alkylamino, [$(C_{1-6})$alkoxy](hydroxy)$(C_{1-6})$alkylamino, [$(C_{1-6})$alkylthio](hydroxy)-$(C_{1-6})$alkylamino, N—[$(C_{1-6})$alkyl]-N-[hydroxy$(C_{1-6})$alkyl]amino, di$(C_{1-6})$alkylamino-$(C_{1-6})$alkylamino, N-[di$(C_{1-6})$alkylamino$(C_{1-6})$alkyl]-N-[hydroxy$(C_{1-6})$alkyl] amino, hydroxy$(C_{1-6})$alkyl$(C_{3-7})$cycloalkylamino, (hydroxy)[$(C_{3-7})$cycloalkyl$(C_{1-6})$alkyl]amino, $(C_{3-7})$heterocycloalkyl$(C_{1-6})$alkylamino, oxo$(C_{3-7})$heterocycloalkyl$(C_{1-6})$alkylamino, $(C_{1-6})$alkylheteroarylamino, heteroaryl$(C_{1-6})$alkylamino, $(C_{1-6})$alkylheteroaryl$(C_{1-6})$alkyl-amino, $C_{2-6}$ alkylcarbonylamino, N—[$(C_{1-6})$alkyl]-N—[$(C_{2-6})$alkylcarbonyl]amino, $(C_{2-6})$alkyl-carbonylamino$(C_{1-6})$alkyl, $C_{3-6}$ alkenylcarbonylamino, bis[$(C_{3-6})$alkenylcarbonyl]amino, N—[$(C_{1-6})$alkyl]-N—[$(C_{3-7})$cycloalkylcarbonyl]amino, $C_{2-6}$ alkoxycarbonylamino, $C_{2-6}$ alkoxycarbonyl$(C_{1-6})$alkylamino, $C_{1-6}$ alkylaminocarbonylamino, $C_{1-6}$ alkylsulphonyl-amino, N—[$(C_{1-6})$alkyl]-N—[$(C_{1-6})$alkylsulphonyl]amino, bis[$(C_{1-6})$alkylsulphonyl]amino, N—[$(C_{1-6})$alkyl]-N-[carboxy$(C_{1-6})$alkyl]amino, carboxy$(C_{3-7})$cycloalkylamino, carboxy-$(C_{3-7})$cycloalkyl$(C_{1-6})$alkylamino, formyl, $C_{2-6}$ alkylcarbonyl, $(C_{3-7})$cycloalkylcarbonyl, phenylcarbonyl, $(C_{2-6})$alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonylmethylidenyl, a carboxylic acid isostere or prodrug moiety Ω, —$(C_{1-6})$alkyl-Ω, aminocarbonyl, $C_{1-6}$ alkylaminocarbonyl, hydroxy$(C_{1-6})$alkylaminocarbonyl, di$(C_{1-6})$alkylaminocarbonyl, aminocarbonyl$(C_{1-6})$alkyl, aminosulphonyl, di$(C_{1-6})$alkylaminosulphonyl, $(C_{1-6})$alkylsulphoximinyl, [$(C_{1-6})$alkyl][N—$(C_{1-6})$alkyl]-sulphoximinyl and heteroaryl. Additional examples of optional substituents on $R^1$, $R^2$, $R^{5a}$ and $R^{5b}$ include $(C_{3-7})$cycloalkyl-sulphonyl and hydroxy $(C_{1-6})$alkylaminosulphonyl.

Examples of particular substituents on $R^1$, $R^2$, $R^{5a}$ and $R^{5b}$ include fluoro, chloro, bromo, fluoromethyl, fluoroisopropyl, cyano, cyanoethyl, nitro, nitromethyl, methyl, ethyl, isopropyl, isobutyl, tert-butyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, cyclopropyl, (cyclopropyl)

(hydroxy)propylamino, morpholinylethyl-amino, oxopyrrolidinylmethylamino, ethyloxadiazolylamino, methylthiadiazolylamino, thiazolylmethylamino, thiazolylethylamino, pyrimidinylmethylamino, methylpyrazolyl-methylamino, acetylamino, N-acetyl-N-methylamino, N-isopropylcarbonyl-N-methyl-amino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylaminocarbonyl, hydroxyethylaminocarbonyl, dimethylaminocarbonyl, aminocarbonylmethyl, aminosulphonyl, methylaminosulphonyl, dimethylaminosulphonyl, methylsulphoximinyl, (methyl)(N-methyl)sulphoximinyl and triazolyl. Additional examples of particular substituents on $R^1$, $R^2$, $R^{5a}$, and $R^{5b}$ include cyanosisopropyl, cyclopropyl-sulphonyl, isopropylsulphonyl and (hydroxy)ethylaminosulphonyl.

Suitable examples of particular substituents on $R^1$, $R^2$, $R^{5a}$ and $R^{5b}$ include fluoro, hydroxy, methyl-sulphonyl, methyl, isopropyl, methoxy, ethoxycarbonyl, cyclpropyl, cyclobutyl, carboxy, methylsulphoximinyl, acetyl, cyanosiopropyl, cyclopropyl-sulphonyl, isopropylsulphonyl and (hydroxy)ethylaminosulphonyl.

Generally, $R^1$ represents $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Appropriately, $R^1$ represents aryl, $(C_{3-7})$heterocycloalkenyl-, heteroaryl, $(C_{3-7})$heterocycloalkyl-heteroaryl-, $(C_{4-9})$heterobicycloalkyl-heteroaryl- or $(C_{4-9})$spiroheterocycloalkyl-heteroaryl, any of which groups may be optionally substituted by one or more substituents.

More generally, $R^1$ represents aryl, heteroaryl, or $(C_{3-7})$heterocycloalkyl-heteroaryl-, either of which groups may be optionally substituted by one or more substituents.

In a first embodiment, $R^1$ represents halogen. In one aspect of that embodiment, $R^1$ represents bromo.

In a second embodiment, $R^1$ represents cyano.

In a third embodiment, $R^1$ represents optionally substituted $C_{1-6}$ alkyl. In one aspect of that embodiment, $R^1$ represents optionally substituted ethyl.

In a fourth embodiment, $R^1$ represents optionally substituted $C_{2-6}$ alkynyl. In one aspect of that embodiment, $R^1$ represents optionally substituted butynyl.

In a fifth embodiment, $R^1$ represents optionally substituted aryl. In one aspect of that embodiment, $R^1$ represents optionally substituted phenyl.

In an sixth embodiment, $R^1$ represents optionally substituted $C_{3-7}$ heterocycloalkyl.

In a seventh embodiment, $R^1$ represents optionally substituted $C_{3-7}$ heterocycloalkenyl. In one aspect of this embodiment $R^1$ represents optionally substituted 1-H-pyridin-2-one.

In an eighth embodiment, $R^1$ represents optionally substituted heteroaryl. In selected aspects of that embodiment, $R^1$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In a ninth embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a tenth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In an eleventh embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-.

In a seventh aspect of that embodiment, $R^1$ represents optionally substituted cyclohexylpyrazinyl-. In an eighth aspect of that embodiment, $R^1$ represents optionally substituted cyclopropylpyridinyl.

In a twelfth embodiment, $R^1$ represents optionally substituted $(C_{4-7})$-cycloalkenyl-heteroaryl-.

In a thirteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, R represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, R represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinylpyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanylpyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl. In twenty-third aspect of that embodiment, $R^1$ represents (imino)(oxo)thiazinanyl-pyrimidinyl. In twenty-fourth aspect of that embodiment, $R^1$ represents (oxo)thiazinanyl-pyrimidinyl. In twenty-fifth aspect of that embodiment, $R^1$ represents and (dioxo)thiazinanyl-pyrimidinyl.

In a fourteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a fifteenth embodiment, $R^1$ represents optionally substituted $(C_{3-7})$-heterocycloalkenyl-heteroaryl-.

In a sixteenth embodiment, $R^1$ represents optionally substituted $(C_{4-9})$-heterobicycloalkyl-heteroaryl-. In one aspect of this embodiment $R^1$ represents 3-azabicyclo[3.2.1]octanylpyrimidinyl. In another aspect of that embodiment, $R^1$ represents optionally substituted 3,7-dioxa-9-azabicyclo[3.3.1]nonanyl-pyrimidinyl.

In seventeenth embodiment, $R^1$ represents optionally substituted $(C_{4-9})$-spiroheterocycloalkyl-heteroaryl-. In one aspect of that embodiment, $R^1$ represents optionally substituted 2-oxa-7-aza-spiro[3,5]nonanyl-pyrimidinyl.

In an eighteenth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a nineteenth embodiment, $R^1$ represents optionally substituted $(C_{4-9})$-bicycloalkyl-heteroaryl-.

Appositely, $R^1$ represents bromo, or cyano; or ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexyl-pyrimidinyl, cyclohexylpyrazinyl, cyclohexylmethylpyrimidinyl, cyclohexenylpyridinyl, cyclopropylpyridinyl, cyclohexenylpyrimidinyl, bicyclo[3.1.0]hexanylpyridinyl, bicyclo[3.1.0] hexanyl-pyrimidinyl, bicyclo[4.1.0]heptanylpyrimidinyl, bicyclo[2.2.2]octanylpyrimidinyl, pyrrolidinylpyridinyl, tetrahydropyranylpyridinyl, piperidinylpyridinyl, piperazinylpyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinyl-pyrimidinyl, tetrahydropyranylpyrimidinyl, piperidinylpyrimidinyl, piperazinyl-pyrimidinyl, hexahydro-[1,2,5]thiadiazolo[2,3-a]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinylpyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 3-azabicyclo[4.1.0]heptanylpyridinyl, 3-azabicyclo[4.1.0]heptanyl-pyrimidinyl, 2-oxabicyclo[2.2.2]octanylpyrimidinyl, 3-azabicyclo[3.2.1]octanyl-pyrimidinyl, 8-azabicyclo[3.2.1] octanylpyrimidinyl, 3-oxa-8-azabicyclo[3.2.1]octanylpyrimidinyl, 3,6-diazabicyclo[3.2.2]nonanylpyrimidinyl, 3-oxa-7-azabicyclo[3.3.1]-nonanylpyrimidinyl, 5-azaspiro[2.3]hexanylpyrimidinyl, 5-azaspiro[2.4]heptanyl-pyrimidinyl, 2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl or 2,4,8-triazaspiro[4.5]decanyl-pyrimidinyl, (imino)(oxo)thiazinanyl-pyrimidinyl, (oxo)thiazinanyl-pyrimidinyl and (dioxo)thiazinanyl-pyrimidinyl, any of which groups may be optionally substituted by one or more substituents. Additionally, $R^1$ represents 1H-pyridin-2-one, optionally substituted by one or more substituents.

Appropriately, $R^1$ represents phenyl, tetrahydropyranylpyrimidinyl, oxetanylpyrimidinyl, tetrahydropyranylpyridinyl, pyrimidinyl, pyrazolyl, pyridinyl, pyrimidinyl, morpholinylpyrimidinyl, piperazinylpyridinyl, diazepanylpyrimidinyl, 3-azabicyclo[3.2.1]octanylpyrimidinyl, piperidinylpyrimidinyl, cyclobutypyrimidinyl, (imino)(oxo)thiazinanyl-pyrimidinyl, (oxo)thiazinanyl-pyrimidinyl, (dioxo) thiazinanyl-pyrimidinyl, 2-oxa-7-azaspiro[3.5]nonanylpyrimidinyl, 3,7-dioxa-9-azabicyclo [3.3.1]nonanylpyrimidinyl, 3-azabicyclo [3.2.1]octanyl-pyrimidinyl, or 1H-pyridin-2-one, any of which groups may be optionally substituted by one or more substituents.

Illustratively, $R^1$ represents phenyl, tetrahydropyranylpyrimidinyl, oxetanylpyrimidinyl, tetrahydropyranylpyridinyl, pyrimidinyl, pyrazolyl, pyridinyl, pyrimidinyl, morpholinylpyrimidinyl, piperazinylpyridinyl, diazepanylpyrimidinyl, (imino)(oxo)thiazinanyl-pyrimidinyl, (oxo)thiazinanyl-pyrimidinyl, (dioxo)thiazinanyl-pyrimidinyl or piperidinylpyrimidinyl, any of which groups may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro $(C_{1-6})$alkyl, $C_{1-6}$ alkyl, $(C_{3-7})$cycloalkyl, trifluoromethyl, trifluoroethyl, $C_{2-6}$ alkenyl, hydroxy, hydroxy$(C_{1-6})$alkyl, $C_{1-6}$ alkoxy, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$ alkyl, oxo, amino, amino-$(C_{1-6})$alkyl, $C_{1-6}$ alkylamino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino$(C_{1-6})$alkyl, $C_{1-6}$ alkylsulphonylamino, N—[$(C_{1-6})$alkyl]-N—[$(C_{1-6})$alkylsulphonyl]amino, bis[$(C_{1-6})$alkylsulphonyl]amino, N—[$(C_{1-6})$alkyl]-N-[carboxy$(C_{1-6})$alkyl]amino, carboxy$(C_{3-7})$cycloalkyl-amino, carboxy$(C_{3-7})$cycloalkyl$(C_{1-6})$alkylamino, formyl, $C_{1-6}$ alkylcarbonyl, $(C_{2-6})$alkyl-carbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonyl-methylidenyl, a carboxylic acid isostere or prodrug moiety Ω as defined herein, —($C_{1-6}$)alkyl-Ω, aminocarbonyl, aminosulphonyl, ($C_{1-6}$)alkylsulphoximinyl, [($C_{1-6}$)alkyl][N—($C_{1-6}$)alkyl]sulphoximinyl and heteroaryl. Additional examples of optional substituents on $R^1$ include ($C_{3-7}$)cycloalkyl-sulphonyl and hydroxy($C_{1-6}$)alkylaminosulphonyl.

Appropriate examples of optional substituents on $R^1$ include one, two or three substituents independently selected from halogen, hydroxy, $C_{1-6}$ alkyl, $C_{1-6}$ alkoxy, $C_{1-6}$ alkylcarbonyl, (hydroxy)$C_{1-6}$alkyl, ($C_{3-7}$)cycloalkyl, $C_{1-6}$ alkylsulphonyl, ($C_{1-6}$)alkylsulphonyl($C_{1-6}$)alkyl, ($C_{1-6}$)alkylsulphoximinyl, heteroaryl, oxo, carboxy, (cyano)$C_{1-6}$alkyl, (halo)$C_{1-6}$alkyl, aminosulphonyl, ($C_{3-7}$)cycloalkyl-sulphonyl and hydroxy($C_{1-6}$)alkylaminosulphonyl.

Suitable examples of optional substituents on $R^1$ include one, two or three substituents independently selected from halogen, hydroxy, $C_{1-6}$ alkyl, $C_{1-6}$ alkoxy, $C_{1-6}$ alkylcarbonyl, (hydroxy)$C_{1-6}$alkyl, ($C_{3-7}$)cycloalkyl, $C_{1-6}$ alkylsulphonyl, ($C_{1-6}$)alkylsulphonyl($C_{1-6}$)alkyl, ($C_{1-6}$)alkylsulphoximinyl, oxo and carboxy.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl, (methyl)(N-methyl)sulphoximinyl and triazolyl. Additional examples of particular substituents on $R^1$ include cyanoisopropyl, cyclopropyl-sulphonyl, isopropylsulphonyl and (hydroxy)ethylaminosulphonyl.

Particular examples of substituents on $R^1$ include one, two or three substituents independently selected from fluoro, methyl, isopropyl, isopropylmethyl, methylsulphonylmethyl, hydroxy, hydroxyisopropyl, cyclopropyl, methylsulphonyl, carboxy, hydroxymethyl, acetyl, methylsulphoximinyl, oxo, methoxy, amino-sulphonyl, cyanoisopropyl, cyclopropyl-sulphonyl, isopropylsulphonyl and (hydroxy)ethylaminosulphonyl.

In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

In second particular embodiment, $R^1$ is substituted by $C_{1-6}$ alkylsulphonyl. In one aspect of this embodiment, $R^1$ is substituted by methylsulphonyl.

In a third particular embodiment $R^1$ is substituted by a halogen. In one aspect of this embodiment, $R^1$ is substituted by a fluoro.

In a fourth particular embodiment, $R^1$ is substituted by ($C_{1-6}$)alkylsulphoximinyl. In one aspect of this particular embodiment, $R^1$ is substituted by methylsulphoximinyl.

Selected values of $R^1$ include bromo, cyano, methoxycarbonyl-ethyl, ethoxycarbonylethyl, hydroxybutynyl, chlorophenyl, hydroxyphenyl, methyl-sulphonylphenyl, (methylsulphonyl)methylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (methoxycarbonyl)(methyl)pyrrolidinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, tetrahydropyranylpyridinyl, fluoro-pyridinyl, cyanopyridinyl, methylpyridinyl, (cyano)(methyl)pyridinyl, dimethylpyridinyl, cyclopropylpyridinyl, trifluoromethylpyridinyl, ethenylpyridinyl, hydroxyisopropylpyridinyl, hydroxymethylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, methylsulphonylmethylpyridinyl, oxopyridinyl, (methyl)(oxo)-pyridinyl, (dimethyl)(oxo)pyridinyl, aminopyridinyl, methylaminopyridinyl, dimethyl-aminopyridinyl, methoxyethylaminopyridinyl, N-(hydroxyethyl)-N-(methyl)amino-pyridinyl, methylsulphonylaminopyridinyl, [bis(methylsulphonyl)amino]pyridinyl, carboxypyridinyl, quinolinyl, hydroxypyridazinyl, pyrimidinyl, isopropylpyrimidinyl, fluoroisopropyl-pyrimidinyl, hydroxyisopropylpyrimidinyl, methoxypyrimidinyl, carboxycyclobutyloxy-pyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxy-cyclohexylpyrazolyl, carboxycyclohexylpyridinyl, fluoromethylcyclopropylpyrimidinyl, acetylaminomethylcyclopropylpyrimidinyl, hydroxycyclobutylpyrimidinyl, carboxy-cyclopentylpyrimidinyl, carboxycyclohexylpyrimidinyl, (carboxy)(methyl)cyclohexylpyrimidinyl, (carboxy)(hydroxy)cyclohexylpyrimidinyl, carboxymethylcyclohexyl-pyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxy-cyclohexylpyrazinyl, carboxycyclohexylmethylpyrimidinyl, carboxycyclohexenyl-pyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)(methyl)pyridinyl, methylpiperazinylpyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanyl-pyridinyl, fluorooxetanylpyrimidinyl, hydroxyoxetanylpyrimidinyl, hydroxyazetidinyl-pyrimidinyl, (hydroxy)(methyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxy-pyrrolidinylpyrimidinyl, (carboxy)(methyl)pyrrolidinylpyrimidinyl, carboxymethyl-pyrrolidinylpyrimidinyl, ethoxycarbonylpyrrolidinylpyrimidinyl, fluoro-tetrahydropyranylpyrimidinyl, hydroxytetrahydropyranylpyrimidinyl, difluoropiperidinylpyrimidinyl, (cyano)(methyl)piperidinylpyrimidinyl, (hydroxy)(nitromethyl)piperidinyl-pyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinyl-pyrimidinyl, (carboxy)(methyl)piperidinylpyrimidinyl, (carboxy)(ethyl)piperidinyl-pyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxymethylpiperidinylpyrimidinyl, methoxycarbonylpiperidinylpyrimidinyl, ethoxycarbonylpiperidinylpyrimidinyl, (ethoxycarbonyl)(fluoro)piperidinylpyrimidinyl, (methoxy-carbonyl)(methyl)piperidinylpyrimidinyl, (ethyl)(methoxycarbonyl)piperidinylpyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylaminosulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethyl-piperazinylpyrimidinyl, tert-butoxycarbonylpiperazinylpyrimidinyl, tetrazolylmethyl-piperazinylpyrimidinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, isopropylmethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo [3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanyl-pyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, oxo-3,6-diazabicyclo[3.2.2]nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanyl-pyrimidinyl, carboxy-2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, (dioxo)(methyl)-2,4,8-triazaspiro[4.5]decanylpyrimidinyl, methylsulphoximinylphenyl, (methyl)cyclobutyldiol-pyrimidinyl, (imino)(oxo)thiazinanyl-pyrimidinyl, (oxo)thiazinanyl-pyrimidnyl and (dioxo)thiazinanyl-pyrimidinyl. Additional values of $R^1$ include cyanoisopropyl-pyrimidinyl, 3-azabicyclo [3.2.1]octanylpyrimidinyl, 1H-pyridin-2-one, (methyl)-1H-pyridin-2-one, (cyclopropyl)-1H-pyridine-2-one, (cyclopropyl)sulphonyl-phenyl, aminosulphonyl-phenyl, (isopropyl)sulphonylphenyl and (hydroxy)ethylaminosulphonyl-phenyl. Appropriate values of $R^1$ include bromo, fluoro-tetrahydropyranylpyrimidinyl, fluoro-oxetanylpyrimidinyl, tetrahydropyranylpyridinyl, isopropylpyridinyl, isopropylmethylpyrazolyl, methylsulphonylmethylpyridinyl, morpholinylpyrimidinyl, hydroxyisopropylpyrimidinyl, cyclopropylpyridinyl, (methyl)cyclobutyldiol-pyrimidinyl, hydroxyisopropylpyridinyl, carboxy-3-azabicyclo[3.2.1]octanyl, methyl-sulphonylphenyl, hydroxymethylpyridinyl, methylsulphonylpyridinyl, methylsulphonylpiperazinylpyridinyl, methylpiperazinylpyridinyl, acetylpiperazinylpyridinyl, dimethylpyridinyl, methylpyrazolyl, oxodiazepanylpyrimidinyl, piperazinylpyridinyl, pyridinyl, (carboxy)(methyl)piperidinylpyrimidinyl, methoxypyridinyl, oxopyridinyl, (methylsulphonyl)methylphenyl, methylsulphoximinylphenyl, (imino)(oxo)thiazinanyl, (oxo)thiazinanyl, (dioxo)thiazinanyl, tetrahydropyranyl-pyrimidinyl; 2-oxa-7-azaspiro[3.5]nonanylpyrimidinyl, cyanoisopropyl-pyrimidinyl, (hydroxy)oxetanyl-pyridmidinyl, fluoroisopropylpyrimidinyl, 3,7-dioxa-9-azabicyclo [3.3.1]nonanyl-pyrimidinyl, 3-azabicyclo [3.2.1]octanylpyrimidinyl, 1H-pyridin-2-one, (methyl)-1H-pyridin-2-one, (cyclopropyl)-1H-pyridine-2-one, (cyclopropyl)sulphonyl-phenyl, (isopropyl)sulphonylphenyl, amino sulphonyl-phenyl, and (hydroxy)ethylaminosulphonyl-phenyl.

Illustrative values of $R^1$ include bromo, fluoro-tetrahydropyranylpyrimidinyl, fluoro-oxetanylpyrimidinyl, tetrahydropyranylpyridinyl, isopropylpyrimidinyl, isopropylmethylpyrazolyl, methylsulphonylmethylpyridinyl, morpholinylpyrimidinyl, hydroxyisopropylpyrimidinyl, cyclopropylpyridinyl, hydroxyisopropylpyridinyl, carboxy-3-azabicyclo[3.2.1]octanylpyrimidinyl, methyl-sulphonylphenyl, hydroxymethylpyridinyl, methylsulphonylpyridinyl, methylsulphonylpiperazinylpyridinyl, methylpiperazinylpyridinyl, acetylpiperazinylpyridinyl, dimethylpyridinyl, methylpyrazolyl, oxodiazepanylpyrimidinyl, piperazinylpyridinyl, pyridinyl, (carboxy)(methyl) piperidinylpyrimidinyl, methoxypyridinyl, oxopyridinyl, and (methylsulphonyl)methylphenyl.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen.

In a second embodiment, $R^2$ represents halogen. In one aspect of that embodiment, $R^2$ represents fluoro. In another aspect of that embodiment, $R^2$ represents chloro.

In a third embodiment, $R^2$ represents trifluoromethyl.

In a fourth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl. In a fifth embodiment, $R^2$ represents cyano.

Typical values of $R^2$ include hydrogen, fluoro, chloro, trifluoromethyl, methyl and ethoxycarbonylethyl.

Particular values of $R^2$ include hydrogen and fluoro.

In a first embodiment, X represents an oxygen atom. In a second embodiment X represents a sulphur atom.

In a third embodiment, X represents —S(O).

In a fourth embodiment, X represents an optionally substituted straight or branched $C_{1-4}$ alkylene chain. Typical values of X according to this embodiment include methylene (—CH$_2$—), (methyl)methylene, ethylene (—CH$_2$CH$_2$—), (ethyl)methylene, (dimethyl)-methylene, (methyl)ethylene, propylene (—CH$_2$CH$_2$CH$_2$—), (propyl)methylene and (dimethyl)ethylene, any of which chains may be optionally substituted by one or more substituents. In one aspect of this embodiment X represents an unsubstituted straight or branched $C_{1-4}$ alkylene chain. In a second aspect of this embodiment, X represents a monosubstituted straight or branched $C_{1-4}$ alkylene chain. In a third aspect of this embodiment, X represents a disubstituted straight or branched $C_{1-4}$ alkylene chain.

In a particular aspect of this embodiment, X represents an unsubstituted methylene.

In a fifth embodiment, X represents —NR$^d$. In a particular aspect of this embodiment, X represents —NH.

In a sixth embodiment X represents a carbonyl.

Examples of typical substituents on the alkylene chain which may be present in a compound in accordance with the invention include halogen, hydroxy, $C_{1-6}$ alkoxy, aryl, —C(O)R$^d$, —CO$_2$R$^d$, —CONR$^b$R$^c$—S(O)(N—R$^d$)R$^a$, or —SO$_2$NR$^b$R$^c$.

Particular values of X include methylene, —S(O), oxygen atom and sulphur atom.

In a first embodiment, $R^{5a}$ represents hydrogen. In a second embodiment, $R^{5a}$ represents hydroxy. In a third embodiment, $R^{5a}$ represents halogen. In one aspect of this embodiment, $R^{5a}$ represents fluoro. In a fourth embodiment, $R^{5a}$ represents trifluoromethyl. In a fifth embodiment, $R^{5a}$ represents —NR$^b$R$^c$. In one aspect of that embodiment, $R^{5a}$ represents —NH$_2$. In a sixth embodiment, $R^{5a}$ represents —NR$^c$C(O)R$^d$. In a seventh embodiment, $R^{5a}$ represents —C(O)—NR$^c$R$^d$. In an eighth embodiment, $R^{5a}$ represents —NHS(O)$_2$R$^e$. In a ninth embodiment, $R^{5a}$ represents —S—R$^a$. In a tenth embodiment, $R^{5a}$ represents —S(O)—Ra. In an eleventh embodiment, $R^{5a}$ represents —S(O)$_2$R$^a$. In a particular aspect of this embodiment, $R^{5a}$ represents —S(O)$_2$—CH3. In a twelfth embodiment, $R^{5a}$ represents —S(O)(N—R$^d$)R$^a$. In a thirteenth embodiment, $R^{5a}$ represents —S(O)$_2$(N—R$^d$). In a fourteenth embodiment, $R^{5a}$ represents —OR$^a$. In one aspect of this embodiment, R$^a$ is an optionally substituted $C_{1-6}$ alkyl. In second aspect of this embodiment R$^a$ is an optionally substituted aryl. In a third aspect of this embodiment, R$^a$ is an optionally substituted heteroaryl. In a fifteenth embodiment, $R^{5a}$ represents —O—(CO)—R$^d$. In a particular aspect of this embodiment, $R^{5a}$ represents —O—(CO)—CH$_3$. In a sixteenth embodiment, —C(O)—OR$^d$. In a seventeenth embodiment, $R^{5a}$ represents optionally substituted $C_{1-6}$ alkyl. In one aspect of that embodiment, $R^{5a}$ represents substituted $C_{1-6}$ alkyl. In a second aspect of this embodiment, $R^{5a}$ represents unsubstituted $C_{1-6}$ alkyl. In a particular aspect of this embodiment, $R^{5a}$ represents methyl. In an eighteenth embodiment, $R^{5a}$ represents an optionally substituted $C_{2-6}$ alkynyl. In a nineteenth embodiment, $R^{5a}$ represents an optionally substituted heteroaryl.

In a twentieth embodiment $R^{5a}$ represents an optionally substituted aryl. In a twenty-first embodiment, R$^a$ represents an optionally substituted $C_{2-6}$ alkenyl.

In a twenty-second embodiment, $R^{5a}$ represents cyano.

Particular values of $R^{5a}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl, methoxy, (hydroxy) ethoxy, (hydroxy)propoxy and 2-oxo-1-pyrrolidinyl-.

Selected values of $R^{5a}$ include hydrogen, hydroxy, fluoro, trifluoromethyl, —N(CH$_3$)$_2$, —NH(CO)CH$_3$, —SO$_2$—CH$_3$, —O—(CO)—CH$_3$, methyl and methoxy.

In a first embodiment, $R^{5b}$ represents hydrogen. In a second embodiment, $R^{5b}$ represents hydroxy. In a third embodiment, $R^{5b}$ represents halogen. In one aspect of this embodiment, $R^{5a}$ represents fluoro. In a fourth embodiment, $R^{5b}$ represents cyano. In a fifth embodiment, $R^{5b}$ represents trifluoromethyl.

In a sixth embodiment, $R^{5b}$ represents optionally substituted $C_{1-6}$ alkyl. In one aspect of that embodiment, $R^{5a}$ represents substituted $C_{1-6}$ alkyl. In a second aspect of this embodiment, $R^{5b}$ represents unsubstituted $C_{1-6}$ alkyl. In a particular aspect of this embodiment, $R^{5b}$ represents methyl.

Selected values of $R^{5b}$ include hydrogen and methyl.

In a particular alternative embodiment, $R^{5a}$ and $R^{5b}$ when taken together with the carbon to which they are attached represent a carbonyl.

In second particular alternative embodiment, $R^{5a}$ and $R^{5b}$ when taken together with the carbon to which they are attached represent a thiocarbonyl.

In third particular alternative embodiment, $R^{5a}$ and $R^{5b}$ when taken together with the carbon to which they are attached represent-C=N—OH.

In a particular embodiment, $R^{5a}$ is as defined above and $R^{5b}$ represents hydrogen. In a particular aspect of this embodiment, $R^{5a}$ is hydroxy.

In another particular embodiment $R^{5a}$ is as defined above and $R^{5b}$ represents $C_{1-4}$ alkyl, preferably methyl. In a particular aspect of this embodiment, $R^{5a}$ is hydroxy.

A particular sub-group of the compounds of formula (IIB) above is represented by the compounds of formula (IIC) and N-oxides thereof, and pharmaceutically acceptable salts and solvates thereof, and glucuronide derivatives thereof, and co-crystals thereof:

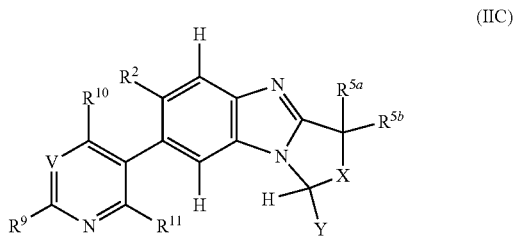

(IIC)

Wherein

V represents C—$R^{12}$ or N;

$R^9$ represents hydrogen, halogen, halo($C_{1-6}$)alkyl, cyano, cyano($C_{1-6}$)alkyl, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl] amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl] amino, bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, aminocarbonyl, aminosulphonyl, ($C_{1-6}$)alkylsulphoximinyl, [($C_{1-6}$)alkyl][N—($C_{1-6}$)alkyl]sulphoximinyl; or $R^9$ represents ($C_{3-7}$)cycloalkyl, ($C_{3-7}$)cycloalkyl($C_{1-6}$)alkyl, ($C_{4-7}$)cycloalkenyl, ($C_{4-9}$)bicycloalkyl, ($C_{3-7}$)heterocycloalkyl, ($C_{3-7}$)heterocycloalkenyl, ($C_{4-9}$)heterobicycloalkyl, ($C_{4-9}$)spiroheterocycloalkyl or heteroaryl, any of which groups may be optionally substituted by one or more substituents; or $R^9$ represents optionally substituted ($C_{1-6}$)alkylaminosulphonyl.

$R^{10}$ and $R^{11}$ independently represents hydrogen, halogen, cyano, trifluoromethyl, hydroxy; or —$NR^bR^c$, —$OR^a$; or $C_{1-6}$ alkyl, $C_{1-6}$ alkylsulphonyl.

$R^{12}$ represents hydrogen, halogen or $C_{1-6}$ alkyl; and

X, $R^2$, $R^{5a}$, $R^{5b}$, $R^a$, $R^b$, $R^c$ are as defined above.

In one embodiment, V represents C—$R^{12}$. In another embodiment, V represents N.

Typically, $R^9$ represents hydrogen, halogen, halo($C_{1-6}$)alkyl, cyano, $C_{1-6}$ alkyl, trifluoromethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, amino, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]-amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, $C_{1-6}$ alkylsulphonylamino, ($C_{2-6}$)alkylcarbonyl-oxy($C_{1-6}$)alkyl, carboxy, morpholinyl($C_{1-6}$)alkoxycarbonyl, $C_{2-6}$ alkoxycarbonyl($C_{1-6}$)alkyl, $C_{2-6}$ alkoxycarbonylmethylidenyl, or ($C_{1-6}$)alkylsulphoximinyl; or $R^9$ represents ($C_{3-7}$)cycloalkyl, ($C_{3-7}$)cycloalkyl-($C_{1-6}$)alkyl, ($C_{4-7}$)cycloalkenyl, ($C_{4-9}$)bicycloalkyl, ($C_{3-7}$)heterocycloalkyl, ($C_{4-9}$)heterobicycloalkyl, ($C_{4-9}$)spiroheterocycloalkyl, or heteroaryl, any of which groups may be optionally substituted by one or more substituents. Additionally, $R^9$ represents cyano($C_{1-6}$)alkyl, ($C_{3-7}$)cycloalkylsulphonyl or ($C_{1-6}$)alkylaminosulphonyl, any of which groups may be optionally substituted by one or more substituents. Appropriately, $R^9$ represents hydrogen, hydroxy, $C_{1-6}$ alkyl, (hydroxy)$C_{1-6}$alkyl, $C_{1-6}$ alkoxy, $C_{2-6}$ alkylcarbonyl, $C_{1-6}$ alkylsulphonyl, ($C_{1-6}$)alkylsulphonyl($C_{1-6}$)alkyl, ($C_{1-6}$)alkylsulphoximinyl, oxo or carboxy; or $R^9$ represents ($C_{3-7}$)cycloalkyl, ($C_{3-7}$)heterocycloalkyl or ($C_{4-9}$)heterobicycloalkyl; or cyano($C_{1-6}$)alkyl, ($C_{3-7}$)cycloalkylsulphonyl or ($C_{1-6}$)alkylaminosulphonyl, any of which groups may be optionally substituted by one or more substituents.

Suitably, $R^9$ represents hydrogen, hydroxy, $C_{1-6}$ alkyl, (hydroxy)$C_{1-6}$ alkyl, $C_{1-6}$ alkoxy, $C_{2-6}$ alkylcarbonyl, $C_{1-6}$ alkylsulphonyl, ($C_{1-6}$)alkylsulphonyl($C_{1-6}$)alkyl, ($C_{1-6}$) alkylsulphoximinyl, oxo or carboxy; or $R^9$ represents ($C_{3-7}$)cycloalkyl, ($C_{3-7}$)heterocycloalkyl or ($C_{4-9}$)heterobicycloalkyl, any which group may be optionally substituted by one or more substituents.

Where $R^9$ represents an optionally substituted ($C_{3-7}$)cycloalkyl group, typical values include cyclopropyl, cyclobutyl, cyclopentyl, cyclohexyl and cycloheptyl, any of which groups may be optionally substituted by one or more substituents.

Where $R^9$ represents an optionally substituted ($C_{3-7}$)cycloalkyl($C_{1-6}$)alkyl group, a typical value is cyclohexylmethyl, which group may be optionally substituted by one or more substituents.

Where $R^9$ represents an optionally substituted ($C_{4-7}$)cycloalkenyl group, typical values include cyclobutenyl, cyclopentenyl, cyclohexenyl and cycloheptenyl, any of which groups may be optionally substituted by one or more substituents.

Where $R^9$ represents an optionally substituted ($C_{4-9}$)bicycloalkyl group, typical values include bicyclo[3.1.0]hexanyl, bicyclo[4.1.0]heptanyl and bicyclo[2.2.2]octanyl, any of which groups may be optionally substituted by one or more substituents.

Where $R^9$ represents an optionally substituted ($C_{3-7}$)heterocycloalkyl group, typical values include oxetanyl, azetidinyl, tetrahydrofuranyl, pyrrolidinyl, tetrahydro-pyranyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, (imino)(oxo)thiazinanyl, (oxo)thiazinanyl, (dioxo)thiazinanyl, any of which groups may be optionally substituted by one or more substituents.

Where $R^9$ represents an optionally substituted ($C_{3-7}$)heterocycloalkenyl group, a typical value is optionally substituted 1,2,3,6-tetrahydropyridinyl.

Where $R^9$ represents an optionally substituted ($C_{4-9}$)heterobicycloalkyl group, typical values include 3-azabicyclo [3.1.0]hexanyl, 2-oxa-5-azabicyclo[2.2.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,9-diazabicyclo-[4.2.1] nonanyl, and 3,7-dioxa-9-azabicyclo [3.3.1]nonanyl, any of which groups may be optionally substituted by one or more substituents.

Where $R^9$ represents an optionally substituted ($C_{4-9}$)spiroheterocycloalkyl group, typical values include 5-azaspiro [2.3]hexanyl, 5-azaspiro[2.4]heptanyl, 2-azaspiro[3.3]-heptanyl, 2-oxa-6-azaspiro[3.3]heptanyl, 2-oxa-6-azaspiro[3.4] octanyl, 2-oxa-6-azaspiro-[3.5]nonanyl, 2-oxa-7-azaspiro

[3.5]nonanyl and 2,4,8-triazaspiro[4.5]-decanyl, any of which groups may be optionally substituted by one or more substituents.

When $R^9$ represents an optionally substituted heteroaryl, typical values include triazolyl and (methyl)triazolyl.

Illustratively, $R^9$ represents hydrogen, isopropyl, isopropylmethyl, hydroxy, hydroxymethyl, hydroxyisopropyl, methoxy, carboxy-cyclobutyloxy, methylthio, methylsulphonyl, methylsulphonylmethyl, methylamino, N-[carboxyethyl]-N-methyl-amino, carboxycyclopentylamino, carboxycyclopropylmethylamino or ethoxycarbonylethyl; or $R^9$ represents cyclopropyl, cyclobutyl, cyclopentyl, cyclohexyl, cyclohexylmethyl, cyclohexenyl, bicyclo[3.1.0]hexanyl, bicyclo[4.1.0]heptanyl, bicyclo[2.2.2]-octanyl, oxetanyl, azetidinyl, tetrahydrofuranyl, pyrrolidinyl, tetrahydropyranyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, 3-azabicyclo[3.1.0]-hexanyl, 2-oxa-5-azabicyclo[2.2.1]heptanyl, 3-azabicyclo[3.1.1]heptanyl, 3-azabicyclo-[4.1.0]heptanyl, 2-oxabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,6-diazabicyclo[3.2.2]nonanyl, 3-oxa-7-azabicyclo[3.3.1]nonanyl, 5-azabicyclo[2.3]hexanyl, 5-azaspiro[2.4]heptanyl or 2-azaspiro-[3.3]heptanyl, any of which groups may be optionally substituted by one or more substituents. Additionally, $R^9$ represents 3,7-dioxa-9-azabicyclo [3.3.1]nonanyl, cyanoisopropyl, fluoroisopropyl, mehtylsulphoximinyl, cyclopropylsulphonyl, aminosulphonyl, isopropylsulphonyl, or (hydroxy)ethylaminosulphonyl, Appropriately, $R^9$ represents hydrogen, isopropyl, isopropylmethyl, hydroxymethyl, hydroxyisopropyl, methoxy, methylsulphonyl, methylsulphonylmethyl; or $R^9$ represents cyclopropyl, oxetanyl, tetrahydrofuranyl, tetrahydropyranyl, piperidinyl, piperazinyl, morpholinyl, diazepanyl, and 3-azabicyclo[3.2.1]octanyl, any of which groups may be optionally substituted by one or more substituents; or $R^9$ represents 3,7-dioxa-9-azabicyclo[3.3.1]nonanyl, cyanoisopropyl, fluoroisopropyl, mehtylsulphoximinyl, cyclopropylsulphonyl, aminosulphonyl, isopropylsulphonyl, or (hydroxy)ethylaminosulphonyl.

Appositely $R^9$ represents hydrogen, isopropyl, isopropylmethyl, hydroxymethyl, hydroxyisopropyl, methoxy, methylsulphonyl, methylsulphonylmethyl; or $R^9$ represents cyclopropyl, oxetanyl, tetrahydrofuranyl, tetrahydropyranyl, piperidinyl, piperazinyl, morpholinyl, diazepanyl, and 3-azabicyclo[3.2.1]octanyl, any of which groups may be optionally substituted by one or more substituents.

Examples of optional substituents which may be present on $R^9$ include one, two or three substituents independently selected from halogen, halo($C_{1-6}$)alkyl, cyano, cyano-($C_{1-6}$)alkyl, nitro, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$)alkylamino, $C_{2-6}$ alkylcarbonylamino, ($C_{2-6}$)alkylcarbonylamino-($C_{1-6}$)alkyl, $C_{2-6}$ alkoxycarbonylamino, $C_{1-6}$ alkylsulphonylamino, formyl, $C_{1-6}$ alkylcarbonyl, carboxy, carboxy($C_{1-6}$)alkyl, $C_{2-6}$ alkoxycarbonyl, morpholinyl-($C_{1-6}$)alkoxycarbonyl, $C_{2-6}$ alkoxycarbonyl($C_{1-6}$)alkyl, $C_{2-6}$ alkoxycarbonylmethylidenyl, a carboxylic acid isostere or prodrug moiety Ω as defined herein, —($C_{1-6}$)alkyl-Ω, aminocarbonyl, $C_{1-6}$ alkylaminocarbonyl, di($C_{1-6}$)alkylaminocarbonyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

Selected examples of optional substituents on $R^9$ include one, two or three substituents independently selected from halogen, $C_{1-6}$ alkyl, $C_{1-6}$ alkylsulphonyl, $C_{1-6}$ alkylcarbonyl, oxo and carboxy.

Suitable examples of particular substituents on $R^9$ include one, two or three substituents independently selected from fluoro, fluoromethyl, chloro, bromo, cyano, cyanomethyl, cyanoethyl, nitro, nitromethyl, methyl, ethyl, isopropyl, trifluoromethyl, trifluoroethyl, ethenyl, hydroxy, hydroxymethyl, methoxy, ethoxy, difluoromethoxy, trifluoromethoxy, trifluoroethoxy, methylthio, methylsulphonyl, methylsulphonylmethyl, methylsulphonylethyl, oxo, amino, methylamino, dimethylamino, acetylamino, acetylaminomethyl, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, n-butoxycarbonyl, tert-butoxycarbonyl, morpholinylethoxycarbonyl, methoxycarbonylmethyl, ethoxycarbonylmethyl, ethoxycarbonylethyl, ethoxycarbonylmethylidenyl, acetylaminosulphonyl, methoxyaminocarbonyl, tetrazolyl, tetrazolylmethyl, hydroxyoxadiazolyl, aminocarbonyl, methylaminocarbonyl, dimethylaminocarbonyl, methylsulphonylaminocarbonyl, aminosulphonyl, methylaminosulphonyl, dimethylaminosulphonyl, methylsulphoximinyl and (methyl)(N-methyl)sulphoximinyl.

Selected examples of particular substituents on $R^9$ include one, two or three substituents independently selected from fluoro, methyl, acetyl, oxo and carboxy. Additional examples of particular substitutents on $R^9$ include hydroxy.

Typically, $R^9$ represents hydrogen, fluoro, fluoroisopropyl, cyano, methyl, isopropyl, trifluoromethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, amino, methylamino, dimethylamino, methoxyethylamino, N-(hydroxyethyl)-N-(methyl)amino, N-[carboxy-ethyl]-N-methylamino, carboxycyclopentylamino, carboxycyclopropylmethylamino, methylsulphonylamino, acetoxyisopropyl, carboxy, ethoxycarbonylethyl, cyclopropyl, fluoromethylcyclopropyl, acetylaminomethylcyclopropyl, hydroxycyclobutyl, carboxycyclopentyl, carboxycyclohexyl, (carboxy)(methyl)cyclohexyl, (carboxy)(hydroxy)cyclohexyl, carboxymethylcyclohexyl, ethoxycarbonylcyclohexyl, (methoxycarbonyl)(methyl)-cyclohexyl, (ethoxycarbonyl) (methyl)cyclohexyl, carboxycyclohexylmethyl, carboxycyclohexenyl, ethoxycarbonylcyclohexenyl, carboxybicyclo[3.1.0]hexanyl, ethoxycarbonylbicyclo[3.1.0]hexanyl, carboxybicyclo[4.1.0]heptanyl, carboxybicyclo-[2.2.2]octanyl, fluorooxetanyl, hydroxyoxetanyl, hydroxyazetidinyl, (hydroxy)(methyl)-azetidinyl, carboxyazetidinyl, (tert-butoxycarbonyl)(hydroxy)azetidinyl, tetrazolyl-azetidinyl, hydroxytetrahydrofuranyl, pyrrolidinyl, hydroxypyrrolidinyl, carboxy-pyrrolidinyl, (carboxy)(methyl)pyrrolidinyl, carboxymethylpyrrolidinyl, ethoxycarbonyl-pyrrolidinyl, fluorotetrahydropyranyl, hydroxytetrahydropyranyl, piperidinyl, difluoropiperidinyl, (cyano)(methyl)piperidinyl, (hydroxy)(nitromethyl)piperidinyl, (hydroxy)-(methyl)piperidinyl, (hydroxy)(trifluoromethyl)piperidinyl, (hydroxymethyl)(methyl)-piperidinyl, methylsulphonylpiperidinyl, oxopiperidinyl, (formyl)(methyl)piperidinyl, acetylpiperidinyl, carboxypiperidinyl, (carboxy)(fluoro)piperidinyl, (carboxy)(methyl)-piperidinyl, (carboxy)(ethyl)piperidinyl, (carboxy)(trifluoromethyl)piperidinyl, (carboxy)-(hydroxy)piperidinyl, (carboxy)(hydroxymethyl) piperidinyl, (carboxy)(methoxy)-piperidinyl, (amino)(carboxy)piperidinyl, carboxymethylpiperidinyl, methoxycarbonyl-piperidinyl, (methoxycarbonyl)(methyl)

piperidinyl, (ethyl)(methoxycarbonyl)piperidinyl, (isopropyl)(methoxycarbonyl)piperidinyl, (methoxy)(methoxycarbonyl)piperidinyl, (carboxy)(methoxycarbonyl)piperidinyl, ethoxycarbonylpiperidinyl, (ethoxycarbonyl)-(fluoro)piperidinyl, (ethoxycarbonyl)(methyl)piperidinyl, (ethoxycarbonyl)(trifluoro-methyl)piperidinyl, (ethoxycarbonyl)(hydroxymethyl)piperidinyl, (n-butoxycarbonyl)-(methyl)piperidinyl, (methyl)(morpholinylethoxycarbonyl)piperidinyl, ethoxycarbonylmethylpiperidinyl, methylsulphonylaminocarbonylpiperidinyl, acetylaminosulphonyl-piperidinyl, methoxyaminocarbonylpiperidinyl, tetrazolylpiperidinyl, hydroxyoxadiazolyl-piperidinyl, aminosulphonylpiperidinyl, piperazinyl, methylpiperazinyl, cyanoethylpiperazinyl, trifluoroethyl-piperazinyl, methylsulphonylpiperazinyl, methylsulphonylethylpiperazinyl, oxopiperazinyl, acetylpiperazinyl, carboxypiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, tetrazolylmethylpiperazinyl, trioxohexahydro-[1,2,5]thiadiazolo[2,3-a]pyrazinyl, morpholinyl, dimethylmorpholinyl, hydroxymethyl-morpholinyl, carboxymorpholinyl, (carboxy)(methyl)morpholinyl, carboxymethyl-morpholinyl, thiomorpholinyl, oxothiomorpholinyl, dioxothiomorpholinyl, carboxy-azepanyl, carboxyoxazepanyl, oxodiazepanyl, (methyl)(oxo)diazepanyl, dioxo-thiadiazepanyl, carboxy-3-azabicyclo[3.1.0]hexanyl, (carboxy)(methyl)-3-azabicyclo-[3.1.0]hexanyl, methoxycarbonyl-3-azabicyclo[3.1.0]hexanyl, ethoxycarbonyl-3-azabicyclo[3.1.0]hexanyl, 2-oxa-5-azabicyclo[2.2.1]heptanyl, carboxy-2-oxa-5-azabicyclo[2.2.1]heptanyl, carboxy-3-azabicyclo[3.1.1]heptanyl, carboxy-3-azabicyclo-[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]octanyl, carboxy-3-azabicyclo[3.2.1]octanyl, methoxycarbonyl-3-azabicyclo[3.2.1]octanyl, oxo-8-azabicyclo[3.2.1]octanyl, ethoxycarbonylmethylidenyl-8-azabicyclo[3.2.1]octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, carboxy-5-azaspiro[2.3]hexanyl, (carboxy)(methyl)-5-azaspiro-[2.3]hexanyl, carboxy-5-azaspiro[2.4]heptanyl, carboxy-2-azaspiro[3.3]heptanyl, 2-oxa-6-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl, (dioxo)(methyl)-2,4,8-triazaspiro[4.5]decanyl, (methyl)cyclobutyldiol, (imino)(oxo)thiazinanyl, (oxo)thiazinanyl or (dioxo)thiazinanyl. Additionally, $R^9$ represents 3,7-dioxa-9-azabicyclo[3.3.1]nonanyl, cyanoisopropyl, fluoroisopropyl, methylsulphoximinyl, cyclopropylsulphonyl, aminosulphonyl, isopropylsulphonyl, or (hydroxy)ethylaminosulphonyl, Appropriate values of $R^9$ include fluorotetrahydropyranyl, fluorooxetanyl, tetrahydropyranyl, isopropyl, methylsulphonyl, hydroxyisopropyl, morpholinyl, cyclopropyl, carboxy-3-azabicyclo[3.2.1]octanyl, piperazinyl, methylpiperazinyl, acetylpiperazinyl, oxodiazepanyl, and (methyl)(carboxy)piperidinyl, hydroxyoxetanyl, methylsulphoximinyl, 2-oxa-7-aza-spiro[3,5]nonanyl, 3,7-dioxa-9-azabicyclo[3.3.1]nonanyl, 3,7-dioxa-9-azabicyclo[3.3.1]nonanyl, -azabicyclo[3.2.1]octanyl, cyanoisopropyl, fluoroisopropyl, methylsulphoximinyl, cyclopropylsulphonyl, aminosulphonyl, isopropylsulphonyl, and (hydroxy)ethylaminosulphonyl.

Illustrative values of $R^9$ include fluorotetrahydropyranyl, fluorooxetanyl, tetrahydropyranyl, isopropyl, methylsulphonyl, hydroxyisopropyl, morpholinyl, cyclopropyl, carboxy-3-azabicyclo[3.2.1]octanyl, piperazinyl, methylpiperazinyl, acetylpiperazinyl, oxodiazepanyl, and (methyl)(carboxy)piperidinyl.

In one embodiment $R^{10}$ represents hydrogen. In a second embodiment, $R^{10}$ represents halogen. In a third embodiment, $R^{10}$ represents cyano. In a fourth embodiment, $R^{10}$ represents trifluormethyl. In a fifth embodiment, $R^{10}$ represents hydroxy. In a sixth embodiment, $R^{10}$ represents —$NR^bR^c$. In one aspect of this embodiment $R^{10}$ represents —$NH_2$. In a seventh embodiment, $R^{10}$ represents —$OR^a$. In one aspect of that embodiment, $R^{10}$ represents methoxy. In an eighth embodiment, $R^{10}$ represents $C_{1-6}$ alkyl. In one aspect of that embodiment, $R^{10}$ represents methyl. In a ninth embodiment, $R^{10}$ represents $C_{1-6}$ alkylsulphonyl. In one aspect of that embodiment, $R^{10}$ represents methylsulphonyl.

In one embodiment $R^{11}$ represents hydrogen. In a second embodiment, $R^{11}$ represents halogen. In a third embodiment, $R^{11}$ represents cyano. In a fourth embodiment, $R^{11}$ represents trifluormethyl. In a fifth embodiment, $R^{11}$ represents hydroxy. In a sixth embodiment, $R^{11}$ represents —$NR^bR^c$. In one aspect of this embodiment $R^{11}$ represents —$NH_2$. In a seventh embodiment, $R^{11}$ represents —$OR^a$. In one aspect of that embodiment, $R^{11}$ represents methoxy. In an eighth embodiment, $R^{11}$ represents $C_{1-6}$ alkyl. In one aspect of that embodiment, $R^{11}$ represents methyl. In a ninth embodiment, $R^{11}$ represents $C_{1-6}$ alkylsulphonyl. In one aspect of that embodiment, $R^{11}$ represents methylsulphonyl.

Particular values of $R^{10}$ and $R^{11}$ include independently hydrogen, methyl and methylsulphonyl.

Generally, $R^{12}$ is hydrogen or $C_{1-6}$ alkyl.

Particular values of $R^{12}$ include hydrogen and methyl.

Particular sub-groups of the compounds of formula (IIC) above are represented by the compounds of formula (IID), (IIE), (IIF), (IIG), (IIH), (IIJ), (IIK), (IIL), (IIM) and (IIN), and N-oxides thereof, and pharmaceutically acceptable salts and solvates thereof, and glucuronide derivatives thereof, and co-crystals thereof:

(IID)

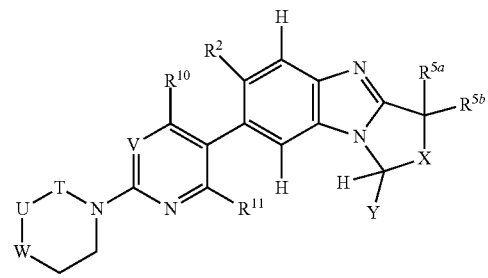

(IIE)

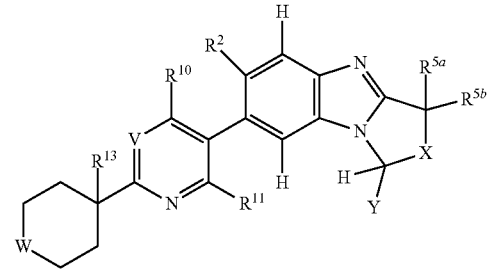

-continued (IIF)
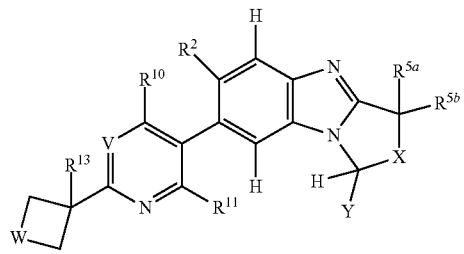

(IIG)
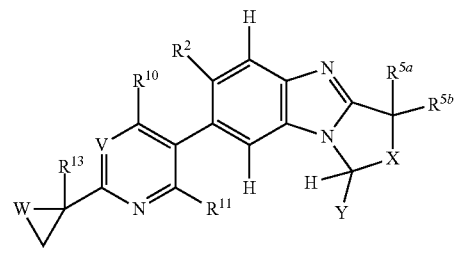

(IIH)
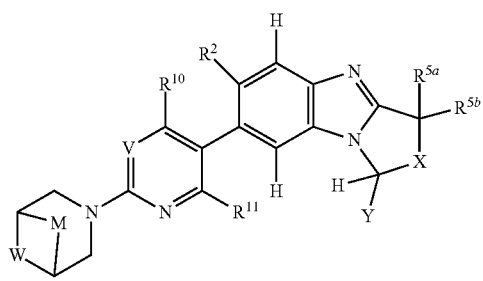

(IIJ)
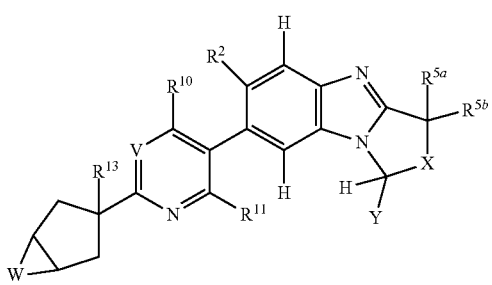

(IIK)
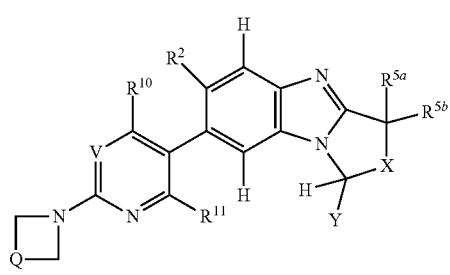

-continued (IIL)
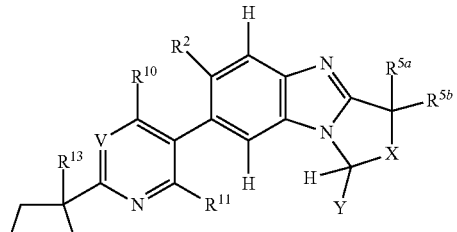

(IIM)
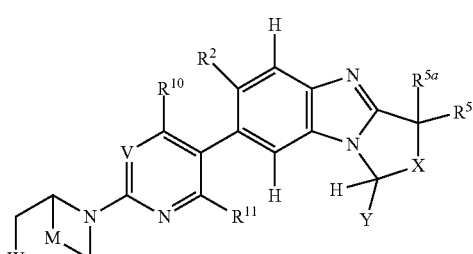

(IIN)
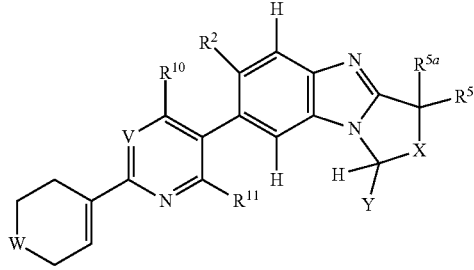

wherein
T represents —CH$_2$— or —CH$_2$—CH$_2$—;
U represents C(O) or S(O$_2$);
W represents O, S, S(O), S(O)$_2$, S(O)(N—R$^d$), N(R$^{14}$) or C(R$^{15}$)(R$^{16}$);
-M- represents —CH$_2$—, —CH$_2$CH$_2$— or —CH$_2$—W—CH$_2$;
Q represents C(R$^{15}$)(R$^{16}$);
R$^{13}$ represents hydrogen, cyano, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$)alkyl, (C$_{1-6}$)alkyl-sulphonylamino or (C$_{1-6}$) alkylsulphonylamino(C$_{1-6}$)alkyl;
R$^{14}$ represents hydrogen, cyano(C$_{1-6}$)alkyl, C$_{1-6}$ alkyl, trifluoromethyl, trifluoro-ethyl, C$_{1-6}$ alkylsulphonyl, (C$_{1-6}$) alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω, —(C$_{1-6}$)alkyl-Ω, aminocarbonyl, C$_{1-6}$ alkylaminocarbonyl, di(C$_{1-6}$)alkylaminocarbonyl, aminosulphonyl or di(C$_{1-6}$)alkylaminosulphonyl;
R$^{15}$ represents hydrogen, halogen, cyano, hydroxy, hydroxy(C$_{1-6}$)alkyl, C$_{1-6}$ alkylsulphonyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, a carboxylic acid isostere or prodrug moiety Ω, or —(C$_{1-6}$)alkyl-Ω; and $R^{16}$ represents hydrogen, halogen, $C_{1-6}$ alkyl, $C_{3-7}$ cycloalkyl, trifluoromethyl, hydroxy, hydroxy-($C_{1-6}$)alkyl, $C_{1-6}$ alkoxy, amino or carboxy;

V, X, $R^2$, $R^{5a}$, $R^{5b}$, $R^{10}$ and $R^{11}$ are as defined above.

Generally, W represents O, S(O)$_2$, N($R^{14}$), S(O)(N—$R^d$), or C($R^{15}$)($R^{16}$).

Typically, W represents O, N($R^{14}$) or C($R^{15}$)($R^{16}$).

In a first embodiment, W represents O. In a second embodiment, W represents S. In a third embodiment, W represents S(O). In a fourth embodiment, W represents S(O)$_2$. In a fifth embodiment, W represents N($R^{14}$). In a sixth embodiment, W represents C($R^{15}$)($R^{16}$). In a seventh embodiment, W represents S(O)(N—$R^d$).

In one embodiment, -M- represents —CH$_2$—. In a second embodiment, -M-represents —CH$_2$CH$_2$—. In a third embodiment M represents CH$_2$—W—CH$_2$. In one aspect of that embodiment, M represents CH$_2$—O—CH$_2$. In a second aspect of that embodiment, M represents CH$_2$—S(O)(N—$R^d$)—CH$_2$. In a third aspect of that embodiment, M represents CH$_2$—S—CH$_2$. In a fourth aspect of that embodiment, M represents CH$_2$—S(O)—CH$_2$. In a fifth aspect of that embodiment, M represents CH$_2$—S(O)$_2$—CH$_2$. In a sixth aspect of that embodiment, M represents CH$_2$—N($R^{14}$)—CH$_2$. In a seventh aspect of that embodiment, M represents CH$_2$—C($R^{15}$)($R^{16}$)—CH$_2$.

In a first embodiment, $R^{13}$ represents hydrogen.

In a second embodiment, $R^{13}$ represents halogen. In one aspect of that embodiment, $R^{13}$ represents fluoro.

In a third embodiment, $R^{13}$ represents halo($C_{1-6}$)alkyl. In one aspect of that embodiment, $R^{13}$ represents fluoromethyl.

In a fourth embodiment, $R^{13}$ represents hydroxy.

In a fifth embodiment, $R^{13}$ represents $C_{1-6}$ alkoxy. In a particular aspect of that embodiment, $R^{13}$ represents methoxy.

In a sixth embodiment, $R^{13}$ represents $C_{1-6}$ alkylthio. In a particular aspect of that embodiment, $R^{13}$ represents methylthio.

In a seventh embodiment, $R^{13}$ represents $C_{1-6}$ alkylsulphinyl. In a particular aspect of that embodiment, $R^{13}$ represents methylsulphinyl.

In an eighth embodiment, $R^{13}$ represents $C_{1-6}$ alkylsulphonyl. In a particular aspect of that embodiment, $R^{13}$ represents methylsulphonyl.

In a ninth embodiment, $R^{13}$ represents amino.

In a tenth embodiment, $R^{13}$ represents $C_{1-6}$ alkylamino. In a particular aspect of that embodiment, $R^{13}$ represents methylamino.

In an eleventh embodiment, $R^{13}$ represents di($C_{1-6}$)alkylamino. In a particular aspect of that embodiment, $R^{13}$ represents dimethylamino.

In a twelfth embodiment, $R^{13}$ represents ($C_{2-6}$)alkylcarbonylamino. In a particular aspect of that embodiment, $R^{13}$ represents acetylamino.

In a thirteenth embodiment, $R^{13}$ represents ($C_{2-6}$)alkylcarbonylamino($C_{1-6}$)alkyl. In a particular aspect of that embodiment, $R^{13}$ represents acetylaminomethyl.

In a fourteenth embodiment, $R^{13}$ represents ($C_{1-6}$)alkylsulphonyl-amino. In a particular aspect of that embodiment, $R^{13}$ represents methylsulphonylamino.

In a fifteenth embodiment, $R^{13}$ represents ($C_{1-6}$)alkylsulphonylamino($C_{1-6}$)alkyl. In a particular aspect of that embodiment, $R^{13}$ represents methylsulphonylaminomethyl.

In a sixteenth embodiment, $R^{13}$ represents cyano.

Typically, $R^{13}$ represents hydrogen, halogen, halo($C_{1-6}$) alkyl, hydroxy or ($C_{2-6}$)alkylcarbonylamino($C_{1-6}$)alkyl.

Selected values of $R^{13}$ include hydrogen, fluoro, fluoromethyl, hydroxy, methoxy, methylthio, methylsulphinyl, methylsulphonyl, amino, methylamino, dimethylamino and acetylaminomethyl.

Particular values of $R^{13}$ include hydrogen, fluoro, fluoromethyl, hydroxy and acetylaminomethyl.

Suitably, $R^{13}$ represents hydrogen or fluoro.

Typically, $R^{14}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$)alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl-($C_{1-6}$)alkyl, tetrazolyl($C_{1-6}$)alkyl, aminocarbonyl, $C_{1-6}$alkylaminocarbonyl, di($C_{1-6}$)alkylaminocarbonyl, aminosulphonyl, $C_{1-6}$ alkylaminosulphonyl or di($C_{1-6}$)alkylaminosulphonyl.

Suitably, $R^{14}$ represents hydrogen, $C_{1-6}$ alkyl or $C_{2-6}$ alkylcarbonyl.

Typical values of $R^{14}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolylmethyl, aminocarbonyl, methylamino-carbonyl, dimethylaminocarbonyl, aminosulphonyl, methylaminosulphonyl and dimethylamino sulphonyl.

Particular values of $R^{14}$ include hydrogen, methyl and acetyl.

In a particular embodiment $R^{14}$ represents hydrogen.

In a selected embodiment, $R^{14}$ represents $C_{1-6}$ alkyl.

In yet another particular embodiment, $R^{14}$ represents $C_{2-6}$ alkylcarbonyl.

Generally, $R^{15}$ represents halogen, carboxy, carboxy ($C_{1-6}$)alkyl, $C_{2-6}$ alkoxycarbonyl, $C_{2-6}$ alkoxycarbonyl($C_{1-6}$) alkyl, a carboxylic acid isostere or prodrug moiety Ω, or —($C_{1-6}$)alkyl-Ω.

Typically, $R^{15}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylaminosulphonyl, ($C_{1-6}$)alkoxyaminocarbonyl, tetrazolyl or hydroxyoxadiazolyl.

Typical values of $R^{15}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl.

In a selected embodiment, $R^{15}$ represents carboxy.

Generally, $R^{16}$ represents hydrogen, halogen, $C_{3-7}$cycloalkyl, or $C_{1-6}$ alkyl.

Suitably, $R^{16}$ represents hydrogen or $C_{1-6}$ alkyl.

Selected values of $R^{16}$ include hydrogen, fluoro, methyl, ethyl, isopropyl, cyclopropyl, trifluoromethyl, hydroxy, hydroxymethyl, methoxy, amino and carboxy.

Particular values of $R^{16}$ include hydrogen and methyl.

In a first embodiment, $R^{16}$ represents hydrogen.

In a second embodiment, $R^{16}$ represents halogen. In one aspect of that embodiment, $R^{16}$ represents fluoro.

In a third embodiment, $R^{16}$ represents $C_{1-6}$ alkyl. In a first aspect of that embodiment, $R^{16}$ represents methyl. In a second aspect of that embodiment, $R^{16}$ represents ethyl. In a third aspect of that embodiment, $R^{16}$ represents isopropyl.

In a fourth embodiment, $R^{16}$ represents trifluoromethyl.

In a fifth embodiment, $R^{16}$ represents hydroxy.

In a sixth embodiment, $R^{16}$ represents hydroxy($C_{1-6}$) alkyl. In one aspect of that embodiment, $R^{16}$ represents hydroxymethyl.

In a seventh embodiment, $R^{16}$ represents $C_{1-6}$ alkoxy. In one aspect of that embodiment, $R^{16}$ represents methoxy.

In an eighth embodiment, $R^{16}$ represents amino.

In a ninth embodiment, $R^{16}$ represents carboxy.

In a tenth embodiment, $R^{16}$ represents a $C_{3-7}$cycloalkyl. In one aspect of this embodiment, $R^{16}$ represents cyclopropyl.

Another particular sub-group of the compounds of formula (IIB) above is represented by the compounds of formula (IIP) and N-oxides thereof, and pharmaceutically acceptable salts and solvates thereof, and glucuronide derivatives thereof, and co-crystals thereof:

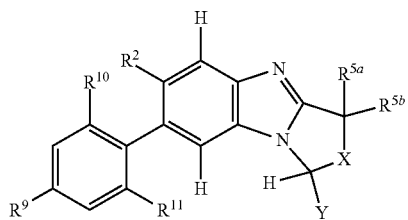

(IIP)

X, Y, $R^2$, $R^{5a}$, $R^{5b}$, $R^9$, $R^{10}$ and $R^{11}$ are as defined above.

In a particular embodiment of compounds of formula (IIP), X represents methylene.

In a particular embodiment of compounds of formula (IIP), Y represents 2-difluromethoxy-phenyl. In another particular embodiment of compounds of formula (IIN), Y represents 2-difluromethoxy-5-chloro-phenyl.

In a particular embodiment of compounds of formula (IIP), $R^2$ represents hydrogen. In a particular embodiment of compounds of formula (IIP), $R^2$ represents flurorine.

In a particular embodiment of compounds of formula (IIP), $R^{5a}$ represents hydroxy.

In a particular embodiment of compounds of formula (IIP), $R^{5b}$ represents hydrogen.

In a particular embodiment of compounds of formula (IIP), $R^9$ represents $C_{1-6}$ alkylsulphonyl. In a particular aspect of that embodiment, $R^9$ represents methyl sulphonyl. In another particular embodiment of compounds of compounds of formula (IIP), $R^9$ represents $C_{3-7}$ cycloalkysulphonyl. In a particular aspect of this embodiment, $R^9$ represents cyclopropyl sulphonyl. In a further particular embodiment of compound of formula (IIP), $R^9$ represents aminosulphonyl. In another further particular embodiment of compound of formula (IIP), $R^9$ represents methylsulphoximinyl. In yet a further particular embodiment of compound of formula (IIP), $R^9$ represents optionally substituted $C_{1-6}$ alkylaminosulphonyl. In a particular aspect of this embodiment $R^9$ represents (hydroxy)ethylaminosulphonyl.

In a particular embodiment of compounds of formula (IIN), $R^{10}$ represents hydrogen.

In a particular embodiment of compounds of formula (IIN), $R^{11}$ represents hydrogen.

Another sub-class of compounds of formula (I) according to the invention is represented by the compounds of formula (IIQ) and N-oxides thereof, and pharmaceutically acceptable salts and solvates thereof, and glucuronide derivatives thereof, and co-crystals thereof:

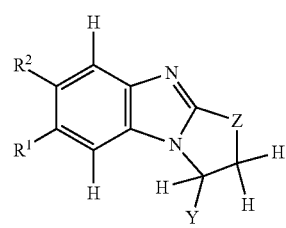

(IIQ)

wherein

Z represents an heteroatom; or —S(O), —S(O)$_2$, —S(O)(N—$R^d$), —NC(O)$R^d$, —N(CO)—O$R^d$, —NS(O)$_2R^d$, —N($R^d$); or an optionally substituted straight or branched $C_{1-4}$ alkylene chain; and $R^1$, $R^2$, and Y are as defined above.

Typically, Z represents a heteroatom; or —NC(O)$R^d$, —N(CO)—O$R^d$, —NS(O)$_2R^d$, —N($R^d$).

Typically, $R^d$ represents hydrogen; or $C_{1-6}$ alkyl.

In one embodiment, $R^d$ represents hydrogen. In another embodiment, $R^d$ represents $C_{1-6}$ alkyl. In a particular aspect of that embodiment, $R^d$ represents methyl.

In a first embodiment, Z represents an heteroatom. In one aspect of that embodiment Z is an oxygen atom. In a second aspect Z is sulphur. In a second embodiment, Z represents —S(O).

In a third embodiment, Z represents —S(O)$_2$. In a fourth embodiment, Z represents —S(O)(N—$R^d$). In a fifth embodiment, Z represents —NC(O)$R^d$. In a sixth embodiment, Z represents —N(CO)—O$R^d$. In a seventh embodiment, Z represents —NS(O)$_2R^d$. In an eighth embodiment, Z represents —N($R^d$).

Typical values of Z include oxygen, sulphur, —NH, —NCH$_3$, —N—(SO$_2$)—CH$_3$, —N—(CO)—CH$_3$ and —N—(CO)—O—CH$_3$.

A particular value of Z is sulphur.

Another sub-class of compounds of formula (I) according to the invention is represented by the compounds of formula (IIR) and N-oxides thereof, and pharmaceutically acceptable salts and solvates thereof, and glucuronide derivatives thereof, and co-crystals thereof:

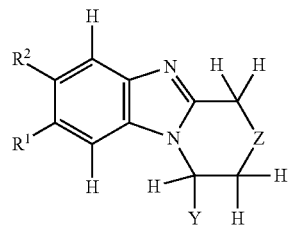

(IIR)

wherein

Z represents an heteroatom; or —S(O), —S(O)$_2$, —S(O)(N—$R^d$), —NC(O)$R^d$, —N(CO)—O$R^d$, —NS(O)$_2R^d$, —N($R^d$); or an optionally substituted straight or branched $C_{1-4}$ alkylene chain; and Y, $R^1$ and $R^2$ are as defined above.

Typically, Z represents an heteroatom; or —NC(O)$R^d$, —N(CO)—O$R^d$, —NS(O)$_2R^d$, —N($R^d$).

Typically, $R^d$ represents hydrogen, $C_{1-6}$ alkylsulphonyl, or $C_{1-6}$ alkyl.

In one embodiment, $R^d$ represents hydrogen. In a second embodiment, $R^d$ represents $C_{1-6}$ alkyl. In a particular aspect of that embodiment, $R^d$ represents methyl.

In a first embodiment, Z represents an heteroatom. In one aspect of that embodiment Z is an oxygen atom. In a second aspect Z is sulphur. In a second embodiment, Z represents —S(O).

In a third embodiment, Z represents —S(O)$_2$. In a fourth embodiment, Z represents —S(O)(N—$R^d$). In a fifth embodiment, Z represents —NC(O)$R^d$. In a sixth embodiment, Z represents —N(CO)—OR$^d$. In a seventh embodiment, Z represents —NS(O)$_2R^d$. In an eighth embodiment, Z represents —N($R^d$).

Typical values of Z include oxygen, —NH, —NCH$_3$, —N—(SO$_2$)—CH$_3$, —N—(CO)—CH$_3$ and —N—(CO)—O—CH$_3$.

A particular sub-group of the compounds of formula (IIR) above is represented by the compounds of formula (IIS) and N-oxides thereof, and pharmaceutically acceptable salts and solvates thereof, and glucuronide derivatives thereof, and co-crystals thereof:

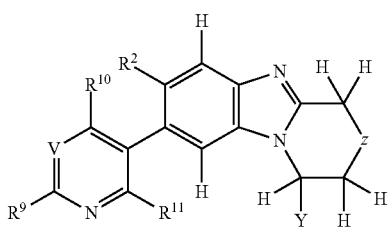

(IIS)

Wherein

Z represents an heteroatom; or —S(O), —S(O)$_2$, —S(O)(N—$R^d$), —NC(O)$R^d$, —N(CO)—OR$^d$, —NS(O)$_2R^d$, —N($R^d$); or an optionally substituted straight or branched $C_{1-4}$ alkylene chain; and V, Y, $R^2$, $R^9$, $R^{10}$ and $R^{11}$ are as defined above.

Typically, Z represents a heteroatom; or —NC(O)$R^d$, —N(CO)—OR$^d$, —NS(O)$_2R^d$, —N($R^d$).

Typically, $R^d$ represents hydrogen, $C_{1-6}$ alkylsulphonyl, or $C_{1-6}$ alkyl.

In one embodiment, $R^d$ represents hydrogen. In a second embodiment, $R^d$ represents $C_{1-6}$ alkyl. In a particular aspect of that embodiment, $R^d$ represents methyl.

In a first embodiment, Z represents an heteroatom. In one aspect of that embodiment Z is an oxygen atom. In a second aspect Z is sulphur. In a second embodiment, Z represents —S(O).

In a third embodiment, Z represents —S(O)$_2$. In a fourth embodiment, Z represents —S(O)(N—$R^d$). In a fifth embodiment, Z represents —NC(O)$R^d$. In a sixth embodiment, Z represents —N(CO)—OR$^d$. In a seventh embodiment, Z represents —NS(O)$_2R^d$. In an eighth embodiment, Z represents —N($R^d$).

Typical values of Z include oxygen, —NH, —NCH$_3$, —N—(SO$_2$)—CH$_3$, —N—(CO)—CH$_3$ and —N—(CO)—O—CH$_3$.

Another particular sub-group of the compounds of formula (IIR) above is represented by the compounds of formula (IIT) and N-oxides thereof, and pharmaceutically acceptable salts and solvates thereof, and glucuronide derivatives thereof, and co-crystals thereof:

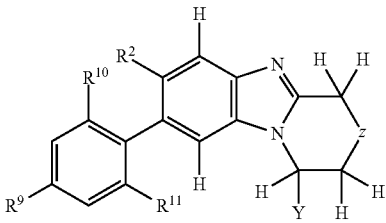

(IIT)

Wherein Z, Y, $R^2$, $R^9$, $R^{10}$ and $R^{11}$ are as defined above.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

It will be apparent to the person skilled in the art that there are various synthetic pathways that can lead to the compounds according to the invention. The following processes are aimed at illustrating some of these synthetic pathways but should not be construed in any way as a limitation on how the compounds according to the invention should be made.

It will also be apparent to the one skilled in the art that synthetic pathways may be different depending on the sub-classes of compounds of formula (I).

Compounds of formula (IIA) above may be prepared by a process which includes reacting an intermediate of formula (III) with an intermediate of formula (IV) as shown in scheme 1, to afford a compound of formula (V), wherein $R^1$, $R^2$, $R^3$, $R^4$, $R^{5a}$, $R^{5b}$, $R^6$, X and Y are as defined above for compound of formula (IIA).

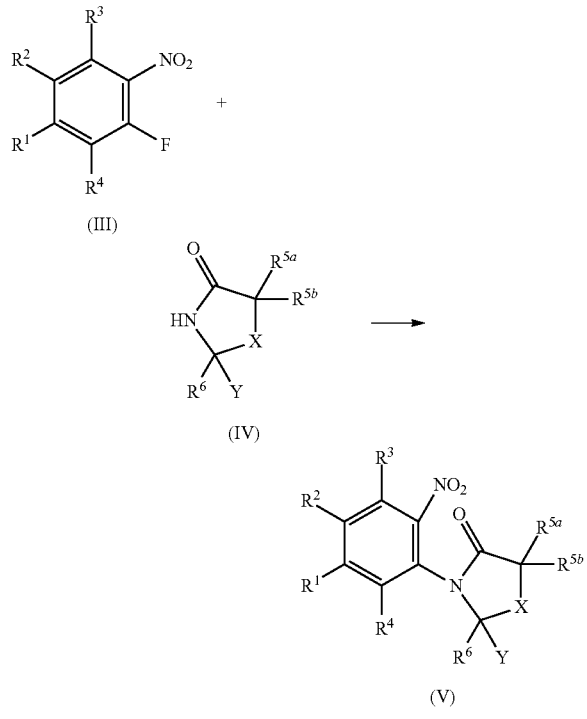

Scheme 1

The reaction is advantageously performed in the presence of a base e.g. sodium hydride, potassium carbonate, cesium carbonate. The reaction is performed in a suitable solvent, e.g. dimethylformamide or acetonitrile, at room temperature.

Where they are not available commercially, compounds of formula (IV) can be prepared by methods analogous to those described in the Examples or other methods known to the skilled in the art.

Such methods may vary depending on the nature of some of the groups present on compound of formula (IV).

For example:

(i) Compound of formula (IV), wherein $R^6$ is hydrogen, can be prepared in a few steps from compound of formula Y—(CO)—H. Said compound can be conveniently treated with a $C_{1-4}$ alkoxycyclopropoxy-trimethylsilane in the presence of $TiCl_4$ in a suitable solvent, e.g. dichloromethane. The intermediate thereby obtained is reacted with a protected amine in a suitable solvent, e.g. toluene, at high temperature.

(ii) Alternatively, compounds of formula (IV) may be prepared by cyclization of an intermediate of formula (VI), in a suitable solvent e.g. ethanol in the presence of Ni Raney, followed by subsequent decarbalkoxylation.

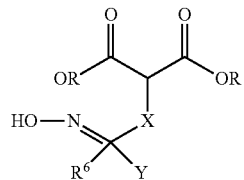

(iii) Alternatively, compound of formula (IV) may be prepared by reacting a succinimide with a reducing agent, e.g. sodium borohydride in the presence of an acid and R—OH, R being a $C_{1-4}$ alkyl, 5-Alkoxy pyrrolidine-2-one thereby obtained is reacted with magnesium in the presence of Y—Br, in a suitable solvent, e.g. THF.

(iv) Alternatively, compounds of formula (IV), wherein $R^6$ is hydrogen, and X is —S, may be prepared by reacting a compound of formula Y—(CO)—H with 2-sulfanylacetic acid in the presence of an ammonium salt, e.g. ammonium carbonate. The reaction is performed in suitable solvent, e.g. toluene, at high temperature.

As an alternative to the process of preparation set out in scheme 1, compounds of formula (V) may be prepared according to the following scheme 3, by reacting intermediate (VII) with intermediate (VIII) in the presence of an acid e.g. sulphuric acid, in a suitable solvent, e.g. toluene, at high temperature, $R^1$, $R^2$, $R^3$, $R^4$, $R^6$, X and Y being as defined above and $L^1$ being a leaving group. An example of a leaving group is alkoxy.

Scheme 3

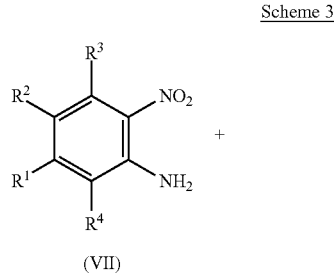

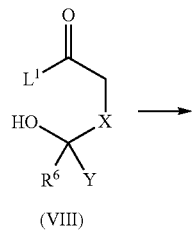

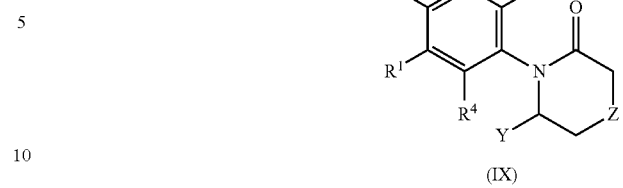

In a similar fashion to what is described above for the preparation of compounds of formula (V), preparation compounds of formula (IIN) may include the preparation of intermediates of formula (IX) wherein $R^1$, $R^2$, $R^3$, $R^4$, $R^6$, Y and Z are as defined above for compounds of formula (IIN).

Scheme 3'

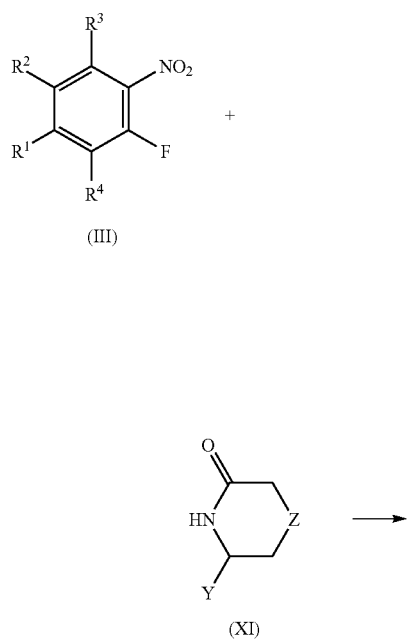

Preparation of compounds of formula (IIK), wherein Z is —$NR^d$ and, $R^1$, $R^2$, $R^7$, $R^8$ are as defined above may include the preparation of intermediate of formula (XV) according to scheme 4.

Step (i) is typically achieved by reacting compound of formula (XII) with an hydroxyl amine salt, in the presence of a base, e.g. triethylamine.

Step (ii) comprises catalytic hydrogenation of intermediate (XIII) performed in the presence of Pd/C in a suitable solvent e.g. methanol, under high pressure.

Step (iii) includes reacting intermediate (XIV) with protecting agent, e.g. di-ter-butylcarbonate in a suitable solvent e.g. dichloromethane, followed by a cyclization in the presence of 1,1'-carnonyldiimidazole, in a suitable solvent, e.g. dichloromethane.

Compounds of formula (V) wherein X is a $C_{1-4}$ alkylene chain or a sulphur atom may be transformed into the corresponding compound of formula (IIA), in the presence of iron powder. Conveniently this reaction is performed in an acetic acid at high temperature.

Alternatively, when X is nitrogen, a similar transformation may be made in the presence of $P_2S_5$.

Compounds of formula (V) wherein X is N—$R^d$ can be conveniently transformed into corresponding compounds of formula (IIA) by initial reduction of the nitro group with iron powder in the presence of an acid, e.g. acetic acid, followed by a cyclization performed in the presence of P₂S₅ in a suitable solvent e.g. THF at high temperature.

Compounds of formula (IIA) wherein R$^{5a}$ is hydroxy and R$^{5b}$ is hydrogen above may be prepared by a process which comprises reacting an intermediate of formula (XVI).

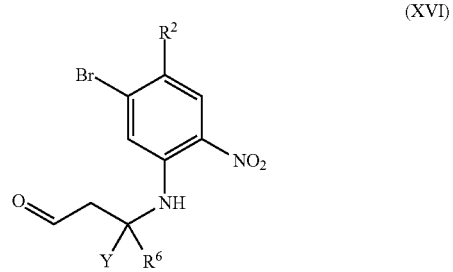

(XVI)

Advantageously, said intermediate is reacted with trimethylsilane cyanide in a suitable solvent e.g. dichloromethane. The intermediate thereby obtained may subsequently be reacted with iron powder in acetic acid similarly to compound (V) above or alternatively with stannylchloride(II) at high temperature to afford the desired compound of formula (IIA). The hydroxy group may be further functionalized according to method analogous to the Examples or known to the one skilled in the art, to afford a variety of R$^a$ groups.

Intermediate of formula (XVI) may obtained by reaction of an intermediate of formula (III), as defined here above, with a compound of formula NH₂—CH(Y)—CH₂—CO-OR$^d$, wherein Y and R$^d$ are as defined here above. The reaction is conveniently effected in the presence of a base, e.g. potassium carbonate, in a suitable solvent, e.g. acetonitrile, at high temperature. The resulting compound is subsequently treated with a reducing agent, e.g. DIBAL-H.

Where they are not commercially available, the starting materials (III), (IV), (VI), (VII), (XI) and (XII) may be prepared by methods analogous to those described in the accompanying Examples, or by standard methods well known from the art.

References to compound of formula (I) below will be understood as including all potential the subclasses and subgroups mentioned here above.

A compound of formula (I) which contains a hydroxy group may be alkylated by treatment with the appropriate alkyl halide in the presence of a base, e.g. sodium hydride, or silver oxide. A compound of formula (I) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound of formula (I) which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound of formula (I) which contains an N—H moiety may be methylated by treatment with formaldehyde in the presence of a reducing agent, e.g. sodium triacetoxyborohydride.

A compound of formula (I) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound of formula (I) substituted by amino (—NH₂) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound of formula (I) substituted by hydroxy (—OH) may be converted into the corresponding compound substituted by $C_{1-6}$ alkyl-sulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound of formula (I) containing the moiety —S— may be converted into the corresponding compound containing the moiety —S(O)— by treatment with 3-chloroperoxybenzoic acid. Likewise, a compound of formula (I) containing the moiety —S(O)— may be converted into the corresponding compound containing the moiety —S(O)₂— by treatment with 3-chloroperoxybenzoic acid. Alternatively, a compound of formula (I) containing the moiety —S— may be converted into the corresponding compound containing the moiety —S(O)₂— by treatment with Oxone® (potassium peroxymonosulfate).

A compound of formula (I) containing an aromatic nitrogen atom may be converted into the corresponding N-oxide derivative by treatment with 3-chloroperoxybenzoic acid.

A compound of formula (I) which contains a carbonyl may be converted into the corresponding alcohol by treatment with a suitable borohydride, e.g. lithium-tri-sec-butylborohydride or sodium borohydride, in a suitable solvent e.g. THF.

A bromophenyl derivative of formula (I) may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A chlorophenyl derivative of formula (I) may be converted into the corresponding butyloxycarbonylphenyl derivative by treatment with butanol, under high pressure of CO and at high temperature. The reaction is conveniently effected in the presence of dichloro[bis(dicyclohexylphosphino)propane]Pd(II) and sodium carbonate.

A chlorophenyl derivative of formula (I) may be converted into the corresponding cyanophenyl derivative by treatment with zinc cyanide in the presence of tetrakis-(triphenylphosphine)palladium(0). The reaction is conveniently effected in a suitable solvent, e.g. DMF, at high temperature and using microwave technology. A compound of formula (I) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium(II), tetrakis(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate or potassium carbonate, or potassium phosphate.

A compound of formula (I) wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato)diboron or bis(neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis-(diphenylphosphino)ferrocene]dichloropalladium (II), or bis[3-(diphenylphosphanyl)-cyclopenta-2,4-dien-1-yl]iron-dichloropalladium-dichloromethane complex. Step (ii) is conveniently effected in the presence of a transition metal catalyst such as tetrakis-(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate or potassium carbonate.

A compound of formula (I) wherein $R^1$ represents halogen, e.g. bromo, may be converted into the corresponding compound wherein $R^1$ represents an optionally substituted aryl, heteroaryl or heterocycloalkenyl, via a two-step procedure which comprises: (i) reaction with the corresponding optionally substituted 4, 4, 5, 5-tetramethyl-1, 3,2-dioxaborolane derivative, in a suitable solvent, e.g. 1,4-dioxane, in the presence of an inorganic base e.g. sodium carbonate, and (ii) addition of (tris)(benzylideneacetone)dipalladium (0) and tri-tert-butylphoshonium tetrafluoroborate. The reaction is conveniently effected a high temperature using microwave technology.

A compound of formula (I) wherein $R^1$ represents halogen, e.g. bromo, may be converted into the corresponding compound wherein $R^1$ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine)palladium(0), typically in the presence of copper(I) iodide and a base, e.g. an organic base such as triethylamine.

A compound of formula (I) wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper(II) acetate and an organic base such as N,N,N',N'-tetramethylethylenediamine (TMEDA).

A compound of formula (I) wherein $R^1$ represents halogen, e.g. bromo, may be converted into the corresponding compound wherein $R^1$ represents 2-(methoxycarbonyl)-ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate or bis(dibenzylideneacetone)palladium(0), and a reagent such as tri(ortho-tolyl)phosphine.

A compound of formula (I) containing an hydroxy-phenyl moiety may be transformed into the corresponding compound of formula (I) containing a difluoromethoxy-phenyl moiety by treatment with diethyl(bromodifluoromethyl) phosphontae in the presence of a suitable base, e.g. potassium hydroxide, in a suitable solvent, e.g. acetonitrile.

In general, a compound of formula (I) containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) wherein $R^1$ represents 6-methoxypyridin-3-yl may be converted into the corresponding compound wherein $R^1$ represents 2-oxo-1,2-dihydropyridin-5-yl by treatment with pyridine hydrochloride; or by heating with a mineral acid such as hydrochloric acid. By utilising similar methodology, a compound of formula (I) wherein $R^1$ represents 6-methoxy-4-methylpyridin-3-yl may be converted into the corresponding compound wherein $R^1$ represents 4-methyl-2-oxo-1,2-dihydropyridin-5-yl; and a compound of formula (I) wherein $R^1$ represents 6-methoxy-5-methylpyridin-3-yl may be converted into the corresponding compound wherein $R^1$ represents 3-methyl-2-oxo-1,2-dihydropyridin-5-yl.

A compound of formula (I) wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—CO$_2$H) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—CO$_2$H) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C=O) moiety may be converted into the corresponding compound containing a —C(CH$_3$)(OH)— moiety by treatment with methylmagnesium bromide. Similarly, a compound of formula (I) containing a carbonyl (C=O) moiety may be converted into the corresponding compound containing a —C(CF$_3$)(OH)— moiety by treatment with (trifluoromethyl)trimethylsilane and cesium fluoride. A compound of formula (I) containing a carbonyl (C=O) moiety may be converted into the corresponding compound containing a —C(CH$_2$NO$_2$)(OH)— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) wherein R$^1$ represents a substituent containing at least one nitrogen atom, which substituent is linked to the remainder of the molecule via a nitrogen atom, may be prepared by reacting a compound of formula (I) wherein R$^1$ represents halogen, e.g. bromo, with the appropriate compound of formula R$^1$—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropyl-biphenyl (XPhos) or 2,2'-bis(diphenylphosphino)-1,1'-binaphthalene (BINAP) and a base, e.g. an inorganic base such as sodium tert-butoxide. Alternatively, the reaction may be effected using palladium diacetate, in the presence of a reagent such as [2',6'-bis(propan-2-yloxy)biphenyl-2-yl](dicyclohexyl)phosphane and a base, e.g. an inorganic base such as cesium carbonate.

A compound of formula (I) containing an oxo moiety can be converted into the corresponding compound containing an ethoxycarbonylmethylidene moiety by treatment with triethyl phosphonoacetate in the presence of a base such as sodium hydride.

A compounds of formula (IIC), (IIP), (IIS) or (IIT) wherein R$^9$ represents ethenyl may be prepared by reacting a compound of (IIC), (IIP), (IIS) or (IIT) wherein R$^9$ represents halogen, e.g. chloro, with potassium vinyl trifluoroborate. The reaction is typically effected in the presence of a transition metal catalyst, e.g. [1,1'-bis(diphenylphosphino)ferrocene]dichloropalladium(II), and a base, e.g. an organic base such as triethylamine.

A compound of formula (IIC), (IIP), (IIS) or (IIT) wherein R$^9$ represents halogen, e.g. chloro, may be converted into the corresponding compound wherein R$^9$ represents an optionally substituted C$_{4-7}$ cycloalkenyl moiety by treatment with the appropriately substituted cycloalkenyl boronic acid or a cyclic ester thereof formed with an organic diol, e.g. pinacol, 1,3-propanediol or neopentyl glycol. The reaction is typically effected in the presence of a transition metal catalyst, e.g. bis[3-(diphenylphosphanyl)cyclopenta-2,4-dien-1-yl] iron-dichloropalladium-dichloromethane complex, and a base, e.g. an inorganic base such as potassium carbonate.

A compound of formula (IIC), (IIP), (IIS) or (IIT) wherein R$^9$ represents a substituent containing at least one nitrogen atom, which substituent is linked to the remainder of the molecule via a nitrogen atom, may be prepared by reacting a compound of formula (IIC), (IIP), (IIS) or (IIT) wherein R$^9$ represents halogen, e.g. chloro, with the appropriate compound of formula R$^9$—H [e.g. 2-methoxyethylamine, N-methyl-L-alanine, 2-aminocyclopentanecarboxylic acid, 3-aminocyclopentanecarboxylic acid, 1-(aminomethyl)cyclopropanecarboxylic acid, methyl azetidine-3-carboxylate, pyrrolidin-3-ol, pyrrolidine-3-carboxylic acid, piperidine-2-carboxylic acid, piperidine-3-carboxylic acid, 4-(1H-tetrazol-5-yl)piperidine, piperazine, 1-(methylsulfonyl)piperazine, piperazin-2-one, 2-(piperazin-1-yl)propanoic acid, morpholine, morpholine-2-carboxylic acid, thiomorpholine, thiomorpholine 1,1-dioxide, 1,4-diazepan-5-one, 2-oxa-5-azabicyclo[2.2.1]heptane or an appropriately substituted azaspiroalkane], optionally in the presence of a base, e.g. an organic base such as triethylamine or N,N-diisopropylethylamine and/or 1-methyl-2-pyrrolidinone, or pyridine, or an inorganic base such as potassium carbonate.

It will be apparent to the person skilled in the art that the synthesis of compounds of formula (I) with specific R$^1$ and R$^9$ groups or with specific substituents, which synthesis is not detailed here above, can be prepared according to the specific protocols described here after in the Examples.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W.

Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the binding of a fluorescence conjugate to TNFα when tested in the fluorescence polarisation assay described below. Moreover, certain compounds in accordance with this invention potently inhibit TNFα-induced NF-κB activation in the reporter gene assay described below.

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229 (published 19 Dec. 2013); or by a procedure analogous thereto.

Preparation of Fluorescence Conjugate

Compound (A) (27.02 mg, 0.0538 mmol) was dissolved in DMSO (2 mL). 5 (-6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, the compounds of the accompanying Examples were all found to exhibit IC$_{50}$ values of 50 μM or better.

Reporter Gene Assay

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNF. Compounds were diluted from 10 mM DMSO stocks (final assay concentration 0.3% DMSO) to generate a 10-point 3-fold serial dilution curve (e.g., 30,000 nM to 2 nM final concentration). Diluted compound was preincubated with TNFα for 60 minutes prior to addition to a 384-well microtitre plate and incubated for 18 h. The final TNF concentration in the assay plate was 0.5 ng/mL. SEAP activity was determined in the supernatant using a colorimetric substrate, e.g., QUANTI-Blue™ or HEK-Blue™ Detection media (InvivoGen). Percentage inhibitions for compound dilutions were calculated between a DMSO control and maximum inhibition (by excess control compound) and an IC$_{50}$ value calculated using XLfit™ (4 parameter logistic model) in ActivityBase.

When tested in the reporter gene assay, certain compounds of the accompanying Examples were found to exhibit IC$_{50}$ values of 50 μM or better.

EXAMPLES

Nomenclature

Compounds were named with the aid of ACD/Name Batch (Network) ver. 12.0 or Accelyrs Draw 4.0

Abbreviations

DCM: Dichloromethane
DMF: N,N-Dimethylformamide
DMSO: Dimethylsulfoxide
Et$_2$O: Diethyl ether
THF: Tetrahydrofuran
r.t.: Room temperature
br.: Broad
M: Mass
Brine: Saturated aqueous sodium chloride solution
HPLC: High Performance Liquid Chromatography
LCMS: Liquid Chromatography Mass Spectrometry
ES+: Electrospray Positive Ionisation
TEA: Triethylamine
DIPEA: N,N-di-iso-propylethylamine
DIAD: Diisopropyl (E)-1,2-diazenedicarboxylate
CDI: Carbonyl diimidazole
bs.: Broad singlet
Boc$_2$O: Di-tert butyl dicarbonate
DME dimethoxy ethane
EtOAc: Ethyl acetate
MeOH: Methanol
SiO$_2$: Silica h: Hour
AcOH: Acetic acid
RT: retention time
TLC thin layer chromatography
sat. Saturated
Hex hexane
aq. Aqueous
TMSCN: trimethylsilyl cyanide
DAST: diethylaminosulphur trifluoride
The methanolic ammonia solution is made by mixing 100 mL of an aq. solution of 37% w/w of $NH_4OH$ in 900 mL of MeOH.

Analytical Conditions

All NMRs were obtained either at 300 MHz or 400 MHz. All reactions involving air- or moisture-sensitive reagents were performed under a nitrogen atmosphere using dried solvents and glassware.
All compound GCMS data were determined by using the method below:
Method 1:
ITQ 900 Ion Trap Finnigan mass spectrometer is used for GC-MS analysis. This spectrometer is equipped with a gas chromatograph model Trace GC ultra (Finnigan) fitted with a split/splitless injector. The separation is carried on a FactorFOUR fused-silica column (VF-5MS 15 m×0.25 33 I.D., 1 µm) from Varian. Helium (purity 99.999%) is used as carried gas. Sample (1 µL) is injected in splitless mode and the oven temperature is programmed as follows: 50° C. for 5 min, increasing to 280° C. (23° C./min) and holding for 10 min. The ITQ 900 spectrometer operates in electron impact (EI) or chemical ionization (CI—CH4). The source temperature is set at 150° C.
All compound LCMS data were determined by using the method below.
Method 2:
Waters Acquity-SQD, Waters Acquity UPLC BEH C18, 2.1×50 mm, 1.7 µm column
Mobile phase A: 10 mM Ammonium Formate+0.1% Ammonia
Mobile phase B: 95% MeCN+5% H2O+0.1% Ammonia
Gradient program (Flow Rate 1.0 mL/min, Column Temperature 40° C.):

| Time | A % | B % |
|---|---|---|
| 0.00 | 95 | 5 |
| 0.50 | 95 | 5 |
| 1.75 | 5 | 95 |
| 2.00 | 5 | 95 |
| 2.25 | 95 | 5 |

Method 1b:
Waters Acquity-SDS, Waters Acquity BEH C18, 2.1×50 mm, 1.7 µm column
Mobile phase A: water+0.5% formic acid
Mobile phase B: MeCN+0.035% formic acid
Gradient program (Flow Rate 0.9 mL/min, column temperature 55° C.):

| Time | A % | B % |
|---|---|---|
| 0.00 | 95 | 5 |
| 2.00 | 5 | 95 |
| 2.60 | 5 | 95 |
| 2.70 | 95 | 5 |
| 3.00 | 95 | 5 |

Preparative HPLC
Method 2b:
Column: Merck Purosphere® STAR-RP18; 25 mm×250 mm, 10µ at ambient temperature
Eluent: MeCN:$H_2O$+0.05% TFA (flow rate 25 ml/min)
Gradient: 5:95 (0 min)→95:5 (45 min),
Method 2d:
Column: Agilent Prep C-18, 30 mm×250 mm, 10 g at ambient temperature
Eluent: MeCN:$H_2O$ (flow rate 75 ml/min)
Gradient: 10:90 (0 min)→90:10 (12.5 min)→90:10 (15 min)
It will be apparent to the one skilled in the art that different retention times (RT) may be obtained for GCMS and LCMS data may be obtained id different analytical conditions are used.

Intermediate 1

Ethyl 4-(2,5-dimethylphenyl)-4-hydroxy-butanoate

To a solution of 2,5-dimethylbenzaldehyde (5.00 g, 37.27 mmol) in DCM (75 mL) at −78° C. was added $TiCl_4$ (41.0 mL, 40.99 mmol, 1 M in DCM). A solution of (1-ethoxy-cyclopropoxy)-trimethyl-silane (7.79 g, 44.72 mmol) in DCM (30 mL) was added and the reaction was stirred at −78° C. for 30 min and warmed to r.t. for 18 h. The reaction was treated with a sat. aq. solution of $NH_4Cl$ (100 mL) and extracted with DCM (100 mL). The organic layer was separated, dried ($MgSO_4$) and concentrated in vacuo to afford the title compound (8.25 g, 94%). $^1$H NMR (400 MHz, $CDCl_3$) δ 7.31 (m, 1H), 7.06 (m, 2H), 5.26 (m, 1H), 4.15 (m, 3H), 2.57 (m, 2H), 2.39 (m, 8H), 1.28 (m, 3H). GC-MS m/z 218.1 (M-18).

Intermediate 2

5-(2,5-dimethylphenyl)-1-[(4-methoxyphenyl) methyl]pyrrolidin-2-one

To a solution of Intermediate 1 (2.00 g, 8.46 mmol) in toluene (35 mL) was added (4-methoxyphenyl)methanamine (11.61 g, 84.6 mmol) and the reaction was heated to 150° C. in a sealed tube for 4 h. The reaction was cooled and treated with water (50 mL) and DCM (50 mL), the organic layer was separated, dried ($MgSO_4$) and concentrated in vacuo. The residue was purified by column chromatography ($SiO_2$, 0-3% methanolic ammonia/DCM), yielding the title compound (1.20 g, 40%). $^1$H NMR (400 MHz, $CDCl_3$) δ 7.04 (m, 4H), 6.92 (s, 1H), 6.82 (d, J 8.6 Hz, 2H), 5.12 (m, 1H), 4.62 (m, 1H), 3.79 (m, 3H), 3.48 (m, 1H), 2.62 (m, 1H), 2.49 (m, 1H), 2.37 (m, 5H), 2.10 (m, 3H). LCMS ($ES^+$) 310.3 $(M+H)^+$.

Intermediate 3

5-(2,5-dimethylphenyl)pyrrolidin-2-one

Intermediate 2 (1.00 g, 3.23 mmol) and molecular sieves (4 Å, 1.5 g) were suspended in a solution of TFA (4 mL) and anisole (2 mL). The reaction mixture was heated at 110° C.

for 18 h in a sealed tube. The reaction mixture was cooled and extracted with DCM (20 mL), washed with water (20 mL), brine (20 mL) and the organic layer was separated, dried (MgSO$_4$) and concentrated in vacuo. The residue was purified by column chromatography (SiO$_2$, 0-3% methanolic ammonia/DCM), yielding the title compound (0.12 g, 20%). $^1$H NMR (400 MHz, CDCl$_3$) δ 7.28 (m, 1H), 7.19 (m, 1H), 7.11 (m, 1H), 6.55 (m, 1H), 5.04 (m, 1H), 2.75 (m, 1H), 2.57 (m, 2H), 2.46 (s, 3H), 2.43 (s, 3H), 1.99 (m, 1H). LCMS (ES$^+$) 190.2 (M+H)$^+$.

Intermediate 4 (Method A)

1-(5-bromo-2-nitro-phenyl)-5-(2,5-dimethylphenyl)pyrrolidin-2-one

To a solution of Intermediate 3 (0.14 g, 0.74 mmol) in dry DMF (6 mL), was added sodium hydride (0.04 g, 0.89 mmol) and the reaction mixture was stirred at r.t. for 10 min. A solution of 2-fluoro-4-bromo-nitrobenzene (0.18 g, 0.81 mmol) in DMF (2 mL) was then added and the reaction stirred at r.t. for 18 h. The reaction mixture was diluted with DCM (20 mL), washed with water (20 mL), brine (20 mL) and the organic layer was separated, dried (MgSO$_4$) and concentrated in vacuo. The residue was triturated with Et$_2$O yielding the title compound (0.11 g, 38%). $^1$H NMR (400 MHz, CDCl$_3$) δ 7.80 (m, 1H), 7.46 (m, 1H), 7.33 (m, 1H), 7.06 (m, 4H), 5.47 (m, 1H), 2.72 (m, 3H), 2.35 (m, 3H), 2.28 (m, 3H). LCMS (ES$^+$) 389.2/391.2 (M+H)$^+$.

Intermediate 5

2-bromo-1-[2-(difluoromethoxy)phenyl]ethanone

To a solution of 2'-(difluoromethoxy)acetophenone (2.00 g, 10.74 mmol) in MeOH (40 mL) was added, dropwise, bromine (1.72 g, 10.74 mmol) in MeOH (5 mL). The mixture was stirred at 70° C. for 30 min. The reaction was concentrated in vacuo and the residue was washed with water (10 mL) and extracted with DCM (20 mL), dried (MgSO$_4$) and concentrated in vacuo yielding the title compound (2.58 g, 88%). $^1$H NMR (400 MHz, CDCl$_3$) δ 7.86 (m, 1H), 7.62 (m, 1H), 7.38 (m, 1H), 7.21 (m, 1H), 6.67 (m, 1H), 4.54 (m, 2H). GC-MS m/z 265.0/267.0 (M+H)$^+$.

Intermediate 6

Diethyl 2-[2-[2-(difluoromethoxy)phenyl]-2-oxo-ethyl]propanedioate

To a solution of Intermediate 5 (2.50 g, 9.41 mmol) in dry THF (50 mL) was added sodium hydride (0.56 g, 14.12 mmol), the reaction mixture was stirred at 0° C. for 1 h and a solution of diethylmalonate (1.81 g, 11.3 mmol) in THF (5 mL) was added drop wise. The reaction was stirred at r.t. for 18 h. The reaction mixture was diluted with EtOAc (20 mL) and washed with water (20 mL) and brine (20 mL). The organic layer was separated, dried (MgSO$_4$) and concentrated in vacuo, yielding the title compound (1.52 g, 46%). $^1$H NMR (400 MHz, DMSO-d$_6$) δ 7.77 (dd, J 7.8 Hz, J 1.7 Hz, 1H), 7.68 (m, 1H), 7.35 (m, 3H), 4.14 (m, 6H), 3.93 (t, J 7.1 Hz, 1H), 3.54 (d, J 7.1 Hz, 2H), 1.19 (m, 4H). LCMS (ES$^+$) 345.2 (M+H)$^+$.

Intermediate 7

Diethyl 2-[2-[2-(difluoromethoxy)phenyl]-2-hydroxyimino-ethyl]propanedioate

To a solution of Intermediate 6 (1.30 g, 3.78 mmol) in pyridine (10 mL) was added hydroxylamine hydrochloride (0.52 g, 7.55 mmol), the reaction mixture was stirred at 60° C. for 20 h and concentrated in vacuo, yielding the title compound (2.00 g, quantitative yield). LCMS (ES$^+$) 360.3 (M+H)$^+$.

Intermediate 8

Ethyl 5-[2-(difluoromethoxy)phenyl]-2-oxo-pyrrolidine-3-carboxylate

To a solution of Intermediate 7 (2.00 g, 3.78 mmol) in EtOH (50 mL), Ni Raney was added (10% mol). The autoclave was sealed and heated at 60° C., under 10 bar of hydrogen for 18 h. The reaction was filtered through celite and washed with EtOH (20 mL). The filtrate was concentrated in vacuo. The residue was purified by column chromatography (SiO$_2$, 0-3% methanolic ammonia/DCM), yielding the title compound (0.36 g, 32%). $^1$H NMR (400 MHz, CDCl$_3$) δ 7.06 (m, 4H), 6.34 (m, 1H), 4.92 (m, 1H), 3.92 (m, 2H), 3.18 (m, 1H), 2.68 (m, 1H), 2.06 (m, 1H), 1.39 (m, 1H), 1.02 (m, 3H). LCMS (ES$^+$) 300.2 (M+H)$^+$.

Intermediate 9

5-[2-(difluoromethoxy)phenyl]pyrrolidin-2-one

To a solution of Intermediate 8 (4.0 g, 13.0 mmol) in EtOH (150 mL), 1 N sodium hydroxide (15 mL, 15 mmol) was added. The mixture was stirred at r.t. for 18 h. The reaction mixture was diluted with water (20 mL) and washed with DCM (50 mL). The organic layer was discarded, the aq. layer was treated with 1N HCl (15 mL, 15 mmol) and extracted with DCM (50 mL). The organic layer was separated, dried (MgSO$_4$) and concentrated in vacuo. The residue was dissolved in toluene (50 mL) and the mixture stirred at 110° C. for 18 h. The reaction was diluted with water (20 mL) and extracted with DCM (50 mL); the organic layer was separated, dried (MgSO$_4$) and concentrated in vacuo. The residue was purified by column chromatography (SiO$_2$, 0-3% methanolic ammonia/DCM), yielding the title compound (0.64 g, 21%). $^1$H NMR (400 MHz, CDCl$_3$) δ 7.44 (m, 1H), 7.35 (m, 1H), 7.24 (m, 1H), 7.14 (m, 1H), 6.59 (m, 1H), 6.18 (m, 1H), 5.15 (m, 1H), 2.67 (m, 1H), 2.46 (m, 2H), 1.97 (m, 1H). LCMS (ES$^+$) 228.1 (M+H)$^+$.

Intermediate 10

1-(5-bromo-2-nitro-phenyl)-5-[2-(difluoromethoxy)phenyl]pyrrolidin-2-one

The title compound was prepared from Intermediate 9 (0.13 g, 0.57 mmol) and 2-fluoro-4-bromo-nitrobenzene (0.14 g, 0.63 mmol) by the Method A, (0.09 g, 37%). $^1$H NMR (400 MHz, CDCl$_3$) δ 7.81 (m, 1H), 7.65 (m, 1H), 7.41 (m, 1H), 7.31 (m, 1H), 7.22 (m, 2H), 7.14 (m, 1H), 6.64 (m, 1H), 5.74 (m, 1H), 2.71 (m, 3H), 2.16 (m, 1H). LCMS (ES$^+$) 427.2/429.2 (M+H)$^+$.

Intermediates 11 and 12

Enantiomer 1 (5 S or R)-5-[2-(difluoromethoxy) phenyl]pyrrolidin-2-one and enantiomer 2 (5R or S)-5-[2-(difluoromethoxy)phenyl]pyrrolidin-2-one The following title compounds were isolated from Intermediate 9 (0.47 g) by purification under SFC conditions on Chiralpak IA (50*226, 360 mL/min, 25° C., $CO_2$+10% MeOH, con: 20 g/l), yielding Intermediate 11 (RT 3.9 min, 0.20 g) and Intermediate 12 (RT 5.4 min, 0.22 g) respectively.

Intermediate 13

Enantiomer 1 (5S or R)-1-(5-bromo-2-nitro-phenyl)-5-[2-(difluoromethoxy)phenyl]pyrrolidin-2-one The title compound was prepared from Intermediate 11 (0.20 g) and 2-fluoro-4-bromo-nitrobenzene by the Method A, (0.40 g, quantitative yield). LCMS (ES$^+$) 427.2/429.2 (M+H)$^+$.

Intermediate 14

Enantiomer 2 (5R or S)-1-(5-bromo-2-nitro-phenyl)-5-[2-(difluoromethoxy)phenyl]pyrrolidin-2-one The title compound was prepared from Intermediate 12 (0.22 g) and 2-fluoro-4-bromo-nitrobenzene by the Method A, (0.40 g, 91%). LCMS (ES$^+$) 427.2/429.2 (M+H)$^+$.

Intermediate 15

Ethyl 4-hydroxy-4-(o-tolyl)butanoate

To a solution of 2-methylbenzaldehyde (3.0 g, 25.0 mmol) in DCM (60 mL) at −78° C. was added TiCl$_4$ (40.0 mL, 40 mmol, 1 M in DCM). A solution of (1-ethoxycyclopropoxy)-trimethyl-silane (8.70 g, 50.0 mmol) in DCM (20 mL) was added and the reaction was stirred at −78° C. for 30 min and warmed to r.t. for 18 h. The reaction was treated with a sat. aq. solution of NH$_4$Cl (100 mL) and extracted with DCM (100 mL). The organic layer was separated, dried (MgSO$_4$) and concentrated in vacuo. The residue was purified by column chromatography (SiO$_2$, 0-10% EtOAc/hexanes), yielding the title compound as a yellow oil (4.40 g, 79%). $^1$H NMR (400 MHz, CDCl$_3$) δ 7.50 (d, 1H), 7.20-7.10 (m, 3H), 5.22 (m, 1H), 4.15 (q, 2H), 2.50 (m, 2H), 2.30 (m, 2H), 2.35 (s, 3H), 1.25 (t, 3H).

Intermediate 16

1-[(4-methoxyphenyl)methyl]-5-(o-tolyl)pyrrolidin-2-one

To a solution of Intermediate 15 (4.40 g, 19.8 mmol) in toluene (20 mL) was added (4-methoxyphenyl)methanamine (27.1 g, 198.0 mmol) and the reaction was heated to 150° C. in a sealed tube for 18 h. The reaction was cooled and treated with water (50 mL) and DCM (50 mL), the organic layer was separated, dried (MgSO$_4$) and concentrated in vacuo. The residue was purified by column chromatography (SiO2, 0-35% EtOAc/hexanes), yielding the title compound as a white solid (3.20 g, 55%). $^1$H NMR (400 MHz, CDCl$_3$) δ 7.25-7.1 (m, 4H), 6.95 (d, 2H), 6.8 (d, 2H), 5.1 (d, 1H), 4.65 (m, 1H), 5.8 (s, 3H), 3.4 (d, 2H), 2.45-2.3 (m, 4H), 2.1 (s, 3H). LCMS (ES$^+$) 296.0 (M+H)$^+$.

Intermediate 17

5-(o-tolyl)pyrrolidin-2-one

A solution of Intermediate 16 (3.2 g, 10.0 mmol) in TFA (25 mL) was heated at 150° C. for 18 h in a sealed tube. The cooled reaction mixture was concentrated in vacuo. The residue was purified by column chromatography (SiO$_2$, 0-3% MeOH/DCM), yielding the title compound as a yellow solid (1.5 g, 79%). $^1$H NMR (400 MHz, CDCl$_3$) δ 7.20-7.10 (m, 4H), 4.85 (m, 1H), 3.50 (m, 2H), 2.25 (s, 3H), 2.20 (m, 2H). LCMS (ES$^+$) 176.0 (M+H)$^+$.

Intermediate 18

1-(5-bromo-2-nitro-phenyl)-5-(o-tolyl)pyrrolidin-2-one

The title compound was prepared from Intermediate 17 (0.75 g, 4.28 mmol) and 2-fluoro-4-bromo-nitrobenzene by the Method A, (0.50 g, 31%). $^1$H NMR (400 MHz, CDCl$_3$) δ 7.80 (d, 1H), 7.50 (d, 1H), 7.40 (d, 1H), 7.15 (m, 3H), 7.05 (s, 1H), 5.50 (m, 1H), 2.60-2.70 (m, 3H), 2.35 (s, 3H), 2.10 (m, 1H). LCMS (ES$^+$) 375.0/377.0 (M+H)$^+$.

Intermediate 19

Ethyl 4-hydroxy-4-phenyl-butanoate

The title compound was prepared in a similar manner to Intermediate 15. To a solution of benzaldehyde (1.00 g, 9.43 mmol) in DCM (30 mL) at −78° C. was added TiCl$_4$ (15.0 mL, 15.0 mmol, 1 M in DCM). A solution of (1-ethoxycyclopropoxy)-trimethyl-silane (2.90 g, 14.10 mmol) in DCM (20 mL) was added and the reaction was stirred at −78° C. for 30 min and warmed to r.t. for 18 h. The reaction was treated with sat. aq. NH$_4$Cl (20 mL) and extracted with DCM (20 mL). The organic layer was separated, dried (MgSO$_4$) and concentrated in vacuo. The residue was purified by column chromatography (SiO$_2$, 0-10% EtOAc/hexanes), yielding the title compound as a yellow oil (1.60 g, 84%). $^1$H NMR (400 MHz, CDCl$_3$) δ 7.30-7.20 (m, 5H), 4.95 (m, 1H), 4.10 (q, 2H), 2.45-2.30 (m, 4H), 1.25 (t, 3H).

Intermediate 20

1-[(4-methoxyphenyl)methyl]-5-phenyl-pyrrolidin-2-one

To a solution of Intermediate 19 (2.00 g, 9.61 mmol) in toluene (20 mL) was added (4-methoxyphenyl)methanamine (13.20 g, 96.5 mmol) and the reaction was heated to 150° C. in a sealed tube for 18 h. The reaction was cooled and treated with water (50 mL) and DCM (50 mL), the organic layer was separated, dried (MgSO$_4$) and concentrated in vacuo. The residue was purified by column chromatography (SiO$_2$, 0-35% EtOAc/hexanes), yielding the title compound as a yellow solid (2.0 g, 74%). $^1$H NMR (400 MHz, CDCl$_3$) δ 7.30-7.40 (m, 3H), 7.15 (d, 2H), 7.00 (d, 2H), 6.80 (d, 2H), 5.05 (d, 1H), 4.40 (m, 1H), 3.80 (s, 3H), 3.40 (d, 1H), 2.50-2.35 (m, 3H), 1.9 (m, 1H). LCMS (ES$^+$) 282.0 (M+H)$^+$.

Intermediate 21

5-phenylpyrrolidin-2-one

A solution of Intermediate 20 (2.00 g, 7.11 mmol) in TFA (15 mL) was heated at 150° C. for 18 h in a sealed tube. The reaction mixture was cooled and concentrated in vacuo. The residue was purified by column chromatography (SiO$_2$, 0-3% MeOH/DCM), yielding the title compound as a yellow solid (0.80 g, 70%). $^1$H NMR (400 MHz, CDCl$_3$) δ 8.10 (br s, 1H), 7.30-7.40 (m, 5H), 4.65 (m, 1H), 2.50 (m, 1H), 2.20 (m, 2H), 1.75 (m, 1H). LCMS (ES$^+$) 162.0 (M+H)$^+$.

Intermediate 22

1-(5-bromo-2-nitro-phenyl)-5-phenyl-pyrrolidin-2-one

The title compound was prepared from Intermediate 21 (0.50 g, 3.10 mmol) and 2-fluoro-4-bromo-nitrobenzene by the Method A, (0.25 g, 23%). $^1$H NMR (400 MHz, CDCl$_3$) δ 7.80 (d, 1H), 7.30-7.40 (m, 6H), 7.10 (s, 1H), 5.15 (m, 1H), 2.60-2.70 (m, 3H), 2.20 (m, 1H). LCMS (ES$^+$) 361.0/362.0 (M+H)$^+$.

Intermediate 23 (Method B)

7-bromo-1-phenyl-2,3-dihydro-1H-pyrrolo[1,2-a]benzimidazole

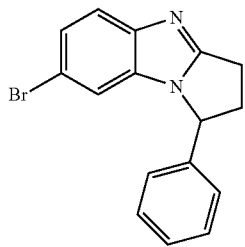 [SMILES: Brc1ccc2nc3n(c2c1)C(c1ccccc1)CC3]

To a solution of Intermediate 22 (0.50 g, 1.38 mmol) in AcOH (5 mL) was added iron powder (0.39 g, 6.94 mmol). The reaction was heated to reflux for 18 h. The reaction mixture was filtered through celite and concentrated in vacuo. The residue was treated with a sat. aq. solution of NaHCO$_3$ and extracted with EtOAc (10 mL). The organics were washed with water (10 mL) and brine (10 mL), the organic layer was separated, dried (MgSO$_4$) and concentrated in vacuo. The residue was purified by column chromatography (SiO$^2$, 0-3% methanolic ammonia/DCM), yielding the title compound (0.38 g, 87%). $^1$H NMR (400 MHz, CDCl$_3$) δ 7.60 (d, 1H), 7.45-7.40 (m, 4H), 7.35-7.30 (m, 2H), 6.90 (s, 1H), 5.40 (m, 1H), 3.20-3.05 (m, 3H), 2.50 (m, 1H). LCMS (ES$^+$) 312.0/314.0 (M+H)$^+$.

Intermediate 24

(E/Z)-1-(difluoromethoxy)-2-(2-nitrovinyl) benzene

To a solution of 2-(difluoromethoxy)benzaldehyde (10 g, 57.8 mmol) in AcOH (30 mL) was added nitromethane (7.05 g, 115.6 mmol) and ethylenediamine (1.73 g, 28.9 mmol) at 10° C. The reaction mixture was heated at 50° C. for 18 h. After completion of reaction, ice cold water was added and the mixture was stirred vigorously for 1 h. The precipitate was filtered, washed with water and dried in vacuo, yielding the title compound as a yellow solid (11 g, 92%). $^1$H NMR (400 MHz, CDCl$_3$) 8.18 (d, J 13.6 Hz, 1H), 7.49-7.71 (m, 3H), 7.22-7.31 (m, 2H), 6.45-6.81 (t, 1H).

Intermediate 25

N-(1-(2-(difluoromethoxy)phenyl)-2-nitroethyl)hydroxylamine

To a solution of Intermediate 24 (11.5 g, 53.48 mmol) in EtOH (40 mL), was added hydroxylamine hydrochloride (7.38 mg, 106.9 mmol) and triethylamine (14.61 mL, 106.9 mmol) at 0° C. The reaction mixture was stirred at r.t. for 18 h. Water was added, extracted with EtOAc and concentrated in vacuo. The residue was purified by column chromatography (SiO$_2$, 0-65% EtOAc/hexanes) yielding the title compound as a yellow oil (9 g, 77%). $^1$H NMR (400 MHz, CDCl$_3$) 7.36-7.41 (m, 2H), 7.16-7.25 (m, 2H), 6.41-6.77 (t, 1H), 5.12 (q, J 8.0 Hz, 1H), 4.99 (m, 1H), 4.71 (q, J 12.8 Hz, 1H).

Intermediate 26

1-(2-(difluoromethoxy) phenyl)ethane-1,2-diamine

To a solution of Intermediate 25 (6 g, 24.19 mmol) in MeOH (150 mL), was added 10% palladium on carbon (1.5 g) at 0° C. The reaction mixture was stirred at r.t. under hydrogen atmosphere (100 psi pressure) for 18 h. The reaction mixture was filtered through a celite bed, the filter cake washed with MeOH and the filtrate concentrated in vacuo yielding the title compound as a pale yellow oil (4.7 g, 80%). $^1$H NMR (400 MHz, DMSO-d$_6$) δ 7.60 (d, J 6.8 Hz, 1H), 7.20-7.00 (m, 6H), 4.03 (q, J 11.2 Hz, 1H), 2.83 (dd, J 16.4 Hz, 1H), 2.44 (dd, J 12.4 Hz, 1H), 1.80 (bs, 2H). LCMS (ES$^+$) RT 1.31 min, 203 (M+H)$^+$.

Intermediate 27 tert-butyl (2-amino-2-(2-(difluoromethoxy)phenyl) ethyl) carbamate

To a solution of Intermediate 26 (4 g, 19.7 mmol) in dry DCM (50 mL), was added triethylamine (2.7 mL, 19.7 mmol) and di-tert-butyl dicarbonate (4.3 g, 19.7 mmol) at 0° C. The reaction mixture was stirred at r.t. for 3 h. Water was added and the mixture extracted with DCM. The organic layer was washed with water and brine, dried over (Na$_2$SO$_4$) and concentrated in vacuo. The residue was purified by preparative TLC (5% MeOH in DCM) yielding the title compound as a white solid (3.1 g, 52%). $^1$H NMR (400 MHz, CDCl$_3$) 7.43 (d, J 7.6 Hz, 1H), 7.19-7.28 (m, 2H), 7.07 (d, J 7.6 Hz, 1H), 6.38-6.75 (t, 1H), 4.85 (bs, 1H), 4.35 (m, 1H), 3.36 (m, 2H), 1.80 (bs, 2H), 1.39 (s, 9H). LCMS (ES$^+$) RT 2.09 min, 303 (M+H)$^+$.

Intermediate 28 tert-butyl 4-(2-(difluoromethoxy)phenyl)-2-oxoimidazolidine-1-carboxylate

To a solution of Intermediate 27 (6 g, 19.8 mmol) in DCM (80 mL) was added 1,1'-carbonyldiimidazole (3.8 g, 23.83 mmol) and the reaction mixture was stirred at r.t. for 4 h. The reaction mixture was concentrated in vacuo and the residue was purified by column chromatography (SiO$_2$, 0-50% EtOAc/hexanes), yielding the title compound as a yellow oil (4.2 g, 64%). $^1$H NMR (400 MHz, CDCl$_3$) 7.50 (t, J 7.2 Hz, 1H), 7.36-7.24 (m, 2H), 7.10 (d, J 8 Hz, 1H), 6.76-6.39 (t, 1H), 5.08 (dd, J 16 Hz, 1H), 4.27 (t, J 10 Hz, 1H), 3.58 (dd, J 10.8 Hz, 1H), 1.60 (s, 9H).

Intermediate 29 tert-butyl-3-(5-bromo-4-fluoro-2-nitrophenyl)-4-(2-(difluoromethoxy)phenyl)-2-oxoimidazolidine-1-carboxylate The title compound was prepared in a method similar to Method A. To a solution of Intermediate 28 (2.1 g, 6.4 mmol) in DMF (15 mL) was added Cs$_2$CO$_3$ (6.2 g, 19.2 mmol) and 2,5-difluoro-4-bromonitrobenzene (1.7 g, 7.04 mmol). The contents were heated in a sealed tube at 60° C. for 3 h. The reaction mixture was quenched with ice water and the aq. layer was extracted with EtOAc. The organic layer was dried over (Na$_2$SO$_4$) and concentrated in vacuo. The residue was purified by column (SiO$_2$, 0-30% EtOAc/hexanes) yielding the title compound as a yellow solid (2.6 g, 74%). $^1$H NMR (400 MHz, CDCl$_3$) δ 7.77 (d, J 8 Hz, 1H), 7.63 (d, J 7.6 Hz, 1H), 7.24-7.38 (m, 3H), 7.14 (d, J 8 Hz, 1H), 6.76-6.39 (t, 1H), 5.61 (t, J 16.8 Hz, 1H), 4.38 (t, J 20 Hz, 1H), 3.79 (dd, J 10 Hz, 1H), 1.60 (s, 9H).

Intermediate 30

1-(2-amino-5-bromo-4-fluoro-phenyl)-5-[2-difluoromethoxy)phenyl]imidazolidin-2-one To a solution of Intermediate 29 (500 mg, 0.91 mmol) in AcOH (6 mL) was added iron powder (252 mg, 4.58 mmol) and at 100° C. for 18 h. The reaction was filtered through a celite bed and the filtrate concentrated in vacuo. The residue was purified by column chromatography (SiO$_2$, 0-5% MeOH/DCM), yielding the title compound as an off white solid (210 mg, 55%). $^1$H NMR (400 MHz, CDCl$_3$) δ 7.77 (d, J 10 Hz, 1H), 7.54 (d, J 7.6 Hz, 1H), 7.26-7.10 (m, 3H), 7.08 (t, J 16 Hz, 1H), 6.69-6.32 (t, 1H), 5.76 (q, J 17 Hz, 1H), 5.00 (bs, 2H), 4.08 (t, J 18 Hz, 1H), 3.44 (t, J 16.8 Hz, 1H). LCMS (ES$^+$) RT 2.17 min, 416.1 (M+H)$^+$.

Intermediate 31

6-bromo-3-(2-(difluoromethoxy)phenyl)-7-fluoro-2,3-dihydro-1H-benzo[d]imidazo[1,2-a]imidazole

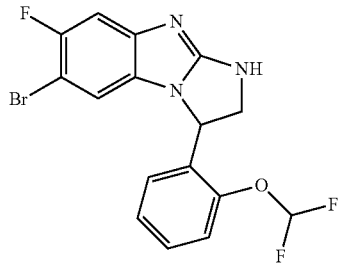 [SMILES: Fc1cc2nc3n(c2cc1Br)C(c1ccccc1OC(F)F)CN3]

The title compound was prepared by a variation of Method B. To a solution of Intermediate 30 (150 mg, 0.36 mmol) in toluene (5 mL) was added P$_2$S$_5$ (160 mg, 0.72 mmol). The reaction mixture was refluxed for 4 h. The reaction mixture was quenched with sat. aq. NaHCO$_3$ and the aq. layer was extracted with EtOAc. The combined organic layers were washed with water, brine and dried over (Na$_2$SO$_4$), and concentrated in vacuo. The residue was purified by preparative TLC (DCM/MeOH 95/5) yielding the title compound as an off white solid (50 mg, 35%). $^1$H NMR (400 MHz, CDCl$_3$) δ 7.40 (t, J 14.4 Hz, 1H), 7.26-7.10 (m, 4H), 6.84-6.46 (t, 1H), 5.86 (t, J 15 Hz, 1H), 5.60 (bs, 1H), 4.58 (t, J 18 Hz, 1H), 3.89 (dd, J 9.6 Hz, 1H). LCMS (ES$^+$) RT 2.06 min, 398/400.0 (M+H)$^+$.

Intermediate 32 tert-butyl 3-(5-bromo-2-nitrophenyl)-4-(2-(difluoromethoxy)phenyl)-2-oxoimidazolidine-1-carboxylate The title compound was prepared in a method similar to Method A. To a solution of Intermediate 28 (200 mg, 0.6 mmol) in DMF (5 mL) were added Cs$_2$CO$_3$ (586 mg, 1.8 mmol) and 2-fluoro-4-bromonitrobenzene (147 mg, 0.67 mmol). The reaction mixture was heated in a sealed tube at 60° C. for 3 h. The reaction mixture was quenched by adding ice water and the aq. layer was extracted with EtOAc. The combined organic layers were washed with water, brine, dried over (Na$_2$SO$_4$), and concentrated in vacuo. The residue was purified by column chromatography (SiO$_2$, 0-30%, EtOAc/hexanes) yielding the title compound as a yellow solid (250 mg, 77%). $^1$H NMR (400 MHz, CDCl$_3$) δ 7.82 (d, J 8.4 Hz, 1H), 7.66 (d, J 7.6 Hz, 1H), 7.42-7.21 (m, 4H), 7.14 (d, J 8.4 Hz, 1H), 6.77-6.41 (t, 1H), 5.66 (t, J 17.2 Hz, 1H), 4.38 (t, J 20 Hz, 1H), 3.76 (t, J 10.4 Hz, 1H), 1.56 (s, 9H).

Intermediate 33

1-(2-amino-5-bromo-phenyl)-5-[2-(difluoromethoxy)phenyl]imidazolidin-2-one

To a solution of Intermediate 32 (500 mg, 0.94 mmol) in AcOH (5 mL) was added iron powder (260 mg, 4.73 mmol) and the reaction mixture was heated at 100° C. for 4 h. The solvent was concentrated in vacuo, the residue diluted with water and the pH was adjusted to 7 by using sat. aq. NaHCO$_3$. The mixture was filtered through a celite bed and the filtrate was extracted with EtOAc. The combined organic layers were washed with water, brine and dried over (Na$_2$SO$_4$), and concentrated in-vacuo. The residue was purified by column chromatography (SiO$_2$, 0-5% MeOH/DCM), yielding the title compound as an off white solid (300 mg, 80%). $^1$H NMR (400 MHz, DMSO-d$_6$) δ 7.70 (d, J 8.4 Hz, 1H), 7.54 (d, J 18 Hz, 1H), 7.42-7.11 (m, 4H), 6.90 (m, 1H), 6.62 (d, J 8.8 Hz, 1H), 5.71 (t, J 15.6 Hz, 1H), 3.86 (t, J 16.4 Hz, 1H), 3.15 (t, J 15.2 Hz, 1H). LCMS (ES$^+$) RT 2.12 min, 398.2 (M+H)$^+$.

Intermediate 34

6-bromo-3-(2-(difluoromethoxy)phenyl)-2,3-dihydro-1H-benzo[d]imidazo[1,2-a]imidazole

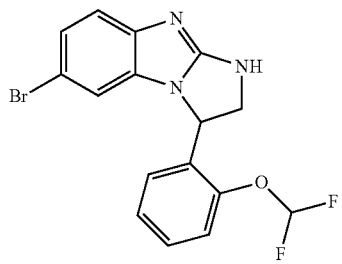 [SMILES: FC(F)Oc1ccccc1C1CNc2nc3ccc(Br)cc3n21]

The title compound was prepared by a variation of Method B. To a solution of Intermediate 33 (500 mg, 1.25 mmol) in toluene (5 mL) was added $P_2S_5$ (279 mg, 1.25 mmol). The reaction mixture was refluxed for 4 h. The reaction mixture was quenched with a sat. aq. solution of $NaHCO_3$ and the aq. layer extracted with EtOAc. The combined organic layers were dried over $(Na_2SO_4)$, and concentrated in vacuo. The residue was purified by column chromatography $(SiO_2, 0\text{-}2\%$ MeOH/DCM$)$, yielding the title compound as an off white solid (55 mg, 11%). $^1$H NMR (400 MHz, $CDCl_3$) δ 7.40 (t, J 14.4 Hz, 1H), 7.30-7.15 (m, 5H), 7.09 (t, J 7.2 Hz, 1H), 6.86-6.45 (t, 1H), 5.86 (t, J 14.8 Hz, 1H), 5.10 (bs, 1H), 4.56 (t, J 18 Hz, 1H), 3.87 (t, J 14.8 Hz, 1H). LCMS $(ES^+)$ RT 2.48 min, 380.0/382.0 $(M+H)^+$.

Intermediate 35

(5R or S)-1-(5-bromo-4-fluoro-2-nitro-phenyl)-5-[2-(difluoromethoxy)phenyl]pyrrolidin-2-one The title compound was prepared in a method similar to Method A. To a solution of Intermediate 12 (5.0 g, 22.0 mmol) in MeCN (48 mL) was added 4-bromo-2,5-difluoronitrobenzene (5.76 g, 23.2 mmol) and $Cs_2CO_3$ (15.77 g, 47.93 mmol). The mixture was stirred at 40° C. for 18 h, and concentrated in vacuo. The residue was treated with brine and partitioned with EtOAc. The aq. layer was extracted with EtOAc, the combined organic phases were dried $(MgSO_4)$, filtered and concentrated in vacuo. The residue was used in the next step without any further purification. LCMS $(ES^+)$ RT 5.0 min, 445.0/447.0 $(M+H)^+$.

Intermediate 36

1-(5-bromo-4-fluoro-2-nitro-phenyl)-5-[2-(difluoromethoxy)phenyl]pyrrolidin-2-one To a solution of Intermediate 9 (3.36 g, 14.8 mmol) and 4-bromo-2,5-difluoronitrobenzene (7.04 g, 29.6 mmol) by the Method A (3.31 g, 50%). $^1$H NMR (DMSO-$d_6$, 400 MHz) δ: 8.10 (d, J 8.3 Hz, 1H), 7.60 (m, 2H), 7.35 (m, 2H), 7.23 (m, 2H), 5.84 (m, 1H), 2.62 (m, 2H), 2.01 (m, 2H). LCMS $(ES^+)$ RT 1.52 min, 445.0/447.0 $(M+H)^+$.

Intermediate 37

1-tert-butyl-4-ethyl 4-methylpiperidine-1,4-dicarboxylate

Ethyl N-Boc-piperidine-4-carboxylate (10.00 g, 36.92 mmol) was dissolved in THF (100 mL) and cooled to −78° C. LDA (47 mmol, 23 mL) was added and the reaction stirred for 1 h. Iodomethane (81.25 mmol, 5.08 mL) was then added and the reaction stirred for a further 1 h before removing the cold bath and allowing the reaction to warm to r.t. for 30 min. The reaction was quenched with sat. aq. $NH_4Cl$ and partitioned with EtOAc, the organics were extracted and dried $(MgSO_4)$ and concentrated in vacuo, (quantitative yield). $^1$H NMR (400 MHz, DMSO-$d_6$) δ: 4.11 (q, J 7.1 Hz, 2H), 3.61 (dt, J 13.4 Hz, J 4.5 Hz, 2H), 2.95 (d, J 0.3 Hz, 2H), 1.91 (d, J 13.6 Hz, 2H), 1.39 (s, 9H), 1.31 (m, 2H), 1.19 (m, 3H), 1.15 (s, 3H).

Intermediate 38 ethyl 4-methylpiperidine-4-carboxylate; hydrochloride

To a solution of Intermediate 37 (11.0 g, 40.5 mmol) dissolved in 1,4-dioxane (30.0 mL) at 0-5° C. was added HCl (15.2 mL, 4 M in 1,4-dioxane). The mixture was allowed to warm to r.t. and stirred for 18 h. The reaction mixture was concentrated in vacuo and residue washed with diethyl ether, yielding the title compound as an orange solid (5.02 g, 59.6%). $^1$H NMR (DMSO-$d_6$) δ: 9.00 (m, 1H), 4.14 (q, J 6.8 Hz, 2H), 3.16 (m, 2H), 2.82 (m, 2H), 2.08 (d, J 14.4 Hz, 2H), 1.65 (m, 2H), 1.22 (m, 6H).

Intermediate 39

[2-(4-ethoxycarbonyl-4-methyl-1-piperidyl)pyrimidin-5-yl]boronic acid

A mixture of 2-chloropyrimidine-5-boronic acid (3.95 g, 24.2 mmol), Intermediate 38 (5.03 g, 24.2 mmol) and triethylamine (60.6 mmol, 8.50 mL) in EtOH (50 mL) was heated at 70° C. for 5 h. The reaction was cooled and partitioned between water (100 mL) and EtOAc (100 mL). The aq. layer was separated and re-extracted with further EtOAc (2×100 mL). The organic layers were combined and washed with brine (100 mL) before separating, drying $(MgSO_4)$, filtering under reduced pressure and concentrating in vacuo, yielding the title compound as a brown foam (quantitative yield). LCMS $(ES^+)$ RT 1.23 min 294.0 $(M+H)^+$.

Intermediate 40

[2-[(1R,5S)-8-methoxycarbonyl-3-azabicyclo[3.2.1]octan-3-yl]pyrimidin-5-yl]boronic acid (1R,5S)-3-tert-butoxycarbonyl-3-azabicyclo[3.2.1]octane-8-carboxylic acid (9.0 g, 35.3 mmol) was suspended in HCl solution (2.25 M in MeOH) and the reaction heated to reflux for 4 h. The reaction was allowed to cool to r.t. and then concentrated in vacuo to give a white solid. (2-chloropyrimidin-5-yl)boronic acid (5.58 g, 35.2 mmol) was added and the mixture suspended in EtOH (130 mL). Triethylamine (9.90 mL, 70.5 mmol) was added and the reaction heated at 80° C. for 5 h. The reaction was allowed to cool to r.t. and then water was added (30 mL). The reaction mixture was concentrated to around ⅓ volume and then more water added (100 mL). An off-white solid precipitated out, which was filtered and washed with water (2×30 mL) to afford the title compound (8.9 g, 86% yield) as an off-white powder. $^1$H NMR (300 MHz, DMSO-$d_6$) δ ppm 8.59 (2H, s), 8.02 (2H, s), 4.45 (2H, dd, J 13.1, 3.4 Hz), 3.62 (3H, s), 2.98 (2H, br d, J 12.4 Hz), 2.77 (1H, s), 2.59 (2H, br s), 1.66-1.63 (2H, m), 1.38-1.33 (2H, m). LCMS (ES$^+$) RT 0.97 min 292.0 (M+H)$^+$.

Intermediates 41 and 42

Enantiomer 1: (5R or S)-5-phenylpyrrolidin-2-one and enantiomer 2: (5S)-5-phenylpyrrolidin-2-one The title compounds were isolated by purification of Intermediate 20 under SFC conditions on Chiralpak IC (50*264 mm*mm, flow 360 mL/min, 25° C., CO$_2$+20% EtOH, injection of 7.6 mL, solution at a concentration of 100 g/L. The first eluting enantiomer (RT 6.2 min) was collected and the fractions were evaporated to yield enantiomer 1 (5R or S)-5-phenylpyrrolidin-2-one (arbitrarily attributed as the (5R) enantiomer, 5.34 g). The second eluting enantiomer (RT 9.0 min) was collected and the fractions were evaporated to yield enantiomer 2 (5S or R)-5-phenylpyrrolidin-2-one (arbitrarily attributed as the (5S) enantiomer, 5.58 g). $^1$H NMR (400 MHz, CDCl$_3$) δ 7.33 (m, 5H), 6.34 (m, 1H), 4.75 (t, 1H, J 7.0 Hz), 2.49 (m, 3H), 1.97 (m, 1H). LCMS (ES$^+$) RT 3.14 min, 162.2 (M+H).

Intermediate 43

Enantiomer 1: (5R or S)-1-(5-bromo-2-nitro-phenyl)-5-phenyl-pyrrolidin-2-one The title compound was prepared in a method similar to Method A. To a solution of Intermediate 42 (5.34 g, 33.1 mmol) in MeCN (400 mL) was added, 4-bromo-2-fluoro-1-nitro-benzene (8.75 g, 39.8 mmol) and Cs$_2$CO$_3$ (23.7 g, 72.9 mmol) and the reaction was heated at 75° C. for 20 h. Water was added and the mixture was extracted three times with EtOAc. The combined organic phases were dried (MgSO$_4$) and concentrated in vacuo to afford the title compound (11.9 g, 100%) which was used in the next step without further purification. $^1$H NMR (400 MHz, CDCl$_3$) δ 8.02 (s, 1H), 7.78 (d, 1H, J 8.7 Hz), 7.41 (m, 5H), 7.13 (d, 1H, J 1.6 Hz), 5.16 (t, 1H, J 7.4 Hz), 2.68 (m, 3H), 2.22 (m, 1H). LCMS (ES$^+$) RT 4.74 min, 361/363 (M+H).

Intermediate 44

Enantiomer 1: (1R or S)-7-bromo-1-phenyl-2,3-dihydro-1H-pyrrolo[1,2-a]benzimidazole

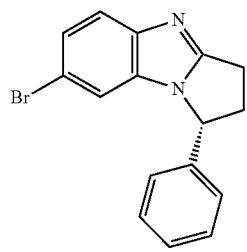 [SMILES: Brc1ccc2nc3n(c2c1)[C@@H](c1ccccc1)CC3]

The title compound was prepared from Intermediate 43 (33.1 mmol) by the -Method B (8.2 g, 84%). LCMS (ES$^+$) RT 4.84 min, 313.0/315.0 (M+H)$^+$.

Intermediate 45

2-[2-(difluoromethoxy)phenyl]thiazolidin-4-one

To a solution of 2-(difluoromethoxy)benzaldehyde (9.87 g, 57.4 mmol) dissolved in toluene (30 mL) were added 2-sulfanylacetic acid (6.87 g, 74.6 mmol) and (NH$_4$)$_2$CO$_3$ (28.66 g, 298.3 mmol). The mixture was stirred at 110° C. for 18 h and concentrated in vacuo. The residue was triturated with EtOAc. The obtained precipitate was filtered to yield the title compound as a white solid (8.07 g, 57%). LCMS (ES$^+$) RT 3.34 min, 246.1 (M+H).

Intermediates 46 and 47

Enantiomer 1: (2R or S)-2-[2-(difluoromethoxy)phenyl]thiazolidin-4-one; enantiomer 2 (2S or R)-2-[2-(difluoromethoxy)phenyl]thiazolidin-4-one The title compounds were isolated by purification of Intermediate 45 under SFC conditions on Chiralpak AD (50*216 mm*mm, flow 360 mL/min, 25° C., CO$_2$+20% EtOH for 1.7 min then 40% EtOH for 3 min, injection of 4.45 mL solution at a concentration of 100 g/L). The first eluting enantiomer (RT 1.7 min) was collected and the fractions were evaporated to yield the compound (arbitrarily attributed as the (2R) enantiomer). The second eluting enantiomer (RT 2.7 min) was collected and the fractions were evaporated to yield the compound (arbitrarily attributed as the (2S) enantiomer).

Intermediate 48

3-(5-bromo-2-nitro-phenyl)-2-[2-(difluoromethoxy)phenyl]thiazolidin-4-one

The title compound was prepared from Intermediate 45 (3.03 g, 12.3 mmol) and 4-bromo-2-fluoro-1-nitro-benzene (5.44 g, 24.7 mmol) by the Method A (3.76 g, 68.0%). LCMS (ES$^+$) RT 4.5 min, 445.0/447.0 (M+H)$^+$.

Intermediate 49

7-bromo-1-[2-(difluoromethoxy)phenyl]-1,3-dihydrothiazolo[3,4-a]benzimidazole

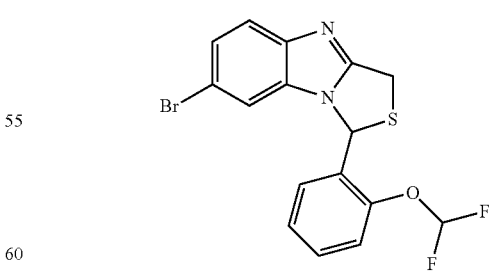

The title compound was prepared from Intermediate 48 (3.01 g, 6.76 mmol) and iron (1.89 g, 33.8 mmol) by the Method B. The residue was used in the next step without any further purification. LCMS (ES$^+$) RT 4.54 min, 397.1/399.1 (M+H)$^+$.

Intermediate 50

5-Ethoxypyrrolidin-2-one

To a solution of succinimide (50 g, 0.50 mol) in EtOH (1.2 L) was added sodium borohydride (48 g, 1.3 mol) at 0° C., and 1M $H_2SO_4$ solution (100 mL) in EtOH was slowly added over a period of 3 h. Then the reaction mixture was cooled to −50° C. and acidified to pH 2 by using 6M solution of $H_2SO_4$. Reaction mixture was stirred at r.t. for 3 h and neutralized by using 2M KOH solution in EtOH. The reaction was concentrated in vacuo. The residue was stirred in chloroform (1.0 L) for 30 min, and filtered through a celite bed. The filtrate was concentrated in-vacuo and the residue was purified by column chromatography ($SiO_2$, 0-2% MeOH/DCM), yielding the title compound as a white solid (25 g, 38%). $^1$H NMR (400 MHz, $CDCl_3$) δ 7.8 (bs, 1H), 4.9 (d, 1H), 3.5-3.6 (m, 1H), 3.3-3.4 (m, 1H), 2.4-2.5 (m, 1H), 2.2-2.3 (m, 2H), 2-2.1 (m, 1H), 1.2 (t, 3H). LCMS ($ES^+$) $(M+H)^+$ 130.

Intermediate 51

[2-(Morpholin-4-yl)pyrimidin-5-yl]boronic acid

A solution of (2-chloropyrimidin-5-yl)boronic acid (1 g, 6.32 mmol), morpholine (2.19 mL, 25.26 mmol) and triethylamine (0.9 mL, 6.32 mmol) in ethanol (25 mL) was stirred at 20° C. for 1 h. Water (50 mL) was slowly added to the reaction mixture to form a precipitate that was collected by filtration, to afford the title compound as a cream solid (950 mg, 70%). δH (250 MHz, DMSO-$d_6$) 8.63 (s, 2H), 8.05 (s, 2H), 3.68 (ddd, J 23.4, 5.7, 3.9 Hz, 8H). LCMS ($ES^+$) 210 $(M+H)^+$.

Intermediate 52

5-(2-methoxyphenyl)pyrrolidin-2-one

Under inert atmosphere, dry magnesium metal (540 mg, 23.25 mmol) was suspended in dry THF (15 mL). At 70° C. 1,2-dibromoethane (0.1 mL) and 2-bromo anisole (2.9 mL, 23.25 mmol) were added in succession. The reaction was stirred at 70° C. for 1 h before cooling to 0° C. A solution of Intermediate 50 (1 g, 7.75 mmol) in THF (10 mL) was added. The reaction mixture was stirred at 70° C. for 5 h, before careful addition of water (10 mL) and AcOH (5 mL). The stirring was continued for 30 min at r.t. and extracted in EtOAc (3×50 mL). The organic layer was dried ($Na_2SO_4$), concentrated in vacuo. The residue was purified by column chromatography ($SiO_2$, 0-2% MeOH/DCM), yielding 5-(2-methoxyphenyl)pyrrolidin-2-one as a white solid (600 mg, 40%). $^1$H NMR (400 MHz, $CDCl_3$) δ 7.30 (m, 2H), 7.00-6.90 (m, 2H), 5.90 (bs, 1H), 5.10 (t, 1H), 3.90 (s, 3H), 2.70-2.32 (m, 3H), 2 (m, 1H).

Intermediate 53

1-(5-bromo-4-fluoro-2-nitrophenyl)-5-(2-methoxyphenyl)pyrrolidin-2-one

The title compound was prepared in a method similar to Method A. To a solution of Intermediate 52 (600 mg, 3.14 mmol) in DMF (10 mL) was added cesium carbonate (3.06 g, 9.42 mmol), 4-bromo-2,5-difluoro nitrobenzene (747 mg, 3.14 mmol, 1 eq) and heated at 90° C. for 18 h. At r.t., the slurry was poured in ice cold water and extracted with EtOAc (3×70 mL). The organic layer was washed with ice cold water and brine, dried ($Na_2SO_4$), concentrated in vacuo. The residue was purified by column chromatography ($SiO_2$, 0-30% EtOAc/hexanes), yielding 1-(5-bromo-4-fluoro-2-nitrophenyl)-5-(2-methoxyphenyl)pyrrolidin-2-one as a yellow solid (600 g, 46%). $^1$H NMR (400 MHz, $CDCl_3$) δ 7.70 (d, 1H), 7.40-7.22 (m, 3H), 7.00-6.90 (m, 2H), 5.60 (t, 1H), 3.90 (s, 3H), 2.80-2.60 (m, 2H), 2.30-2.20 (m, 2H). LCMS ($ES^+$) 409.0/411.0 $(M+H)^+$.

Intermediate 54

7-bromo-6-fluoro-1-(2-methoxyphenyl)-2,3-dihydro-1H-pyrrolo[1,2-a]benzimidazole

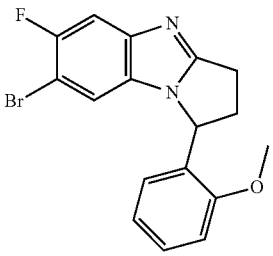 [SMILES: COc1ccccc1C1CCc2nc3cc(F)c(Br)cc3n21]

The title compound was prepared from Intermediate 53 (3 g, 7.3 mmol) and Iron powder (1.3 g, 22 mmol) by the Method B (1.5 g, 57%). $^1$H NMR (400 MHz, $CDCl_3$) δ 7.50 (d, 1H), 7.30 (t, 1H), 7.10 (d, 1H), 6.90 (d, 1H), 6.82 (t, 1H), 6.90 (d, 1H), 5.90 (t, 1H), 3.90 (s, 3H), 3.20-3.00 (m, 3H), 2.60-2.50 (m, 1H). LCMS ($ES^+$) 361.0/363.0 $(M+H)^+$.

Intermediates 55 and 56

Enantiomer 1 (1R or S)-7-bromo-6-fluoro-1-(2-methoxyphenyl)-2,3-dihydro-1H-pyrrolo[1,2-a]benzimidazole; enantiomer 2 (1S or R)-7-bromo-6-fluoro-1-(2-methoxyphenyl)-2,3-dihydro-1H-pyrrolo[1,2-a]benzimidazole

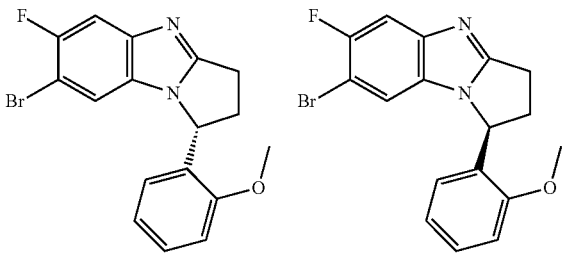 [SMILES: COc1ccccc1[C@H]1CCc2nc3cc(F)c(Br)cc3n21 ; COc1ccccc1[C@@H]1CCc2nc3cc(F)c(Br)cc3n21]

The title compounds were isolated by chiral purification of 2 g of Intermediate 54 under SFC conditions on Chiralpak AD (50*216 mm*mm, flow 360 mL/min, 25° C., CO2+25% MeOH, injection of 25 mL solution at a concentration of 10 g/L). The first eluting enantiomer (RT 3.4 min) was collected and the fractions were evaporated to yield 863 mg of Intermediate 55. The second eluting enantiomer (RT 5.3 min) was collected and the fractions were evaporated to yield 834 mg of Intermediate 56.

Intermediate 57

Ethyl 4-(2-chlorophenyl)-4-hydroxybutanoate

The title compound was prepared by a similar method to Intermediate 1. To a solution of 2-chlorobenzaldehyde (1.5 g, 10.71 mmol) in DCM (12 mL), was added drop wise $TiCl_4$ (11.8 mL, 1M in DCM) and [(1-ethoxycyclopropyl)oxy] (trimethyl)silane (2.6 mL, 12.8 mmol) at −78° C. After stirring at −78° C. for 30 min, the reaction was warmed r.t for 18 h. The reaction was quenched by addition of sat. aq. $NH_4Cl$ (5 mL). The aq. layer was extracted by DCM (2×10 mL) and dried ($Na_2SO_4$), concentrated in vacuo. The residue was purified by column chromatography ($SiO_2$, 0-10% EtOAc/hexanes), yielding the title compound as a yellow oil (1.4 g, 60%). LCMS ($ES^+$) 243.0 $(M+H)^+$.

Intermediate 58

5-bromo-4-fluoro-2-nitroaniline

A solution of 1-bromo-2,5-difluoro-4-nitrobenzene (2 g, 8.43 mmol) in methanolic ammonia (25 mL) was heated at 60° C. in a sealed tube, for 18 h. The reaction was concentrated in vacuo, and the residue purified by column chromatography ($SiO_2$, 0-30% EtOAc/hexanes), yielding the title compound as a yellow solid (1.4 g, 73%). $^1$H NMR (400 MHz, $CDCl_3$) 7.90 (d, 1H), 7.10 (d, 1H), 5.98 (bs, 2H).

Intermediate 59

1-(5-bromo-4-fluoro-2-nitrophenyl)-5-(2-chlorophenyl)pyrrolidin-2-one

In a sealed tube, Intermediate 57 (200 mg, 0.82 mmol), Intermediate 58 (287 mg, 1.23 mmol) and 3 drops of conc. $H_2SO_4$ in toluene were heated at 160° C. for 10 h. The reaction was cooled to r.t and water (10 mL) was added. The aq. layer was extracted with EtOAc (2×10 mL), and the combined organic layer was washed with water, brine, dried ($Na_2SO_4$), concentrated in vacuo. The residue purified by column chromatography ($SiO_2$, 0-40% EtOAc/hexanes), the title compound as a yellow solid (75 mg, 22%). $^1$H NMR (400 MHz, $CDCl_3$) δ 7.78 (d, 1H), 7.60 (d, 1H), 7.40-7.25 (m, 4), 5.78 (m, 1H), 2.80-2.65 (m, 3H), 2.15 (m, 1H). LCMS ($ES^+$) 412.0/414.0 $(M+H)^+$.

Intermediate 60

7-bromo-1-(2-chlorophenyl)-6-fluoro-2,3-dihydro-1H-pyrrolo[1,2-a]benzimidazole

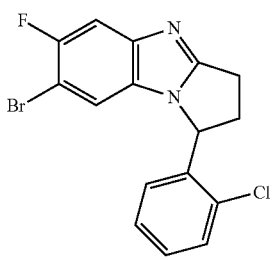 [SMILES: Fc1cc2nc3n(c2cc1Br)C(c1ccccc1Cl)CC3]

The title compound was prepared from Intermediate 59 (500 mg, 1.21 mmol) and Iron powder (203 mg, 3.64 mmol) by the Method B (300 mg, 68%). $^1$H NMR (400 MHz, $CDCl_3$) δ 7.50 (d, 2H), 7.30-7.20 (m, 2H), 7.10 (d, 1H), 6.65 (d, 1H), 5.92 (m, 1H), 3.25-3.15 (m, 3H), 2.56 (m, 1H). LCMS ($ES^+$) 366.0/368.0 $(M+H)^+$.

Intermediates 61 and 62

Enantiomer 1: (1R or S)-7-bromo-1-(2-chlorophenyl)-6-fluoro-2,3-dihydro-1H-pyrrolo[1,2-a]benzimidazole; enantiomer 2 (1S or R)-7-bromo-1-(2-chlorophenyl)-6-fluoro-2,3-dihydro-1H-pyrrolo[1,2-a]benzimidazole

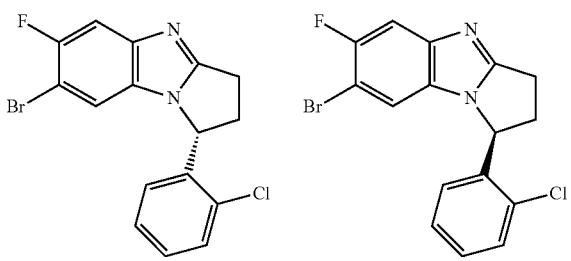 [SMILES: Fc1cc2nc3n(c2cc1Br)[C@@H](c1ccccc1Cl)CC3 ; Fc1cc2nc3n(c2cc1Br)[C@H](c1ccccc1Cl)CC3]

The title compounds were isolated by chiral purification of 478 mg of Intermediate 60 under SFC conditions on Chiralpak IA (50*266 mm*mm, flow 360 mL/min, 25° C., $CO_2$+20% MeOH, injection of 5.33 mL solution at a concentration of 30 g/L). The first eluting enantiomer 1 (RT 6.3 min) was collected and the fractions were evaporated to yield. Intermediate 61. The second eluting enantiomer 2 (RT 8.2 min) was collected and the fractions were evaporated to yield Intermediate 62.

Intermediate 63

5-(4-fluorophenyl)pyrrolidin-2-one

The title compound was prepared by a method similar to the provided procedure for Intermediate 52. To a solution of magnesium metal (1.1 g, 46.5 mmol) in dry THF (20 mL) was added catalytic 1,2-dibromoethane and 4-fluoro bromobenzene (5.1 mL, 46.5 mmol) in THF (5 mL) over a period of 15 min at 60° C. The reaction mixture was refluxed for 1 h. The reaction was cooled to 0° C. and a solution of Intermediate 50 was added drop wise (2 g, 15.5 mmol) in dry THF (10 mL). The reaction mixture was stirred r.t. for 1 h at 0° C. and then refluxed for 5 h. The reaction mixture was cooled and water (4 mL) was added carefully, followed by AcOH (6 mL). The stirring was continued for 30 min at r.t. and extracted in EtOAc (3×50 mL). The organic layer was dried over $Na_2SO_4$, concentrated in vacuo. The residue was purified by column chromatography ($SiO_2$, 0-2% MeOH/DCM), yielding 5-(4-fluorophenyl)pyrrolidin-2-one as a white solid (1.3 g, 47%). $^1$H NMR (400 MHz, $CDCl_3$) δ 7.27 (dd, J 8.7, 4.9 Hz, 2H), 7.05 (t, J 8.5 Hz, 2H), 6.21 (s, 1H), 4.74 (t, J 7.0 Hz, 1H), 2.68-2.33 (m, 3H), 1.94 (dq, J 11.9, 8.1 Hz, 1H). LCMS ($ES^+$) $(M+H)^+$ 180.

Intermediate 64

1-(5-bromo-4-fluoro-2-nitrophenyl)-5-(4-fluorophenyl)pyrrolidin-2-one

The title compound was prepared in a method similar to Method A. To a solution of Intermediate 63 (2.2 g, 12.2 mmol) in dry DMF (15 mL) was added cesium carbonate (9.98 g, 30.7 mmol) and 4-bromo-2,5-difluoro nitrobenzene (3.1 g, 13.5 mmol). The reaction mixture was stirred at r.t. for 18 h. The reaction mixture was treated with the addition of water (30 mL), and extracted with EtOAc (4×20 mL). The organic layer was washed with water and brine, dried (Na2SO4) and concentrated in vacuo. The residue was purified by column chromatography (SiO$_2$, 0-50% EtOAc/hexanes), yielding the title compound as a yellow solid (2.3 g, 47%). $^1$H NMR (400 MHz, CDCl$_3$) δ 7.73 (dd, J=7.6, 2.4 Hz, 1H), 7.35 (ddd, J 8.7, 5.1, 2.4 Hz, 2H), 7.19 (dd, J 6.2, 2.4 Hz, 1H), 7.04 (tt, J 9.7, 2.9 Hz, 2H), 5.17-5.00 (m, 1H), 2.88-2.54 (m, 3H), 2.30-2.10 (m, 1H).

Intermediate 65

7-bromo-6-fluoro-1-(4-fluorophenyl)-2,3-dihydro-1H-pyrrolo[1,2-a]benzimidazole

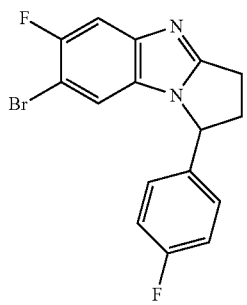 [SMILES: Fc1ccc(C2CCc3nc4cc(F)c(Br)cc4n32)cc1]

The title compound was prepared from Intermediate 64 (2.3 g, 5.8 mmol) and Iron powder (975 mg, 17.4 mmol) by the Method B (1.5 g, 74%). $^1$H NMR (400 MHz, CDCl$_3$) δ 7.47 (d, J 9.2 Hz, 1H), 7.22-7.02 (m, 4H), 6.93 (d, J 6.0 Hz, 1H), 5.40 (t, J 6.8 Hz, 1H), 3.38-3.01 (m, 3H), 2.54 (ddt, J 14.4, 11.7, 5.1 Hz, 1H). LCMS (ES$^+$) 349.0/351.0 (M+H)$^+$.

Intermediates 66 and 67

Enantiomer 1: (1S or R)-7-bromo-6-fluoro-1-(4-fluorophenyl)-2,3-dihydro-1H-pyrrolo[1,2-a]benzimidazole; enantiomer 2 (1R or S)-7-bromo-6-fluoro-1-(4-fluorophenyl)-2,3-dihydro-1H-pyrrolo[1,2-a]benzimidazole

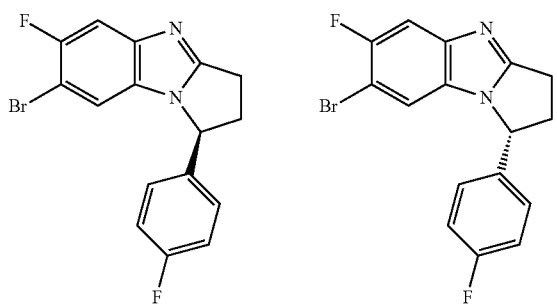 [SMILES: Fc1ccc([C@@H]2CCc3nc4cc(F)c(Br)cc4n32)cc1 ; Fc1ccc([C@H]2CCc3nc4cc(F)c(Br)cc4n32)cc1]

The title compounds were isolated by chiral purification of 2 g of Intermediate 65 under SFC conditions on Chiralpak AD (50*216 mm*mm, flow 360 mL/min, 25° C., CO2+40% EtOH, injection of 10 mL solution at a concentration of 50 g/L). The first eluting enantiomer 1 (RT 1.9 min) was collected and the fractions were evaporated to yield 1.23 g of Intermediate 66. The second eluting enantiomer 2 (RT 3 min) was collected and the fractions were evaporated to yield 1.19 Intermediate 67.

Intermediate 68

1-bromo-2-(methylsulfanyl)benzene

To a solution of NaOH (1.7 g, 42.50 mmol) in EtOH (15 mL) was added 2-bromo thiophenol (5 g, 26.45 mmol). The reaction mixture was stirred at r.t. for 30 min before cooling to 0° C., and methyl iodide (2.4 mL, 39 mmol) was added. The reaction mixture was stirred at r.t. for 10 h. The reaction mixture was treated with iced water, and extracted with DCM (2×20 mL). The organic layer was washed with water and brine, dried (Na$_2$SO$_4$), and concentrated in vacuo. The residue was purified by flash chromatography (SiO$_2$, 0-5% EtOAc/hexanes), yielding the title compound as a yellow oil (4.6 g, 86%). LCMS (ES$^+$) 203.0/205.0 (M+H)$^+$.

Intermediate 69

5-[2-(methylsulfanyl)phenyl]pyrrolidin-2-one

To a solution of magnesium metal (223 mg, 9.30 mmol) in dry THF (10 mL) was added catalytic 1,2-dibromoethane and Intermediate 68 (1.87 g, 9.30 mmol) in THF (5 mL) over a period of 15 min at 60-65° C. The reaction mixture was refluxed for 1 h. The reaction was cooled to 0° C. and a solution of Intermediate 50 was added drop wise (400 mg, 3.10 mmol) in dry THF (5 mL). The reaction mixture was stirred r.t. for 1 h at 0° C. and then refluxed for 5 h. The reaction mixture was cooled and water (1 mL) was added carefully, followed by AcOH (1 mL). The stirring was continued for 30 min at r.t. and extracted in EtOAc (3×50 mL). The organic layer was dried (Na$_2$SO$_4$), concentrated in vacuo. The residue was purified by column chromatography (SiO$_2$, 0-2% MeOH/DCM), yielding the title compound as white solid (300 mg, 46%). $^1$H NMR (400 MHz, CDCl$_3$) δ 7.35-7.20 (m, 4H), 5.95 (bs, 1H), 5.20 (m, 1H), 2.70 (m, 1H), 2.44 (s, 3H), 2.40 (m, 2H), 1.95 (m, 1H). LCMS (ES$^+$) (M+H)$^+$ 208.0.

Intermediate 70

1-(5-bromo-4-fluoro-2-nitrophenyl)-5-[2-(methylsulfanyl)phenyl]pyrrolidin-2-one

The title compound was prepared by a similar variation of Method A. To a solution of Intermediate 69 (300 mg, 1.44 mmol) in dry DMF (6 mL) was added cesium carbonate (1.4 g, 4.32 mmol) and 4-bromo-2,5-difluoro nitrobenzene (376 mg, 1.59 mmol). The reaction mixture was stirred at r.t. for 14 h. The reaction mixture was treated with water (5 mL), and extracted with EtOAc (4×10 mL). The organic layer was washed with water, brine and dried (Na$_2$SO$_4$), concentrated in vacuo. The residue was purified by column chromatography (SiO$_2$, 0-65% EtOAc/hexanes), yielding the title compound as a yellow solid (305 mg, 49%). LCMS (ES$^+$) 425.0/427.0 (M+H)$^+$.

Intermediate 71

7-bromo-6-fluoro-1-[2-(methylsulfanyl)phenyl]-2,3-dihydro-1H-pyrrolo[1,2-a]benzimidazole

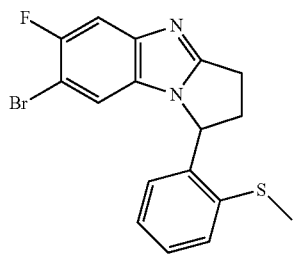 [SMILES: CSc1ccccc1C1CCc2nc3cc(F)c(Br)cc3n21]

The title compound was prepared from Intermediate 70 (300 mg, 0.707 mmol) and Iron powder (118 mg, 2.12 mmol) by the Method B (205 mg, 77%). LCMS (ES$^+$) 377.0/379.0 (M+H)$^+$.

Intermediate 72

7-bromo-6-fluoro-1-[2-(methylsulfonyl)phenyl]-2,3-dihydro-1H-pyrrolo[1,2-a]benzimidazole

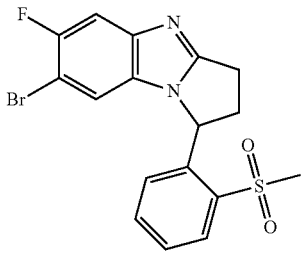 [SMILES: CS(=O)(=O)c1ccccc1C1CCc2nc3cc(F)c(Br)cc3n21]

To a solution of Intermediate 71 (1.9 g, 5.03 mmol) in DCM (25 mL) was added m-CPBA (2.58 g, 15.09 mmol) at 0° C., portion wise. The reaction mixture was stirred at r.t. for 2 h. 5 mL sat. aq. NaHCO$_3$ was added, and the aq. layer was extracted with DCM (2×10 mL). The organic layer was washed with water, brine and dried (Na$_2$SO$_4$), concentrated in vacuo. The residue was purified by flash chromatography (SiO$_2$, 0-100% EtOAc/hexanes), yielding the title compound as a yellow solid (1.25 g, 60%). $^1$H NMR (400 MHz, CDCl$_3$) δ 8.2 (d, 1H), 7.55-7.60 (m, 3H), 6.82-6.9 (m, 2H), 6.4 (m, 1H), 3.4 (m, 1H), 3.25 (s, 3H), 3.15-3.21 (m, 2H), 2.5 (m, 1H). LCMS (ES$^+$) 409.0/411.0 (M+H)$^+$.

Intermediates 73 and 74

Enantiomer 1: (1S or R)-7-bromo-6-fluoro-1-(2-methylsulfonylphenyl)-2,3-dihydro-1H-pyrrolo[1,2-a]benzimidazole; enantiomer 2 (1R or S)-7-bromo-6-fluoro-1-(2-methylsulfonylphenyl)-2,3-dihydro-1H-pyrrolo[1,2-a]benzimidazole

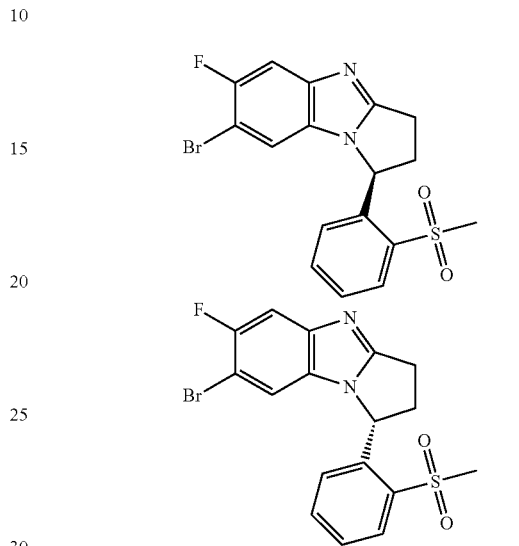

The title compounds were isolated by chiral purification of 2.35 g of Intermediate 72 under LC conditions on Chiralpak AD (100*500 mm*mm, flow 300 mL/min, 30° C., CO2+heptane-i-PrOH (1:1), injection of 972 mL solution at a concentration of 1 g/L). The first eluting enantiomer 1 (RT 25 min) was collected and the fractions were evaporated to yield Intermediate 73. The second eluting enantiomer 2 (RT 47 min) was collected and the fractions were evaporated to yield Intermediate 74.

Intermediate 75

5-[2-(trifluoromethyl)phenyl]pyrrolidin-2-one

The title compound was prepared by a method similar to that previously described for Intermediate 52. To a solution of magnesium metal (2.78 g, 116 mmol) in dry THF (80 mL) was added catalytic 1,2-dibromoethane and 2-bromobenzotrifluoride (26 g, 116 mmol) in THF (10 mL) over a period of 20 min at 60-65° C. The reaction mixture was refluxed for 1 h. The reaction was cooled to 0° C. and a solution of Intermediate 50 was added drop wise (5 g, 38.7 mmol) in dry THF (10 mL). The reaction mixture was stirred r.t. for 1 h at 0° C. and then refluxed for 5 h. The reaction mixture was cooled and water (10 mL) was added carefully, followed by AcOH (20 mL). The stirring was continued for 30 min at r.t. and extracted in EtOAc (3×50 mL). The organic layer was dried (Na$_2$SO$_4$), concentrated in vacuo. The residue was purified by column chromatography (SiO$_2$, 0-2% MeOH/DCM), yielding the title compound as a yellow solid (1.1 g, 13%). $^1$H NMR (400 MHz, CDCl$_3$) δ 7.70-7.60 (m, 3H), 7.42 (m, 1H), 5.94 (bs, 1H), 5.18 (m, 1H), 2.70-2.40 (m, 3H), 1.95 (m, 1H). LCMS (ES$^+$) 230.0 (M+H)$^+$.

Intermediate 76

1-(5-bromo-4-fluoro-2-nitrophenyl)-5-[2-(trifluoromethyl)phenyl]pyrrolidin-2-one The title compound was prepared by a similar variation of Method A. To a solution of Intermediate 75 (2.7 g, 11.7 mmol) in dry DMF (30 mL) was added cesium carbonate (9.57 g, 29.4 mmol) and 4-bromo-2,5-difluoro nitrobenzene (3 g, 12.9 mmol). The reaction mixture was stirred at r.t. for 18 h. The reaction mixture was treated with the addition of water (5 mL), and extracted with EtOAc (4×10 mL). The organic layer was washed with water and brine, dried ($Na_2SO_4$), and concentrated in vacuo. The residue was purified by column chromatography ($SiO_2$, 0-50% EtOAc/hexanes), yielding the title compound as a yellow solid (2.5 g, 47%). LCMS ($ES^+$) 447.0/449.0 $(M+H)^+$.

Intermediate 77

7-bromo-6-fluoro-1-[2-(trifluoromethyl)phenyl]-2,3-dihydro-1H-pyrrolo[1,2-a]benzimidazole

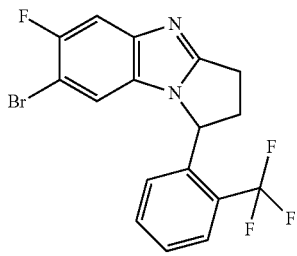 [SMILES: Fc1cc2nc3n(c2cc1Br)C(c1ccccc1C(F)(F)F)CC3]

The title compound was prepared from Intermediate 76 (2.5 g, 5.6 mmol) and iron powder (941 mg, 16.8 mmol) by the Method B (2 g, 89%). $^1$H NMR (400 MHz, $CDCl_3$) δ 7.80 (m, 1H), 7.50 (m, 3H), 6.90 (d, 1H), 6.80 (m, 1H), 5.88 (m, 1H), 3.30-3.15 (m, 3H), 2.50 (m, 1H). LCMS ($ES^+$) 399.0/401.0 $(M+H)^+$.

Intermediates 78 and 79

Enantiomer 1: (1R or S)-7-bromo-6-fluoro-1-[2-(trifluoromethyl)phenyl]-2,3-dihydro-1H-pyrrolo[1,2-a]benzimidazole; enantiomer 2 (1S or R)-7-bromo-6-fluoro-1-[2-(trifluoromethyl)phenyl]-2,3-dihydro-1H-pyrrolo[1,2-a]benzimidazole

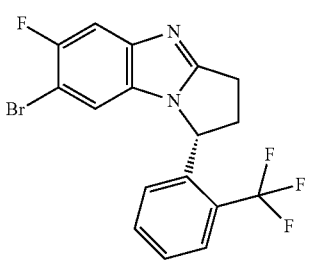

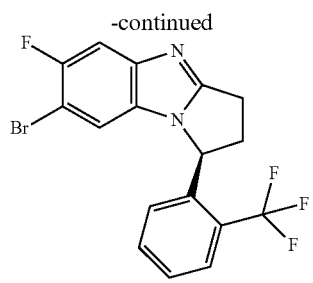

The title compounds were isolated by chiral purification of 1.95 g of Intermediate 77 under LC conditions on Chiralpak AD (100*500 mm*mm, flow 300 mL/min, 30° C., $CO_2$+MeOH 100%, injection of 12.5 mL solution at a concentration of 65 g/L). The first eluting enantiomer 1 (RT 12 min) was collected and the fractions were evaporated to yield 880 mg of Intermediate 78. The second eluting enantiomer 2 (RT 21 min) was collected and the fractions were evaporated to yield 880 mg of Intermediate 79.

Intermediate 80

7-bromo-1-(o-tolyl)-2,3-dihydro-1H-pyrrolo[1,2-a]benzimidazole

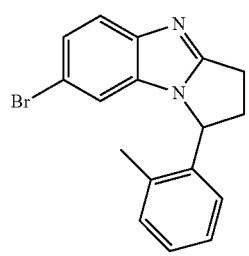 [SMILES: Cc1ccccc1C1CCc2nc3ccc(Br)cc3n21]

The title compound was prepared from Intermediate 18 (0.33 g, 0.88 mmol) and iron powder (0.24 g, 4.4 mmol) by the Method B, (0.20 g, 69%). $^1$H NMR (400 MHz, $CDCl_3$) δ 7.60 (d, 1H), 7.30-7.25 (m, 3H), 7.10 (m, 1H), 7.00 (s, 1H), 6.80 (d, 1H), 5.70 (m, 1H), 3.15-3.05 (m, 3H), 2.50 (m, 1H), 2.45 (s, 3H). LCMS ($ES^+$) 327.0/329.0 $(M+H)^+$.

Intermediate 81 methyl 5-(2,5-dimethylphenyl)-5-oxo-pentanoate

To a solution of p-xylene (21 mL, 170 mmol) and methyl 5-chloro-5-oxo-pentanoate (23.5 mL, 170 mmol), aluminium chloride (24.9 g, 187 mmol) was added slowly portion wise. The reaction was exothermic. After 1 h, p-xylene (40 mL) was added to avoid solidification of the reaction mixture. The reaction was stirred at r.t. for 2 h. DCM (200 mL) was added and the resulting solution was poured on ice and sat. aq. $Na_2CO_3$. The aluminium salts were filtered and the filtrate was decanted. The aq. layer was extracted with DCM, the organics were washed with 0.1 M NaOH, dried ($MgSO_4$) and concentrated in vacuo. The residue (27.8 g, 70%) was used without any purification. $^1$H NMR (400 MHz, $CDCl_3$) δ 7.43 (m, 1H), 7.21 (m, 1H), 7.07 (m, 1H), 3.67 (m, 3H), 2.95 (m, 2H), 2.46 (m, 5H), 2.39 (m, 3H), 2.06 (m, 2H). GC-MS(CI) MH+ 235.18.

Intermediate 82 methyl (5Z)-5-(2,5-dimethylphenyl)-5-hydroxy-imino-pentanoate

To a solution of Intermediate 81 (1.50 g, 6.40 mmol) in pyridine (5 mL), hydroxylamine hydrochloride (0.89 g, 12.8 mmol) was added. The reaction mixture was heated to 60° C. for 20 h in a sealed tube. The reaction mixture was cooled and concentrated in vacuo. The residue was diluted with EtOH (2×10 mL) and concentrated in vacuo, yielding the title compound in quantitative yield (2.0 g). $^1$H NMR (400 MHz, CDCl$_3$) δ 8.42 (m, 1H), 6.96 (m, 2H), 3.66 (m, 3H), 2.73 (m, 1H), 2.48 (m, 1H), 2.38 (m, 2H), 2.30 (m, 3H), 2.21 (m, 3H), 1.84 (m, 2H). LC-MS: MH+ 250.3.

Intermediate 83

6-(2,5-dimethylphenyl)piperidin-2-one

Intermediate 82 (2.0 g, 8.02 mmol) was dissolved in EtOH (50 mL) and placed in an autoclave. Ni Raney (1.0 g) was added to the mixture. The autoclave was charged with hydrogen (10 bar) and heated at 60° C. for 48 h. The reaction mixture was filtered over celite and concentrated in vacuo. DCM was added, the organic layer was washed with water, dried (MgSO$_4$) and concentrated in vacuo. The residue was purified by prep HPLC, yielding 0.25 g of the title compound (19% for the 2 steps) $^1$H NMR (400 MHz, CDCl$_3$) δ 7.16 (m, 1H), 7.00 (m, 2H), 6.04 (m, 1H), 4.75 (m, 1H), 2.47 (m, 2H), 2.27 (m, 6H), 2.09 (m, 1H), 1.94 (m, 1H), 1.79 (m, 1H), 1.59 (m, 1H). LC-MS MH+ 204.2.

Intermediate 84

1-(5-bromo-2-nitro-phenyl)-6-(2,5-dimethylphenyl)piperidin-2-one

The title compound was prepared from Intermediate 83 (0.25 gr, 1.2 mmol) and 4-bromo-2-fluoro-1-nitro-benzene (0.54 g, 2.5 mmol) by the Method A. LCMS (ES$^+$) 403.2/405.2 (M+H)$^+$.

Intermediate 85

2-(2-(difluoromethoxy)phenyl)oxirane

A mixture of 2-(difluoromethoxy)benzaldehyde (110 g, 639 mmol), tetrabutylammonium iodide (2.360 g, 6.39 mmol) and trimethylsulfonium iodide (156 g, 767 mmol) in DCM (900 ml) and aq. NaOH (50%, 600 ml) was vigorously stirred for 6 days. The reaction mixture was diluted with DCM and water and the layers were separated. The water layer was extracted three times with DCM. The organic layers were combined and washed with water and concentrated in vacuo. The residue was diluted with diethylether, washed with aq. Na$_2$S$_2$O$_3$ (1 M, ×2), water (×2) and brine, and dried (Na$_2$SO$_4$) to give the title compound as a yellow oil (135.8 g, 96%). $^1$H NMR (300 MHz, CDCl$_3$-d) δ 7.31 (ddd, J 8.0, 6.4, 2.8 Hz, 1H), 7.27-7.17 (m, 2H), 7.13 (d, J 8.0 Hz, 1H), 6.56 (t, J 73.8 Hz, 1H), 4.18 (dd, J 4.1, 2.6 Hz, 1H), 3.17 (dd, J 5.6, 4.2 Hz, 1H), 2.72 (dd, J 5.7, 2.6 Hz, 1H).

Intermediate 86 tert-butyl (1-(2-(difluoromethoxy)phenyl)-2-hydroxyethyl)carbamate

Sodium azide (13.97 g, 215 mmol) and NH$_4$Cl (11.49 g, 215 mmol) were added to a solution of Intermediate 85 (40 g, 215 mmol) in a mixture of water (80 ml) and MeOH (320 ml). The flask was sealed and the reaction mixture stirred at 50° C. for 18 h. After cooling to r.t. the reaction mixture was flushed with argon and palladium (10 wt % on activated charcoal, 2.287 g, 2.149 mmol) was added. The resulting mixture was stirred under hydrogen atmosphere for 5 hours, purged with argon, filtered over kieselguhr, and rinsed with methanol. To the filtrate, di-tert-butyl dicarbonate (46.9 g, 215 mmol) was added and the mixture was stirred overnight. The mixture was diluted with water and the MeOH was evaporated in vacuo. The formed precipitate was filtered, washed successively with water, taken up in EtOAc, dried (Na$_2$SO$_4$), and concentrated in vacuo. The residue was triturated with diethylether to give the title compound as a white solid. (27.2 g, 40%). $^1$H NMR (300 MHz, DMSO-d$_6$) δ 7.47-7.39 (m, 1H), 7.34-7.20 (m, 3H), 7.19 (t, J 74.0 Hz, 1 Hz), 7.12 (dd, J 7.9, 1.3 Hz, 1H), 4.99-4.80 (m, 2H), 3.53-3.34 (m, 2H), 1.45-1.10 (m, 9H). LCMS (ES$^+$) RT1.962 min, 248 [M-tBuOCO+H]$^+$.

Intermediate 87

2-amino-2-(2-(difluoromethoxy)phenyl)ethanol hydrochloride

Intermediate 86 (84.7 g, 279 mmol) was dissolved in 1,4-dioxane (extra dry, 500 ml) and hydrochloric acid in 1,4-dioxane (4 M, 880 mmol, 220 ml) was added. The mixture was stirred overnight. The formed precipitate was filtered, washed with DCM, and dried in vacuo to give the title compound as a white solid (55.8 g, 79%). $^1$H NMR (300 MHz, DMSO-d$_6$) δ 8.67 (s, 3H), 7.73 (dd, J 7.7, 1.4 Hz, 1H), 7.47 (td, J 8.1, 1.6 Hz, 1H), 7.39-7.22 (m, 2H), 7.29 (t, J 73.6 Hz, 1H), 5.59 (t, J 5.2 Hz, 1H), 4.51 (t, J 6.0 Hz, 1H), 3.78-3.62 (m, 2H). LCMS (ES$^+$): RT 2.33 min, 204 [M-Cl]$^+$.

Intermediate 88

(R)-5-(2-difluoromethoxy-phenyl)-morpholin-3-one

To a suspension of sodium hydride (6.67 g, 167 mmol, 60% dispersion in mineral oil, 4.0 eq.) in THF (200 mL) was added Intermediate 87 (10 g, 41.72 mmol, 10 g) and ethyl chloroacetate (1.2 eq., 50.07 mmol, 6.14 g). The reaction mixture was heated at 75° C. for 14 h and then cooled to r.t. The reaction mixture was taken up in Et$_2$O, washed three times with water and brine, then dried (MgSO$_4$) and concentrated in vacuo. The residue was washed with iso-Hexane, to give the title compound as a yellow solid (8.4 g) used in the next step without any further purification. $^1$H NMR (400 MHz, CDCl$_3$) δ: 7.41 (d, J 7.7 Hz, 1H), 7.29 (m, 1H), 7.21 (m, 1H), 7.06 (m, 1H), 6.51 (m, 1H), 5.05 (m, 1H), 4.02 (m, 1H), 3.67 (m, 1H), 3.59 (dd, J 11.8 Hz, J 6.3 Hz, 1H), 3.40 (q, J 7.0 Hz, 1H). LCMS (ES$^+$) 244.0 (M+H)$^+$.

Intermediate 89

4-(5-bromo-4-fluoro-2-nitro-phenyl)-5-(2-difluoromethoxy-phenyl)-morpholin-3-one The title compound was prepared by Intermediate 88 (10.14 g, 41.69 mmol), DMF (35 mL), sodium hydride (1.2 eq., 50.0 mmol, 2.00 g, 60% dispersion in mineral oil) and 4-bromo-2,5-difluoronitrobenzene (1.0 eq, 41.69 mmol, 9.92 g) by the Method A (5.62 g, 29%). $^1$H NMR (400 MHz, CDCl₃) δ: 7.67 (m, 1H), 7.30 (m, 3H), 7.00 (m, 2H), 6.35 (m, 1H), 4.37 (m, 4H), 3.96 (m, 1H). LCMS (ES⁺) 461/463 (M+H)⁺.

Intermediate 90

6-(2-(difluoromethoxy)phenyl)piperazin-2-one

To a solution of Intermediate 26 (7.3 g, 36.13 mmol, 1 eq.) in MeCN (30 mL), K₂CO₃ (4.98 g, 36.13 mmol, 1 eq.) and ethyl chloroacetate (4.40 g, 36.13 mmol, 1 eq.) were added at 0° C. The reaction mixture was stirred at r.t. for 18 h. Water was added and the reaction mixture extracted with EtOAc. The organic layer was washed with water and brine, dried (Na₂SO₄) and concentrated in vacuo. The residue was purified by column chromatography (SiO₂, 0-4% MeOH/DCM), yielding the title compound as a white solid (3.2 mg, 36%). ¹H NMR (400 MHz, CDCl₃) δ 7.42 (d, J 6.8 Hz, 1H), 7.35-7.23 (m, 2H), 7.10 (d, J 8 Hz, 1H), 6.75-6.38 (t, 1H), 5.01 (m, 1H), 3.56 (s, 2H), 3.30 (d, J 17.6 Hz, 1H), 2.86 (d, J 19.6 Hz, 1H). LCMS (ES⁺) RT 1.29 min, 243.1 (M+H)⁺.

Intermediate 91 tert-butyl 3-(2-(difluoromethoxy)phenyl)-5-oxopiperazine-1-carboxylate

To a solution of Intermediate 90 (3.2 g, 13.22 mmol, 1 eq.) in dry DCM (25 mL), triethylamine (1.6 g, 15.86 mmol, 1.2 eq.) and di-tertbutyl dicarbonate (3.45 g, 15.86 mmol, 1.2 eq.) was added at 0° C. The reaction mixture was stirred at r.t. for 6 h. Water was added and the mixture was extracted with DCM. The organic layer was washed with water and brine, dried (Na₂SO₄) and concentrated in vacuo. The residue was purified by column chromatography (SiO₂, 0-2% MeOH/DCM), yielding the title compound as a white solid (3.2 mg, 71%). ¹H NMR (400 MHz, DMSO-d₆) δ 8.36 (bs, 1H), 7.38 (m, 2H), 7.24 (d, J 6.8 Hz, 1H), 7.17 (d, J 6.8 Hz, 1H), 4.78 (m, 1H), 4.42 (d, J 17.6 Hz, 1H), 3.84 (d, J 12.4 Hz, 1H), 3.77 (d, J 18 Hz, 1H), 3.63 (d, J 11.2 Hz, 1H), 1.10-1.29 (s, 9H). LCMS (ES⁺) RT 2.19 min, 287.1 (M+H-ᵗBu)⁺.

Intermediate 92 tert-butyl 4-(5-bromo-4-fluoro-2-nitrophenyl)-3-(2-(difluoromethoxy) phenyl)-5-oxopiperazine-1-carboxylate The title compound was prepared by a variation of Method A. To a solution of Intermediate 91 (5 g, 14.61 mmol, 1 eq.) in dry MeCN (25 mL), K₂CO₃ (6.05 g, 43.5 mmol, 3 eq.) and 4-bromo-2,5-difluoro nitrobenzene (3.4 g, 14.61 mmol, 1 eq.) was added. The mixture was heated at 90° C. for 20 h in a sealed tube. The reaction mixture was cooled, water was added and the mixture was extracted with DCM. The organic layer was washed with water and brine, dried (Na₂SO₄) and concentrated in vacuo. The residue was purified by column chromatography (SiO₂, 0-30% EtOAc/hexanes), yielding the title compound as a yellow solid (1.5 g, 18%). ¹H NMR (400 MHz, DMSO-d₆) δ 8.30 (s, 1H), 7.66 (d, J 6.8 Hz, 1H), 7.27-7.45 (m, 5H), 5.14 (m, 1H), 4.56 (d, J 16.4 Hz, 1H), 4.03 (d, J 15.2 Hz, 2H), 3.18 (d, J 16 Hz, 1H), 1.08-1.34 (s, 9H).

Intermediate 93 tert-butyl 4-(5-bromo-2-nitrophenyl)-3-(2-(difluoromethoxy)phenyl)-5-oxopiperazine-1-carboxylate The title compound was prepared by a variation of Method A. To a solution of Intermediate 91 (2.92 mmol, 1 eq.) in dry MeCN (15 mL) were added K₂CO₃ (1.2 g, 8.76 mmol, 3 eq.) and 4-bromo-2-fluoro nitrobenzene (511 mg, 3.21 mmol, 1.1 eq.). The mixture was heated at 90° C. in a sealed tube. After 26 h, the reaction mixture was cooled to r.t., water was added and extracted with EtOAc, dried (Na₂SO₄) and concentrated in vacuo. The residue was purified by column chromatography (SiO₂, 0-30% EtOAc/hexanes), yielding the title compound as a yellow solid (225 mg, 15%). ¹H NMR (400 MHz, DMSO-d₆) δ 8.05 (d, J 8.4 Hz, 1H), 7.93 (s, 1H), 7.27-7.63 (m, 6H), 5.43 (m, 1H), 4.29-4.38 (m, 3H), 4.03 (d, J 6.8 Hz, 1H), 1.07-1.23 (s, 9H).

Intermediate 94

2-[2-(difluoromethoxy)phenyl]-2-morpholino-acetonitrile 2-(difluoromethoxy)benzaldehyde (44 g, 255.6 mmol) was added drop wise (temperature kept below 25° C.) to cold (0° C.) morpholine (200 g, 2.3 moles). KCN (20 g, 307.1 mmol, 1.2 eq.) dissolved in 25 mL of water was added and the reaction mixture was stirred for 2.5 h at 80° C. After cooling, the solidified reaction mixture was dissolved in EtOAc (250 mL) and the organic phase was washed with water (250 mL). The aq. layers were extracted 3× with 150 mL of EtOAc. The combined organic layers were washed with water (2×), brine (1×), dried (MgSO₄) and concentrated in vacuo to give the title compound as a pale yellowish oil (65 g) that was used in the next step without any further purification. ¹H NMR (400 MHz, DMSO-d₆) δ: 7.60 (dd, J 7.6 Hz, J 1.0 Hz, 1H), 7.45 (m, 1H), 7.29 (m, 2H), 6.50 (dd, J 79.0 Hz, J 70.2 Hz, 1H), 3.68 (m, 5H), 2.62 (m, 4H).

Intermediate 95

2-[2-(difluoromethoxy)phenyl]-2-morpholino-pentanedinitrile

A methanolic KOH solution (30%, 3 mL) was added to a stirred solution of Intermediate 94 (67 g, 249.7 mmol) in 500 mL of THF. Acrylonitrile (20 g, 373.2 mmol, 1.5 eq.) was then added to the mixture and the resulting solution was stirred at r.t. for 3 h. The mixture was concentrated in vacuo, water was added (50 mL) and the mixture was extracted with EtOAc. The extract was washed with water (150 mL), dried (MgSO₄) and concentrated in vacuo to give the title compound as an orange oil (61 g) used in the next step without any further purification. ¹H NMR (CDCl₃) δ: 7.68 (dd, J 7.7 Hz, J 1.1 Hz, 1 H), 7.47 (td, J 7.9 Hz, J 1.4 Hz, 1H), 7.30 (m, 2H), 6.54 (dd, J 76.0 Hz, J 71.3 Hz, 1H), 3.74 (t, J 4.5 Hz, 4H), 2.80 (ddd, J 13.7 Hz, J 10.5 Hz, J 6.1 Hz, 1H), 2.71 (m, 2H), 2.55 (ddd, J 13.8 Hz, J 10.2 Hz, J 5.3 Hz, 1H), 2.47 (m, 2H), 2.27 (ddd, J 17.0 Hz, J 10.3 Hz, J 5.3 Hz, 1H), 2.05 (ddd, J 17.1 Hz, J 10.3 Hz, J 6.0 Hz, 1H).

Intermediate 96

4-[2-(difluoromethoxy)phenyl]-4-oxo-butanenitrile

Intermediate 95 (82 g, 255 mmol) was dissolved in a mixture of AcOH (300 mL), water (150 mL) and THF (600

Intermediate 97

5-[2-(difluoromethoxy)phenyl]-3,4-dihydro-2H-pyrrole

Intermediate 96 (20 g, 88.8 mmol) was dissolved in 200 mL of EtOH. 12 g of Ni Raney (washed 1× with EtOH) was added and the resulting mixture was hydrogenated at 1 bar at r.t. for 5.5 h. The mixture was degassed with Argon and filtered on a bed of celite. The greenish filtrates were then concentrated in vacuo to yield the title compound as a light green oil (18.5 g, 98%) used without further purification in the next step. $^1$H NMR (400 MHz, DMSO-$d_6$) δ: 7.82 (m, 1H), 7.40 (m, 1H), 7.20 (m, 2H), 6.55 (m, 1H), 4.00 (m, 2H), 2.98 (m, 2H), 2.02 (m, 2H). LCMS (ES$^+$) RT 2.3 min, 212.0 (M+H)$^+$.

Intermediate 98

2-[2-(difluoromethoxy)phenyl]pyrrolidine

Sodium borohydride (3.71 g, 97.1 mmol, 1 eq.) was added portion wise to a solution of Intermediate 97 (20.5 g, 97.1 mmol) in 200 mL of MeOH. After 1 h of reaction, an additional portion of sodium borohydride (1.85 g, 0.5 eq., 48 mmol) was added and the resulting reaction mixture was stirred at r.t. for 5 h. Water was added to the reaction mixture, and extracted with EtOAc (3×). The combined organics were washed with water (1×), then with brine (1×), dried (MgSO$_4$), concentrated in vacuo to yield the title compound as a light orange oil used in the next step without any further purification (19.4 g). LCMS (ES$^+$) RT 2.5 min, 214.0 (M+H)$^+$.

Intermediate 99

1-(5-bromo-4-fluoro-2-nitro-phenyl)-2-[2-(difluoromethoxy)phenyl]pyrrolidine Intermediate 98 (19.41 g, 91.0 mmol) was added to a solution of 1-bromo-2,5-difluoro-4-nitro-benzene (21.66 g, 91.0 mmol, 1.0 eq.) in MeCN (180 mL). K$_2$CO$_3$ (15.25 g, 109.2 mmol, 1.2 eq.) was then added and the resulting reaction mixture was stirred at 80° C. for 14 h. The reaction mixture was filtered and the solvent was concentrated in vacuo to yield orange oil. This residue was taken up in EtOAc and washed with water (1×), dried (MgSO$_4$), concentrated in vacuo to yield the title compound as an orange oil (37 g, 94%) that was used in the next step without any further purification. LCMS (ES$^+$) RT 5.7 min, 431.0/433.0 (M+H)$^+$.

Intermediate 100

1-(5-bromo-2-nitro-phenyl)-2-phenyl-pyrrolidine

The title compound was prepared from 2-phenylpyrrolidine and 4-bromo-2-fluoro-1-nitro-benzene following the method described for Intermediate 99. LCMS (ES$^+$) RT 5.68 min, 347.1/349.2 (M+H)$^+$.

Intermediate 101

(S)—N-[[2-(difluoromethoxy)phenyl]methylene]-2-methyl-propane-2-sulfinamide

To a solution of 2-(difluoromethoxy)benzaldehyde (4.7 g, 0.027 mol) in THF (3.44 mL) was added (S)-2-methyl-2-propanesulfinamide (5.62 g, 0.029 mol). Potassium diphosphate dibasic (0.2 eq.) and K$_3$PO$_4$ (0.8 eq.) were added and the reaction mixture was stirred at r.t. for 4 h. DCM was added, the reaction mixture was washed with water, dried (MgSO$_4$) and concentrated in vacuo to afford the title compound as a yellow oil (7 g, 96%) which was used in the next step without purification.

Intermediate 102 ethyl (3R)-3-[[(S)-tert-butylsulfinyl]amino]-3-[2-(difluoromethoxy)phenyl]propanoate Activated zinc powder (356.4 g, 10 eq.) and dry copper chloride (53.95 g, 1 eq.) in THF (1 L) were heated at reflux for 30 min. A solution of ethyl bromoacetate (227.5 g, 2.5 eq.) in THF (250 mL) was added while keeping a slight and constant reflux. After complete addition, the mixture was heated for 1 h at reflux. At 0° C., a solution of Intermediate 101 (150 g, 1 eq.) in THF (200 mL) was added, the reaction mixture was stirred for 1 h and filtered on celite. Water (300 mL) was added, a solid precipitates, and 1M HCl (1 L) was added until complete dissolution of the precipitate. The mixture was decanted by adding NaCl. The organic phase was washed with brine and concentrated in vacuo. The residue was taken up by DCM (1500 mL), washed with sat. aq. NaHCO$_3$, dried (MgSO$_4$) and concentrated in vacuo to yield ethyl 3-(tert-butylsulfinylamino)-3-[2-(difluoromethoxy)phenyl]propanoate (192 g, 97%) which was used in the next step without further purification.

Intermediate 103 ethyl (3R)-3-amino-3-[2-(difluoromethoxy)phenyl]propanoate

To a solution of Intermediate 102 (1.2 g, 3.30 mmol) in Et$_2$O (10 mL), HCl (4 M in 1,4-dioxane, 6.60 mmol) was added and the mixture was stirred at r.t. for 10 min. Water was added to the reaction mixture and extracted with Et$_2$O. The aq. phase was brought to basic pH with Na$_2$CO$_3$, extracted with EtOAc, dried (MgSO$_4$) and concentrated in vacuo to afford the title compound, 0.8 g (90%). LCMS (ES$^+$) 2.83 min, 260 (M+H)$^+$. The absolute configuration of ethyl (3R)-3-amino-3-[2-(difluoromethoxy)phenyl]propanoate confirmed by derivatization with Mosher's reagents (R)-(+)-alpha-methoxy-alpha-trifluoromethylphenylacetic acid & (S)-(−)-alpha-methoxy-alpha-trifluoromethylphenylacetic acid followed by NMR spectroscopy.

--- mL) and stirred at r.t. for 24 h. The mixture was then concentrated in vacuo, the orange residue was taken up in EtOAc (800 mL), washed with a 1 N aq. solution of NaOH until pH 8, washed with water, brine, dried (MgSO$_4$) and concentrated in vacuo to give an orange oil. Purification by chromatography (SiO$_2$, 0-20% EtOAc/heptane), yield the title compound as a pale yellow oil (45 g, 80%). $^1$H NMR (400 MHz, DMSO-$d_6$) δ: 7.83 (dd, J 7.8 Hz, J 1.4 Hz, 1H), 7.57 (m, 1H), 7.32 (m, 1H), 7.20 (d, J 8.2 Hz, 1H), 6.65 (t, J 72.9 Hz, 1H), 3.37 (t, J 7.0 Hz, 2H), 2.75 (t, J 7.0 Hz, 2H).

Intermediate 104

(3R)-3-amino-3-[2-(difluoromethoxy)phenyl]propan-1-ol

LiBH$_4$ (1.9 g, 2.2 equiv.) was suspended in THF (150 mL) and the mixture was heated at 55-60° C. A solution of Intermediate 103 (10.28 g, 1 eq.) in THF (40 mL) was added drop wise. The reaction mixture was stirred at 65° C. for 1.5 h, an additional amount of LiBH$_4$ (2 eq) was added and heating was continued for 3 h. The reaction mixture was then cooled to 0° C. and HCl 5N was added until pH 4. The mixture was washed with DCM and the aq. phase was brought to basic pH with 50% NaOH at 0° C., extracted with a (8.5:1.5) mixture of DCM:MeOH, dried (MgSO$_4$) and concentrated in vacuo. The residue was purified by UV directed preparative reverse chromatography, yielding the title compound, (1.79 g, 21%). LCMS (ES$^+$) 3.34 min 218 (M+H)$^+$.

Intermediate 105

(3R)-3-(5-bromo-4-fluoro-2-nitro-anilino)-3-[2-(difluoromethoxy)phenyl]propan-1-ol To a solution of 1-bromo-2,5-difluoro-4-nitro-benzene (10.41 g.), Intermediate 104 (1 eq.) in MeCN (200 mL), was added and K$_2$CO$_3$ (2 eq.). The reaction mixture was stirred at 70° C. for 16 h. The reaction mixture was concentrated in vacuo, and the residue was dissolved in (1:1) mixture of EtOAc/water and brought to neutral pH with 1N HCl. The organic phase was dried over (MgSO$_4$) and concentrated in vacuo. The residue was purified by column chromatography (SiO$_2$, 100% DCM) yielding the title compound (11.6 g, 61%).

Intermediate 106

(3R)-3-(5-bromo-4-fluoro-2-nitro-anilino)-3-[2-(difluoromethoxy)phenyl]propanal

Intermediate 105 (8.865 g, 1.0 eq.) was dissolved in DCM (400 mL). TEMPO (0.01 eq.) was added, and the mixture was cooled to 0° C. and a solution of KBr (0.1 eq.) in 1 mL of water was added, followed by a solution of NaHCO$_3$ (0.4 eq.) in 8 mL of water. NaOCl (2 eq.) was added drop wise to the reaction mixture. 0.1N NaOH was added, the mixture was extracted twice by DCM, the combined organic phases were washed with 0.1N HCl, and brine, dried over (MgSO$_4$) and concentrated in vacuo to afford the title compound (8.57 g, 97%).

Intermediate 107

(4R)-4-(5-bromo-4-fluoro-2-nitro-anilino)-4-[2-(difluoromethoxy)phenyl]-2-trimethylsilyloxy-butanenitrile Intermediate 106 (35.92 g, 1.0 eq.) and triethylamine (0.1 eq.) are dissolved in DCM (500 mL). Trimethylsilylcyanide (1.2 eq.) was added and the reaction mixture was stirred at rt for 6 h. Water was added, the mixture was extracted twice with DCM, the organic phases are washed with brine, dried (MgSO$_4$) and concentrated in vacuo to afford the title compound as an oil (40.05 g, 91%).

Intermediate 108

Disteroisomer 1: (1R,3S or R)-7-bromo-1-[2-(difluoromethoxy)phenyl]-6-fluoro-2,3-dihydro-1H-pyrrolo[1,2-a]benzimidazol-3-ol

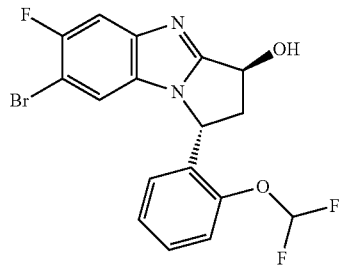 [SMILES: O[C@H]1C[C@H](c2ccccc2OC(F)F)n2c1nc1cc(F)c(Br)cc12]

Intermediate 107 (40.5 g, 1.0 eq.) and iron powder (3 eq.) are dissolved AcOH (70 mL) and the reaction mixture was stirred at 100° C. for 1 h. At r.t., water was added, the mixture was extracted with DCM, the combined organic phases were washed with sat. aq. NaHCO$_3$, dried (MgSO$_4$) and concentrated in vacuo. The residue was purified by chiral chromatography using SFC conditions on Lux-Cell-4 (50*261 mm*mm, flow 360 mL/min, 25° C., CO$_2$+20% MeOH, injection of 3.66 mL solution at a concentration of 30 g/L). The first eluting diastereomer (RT 5.15 min) was collected and the fractions were evaporated to yield the 1R,3R or S diastereisomer (550 mg, 64.4%). The second eluting diastereomer (RT 7.95 min) was collected and the fractions were evaporated to yield the title compound (90 mg, 10.5%). LCMS (ES$^+$) RT 4.49 min, 413.0/415.0 (M+H)$^+$.

Intermediate 109

7-bromo-1-[2-(difluoromethoxy)phenyl]-6-fluoro-3-methyl-1,2-dihydroimidazo[1,2-a]benzimidazole

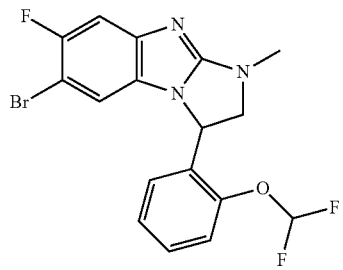 [SMILES: CN1CC(c2ccccc2OC(F)F)n2c1nc1cc(F)c(Br)cc12]

Intermediate 31 (13 mg, 0.033 mmol) was solubilized in 500 μL of DMF. At 0° C., sodium hydride (4 mg, 0.100 mmol, 60 mass %) was added. The reaction was continued for 2 h before addition of iodomethane (10 μL, 0.161 mmol). The reaction was continued at r.t. for 2 h before addition of water (2 mL) and EtOAc (2 mL). The organic layer was washed with brine (2 mL), dried over MgSO$_4$ and concentrated in vacuo. The residue was purified by chromatography (SiO$_2$, 50-100% EtOAc in Heptane) yielding the title compound (6 mg, 44%). LCMS (ES$^+$) RT 4.96 min, 412.0/414.0 (M+H)$^+$.

Intermediate 110

(1R)-7-bromo-1-[2-(difluoromethoxy)phenyl]-8-fluoro-2,3-dihydro-1H-pyrrolo[1,2-a]benzimidazol-3-ol

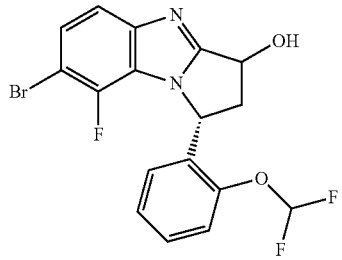 [SMILES: OC1C[C@H](c2ccccc2OC(F)F)n2c1nc1ccc(Br)c(F)c12]

To Intermediate 103 (5 g, 16.8 mmol) in dry MeCN (40 mL) was added K₂CO₃ (6.9 g, 50 mmol) and 4-bromo-2,3-difluoro nitrobenzene (4.8 g, 20.2 mmol). The reaction mixture was stirred at 80° C. for 18 h. The reaction mixture was diluted with water (100 mL) and extracted with EtOAc (2×150 mL). The combined organic layer was washed with water (300 mL), brine (250 mL), dried over Na₂SO₄ and concentrated in vacuo. The residue was purified by chromatography (SiO₂, 10% EtOAc in Heptane) yielding a yellow solid (6.2 g, 77%).

To a solution of the intermediate (6.2 g, 13.02 mmol) in THF (60 mL) at −78° C. was added DIBAL-H (23 mL, 23.5 mmol) drop wise. The reaction mixture was stirred for 2 h at −78° C. After completion of the reaction (monitored by TLC), the reaction mixture was quenched with an aqueous solution of ammonium chloride (200 mL). The reaction mixture was diluted with EtOAc (200 mL) and filtered through celite. The filtrate was washed with water (200 mL) and the organic layer was separated, dried over Na₂SO₄ and concentrated in vacuo to afford 3 g (57% yield) of a yellow oil, which was used in the next step without purification.

To a solution of the previous intermediate (3 g, 6.42 mmol) in DCM (50 mL) was added ZnI₂ (0.2 g, 0.64 mmol), TEA (0.09 mL, 0.64 mmol) and TMSCN (1.6 mL, 12.84 mmol). The reaction mixture was stirred at r.t. for 3 h. After completion of reaction (monitored by TLC), the reaction mixture was diluted with water (100 mL) and the organic layer was separated. The organic layer was washed with water (100 mL), brine (100 mL), dried over Na₂SO₄ and concentrated in vacuo to afford 3.25 g of crude material which was used for the next step without purification.

To a solution of the previous intermediate (3 g, 5.3 mmol) in EtOH (50 mL) was added SnCl₂ (5 g, 26.46 mmol) and the reaction mixture was heated at 80° C. for 2 h. After completion of reaction (monitored by TLC), the reaction mixture was quenched with water (50 mL) and basified to pH-8 using 1N KOH (100 mL). The reaction mixture was diluted with EtOAc (100 mL) and filtered through celite. The organic layer was washed with water (100 mL), brine (100 mL), dried over Na₂SO₄ and concentrated in vacuo. The residue was purified by chromatography (SiO₂, 0-70% EtOAc in hexane) to afford the title compound as a pale brown solid (0.85 g, 36%). LCMS (ES+) RT 2.42 min, 413.0/415.1 (M+H)⁺.

Intermediate 111 and 112

(1R,3R)-7-bromo-1-[2-(difluoromethoxy)phenyl]-3-fluoro-2,3-dihydro-1H-pyrrolo[1,2-a]benzimidazole and (1R,3S)-7-bromo-1-[2-(difluoromethoxy)phenyl]-3-fluoro-2,3-dihydro-1H-pyrrolo[1,2-a]benzimidazole

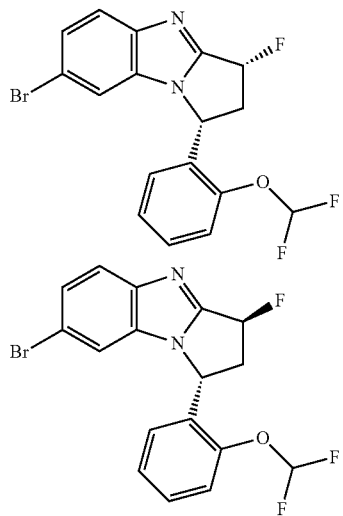

(1R)-7-bromo-1-[2-(difluoromethoxy)phenyl]-2,3-dihydro-1H-pyrrolo[1,2-a]benzimidazol-3-ol was prepared following the procedure described for preparing the intermediate 110 but using 4-bromo-2-fluoro-1-nitro-benzene as reagent in the first step.

To compound (1R)-7-bromo-1-[2-(difluoromethoxy)phenyl]-2,3-dihydro-1H-pyrrolo[1,2-a]benzimidazol-3-ol (100 mg, 0.25 mmol) in DCM (5 mL) was added DAST (0.04 mL, 0.32 mmol) at 0° C. Reaction mixture was stirred for 30 min at the same temperature. After completion of reaction (monitored by TLC), the reaction mixture was quenched with sat. NaHCO₃ solution and extracted with DCM, dried over Na₂SO₄ and concentrated in vacuo. The residue was purified by chromatography (SiO₂, 0-20% EtOAc in hexane) to afford a brown oil (30 mg, 30%). LCMS (ES⁺) 397 (M+H)⁺.

The title intermediate was obtained by chiral purification of the above intermediate by chiral purification under SFC conditions on Chiralpak AD (50*216 mm*mm, flow 360 mL/min, 25° C., CO₂+30% i-PrOH, injection of 11 mL solution at a concentration of 45 g/L). The first eluting diastereoisomer (RT 6.00 min) was collected and the fractions were evaporated to yield the title compound, Intermediate 111 (150 mg, 33%). The second eluting diastereoisomer (RT 9.77 min) was collected and the fractions were evaporated to yield the Intermediate 112 (240 mg, 53%).

Single crystal X-Ray diffraction allowed the determination of the absolute configuration of both chiral centers.

Intermediate 113

4-(5-bromopyrimidin-2-yl)tetrahydropyran-4-ol 5-bromo-2-iodo-pyrimidine (20.02 g, 70.28 mmol) was dissolved in anhydrous toluene (12.5 mL). At −78° C., n-buthyllitium 2.7 mol/L in hexane (28 mL, 76 mmol) was added, followed by a solution of tetrahydro-4H-pyran-4-one (7.39 g, 73.81 mmol) in anhydrous toluene (3.5 mL). The reaction mixture was stirred at −78° C. for 1 h. At 0° C., the reaction mixture was quenched by addition of water (200 mL), extracted by 3×100 mL of EtOAc. Combined organic layers were washed with water (100 mL), a saturated solution of brine (2×100 mL), dried over sodium sulfate and concentrated in vacuo. The residue was purified by chromatography (SiO$_2$, 7-25% EtOAc in heptane) to afford the title compound as a yellow solid (5.2 g, 18%). LCMS basic (ES$^+$) 241.27 (M+H)$^+$.

Intermediate 114

5-bromo-2-(4-fluorotetrahydropyran-4-yl)pyrimidine

Under Argon atmosphere, Intermediate 113 (0.15 g, 0.58 mmol) was dissolved in dichloromethane (10 mL). At 0° C., diethylaminosulfur trifluoride (0.093 g, 0.58 mmol) was added and the mixture was stirred at 0° C. for 30 minutes. The reaction mixture was quenched by addition of water, extracted by DCM (3×20 mL). Combined organic layers were dried over sodium sulfate and concentrated in vacuo. The residue was purified by chromatography (SiO$_2$, 10-20% EtOAc in heptane) to afford the title compound as a white solid (83 mg, 56%). LCMS acid (ES$^+$) 261.00 (M+H)$^+$ Intermediate 115

2-chloro-6-(difluoromethoxy)benzaldehyde

To 2-chloro-6-hydroxy-benzaldehyde (20 g, 128.2 mmol) in MeCN (150 mL) was added an aqueous solution of potassium hydroxide (71.7 g, 1282 mmol) in water (50 mL) at 0° C. and the reaction mixture was stirred at 0° C. for 10 minutes. Diethyl (bromodifluoro methyl) phosphonate (36.4 mL, 205.1 mmol) was added at 0° C. The reaction mixture was stirred at 0° C. for 30 minutes. After completion of reaction (monitored by TLC), the reaction mixture was poured into water (500 mL). The aqueous layer was extracted with ethyl acetate (1 L×2). The organic layer was washed with water (500 mL), brine (500 mL) and dried over anhydrous sodium sulphate. The organic layer was evaporated under reduced pressure to yield the crude product which was purified by column chromatography (SiO$_2$, 5% EtOAc in hexane) yielding the title compound (13.9 g, 53%) as a yellow oil. $^1$H NMR (400 MHz, CDCl$_3$) δ 10.46 (s, 1H), 7.49 (t, J 8.2 Hz, 1H), 7.37 (dd, J 8.1, 1.1 Hz, 1H), 7.20 (m, 1H), 6.61 (t, 1H).

Intermediate 116

N-[[2-chloro-6-(difluoromethoxy)phenyl]methylene]-(S)-2-methyl-propane-2-sulfinamide To a solution of Intermediate 115 (20 g, 97.08 mmol) in dry THF (100 mL) at 0° C. was added (S)-(−)-t-butyl sulfinamide (12.92 g, 106.79 mmol), K$_3$PO$_4$ (61.73 g, 291.2 mmol) and K$_2$HPO$_4$ (50.6 g, 291.2 mmol). Then the reaction mixture was stirred at r.t. for 18 h. After completion of reaction (monitored by TLC), the reaction mixture was filtered through celite and washed with ethyl acetate (1 L). The organic layer was washed with water (500 mL), brine (500 mL) and dried over anhydrous sodium sulphate. The organic layer was evaporated under reduced pressure and the residue was purified chromatography (SiO2, 10% EtOAc in hexane) to afford the title compound (20 g, 87%) as a yellow oil. $^1$H NMR (400 MHz, CDCl$_3$) δ 8.90 (s, 1H), 7.45-7.32 (m, 2H), 7.29-7.15 (m, 1H), 6.82-6.34 (m, 1H), 1.29 (s, 9H). LCMS (ES+) RT 2.73 min, 309.90 (M+H)$^+$ Intermediate 117

Ethyl (3R)-3-[[(S)-tert-butylsulfinyl]amino]-3-[2-chloro-6-(difluoromethoxy)phenyl]propanoate This procedure used activated zinc and THF dried over sodium and benzophenone complex. Activated zinc was prepared using the following procedure: 150 g of zinc powder was taken in 1N HCl (500 mL), stirred for 10 minutes and decanted. The zinc dust powder was further washed with water (3×500 mL) and decanted. The powder was further washed with acetone (3×500 mL), decanted and dried under vacuum to afford 105 g of activated zinc.

To activated zinc dust (105 g, 1618 mmol) in dry THF (150 mL) was added CuCl (19.2 g, 194 mmol) and the reaction mixture was refluxed for 30 minutes. The reaction mixture was cooled to r.t. and ethyl bromoacetate (45 mL, 404 mmol in THF 100 mL) was added drop wise. The reaction mixture was stirred at 50° C. for 30 min. The reaction mixture was cooled to 0° C. and Intermediate 116 (50 g, 161 mmol in THF 100 mL) was added. The reaction mixture was warmed to r.t. and stirred for 3 h. After completion of reaction (monitored by TLC), the reaction mixture was filtered through celite and washed with ethyl acetate (700 mL). The organic layer was washed with 1N citric acid (500 mL), saturated solution of sodium bicarbonate (500 mL), water (500 mL) and brine (500 mL). The organic layer was separated, dried over anhydrous sodium sulphate and evaporated under reduced pressure. The residue was purified by chromatography (SiO$_2$, 40% EtOAc in hexane) to afford the title compound (59 g, 92%) as a yellow oil. $^1$H NMR (400 MHz, CDCl$_3$) δ 7.29-7.21 (m, 2H), 7.05 (d, J 7.3 Hz, 1H), 6.82-6.34 (m, 1H), 5.59 (m, 1H), 4.36 (s, 1H), 4.18-4.02 (m, 2H), 3.25 (dd, J 15.6, 7.5 Hz, 1H), 3.01 (dd, J 15.3, 7.5 Hz, 1H), 1.31-1.11 (m, 12H).

Intermediate 118

Ethyl (3R)-3-amino-3-[2-chloro-6-(difluoromethoxy)phenyl]propanoate hydrochloride To a solution of Intermediate 117 (32 g, 80.6 mmol) in an Ether: EtOH (75 mL, 2:1) mixture was added 4M HCl in 1,4-dioxane (70 mL) and the reaction mixture was stirred at r.t. for 1 h. After completion of reaction (monitored by TLC), the reaction mixture was concentrated under reduced pressure and the residue was washed with diethyl ether (500 mL) to afford the title compound as a yellow solid (22 g, 93%). $^1$H NMR (400 MHz, CDCl$_3$) δ 8.93 (d, J 6.2 Hz, 2H), 7.32-7.10 (m, 3H), 6.96 (s, 1H), 5.42 (m, 1H), 4.08 (q, J 7.0 Hz, 2H), 3.36 (dd, J 16.5, 7.0 Hz, 1H), 3.14 (dd, J 16.5, 7.8 Hz, 1H), 1.34 (t, J 7.1 Hz, 3H).

Intermediate 119

Ethyl (3R)-3-(5-bromo-4-fluoro-2-nitro-anilino)-3-[2-chloro-6-(difluoromethoxy)phenyl]propanoate To a solution of Intermediate 118 (5 g, 17.06 mmol) in MeCN (50 mL) was added potassium carbonate (7.06 g, 51.18 mmol) and 1-bromo-2,5-difluoro-4-nitrobenzene (4.86 g, 20.47 mmol). The reaction mixture was stirred at 80° C. for 16 h. After completion of reaction (monitored by TLC), the reaction mixture was diluted with ethyl acetate (100 mL) and washed with water (100 mL). The organic layer was separated, dried over anhydrous sodium sulphate and concentrated under reduced pressure. The residue was purified by chromatography (SiO$_2$, 20% EtOAc in hexane) to afford the title compound (6 g, 69%) as a yellow viscous liquid.

LCMS (ES+) RT 3.42 min, 510.90/512.90/514.90 (M+H)$^+$

Intermediate 120

(3R)-3-(5-bromo-4-fluoro-2-nitro-anilino)-3-[2-chloro-6-(difluoromethoxy)phenyl]propanal To a solution of Intermediate 119 (6 g, 11.7 mmol) in THF (60 mL) at −78° C. was added DIBAL-H (23 mL, 23.5 mmol) drop wise. The reaction mixture was stirred for 2 h at −78° C. After completion of reaction (monitored by TLC), the reaction mixture was quenched with an aqueous solution of ammonium chloride (200 mL). The reaction mixture was diluted with ethyl acetate (200 mL) and filtered through celite. The filtrate was washed with water (200 mL) and the organic layer was separated, dried over sodium sulphate and evaporated under reduced pressure to afford the title compound (3 g, 57%) as a yellow oil, which was used in the next step without purification.

Intermediate 121

(4R)-4-(5-bromo-4-fluoro-2-nitro-anilino)-4-[2-chloro-6-(difluoromethoxy)phenyl]-2-trimethylsilyloxy-butanenitrile To a solution of Intermediate 120 (3 g, 6.42 mmol) in DCM (50 mL) was added ZnI$_2$ (0.2 g, 0.64 mmol), TEA (0.09 mL, 0.64 mmol) and TMSCN (1.6 mL, 12.84 mmol). The reaction mixture was stirred at r.t. for 3 h. After completion of reaction (monitored by TLC), the reaction mixture was diluted with water (100 mL) and the organic layer was separated. The organic layer was washed with water (100 mL), brine (100 mL), dried over anhydrous sodium sulphate and concentrated under reduced pressure to afford the title compound (3.25 g crude material) which was used for the next step without purification.

Intermediate 122

(1R)-7-bromo-1-[2-chloro-6-(difluoromethoxy)phenyl]-6-fluoro-2,3-dihydro-1H-pyrrolo[1,2-a]benzimidazol-3-ol To a solution of Intermediate 121 (3 g, 5.3 mmol) in EtOH (50 mL) was added SnCl$_2$ (5 g, 26.46 mmol) and the reaction mixture was heated at 80° C. for 2 h. After completion of reaction (monitored by TLC), the reaction mixture was quenched with water (50 mL) and basified to pH-8 using 1N KOH (100 mL). The reaction mixture was diluted with ethyl acetate (100 mL) and filtered through celite. The organic layer was washed with water (100 mL), brine (100 mL), dried over anhydrous sodium sulphate and concentrated under reduced pressure. The residue was purified by chromatography (SiO$_2$, 0-70% EtOAc in hexane) to afford the title compound (1.1 g, 47% yield) as a pale brown solid. $^1$H NMR (400 MHz, CDCl$_3$) δ 7.52 (m, 1H), 7.49-7.30 (m, 2H), 7.04-6.67 (m, 2H), 6.42 (m, 1H), 6.24-5.91 (m, 1H), 5.79-5.52 (m, 1H), 3.71-3.46 (m, 1H), 3.19 (m, 2H). LCMS (ES+) RT 2.39 min, 447.0/449.0/451.0 (M+H)$^+$ Intermediates 123 and 124

(1R,3R)-7-bromo-1-[2-chloro-6-(difluoromethoxy)phenyl]-6-fluoro-2,3-dihydro-1H-pyrrolo[1,2-a]benzimidazol-3-ol and (1R,3S)-7-bromo-1-[2-chloro-6-(difluoromethoxy)phenyl]-6-fluoro-2,3-dihydro-1H-pyrrolo[1,2-a]benzimidazol-3-ol

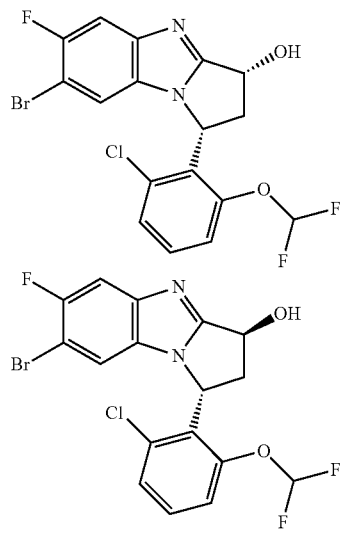

The title compounds were isolated by chiral purification of Intermediate 122 (15 g) under SFC conditions on Chirapak AD (column size: 50*216 mm*mm, flow 360 mL/min, 300 mg/injection/frequency: 8.5 minutes, 25° C., CO$_2$+20% MeOH). Chiral analysis was done on Chiralpak AD-H (column size: 250*4.6 mm, 5 μm, flow 1 mL/min at 30° C. using 80/20 heptane/ethyl acetate containing 0.1% DEA). Under analytical conditions the first eluting diastereoisomers (5.8 and 9.5 minutes) were a mixture of (1R, 3S) and (1R,3R)-7-bromo-1-[2-chloro-6-(difluoromethoxy)phenyl]-6-fluoro-2,3-dihydro-1H-pyrrolo[1,2-a]benzimidazol-3-ol.

(1S,3R) and (1S, 3S)-7-bromo-1-[2-chloro-6-(difluoromethoxy)phenyl]-6-fluoro-2,3-dihydro-1H-pyrrolo[1,2-a]benzimidazol-3-ol were isolated at 12.5 minutes and 21.5 minutes.

The mixture of a mixture of (1R,3S) and (1R,3R)-7-bromo-1-[2-chloro-6-(difluoromethoxy)phenyl]-6-fluoro-2,3-dihydro-1H-pyrrolo[1,2-a]benzimidazol-3-ol was separated by chiral separation under SFC conditions on Chiracel OD (column size: 50*266 mm*mm, flow 360 mL/min, 80 mg/injection/frequency: 4 minutes, 25° C., CO$_2$+20% MeOH). Chiral analysis was done on Chiralpak AD-H (column size: 250*4.6 mm, 5 μm, flow 1 mL/min at 30° C. using 70/30 heptane/ethyl acetate containing 0.1% DEA). Under analytical conditions the first eluting diastereoisomer (4.9 minutes) was the trans isomer, (1R,3S)-7-bromo-1-[2-chloro-6-(difluoromethoxy)phenyl]-6-fluoro-2,3-dihydro-1H-pyrrolo[1,2-a]benzimidazol-3-ol. Combined fractions were evaporated to yield Intermediate 124 (12.7 g, 50%). $^1$H NMR (400 MHz, CDCl3) δ 7.41 (m, 3H), 7.23 (d, J 8.0 Hz, 0.4H), 6.97 (m, 1.2H), 6.85 (d, J 5.8 Hz, 0.4H), 6.73 (t, J 72.3 Hz, 0.4H), 6.41 (m, 1H), 5.95 (dd, J 74.2, 70.8 Hz, 0.6H), 5.71 (m, 0.6H), 5.62 (d, J 7.4 Hz, 0.4H), 3.22 (m, 2H). as a mixture of rotamers 6/4. LCMS basic (ES+) 2.50 min., 446.96/448.95/450.95 (M+H)+.

Under analytical conditions the second eluting diastereoisomer (6.6 minutes) was the cis isomer, (1R,3R)-7-bromo-1-[2-chloro-6-(difluoromethoxy)phenyl]-6-fluoro-2,3-dihydro-1H-pyrrolo[1,2-a]benzimidazol-3-ol. Combined fractions were evaporated to yield Intermediate 123 (6.6 g, 26%). 1H NMR (400 MHz, CDCl3) δ 7.45 (d, J 8.5 Hz, 1H), 7.31 (m, 1.8H), 7.20 (m, 0.6H), 7.08 (d, J 7.9 Hz, 0.6H), 6.88 (d, J 5.5 Hz, 0.6H), 6.74 (d, J 5.2 Hz, 0.4H), 6.61 (t, J 72.5 Hz, 0.4H), 6.15 (t, J 72.0 Hz, 0.6H), 6.08 (m, 1H), 5.63 (m, 1H), 3.56 (m, 0.6H), 3.43 (m, 0.4H), 2.98 (m, 0.4H), 2.80 (m, 0.6H), as a mixture of rotamers 6/4. LCMS acid (ES+) 2.20 min, 446.96/448.95/450.91 (M+H)+.

Under preparative conditions the order of elution was reversed.

Intermediate 125

(1R,3S)-7-bromo-1-[2-chloro-6-(difluoromethoxy)phenyl]-6-fluoro-2,3-dihydro-1H-pyrrolo[1,2-a]benzimidazol-3-ol

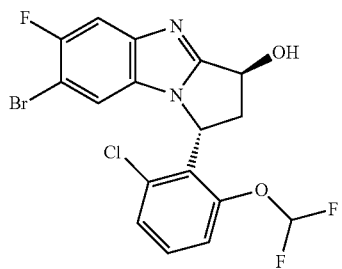 [SMILES: O[C@H]1C[C@H](c2c(Cl)cccc2OC(F)F)n2c1nc1cc(F)c(Br)cc12]

The title compound was also prepared by the following procedure: Intermediate 123 (3.65 g, 8.146 mmol, 1 eq) and triphenylphosphine (2.62 g, 9.775 mmol, 1.2 eq) were solubilized in 8 mL of dry THF, under an inert atmosphere of nitrogen. Acetic acid (513 µL, 8.960 mmol, 1.1 eq) was added and the mixture cooled to 0° C. A solution of DIAD (2.42 mL, 12.220 mmol, 1.5 eq) in 8 mL of dry THF was added drop wise. The reaction was slowly warmed to r.t. and the reaction continued for 2 hours at this temperature. 20 mL of ethyl acetate were added to the reaction mixture before washing with 3×10 mL of a saturated solution of NaHCO3. The organic layer was dried over anhydrous magnesium sulfate and concentrated under vacuum. The residue was purified by chromatography (SiO2, 5% MeOH in DCM) giving 4.8 g (94% yield) of the inverted acetate intermediate which was used directly used in the next step. [(1R,3S)-7-bromo-1-[2-chloro-6-(difluoromethoxy)phenyl]-6-fluoro-2,3-dihydro-1H-pyrrolo[1,2-a]benzimidazol-3-yl]acetate (4.8 g, 9.800 mmol, 1 eq) was solubilized in 48 mL of methanol. Potassium carbonate (1.4 g, 9.800 mmol, 1 eq) was added and the reaction continued for 1 hour at r.t. The reaction was evaporated and the residue was taken up in ethyl acetate (50 mL) and water (20 mL). The organic layer was washed by water (2×20 mL), dried over sodium sulfate, filtered and concentrated under vacuum to give 4.7 g of the crude title compound as a slightly beige solid.

Intermediate 126

Ethyl (3R)-3-(5-bromo-2-nitro-anilino)-3-[2-chloro-6-(difluoromethoxy)phenyl]propanoate Intermediate 126 was prepared from Intermediate 118 (9.3 g, 28.3 mmol) and 4-bromo-2-fluoro-nitrobenzene (7.4 g, 34 mmol), using the same procedure described for preparation of Intermediate 119. The reaction was stirred overnight at 80° C. and purified by chromatography (SiO2, 10% EtOAc in hexane). Intermediate 126 was obtained as a yellow oil (12.5 g, 90%).
LCMS (ES+) 493.0/495.0 (M+H)+

Intermediate 127

(3R)-3-(5-bromo-2-nitro-anilino)-3-[2-chloro-6-(difluoromethoxy)phenyl]propanal

Intermediate 127 was prepared from Intermediate 126 (12.5 g, 25.4 mmol) using the same procedure described for preparation of Intermediate 120. Following work-up the crude Intermediate 127 was purified by chromatography (SiO2, 15% EtOAc in hexane) yielding Intermediate 127 (9 g, 80%) as a yellow oil. 1H NMR (400 MHz, CDCl3) δ 9.80 (d, J 1.3 Hz, 1H), 8.78 (d, J 9.0 Hz, 1H), 7.99 (d, J 9.0 Hz, 1H), 7.27 (d, J 3.2 Hz, 2H), 7.21-7.08 (m, 1H), 6.81-6.66 (m, 2H), 5.93 (m, 1H), 3.56-3.38 (m, 2H), 3.12 (dd, J 17.9, 5.2 Hz, 1H).

Intermediate 128

(4R)-4-(5-bromo-2-nitro-anilino)-4-[2-chloro-6-(difluoromethoxy)phenyl]-2-trimethylsilyloxy-butanenitrile Intermediate 128 was prepared from Intermediate 127 (9 g, 20 mmol) using the same procedure described for preparation of Intermediate 121. The reaction was stirred at r.t. for 2 h. After completion of reaction (monitored by TLC), water (200 mL) was added and extracted with DCM (500 mL). After evaporation of organic layer, the crude product, obtained as a yellow oil (9 g), was used directly for the next step without any purification.

Intermediate 129

(1R)-7-bromo-1-[2-chloro-6-(difluoromethoxy)phenyl]-2,3-dihydro-1H-pyrrolo[1,2-a]benzimidazol-3-ol

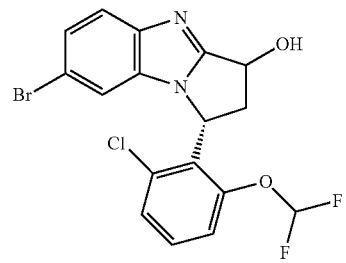 [SMILES: OC1C[C@H](c2c(Cl)cccc2OC(F)F)n2c1nc1ccc(Br)cc12]

Intermediate 129 was prepared from Intermediate 128 (9 g, 16.4 mmol) using the same procedure described for preparation of Intermediate 122. The crude product was purified by chromatography (SiO$_2$, 60% EtOAc in hexane) then triturated with hexane:ethyl acetate to yield the title compound (3 g, 43% yield) as a yellow solid. LCMS (ES$^+$) 429.0/431.0 (M+H)$^+$ Intermediates 130 and 131

(1R,3R)-7-bromo-1-[2-chloro-6-(difluoromethoxy) phenyl]-2,3-dihydro-1H-pyrrolo[1,2-a]benzimidazol-3-ol and (1R,3S)-7-bromo-1-[2-chloro-6-(difluoromethoxy)phenyl]-2,3-dihydro-1H-pyrrolo[1,2-a] benzimidazol-3-ol

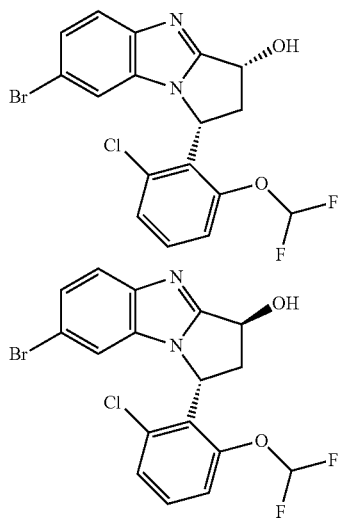

The title compounds were isolated by chiral purification of Intermediate 129 (12.5 g) by 2 successive chiral separation.

First Chiral Separation:
Under SFC conditions on Chiracel OD (column size: 50*266 mm*mm, flow 360 mL/min, 20 mg/injection/frequency: 4 minutes, 25° C., CO$_2$+20% MeOH). Chiral analysis was done on Chiracel OD-H (column size: 250*4.6 mm, flow 1 mL/min at 30° C. using 100% methanol containing 0.1% DEA). Under analytical conditions the first eluting diastereoisomer (3.9 minutes) was either (1S,3R) or (1S, 3S) 7-bromo-1-[2-chloro-6-(difluoromethoxy)phenyl]-2,3-dihydro-1H-pyrrolo[1,2-a]benzimidazol-3-ol. The second eluting diastereoisomers (4.7 minutes) were a mixture of (1R,3S) along with either (1S,3R) or (1S, 3S)-7-bromo-1-[2-chloro-6-(difluoromethoxy)phenyl]-2,3-dihydro-1H-pyrrolo[1,2-a]benzimidazol-3-ol and the third eluting diastereoisomer (5.4 minutes) was (1R,3R)-7-bromo-1-[2-chloro-6-(difluoromethoxy)phenyl]-2,3-dihydro-1H-pyrrolo[1,2-a]benzimidazol-3-ol. Combined fractions of the third eluting diastereomer were evaporated to yield to Intermediate 130 (3.63 g, 29%). $^1$H NMR (400 MHz, DMSO) δ 7.57 (m, 2.3H), 7.45 (m, 0.8H), 7.35 (d, J 8.0 Hz, 0.6H), 7.26 (m, 1H), 7.17 (m, 0.3H), 6.83 (t, J 72.5 Hz, 1H), 6.69 (bs, 1H), 6.15 (m, 1H), 6.07 (m, 1H), 5.38 (m, 1H), 3.38 (m, 1H), 2.67 (m, 1H) as a mixture of rotamers 7/3. LCMS acid (ES$^+$) RT 4.31 min., 429.10/431.08/433.05 (M+H)$^+$.

Second Chiral Separation:
Under SFC conditions on Whelko 01 (R,R) (column size: 50*227 mm*mm, flow 360 mL/min, 690 mg/injection/frequency: 5.5 minutes, 25° C., CO$_2$+20% EtOH). Chiral analysis was done on Chiralcel OD-H (column size: 250*4.6 mm, flow 1 mL/min at 30° C. using 50/50 heptane/isopropyl alcohol containing 0.1% DEA).

Under analytical conditions, the first eluting diastereomer (4.1 minutes) was either (1S,3R) or (1S, 3S)-7-bromo-1-[2-chloro-6-(difluoromethoxy)phenyl]-2,3-dihydro-1H-pyrrolo[1,2-a]benzimidazol-3-ol.

Under analytical conditions, the second eluting diastereomer (5.9 minutes) was the trans isomer, (1R,3S)-7-bromo-1-[2-chloro-6-(difluoromethoxy)phenyl]-2,3-dihydro-1H-pyrrolo[1,2-a]benzimidazol-3-ol. Combined fractions were evaporated to yield Intermediate 131 (4.46 g, 36%). $^1$H NMR (400 MHz, DMSO) δ 7.55 (m, 3.4H), 7.31 (m, 1.4H), 7.12 (d, J 7.8 Hz, 0.6H), 7.03 (t, J 73.0 Hz, 0.6H), 6.89 (s, 0.6H), 6.81 (s, 0.4H), 6.32 (dd, J 8.4, 5.9 Hz, 1H), 6.10 (d, J 6.6 Hz, 1H), 5.32 (m, 0.6H), 5.26 (t, J 6.9 Hz, 0.4H), 3.13 (m, 1H), 2.93 (m, 1H). as a mixture of rotamers 6/4. LCMS acid (ES$^+$) RT 4.40 min., 429.05/431.08/433.05 (M+H)$^+$.

Under preparative conditions the order of elution was reversed.

Intermediate 132

(1R,3S)-7-bromo-1-[2-chloro-6-(difluoromethoxy) phenyl]-2,3-dihydro-1H-pyrrolo[1,2-a]benzimidazol-3-ol

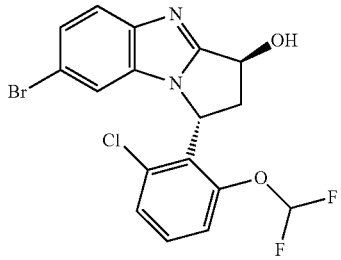 [SMILES: O[C@H]1C[C@H](c2c(Cl)cccc2OC(F)F)n2c1nc1ccc(Br)cc12]

The title compound was prepared from the same procedure described for the preparation of Intermediate 125 starting from Intermediate 130 (3.63 g, 8.450 mmol), triphenylphosphine (2.66 g, 10.14 mmol), and acetic acid (0.5 mL, 9.295 mmol) THF (34 mL), DIAD (2.62 mL, 12.67 mmol) in 5 ml of dry THF giving 3.6 g (91%) of the inverted acetate intermediate which was used directly in the next step. Using the following conditions.

[(1R,3S)-7-bromo-1-[2-chloro-6-(difluoromethoxy)phenyl]-2,3-dihydro-1H-pyrrolo[1,2a]benzimidazol-3-yl]acetate (4.0 g, 8.480 mmol) was solubilized in 40 mL of methanol. Potassium carbonate (1.1 g, 8.48 mmol, 1 eq) was added and the reaction continued for 1 hour at rt. The methanol was evaporated and the residue was taken up in ethyl acetate (50 mL) and water (20 mL). The organic layer was washed by water (2×20 mL), dried over anhydrous sodium sulfate, filtered and concentrated under vacuum to give 4.9 g of crude title compound as a brown oil use without further purification. LCMS (ES$^+$) RT 2.46 min., 428.94/430.96/433.16 (M+H)$^+$.

Intermediate 133

3-(5-bromopyrimidin-2-yl)oxetan-3-ol 5-bromo-2-iodo-pyrimidine (20.02 g, 70.28 mmol) was dissolved in anhydrous toluene (260 mL). At −78° C., n-buthyllitium 1.6 mol/L in hexane (44 mL, 70.0 mmol) was added drop by drop and following a solution of oxetan-3-one (4.5 mL, 73.3 mmol) in anhydrous dry toluene (40 mL) was added drop by drop. The reaction mixture was stirred at −78° C. for 1 h. At 0° C., the reaction mixture was quenched by addition on distilled water (500 mL), extracted by 4×200 mL of ethyl acetate. Combined organic layers were washed with solution 2.5M of ascorbic acid, saturated solution of NaCl (200 mL), dried over sodium sulfate and concentrated in vacuo to give crude product which was filtered on celite. The celite was washed with DCM, hot diisopropyl ether, and combined filtrates was concentrated in vacuo. The crude residue obtained was crystallised in mixture of isopropyl ether and toluene yielding the title compound as a yellow solid (1.8 g, 11%). LCMS (ES$^+$) 231.03 (M+H)$^+$.

Intermediate 134

[3-(5-bromopyrimidin-2-yl)oxetan-3-yl]oxy-trim-ethyl-silane

Intermediate 133 (2.7 g, 12.85 mmol) and imidazole (0.95 g, 13.9 mmol) were mixed in DCM (9 mL/mmol). Chloro-trimethylsilane (1.52 mL, 16.71, 1.3 eq) was added and the reaction mixture was stirred at r.t. for 1.5 h. Chlorotrimethylsilane (1 mL) was added and the stirring was continued for 3 h. Imidazole (0.450 mg) was then added and the reaction mixture was stirred for a additional 1.5 h. The reaction mixture was filtered, the residue washed with DCM (3×100 mL). The filtrate was washed with distilled water (2×100 mL), a saturated solution of NaCl (100 mL), dried over magnesium sulfate and concentrated in vacuo to afford the title compound as a yellow oil (3.7 g, 96%). LCMS (ES$^+$) 303.17 (M+H)$^+$.

Intermediate 135

5-bromo-2-(3-fluorooxetan-3-yl)pyrimidine

Intermediate 134 (3.53 g, 12.1 mmol) was dissolved in DCM (4.2 mL). At −78° C., DAST (1.81 mL, 14.2 mmol) was added drop wise. The reaction mixture was stirred a −78° C. for 0.5 h then stirred at r.t. for 1 h., DAST (0.5 mL, 14.2 mmol) was added and the mixture was stirred 3 h additional. Then DAST (1.0 mL, 7.82 mmol) was added and the mixture was again stirred for 1 h at r.t. A saturated solution of NaHCO$_3$ was added and after decantation the organic layer was dried over magnesium sulfate and concentrated in vacuo. The residue was purified by chromatography (SiO$_2$, 0-20% DCM in heptane) yielding the title compound (0.801 g, 29%). LCMS (ES$^+$) 233.0 (M+H)$^+$.

Intermediate 136

(1R,3S)-1-[2-chloro-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-ol

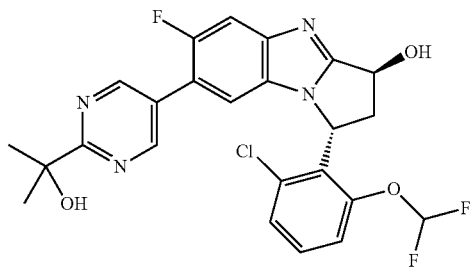 [SMILES: CC(C)(O)c1ncc(-c2cc3c(cc2F)nc2n3[C@@H](c3c(Cl)cccc3OC(F)F)C[C@@H]2O)cn1]

Intermediate 136 was prepared from Intermediate 124 (4.61 g, 10.30 mmol), and 2-[5-(4,4,5,5-tetramethyl-1,3,2-dioxaborolan-2-yl)pyrimidin-2-yl]propan-2-ol (3.00 g, 11.330 mmol), by the Method C (3.6 g, 69%). LCMS (ES$^+$) RT 1.91 min. 505.15/507.15 (M+H)$^+$.

Intermediate 137 Method I

(1R)-7-bromo-1-[2-(difluoromethoxy)phenyl]-3,8-difluoro-2,3-dihydro-1H-pyrrolo[1,2-a]benzimidazole

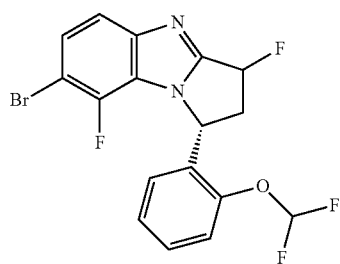 [SMILES: Fc1c(Br)ccc2nc3n(c12)[C@@H](c1ccccc1OC(F)F)CC3F]

Intermediate 110 (1.0 g, 2.420 mmol) was dissolved in DCM (30 mL). At 0° C., DAST (0.384 mL, 2.904 mmol, 1.2 eq) was added drop wise. The reaction mixture was stirred a 0° C. for 0.5 h. A saturated solution of NaHCO$_3$ was added and the mixture was extracted by DCM (2×100 mL) and combined organic layers were dried over sodium sulfate, concentrated in vacuo yielding the title compound (0.94 g, 83%). LCMS acid (ES$^+$) 415.0/417.0 (M+H)$^+$.

Intermediates 138 and 139

(1R,3S or R)-7-bromo-1-[2-(difluoromethoxy)phenyl]-3,8-difluoro-2,3-dihydro-1H-pyrrolo[1,2-a]benzimidazole and (1R,3R or S)-7-bromo-1-[2-(difluoromethoxy)phenyl]-3,8-difluoro-2,3-dihydro-1H-pyrrolo[1,2-a]benzimidazole

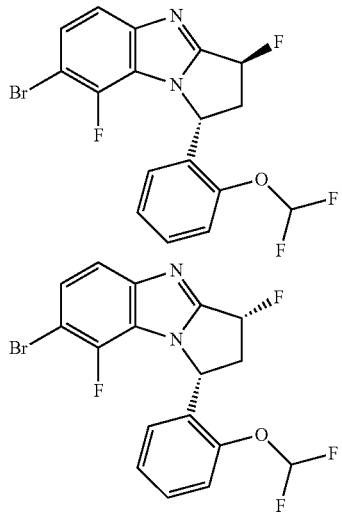

Intermediate 137 was purified by chiral chromatography and the title compounds were isolated under SFC conditions on Chiralpak IA (50*266 mm*mm, flow 360 mL/min, 25° C., CO2/2-PrOH 80/20, injection of 9 mL solution at a concentration of 66 g/L).

The first eluting enantiomer (RT 6 min) was collected and the fractions were evaporated to yield (enantiomer 1) (Intermediate 138).

The second eluting enantiomer (RT 12.19 min) was collected and the fractions were evaporated to yield (enantiomer 2) (Intermediate 139). LCMS (ES$^+$) 417.19 (M+H)$^+$.

Intermediate 140

9-(5-bromopyrimidin-2-yl)-3,7-dioxa-9-azabicyclo[3.3.1]nonane 3,7-dioxa-9-azabicyclo[3.3.1]nonane (0.39 g, 3.0 mmol) and 5-bromo-2-chloropyrimidine (0.61 g, 3.0 mmol) were dissolved in ethanol (5 mL). Triethylamine (0.47 mL, 3.3 mmol) was added and the reaction mixture was heated at 80° C. for 18 h. The reaction mixture was concentrated in vacuo, taken up in EtOAc and remaining starting material was filtered off. The residue was purified by chromatography (SiO$_2$, 0-100% EtOAc in DCM) yielding the title compound (297 mg, 35%). $^1$H NMR (400 MHz, CDCl$_3$) δ ppm 8.33 (s, 2H), 4.48 (s, 2H), 4.11 (d, J 11.2 Hz, 4H), 3.93 (d, J 11.8 Hz, 4H). LCMS (ES$^+$) 286 MH$^+$.

Intermediate 141

N-[(4-Bromophenyl)(methyl)oxo-λ6-sulfanylidene]-2,2,2-trifluoroacetamide

To a suspension of 1-bromo-4-methanesulfinylbenzene (5 g, 22.8 mmol), MgO (3.68 g, 91.3 mmol), tetrakis(acetato-κO)dirhodium(Rh—Rh) (0.25 g, 0.57 mmol) and 2,2,2-trifluoroacetamide (5.16 g, 45.6 mmol) in anhydrous DCM (150 mL) was added bis(acetyloxy)(phenyl)-λ~3~-iodane (11.03 g, 34.2 mmol) at room temperature. The reaction was left to stir at r.t. for 18 h. The reaction mixture was filtered over celite and the filter cake washed with DCM (30 mL). The filtrate was concentrated in vacuo and purified by column chromatography (SiO2, 0-100% EtOAc in heptane) yielding the title compound as a light yellow oil (5.7 g, 97%). $^1$H NMR (250 MHz, CDCl$_3$) δ ppm 7.92-7.75 (m, 4H), 3.45 (s, 3H). LCMS (ES$^+$) RT 1.27 min, 330.0/332.0 (M+H)$^+$.

Intermediate 142

(4-bromophenyl)-imino-methyl-oxo-λ6-sulfane

To a solution of Intermediate 141 (5.7 g, 17.1 mmol) in MeOH (100 mL) was added potassium carbonate (11.6 g, 83.7 mmol). The reaction was left to stir at r.t. for 2 h. The mixture was concentrated in vacuo then diluted with water (50 mL). The product was extracted with EtOAc (3×100 mL). The combined organic fraction was dried (MgSO$_4$) and concentrated in vacuo to yield the title compound as a yellow oil (4.00 g, 96%). $^1$H NMR (500 MHz, CDCl$_3$) δ ppm 7.89-7.83 (m, 2H), 7.70-7.65 (m, 2H), 3.09 (s, 3H), 2.65 (s, 1H). LCMS (ES$^+$) RT 0.81 min, 234.0/236.0 (M+H)$^+$.

Intermediate 143

Imino-methyl-oxo-[4-(4,4,5,5-tetramethyl-1,3,2-dioxaborolan-2-yl)phenyl]-λ-6-sulfane A solution of Intermediate 142 (4 g, 15.4 mmol) in anhydrous 1,4-dioxane (80 mL) was treated with 4,4,4',4',5,5,5',5'-octamethyl-2,2'-bi-1,3,2-dioxaborolane (4.69 g, 18.5 mmol) and potassium acetate (4.53 g, 46.1 mmol). The mixture was degassed thoroughly under a stream of nitrogen for 10 minutes prior to the addition of bis[3-(diphenylphosphanyl)cyclopenta-2,4-dien-1-yl]iron; dichloromethane; dichloropalladium (0.63 g, 0.77 mmol). The reaction was stirred at 80° C. for 75 min. The reaction was concentrated in vacuo, re-dissolved in EtOAc (200 mL) and washed with water (100 mL). The aqueous phase was re-extracted with EtOAc (50 mL) and the combined organic extracts washed with brine (100 mL), dried (Na$_2$SO$_4$) and concentrated in vacuo. The residue was triturated with heptane afforded the title compound as a brown solid (3.05 g, 60%). $^1$H NMR (500 MHz, CDCl$_3$) δ ppm 8.02-7.98 (m, 4H), 3.09 (s, 3H), 1.36 (s, 12H).

Intermediate 144

5-bromo-2-methanesulfinylpyridine

NaIO$_4$ (9.56 g, 44.69 mmol) was added as a slurry in water (10 mL) to a stirred solution of 5-bromo-2-(methylsulfanyl)pyridine (2.4 g, 11.76 mmol) in acetic acid (40 mL) at r.t. The mixture was stirred at r.t. for 2 h. After this time, a colourless precipitate had formed. The mixture was treated with water (50 mL) upon which the precipitate dissolved. The aqueous acidic mixture was basified through addition of saturated aqueous potassium carbonate solution and the product extracted with EtOAc (3×50 mL). The combined organic phase was washed with 10% aqueous sodium thiosulfate solution (50 mL), dried (Na$_2$SO$_4$) and reduced in vacuo to give the crude product as an amber glass (2.52 g) which solidified on standing. Purification by chromatography (SiO$_2$, 0-100% EtOAc in heptane) afforded the title compound as a pale yellow oil (2.04 g, 79%). δH (500 MHz, CDCl$_3$) 8.68 (d, J 2.0 Hz, 1H), 8.08 (dd, J 8.3, 2.2 Hz, 1H), 7.93 (d, J 8.3 Hz, 1H), 2.84 (s, 3H).

Intermediates 145-147

The following intermediates were prepared from the intermediates listed or from commercially available starting materials using methods analogous to the methods described.

| Number | Name | Intermediate used | Method |
|---|---|---|---|
| 145 | N-[(5-bromopyridin-2-yl)(methyl)oxo-λ6-sulfanylidene]-2,2,2-trifluoroacetamide | 144 | Int141 |
| | δH (500 MHz, CDCl$_3$) 8.79 (d, J 1.4 Hz, 1H), 8.22-8.19 (m, 1H), 8.18 (dd, J 8.4, 2.0 Hz, 1H), 3.56 (s, 3H). | | |
| 146 | (5-bromopyridin-2-yl)(imino)methyl-λ6-sulfanone | 145 | Int 142 |
| | δH (500 MHz, DMSO-d6) 8.88 (d, J 2.2 Hz, 1H), 8.37 (dd, J 8.4, 2.3 Hz, 1H), 8.01 (d, J 8.4 Hz, 1H), 4.54 (s, 1H), 3.17 (s, 3H). | | |
| 147 | Imino(methyl)[5-(tetramethyl-1,3,2-dioxaborolan-2-yl)pyridin-2-yl]-λ6-sulfanone | 146 | Int 143 |
| | δH (250 MHz, CDCl$_3$) 8.77 (s, 1H), 8.30 (d, J 6.5 Hz, 1H), 8.04 (d, J 5.3 Hz, 1H), 3.25 (s, 3H), 1.36 (s, 12H). | | |

Intermediates 148 and 149

(1R,3R)-7-bromo-1-[2-(difluoromethoxy)phenyl]-2,3-dihydro-1H-pyrrolo[1,2-a]benzimidazol-3-ol and (1R,3S)-7-bromo-1-[2-(difluoromethoxy)phenyl]-2,3-dihydro-1H-pyrrolo[1,2-a]benzimidazol-3-ol

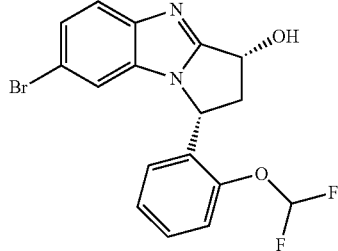

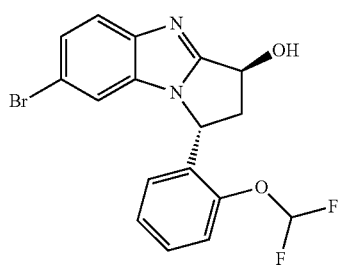

(1R)-7-bromo-1-[2-(difluoromethoxy)phenyl]-2,3-dihydro-1H-pyrrolo[1,2-a]benzimidazol-3-ol was prepared following the procedure described for the intermediate 110 using 4-bromo-2-fluoro-1-nitro-benzene as reagent in the first step.

The title compounds were isolated by purification of (1R)-7-bromo-1-[2-(difluoromethoxy)phenyl]-2,3-dihydro-1H-pyrrolo[1,2-a]benzimidazol-3-ol under SFC conditions on Lux-Cell-4 (50*291 mm*mm, flow 360 mL/min, 25° C., CO2/EtOH 75/25, injection of 9.1 mL solution at a concentration of 33 g/L).

The first eluting enantiomer (RT 3 min) was collected and the fractions were evaporated to yield (distereoisomer 1) (Intermediate 148).

The second eluting enantiomer (RT 5 min) was collected and the fractions were evaporated to yield (distereoisomer 1) (Intermediate 149).

Intermediate 150

2-[(1R,3R)-7-Bromo-1-(2-difluoromethoxy-phenyl)-2,3-dihydro-1H-benzo[d]pyrrolo[1,2-a]imidazol-3-yloxy]-ethanol

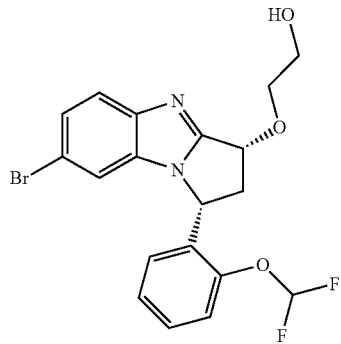 [SMILES: OCCO[C@@H]1C[C@H](c2ccccc2OC(F)F)n2c1nc1ccc(Br)cc12]

NaH (53 mg, 1.33 mmol, 60% in mineral oil) was added to a solution of Intermediate 148 (500 mg, 1.27 mmol) in DMF (1 mL) and the reaction mixture was stirred at r.t. for 30 minutes. 2-(2-Bromoethoxy)tetrahydro-2H-pyran (279 mg, 1.27 mmol) was added and the reaction mixture was stirred for 3 h and distributed between EtOAc (4 mL) and water (4 mL). The phases were separated and the organic phase washed with water (3×2 mL). The organic phase was dried over Na$_2$SO$_4$ and concentrated in vacuo. The residue was dissolved in MeCN (50 mL), 2N HCl (10 mL) was added and the mixture stirred at r.t. for 45 minutes. Evaporation, lyophilisation and purification via preparative HPLC chromatography (Prep-C18 silica gel, MeCN/water: Gradient from 30/70 to 70/30) yielded the title compound (420 mg, 75.6%); LCMS (ES$^+$) RT 1.71 min, 438.99 (M+H)$^+$.

Intermediate 151

3-[(1R,3R)-7-Bromo-1-(2-difluoromethoxy-phenyl)-2,3-dihydro-1H-benzo[d]pyrrolo[1,2-a]imidazol-3-yloxy]-propan-1-ol

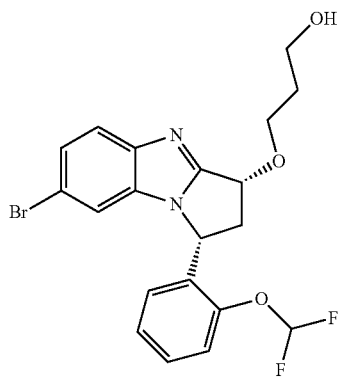 [SMILES: OCCCO[C@@H]1C[C@H](c2ccccc2OC(F)F)n2c1nc1ccc(Br)cc12]

The title compound was prepared from Intermediate 148 (600 mg, 1.52 mmol) and 2-(3-bromopropoxy) tetrahydro-2-H-pyran (339 mg, 1.52 mmol) by the analogous method described for the synthesis of Intermediate 150 (420 mg, 61%). LCMS (ES+) RT 1.73 min, 453.02 (M+H)+.

Intermediate 152

2-[[(1R,3R)-7-bromo-1-[5-chloro-2-(difluoromethoxy)phenyl]-2,3-dihydro-1H-pyrrolo[1,2-a]benzimidazol-3-yl]oxy]ethano1

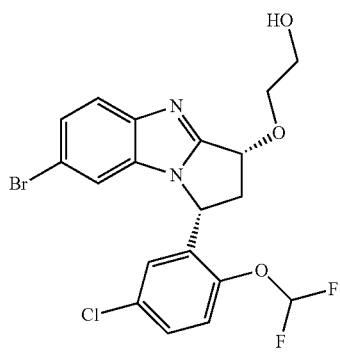 [SMILES: OCCO[C@@H]1C[C@H](c2cc(Cl)ccc2OC(F)F)n2c1nc1ccc(Br)cc12]

The title compound was prepared from Intermediate 161 (350 mg, 0.81 mmol) as described for the synthesis of intermediate 150 (300 mg, 77.7%). LCMS (ES+) RT 1.77 min, 473.04 (M+H)+.

Intermediate 153

1-{2-[(1R,3R)-7-Bromo-1-(2-difluoromethoxy-phenyl)-2,3-dihydro-1H-benzo[d]pyrrolo[1,2-a]imidazol-3-yloxy]-ethyl}-pyrrolidin-2-one

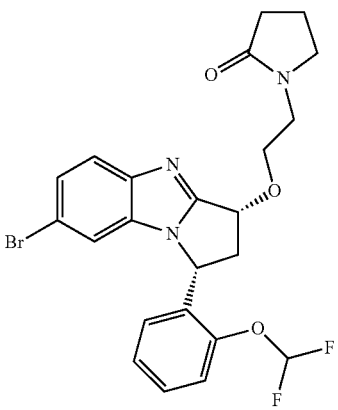 [SMILES: O=C1CCCN1CCO[C@@H]1C[C@H](c2ccccc2OC(F)F)n2c1nc1ccc(Br)cc12]

To a solution of Intermediate 148 (300 mg, 0.76 mmol) in DMF (2 mL), NaH (32 mg, 0.80 mmol; 60% in mineral oil) was added at 0° C. The mixture was stirred at 0° C. for 30 minutes. 1-(2-bromomethyl)pyrrolidin-2-one (153 mg, 0.76 mmol) was added and the mixture stirred for another 30 minutes. NaH (32 mg, 0.80 mmol; 60% in mineral oil) was added at 0° C. The mixture was stirred at 0° C. for 30 minutes and 1-(2-bromomethyl)pyrrolidin-2-one (153 mg, 0.76 mmol) was added and the mixture again stirred for 30 minutes. This procedure was repeated 5 times. The reaction mixture was distributed between EtOAc (4 mL) and water (4 mL), the phases were separated and the organic phase washed with water (3×2 mL). The organic phase was dried over $Na_2SO_4$ and concentrated in vacuo. The residue was purified by column chromatography ($SiO_2$, 5% MeOH in DCM) yielding the desired product (100 mg, 26%). LCMS (ES+) RT 0.816 min, 506.05 (M+H)+.

Intermediate 154

N-[[5-chloro-2-(difluoromethoxy)phenyl]methylene]-2-methyl-propane-2-sulfinamide The title compound was prepared from 5-chloro-2-difluoromethoxy-benzaldehyde and (S)-(−)-t-butyl sulfinamide following the method described for the preparation of Intermediate 116.

Intermediate 155

Ethyl (3R)-3-[[(S)-tert-butylsulfinyl]amino]-3-[5-chloro-2-(difluoromethoxy)phenyl]propanoate The title compound was prepared from Intermediate 154 following the method described for the preparation of Intermediate 117.

Intermediate 156

Ethyl (3R)-3-amino-3-[5-chloro-2-(difluoromethoxy)phenyl]propanoate hydrochloride The title compound was prepared from Intermediate 155 following the method described for the preparation of Intermediate 118.

Intermediate 157

(R)-ethyl-3-((5-bromo-2-nitrophenyl)amino)-3-(5-chloro-2-(difluoromethoxy)phenyl)propanoate The title compound was prepared from Intermediate 156 and 4-bromo-2-fluoro-1-nitro-benzene following the method described for the preparation of Intermediate 119.

Intermediate 158

(3R)-3-(5-bromo-2-nitro-anilino)-3-[5-chloro-2-(difluoromethoxy)phenyl]propanal To a solution of Intermediate 157 (10 g, 20.3 mmol) in anhydrous THF (50 mL) at −78° C. was added DIBAL-H (40.5 mmol, 1M in toluene) drop wise and the mixture was stirred at −78° C. After 3 h at −78° C. further DIBAL-H (40.5 mmol, 1M in toluene) was added. After stirring another 1 h at −78° C., the reaction mixture was quenched with an aqueous solution of ammonium chloride and allowed to warm up to r.t. After further dilution with an aqueous solution of ammonium chloride, DCM was added. After addition of NaCl to the aqueous phase, the organic phase was separated, washed with NaCl solution and dried over $Na_2SO_4$ and concentrated in vacuo yielding the title product (9.99 g, quantitative) which was used for the next step without purification.

Intermediate 159

(4R)-4-((5-bromo-2-nitrophenyl)amino)-4-(5-chloro-2-(difluoromethoxy)phenyl)-2-((trimethylsilyl)oxy)butanenitrile To a solution of Intermediate 158 (9.99 g, 22.22 mmol) in DCM (50 mL) was added $ZnI_2$ (723 mg, 2.22 mmol), TEA (0.313 mL, 2.22 mmol) and TMSCN (6.08 ml, 44.44 mmol). The reaction mixture was stirred at r.t. for 1 h, diluted with water and the organic phase was separated. The organic layer was washed with NaCl solution and dried over $Na_2SO_4$ and concentrated in vacuo to yield the title product (11 g, 90%).

Intermediate 160

(R)-7-Bromo-1-(5-chloro-2-difluoromethoxy-phenyl)-2,3-dihydro-1H-benzo[d]pyrrolo[1,2-a]imidazol-3-ol

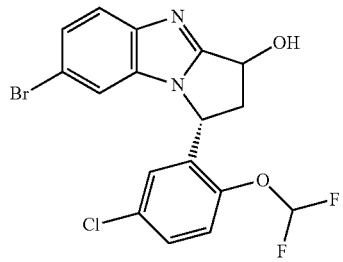 [SMILES: OC1C[C@H](c2cc(Cl)ccc2OC(F)F)n2c1nc1ccc(Br)cc12]

To a solution of Intermediate 159 (11 g, 20.04 mmol) in EtOH (80 ml) $SnCl_2$ (19.39 g, 100.21 mmol) was added and the reaction mixture was heated at 80° C. for 3 h. The reaction mixture was quenched with water (80 mL) and basified to pH 8 using 2 M KOH. The mixture was diluted with EtOAc. After filtration the organic phase was separated, washed with NaCl solution, dried over $Na_2SO_4$ and concentrated in vacuo. The residue was purified by chromatography ($SiO_2$, 30% EtOAc in heptane) yielding the title compound (4.5 g, 52% yield over 3 steps).

Intermediates 161 and 162

(1R,3R)-7-bromo-1-[5-chloro-2-(difluoromethoxy)phenyl]-2,3-dihydro-1H-pyrrolo[1,2-a]benzimidazol-3-ol and (1R,3S)-7-bromo-1-[5-chloro-2-(difluoromethoxy)phenyl]-2,3-dihydro-1H-pyrrolo[1,2-a]benzimidazol-3-ol

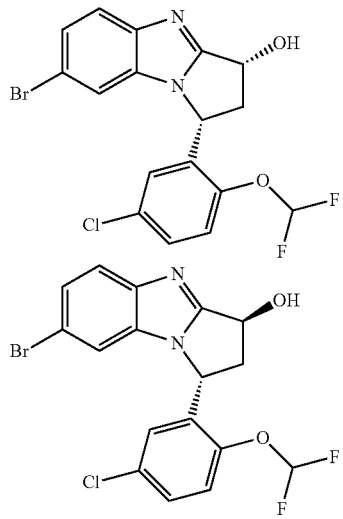

Intermediate 160 was separated by chiral chromatography (Chiralpak AD, 400×100 mm, 20 μM, heptane/ethanol=3/1, flow=300 ml/min). First eluting distereoisomer 1 (9 min): Intermediate 161 (1.75 g, 20%). LCMS (ES$^+$) RT 1.75 min, 429 (M+H)$^+$.

Second eluting distereoisomer (16.3 min): Intermediate 162, (1.98 g, 23%). LCMS (ES⁺) RT 1.74 min, 428.96 (M+H)⁺.

Intermediate 163

Methyl (1R,5S)-3-[5-[(1R,3R)-1-[2-(difluoromethoxy)phenyl]-6-fluoro-3-hydroxy-2,3-dihydro-1H-pyrrolo[1,2-a]benzimidazol-7-yl]pyrimidin-2-yl]-3-azabicyclo[3.2.1]octane-8-carboxylate

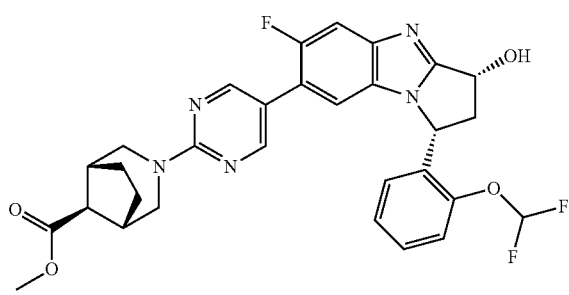 [SMILES: COC(=O)[C@@H]1[C@@H]2CC[C@H]1CN(c1ncc(-c3cc4c(cc3F)nc3n4[C@@H](c4ccccc4OC(F)F)C[C@H]3O)cn1)C2]

The title compound was prepared from Example 160 (500 mg, 1.21 mmol) and Intermediate 40 (493 mg, 1.69 mmol) by the Method C (501 mg, 71%). LCMS (ES+) RT 1.49 min, 580.0 (M+H)⁺

Intermediate 164

(1R,3R or S)-7-bromo-1-[2-(difluoromethoxy)phenyl]-8-fluoro-2,3-dihydro-1H-pyrrolo[1,2-a]benzimidazol-3-ol

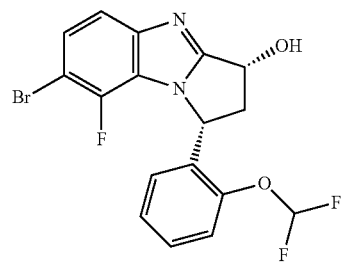 [SMILES: O[C@@H]1C[C@H](c2ccccc2OC(F)F)n2c1nc1ccc(Br)c(F)c12]

Intermediate 107 (40.5 g, 1.0 eq.) and iron powder (3 eq.) are dissolved AcOH (70 mL) and the reaction mixture was stirred at 100° C. for 1 h. At r.t., water was added, the mixture was extracted with DCM, the combined organic phases were washed with sat. aq. NaHCO₃, dried (MgSO₄), and concentrated in vacuo. The residue was purified by chiral chromatography using SFC conditions on Lux-Cell-4 (50*261 mm*mm, flow 360 mL/min, 25° C., CO₂+20% MeOH, injection of 3.66 mL solution at a concentration of 30 g/L). The first eluting diastereomer (RT 5.15 min) was collected and the fractions were evaporated to yield the title compound 1R,3R or S diastereoisomer (550 mg, 64.4%).

Intermediate 165 Method K tert-butyl 4-[2-(difluoromethoxy)phenyl]-8-fluoro-7-[2-(1-hydroxy-1-methyl-ethyl)pyrimidin-5-yl]-3,4-dihydro-1H-pyrazino[1,2-a]benzimidazole-2-carboxylate

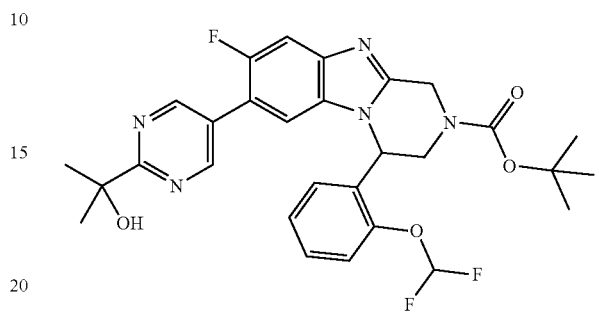

In a microwave vessel (20 ml) Example 12 (300 mg, 586 µmol) was dissolved in 1,4-dioxane (8 mL) and the solution purged with argon. Then sodium carbonate (124 mg, 1.17 mmol), 2-(5-(4,4,5,5-tetramethyl-1,3,2-dioxaborolan-2-yl)pyrimidin-2-yl)propan-2-ol (186 mg, 703 µmol) and water (2 mL) were added. This mixture was again purged with argon before tris(dibenzylideneacetone)dipalladium(0) complex (54 mg, 59 µmol) and tri-tert-butylphosphonium tetrafluoroborate (5 mg, 18 µmol) were added. After heating for 15 minutes at 100° C. in a microwave oven and cooling to r.t. brine and EtOAc were added and after phase separation the aqueous phase was extracted twice with EtOAc. The combined organic phases were washed with brine, dried over sodium sulphate, filtered and concentrated in vacuo. The residue was purified by preparative HPLC (M2d) yielding the title compound (211 mg, 63%). LCMS [M 1b](ES⁺) RT 1.82 min, 570.3 (M+H)⁺.

Example 1

7-bromo-1-(2,5-dimethylphenyl)-2,3-dihydro-1H-pyrrolo[1,2-a]benzimidazole

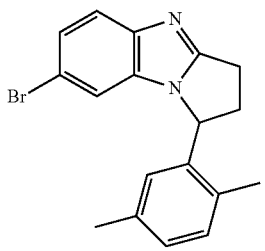 [SMILES: Cc1ccc(C)c(C2CCc3nc4ccc(Br)cc4n32)c1]

The title compound was prepared from a solution of Intermediate 4 (0.09 g, 0.23 mmol) in AcOH (1 mL) with iron powder (0.06 g, 1.15 mmol) by Method B (0.09 g, 38%). ¹H NMR (400 MHz, CDCl₃) δ 7.63 (m, 1H), 7.35 (dd, J 8.5, 1.5 Hz, 1H), 7.17 (m, 1H), 7.04 (m, 2H), 6.48 (m, 1H), 5.65 (m, 1H), 3.21 (m, 3H), 2.53 (m, 1H), 2.39 (m, 3H), 2.22 (m, 3H). LCMS (ES⁺) RT 1.65 min, 341.0/343.0 (M+H)⁺.

Example 2 Method C 1-(2,5-dimethylphenyl)-7-(6-methoxy-3-pyridyl)-2,3-dihydro-1H-pyrrolo[1,2-a]benzimidazole

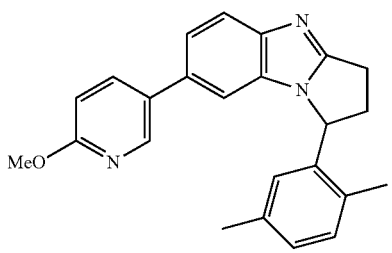 [SMILES: COc1ccc(-c2ccc3nc4n(c3c2)C(c2cc(C)ccc2C)CC4)cn1]

To a solution of Example 1 (0.08 g, 0.23 mmol) and 6-methoxy pyridine 3-yl boronic acid (0.04 g, 0.26 mmol) in 1,4-dioxane/water (6 mL, 10:1) was added K$_2$CO$_3$ (0.10 g, 0.70 mmol). The reaction mixture was degassed for 10 minutes and then Pd(PPh$_3$)$_4$ (0.003 g, 0.01 mmol) was added. The reaction mixture was heated at 100° C. for 20 h. The reaction mixture was diluted with EtOAc (10 mL), washed with water (10 mL), brine (10 mL) and the organic layer was separated, dried (Na$_2$SO$_4$) and concentrated in vacuo. The residue was purified by prep-HPLC yielding the title compound (0.01 g, 15%). $^1$H NMR (400 MHz, CDCl$_3$) δ 8.26 (d, J 2.3 Hz, 1H), 7.84 (m, 1H), 7.70 (m, 1H), 7.43 (dd, J 8.4, 1.5 Hz, 1H), 7.17 (m, 1H), 7.06 (m, 1H), 6.99 (s, 1H), 6.80 (m, 1H), 6.61 (m, 1H), 5.72 (m, 1H), 3.97 (m, 3H), 3.26 (m, 3H), 2.55 (m, 1H), 2.43 (m, 3H), 2.18 (s, 3H). LCMS (ES$^+$) RT 1.62 min, 370.0 (M+H)$^+$.

Examples 3-13

The following Examples were prepared from the assigned precursor by the Method B.

| Example No. | Precursor | Compound Name | LCMS |
|---|---|---|---|
| 3 | Int 10 | 7-bromo-1-[2-(difluoromethoxy)phenyl]-2,3-dihydro-1H-pyrrolo[1,2-a]benzimidazole | LCMS (ES$^+$) RT 1.58 min, 379.0/381.0 (M + H)$^+$. |
| 4 | Int 13 | Enantiomer 1: (1S or R)-7-bromo-1-[2-(difluoromethoxy)phenyl]-2,3-dihydro-1H-pyrrolo[1,2-a]benzimidazole | LCMS (ES$^+$) RT 1.58 min, 379.0/381.0 (M + H)$^+$. |
| 5 | Int 14 | Enantiomer 2: (1R or S)-7-bromo-1-[2-(difluoromethoxy)phenyl]-2,3-dihydro-1H-pyrrolo[1,2-a]benzimidazole | LCMS (ES$^+$) RT 1.58 min, 379.0/381.0 (M + H)$^+$. |
| 6 | Int 35 | Enantiomer 2: (1R or S)-7-bromo-1-[2-(difluoromethoxy)phenyl]-6-fluoro-2,3-dihydro-1H-pyrrolo[1,2-a]benzimidazole | LCMS (ES$^+$) RT 4.8 min, 397.0/399.0 (M + H)$^+$. |

| Example No. | Precursor | Compound Name | LCMS |
|---|---|---|---|
| 9 | Int 84 | 8-bromo-1-(2,5-dimethylphenyl)-1,2,3,4-tetrahydropyrido[1,2-a]benzimidazole | LCMS (ES+) RT 5.1 min, 355.1/357.1 (M + H)+. |

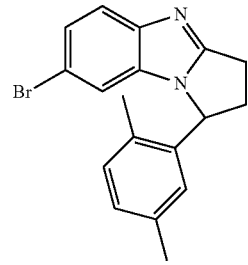

| 10 | Int 89 | 6-bromo-4-(2-difluoromethoxy-phenyl)-7-fluoro-3,4-dihydro-1H-2-oxa-4a,9-diaza-fluorene | LCMS (ES+) RT 4.8 min, 413.0/415.0 (M + H)+ |

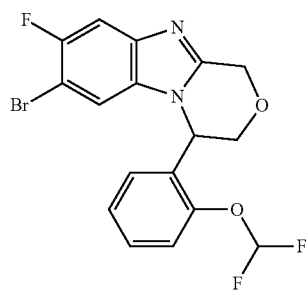

| 11 | Int 36 | 7-bromo-1-[2-(difluoromethoxy)phenyl]-6-fluoro-2,3-dihydro-1H-pyrrolo[1,2-a]benzimidazole | LCMS (ES+) RT 1.53 min, 397.0/399.0 (M + H)+. |

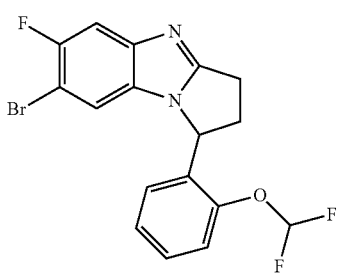

| Example No. | Precursor | Compound Name | LCMS |
|---|---|---|---|
| 12 | Int 92 | tert-butyl 7-bromo-4-(2-(difluoromethoxy)phenyl)-8-fluoro-3,4-dihydrobenzo[4,5]imidazo[1,2-a]pyrazine-2(1H)-carboxylate | LCMS (ES+) RT 2.85 min, 512.0/514.0 (M + H)+. |

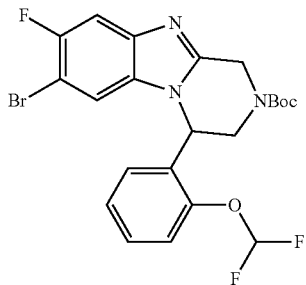

| 13 | Int 93 | tert-butyl 7-bromo-4-(2-(difluoromethoxy)phenyl)-3,4-dihydrobenzo[4,5]imidazo[1,2-a]pyrazine-2(1H)-carboxylate | LCMS (ES+) RT 2.73 min, 494.0/496.0 (M + H)+. |

Examples 14-102

The following Examples were prepared using Method C from the assigned precursor using the appropriate boronate ester or boronic acid, either available commercially or prepared as set out in the Intermediates above.

| Example No. | Precursor | Compound Name | LCMS |
|---|---|---|---|
| 14 | Ex 4 | Enantiomer 1: (1S or R)-1-[2-(difluoromethoxy)phenyl]-7-(6-methoxy-3-pyridyl)-2,3-dihydro-1H-pyrrolo[1,2-a]benzimidazole | LCMS (ES+) RT 1.55 min, 408.0 (M + H)+. |
| 15 | Ex 5 | Enantiomer 2: (1R or S)-1-[2-(difluoromethoxy)phenyl]-7-(6-methoxy-3-pyridyl)-2,3-dihydro-1H-pyrrolo[1,2-a]benzimidazole | LCMS (ES+) RT 1.55 min, 408.0 (M + H)+. |
| 16 | Ex 4 | Enantiomer 1: 4-[5-[(1S or R)-1-[2-(difluoromethoxy)phenyl]-2,3-dihydro-1H-pyrrolo[1,2-a]benzimidazol-7-yl]pyrimidin-2-yl]morpholine | LCMS (ES+) RT 1.5 min, 464.0 (M + H)+. |
| 17 | Ex. 5 | Enantiomer 2: (4-[5-[(1R or S)-1-[2-(difluoromethoxy)phenyl]-2,3-dihydro-1H-pyrrolo[1,2-a]benzimidazol-7-yl]pyrimidin-2-yl]morpholine | LCMS (ES+) RT 1.5 min, 464.0 (M + H)+. |

| Example No. | Precursor | Compound Name | LCMS |
|---|---|---|---|
| 18 | Int 80 | 7-(6-methoxypyridin-3-yl)-1-(2-methylphenyl)-2,3-dihydro-1H-pyrrolo[1,2-a]benzimidazole | LCMS (ES$^+$) RT 1.58 min, 356.0 (M + H)$^+$. |
| 19 | Int 80 | 1-(2-methylphenyl)-7-[2-(morpholin-4-yl)pyrimidin-5-yl]-2,3-dihydro-1H-pyrrolo[1,2-a]benzimidazole | LCMS (ES$^+$) RT 1.52 min, 412.0 (M + H)$^+$. |
| 20 | Int 23 | 7-(6-methoxypyridin-3-yl)-1-phenyl-2,3-dihydro-1H-pyrrolo[1,2-a]benzimidazole | LCMS (ES$^+$) RT 1.53 min, 342.0 (M + H)$^+$. |
| 21 | Int 23 | 7-[2-(morpholin-4-yl)pyrimidin-5-yl]-1-phenyl-2,3-dihydro-1H-pyrrolo[1,2-a]benzimidazole | LCMS (ES$^+$) RT 1.47 min, 398.0 (M + H)$^+$. |

-continued

| Example No. | Precursor | Compound Name | LCMS |
|---|---|---|---|
| 22 | Int 31 | 1-[2-(difluoromethoxy)phenyl]-6-fluoro-7-(4-methylsulfonylphenyl)-2,3-dihydro-1H-imidazo[1,2-a]benzimidazole | LCMS (ES+) RT 1.39 min, 474.0 (M + H)+. |
| 23 | Int 34 | 1-[2-(difluoromethoxy)phenyl]-7-(4-methylsulfonylphenyl)-2,3-dihydro-1H-imidazo[1,2-a]benzimidazole | LCMS (ES+) RT 1.36 min, 456.0 (M ' H)+. |
| 24 | Ex 6 | Enantiomer 2: tert-butyl 4-[5-[(1R or S)-1-[2-(difluoromethoxy)phenyl]-6-fluoro-2,3-dihydro-1H-pyrrolo[1,2-a]benzimidazol-7-yl]-2-pyridyl]piperazine-1-carboxylate | LCMS (ES+) RT 4.66 min, 580.44 (M + H)+. |
| 25 | Ex 6 | Enantiomer 2: (1R or S)-1-[2-(difluoromethoxy)phenyl]-6-fluoro-7-(6-methoxy-3-pyridyl)-2,3-dihydro-1H-pyrrolo[1,2-a]benzimidazole | LCMS (ES+) RT 1.54 min, 426.0 (M + H)+. |

| Example No. | Precursor | Compound Name | LCMS |
|---|---|---|---|
| 26 | Ex 6 | Enantiomer 2: (1R or S)-1-[2-(difluoromethoxy)phenyl]-6-fluoro-7-(3-pyridyl)-2,3-dihydro-1H-pyrrolo[1,2-a]benzimidazole<br>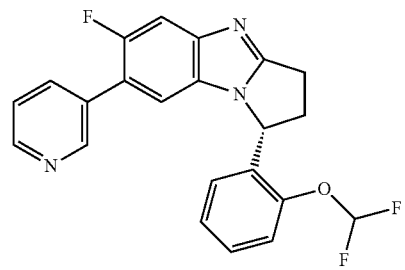 | LCMS (ES+) RT 1.40 min, 396.0 (M + H)+. |
| 27 | Ex 6 | Enantiomer 2: (1R or S)-1-[2-(difluoromethoxy)phenyl]-6-fluoro-7-(3-methylsulfonylphenyl)-2,3-dihydro-1H-pyrrolo[1,2-a]benzimidazole<br>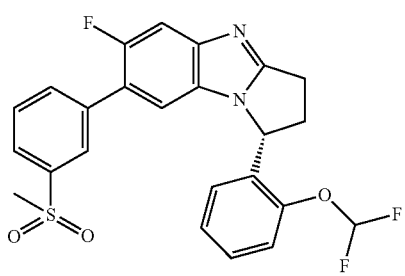 | LCMS (ES+) RT 1.45 min, 473.0 (M + H)+. |
| 28 | Ex 6 | Enantiomer 2: (1R or S)-1-[2-(difluoromethoxy)phenyl]-6-fluoro-7-(2-methylsulfonyl-4-pyridyl)-2,3-dihydro-1H-pyrrolo[1,2-a]benzimidazole<br>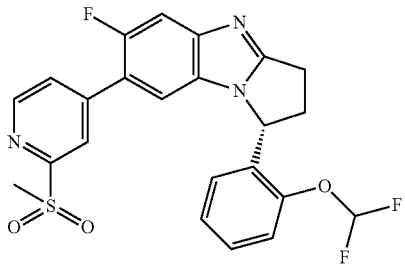 | LCMS (ES+) RT 1.41 min, 474.0 (M + H)+. |

-continued

| Example No. | Precursor | Compound Name | LCMS |
|---|---|---|---|
| 29 | Ex 6 | Enantiomer 2: (1R or S)-1-[2-(difluoromethoxy)phenyl]-6-fluoro-7-(6-methylsulfonyl-3-pyridyl)-2,3-dihydro-1H-pyrrolo[1,2-a]benzimidazole | LCMS (ES+) RT 1.41 min, 474.0 (M + H)+. |
| 30 | Ex 6 | Enantiomer 2: (1R or S)-1-[2-(difluoromethoxy)phenyl]-7-(2,5-dimethyl-3-pyridyl)-6-fluoro-2,3-dihydro-1H-pyrrolo[1,2-a]benzimidazole | LCMS (ES+) RT 1.48 min, 424.0 (M + H)+. |
| 31 | Ex 6 | Enantiomer 2: (1R or S)-1-[2-(difluoromethoxy)phenyl]-6-fluoro-7-(5-methylsulfonyl-3-pyridyl)-2,3-dihydro-1H-pyrrolo[1,2-a]benzimidazole | LCMS (ES+) RT 1.41 min, 474.0 (M + H)+. |
| 32 | Int 44 | Enantiomer 1: (1R or S)-7-(6-methylsulfonyl-3-pyridyl)-1-phenyl-2,3-dihydro-1H-pyrrolo[1,2-a]benzimidazole | LCMS (ES+) RT 1.34 min, 390.0 (M + H)+. |

-continued

| Example No. | Precursor | Compound Name | LCMS |
|---|---|---|---|
| 33 | Int 44 | Enantiomer 1: [5-[(1R or S)-1-phenyl-2,3-dihydro-1H-pyrrolo[1,2-a]benzimidazol-7-yl]-2-pyridyl]methanol | LCMS (ES+) RT 1.32 min, 342.0 (M + H)+. |
| 34 | Ex 116 | [1-[2-(difluoromethoxy)phenyl]-6-fluoro-7-(4-methylsulfonylphenyl)-2,3-dihydro-1H-pyrrolo[1,2-a]benzimidazol-3-yl]acetate | LCMS (ES+) RT 4.4 min, 531.2 (M + H)+. |
| 35 | Ex 5 | Enantiomer 2: tert-butyl 4-[5-[(1R or S)-1-[2-(difluoromethoxy)phenyl]-2,3-dihydro-1H-pyrrolo[1,2-a]benzimidazol-7-yl]-2-pyridyl]piperazine-1-carboxylate | LCMS (ES+) RT 4.08 min, 562.51 (M + H)+. |

| Example No. | Precursor | Compound Name | LCMS |
|---|---|---|---|
| 36 | Ex 5 | Enantiomer 2: (1R or S)-7-(6-cyclopropyl-3-pyridyl)-1-[2-(difluoromethoxy)phenyl]-2,3-dihydro-1H-pyrrolo[1,2-a]benzimidazole 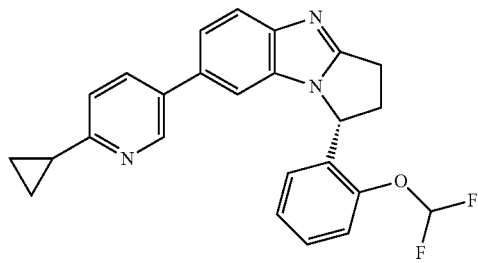 | LCMS (ES+) RT 2.29 min, 418.0 (M + H)+. |
| 37 | Ex 5 | Enantiomer 2: (1R or S)-1-[2-(difluoromethoxy)phenyl]-7-(3-pyridyl)-2,3-dihydro-1H-pyrrolo[1,2-a]benzimidazole 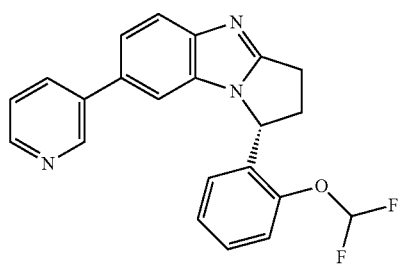 | LCMS (ES+) RT 1.39 min, 378.0 (M + H)+. |
| 38 | Ex 5 | Enantiomer 2: (1R or S)-1-[2-(difluoromethoxy)phenyl]-7-(6-methylsulfonyl-3-pyridyl)-2,3-dihydro-1H-pyrrolo[1,2-a]benzimidazole 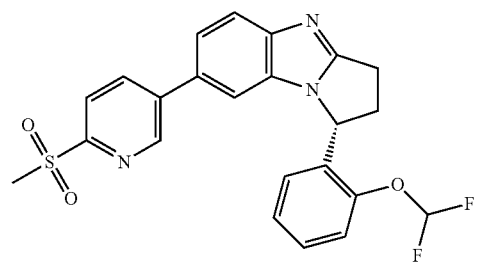 | LCMS (ES+) RT 1.38 min, 456.0 (M + H)+. |
| 39 | Ex. 5 | Enantiomer 2: (1R or S)-1-[2-(difluoromethoxy)phenyl]-7-(1-methylpyrazol-4-yl)-2,3-dihydro-1H-pyrrolo[1,2-a]benzimidazole 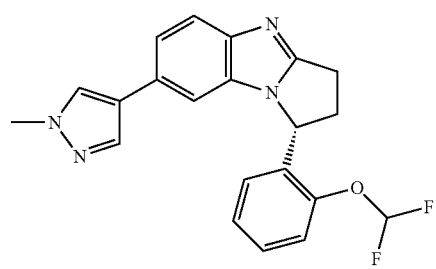 | LCMS (ES+) RT 1.35 min, 381.0 (M + H)+. |

-continued

| Example No. | Precursor | Compound Name | LCMS |
|---|---|---|---|
| 40 | Ex 6 | Enantiomer 2: (1R or S)-1-[2-(difluoromethoxy)phenyl]-6-fluoro-7-(5-fluoro-3-pyridnyl)-2,3-dihydro-1H-pyrrolo[1,2-a]benzimidazole | LCMS (ES+) RT 1.48 min, 414.0 (M + H)+. |
| 41 | Ex 6 | Enantiomer 2: (1R or S)-1-[2-(difluoromethoxy)phenyl]-6-fluoro-7-(4-methyl-3-pyridyl)-2,3-dihydro-1H-pyrrolo[1,2-a]benzimidazole | LCMS (ES+) RT 1.50 min, 410.0 (M + H)+. |
| 42 | Int 44 | Enantiomer 1: tert-butyl 4-[5-[(1R or S)-1-phenyl-2,3-dihydro-1H-pyrrolo[1,2-a]benzimidazol-7-yl]-2-pyridyl]piperazine-1-carboxylate | LCMS (ES+) RT 4.66 min, 496.0 (M + H)+. |

| Example No. | Precursor | Compound Name | LCMS |
|---|---|---|---|
| 43 | Ex 133 | enantiomer 2: (4R or S)-4-[2-(difluoromethoxy)phenyl]-8-fluoro-7-(4-methylsulfonylphenyl)-3,4-dihydro-1H-[1,4]oxazino[4,3-a]benzimidazole 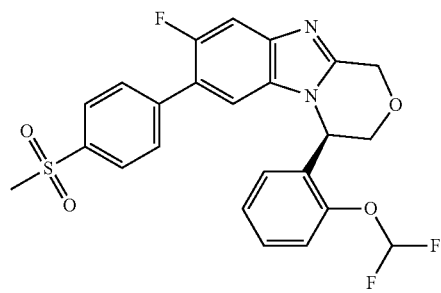 | LCMS (ES+) RT 1.39 min, 489.0 (M + H)+. |
| 44 | Ex 132 | enantiomer 1: (4S or R)-4-[2-(difluoromethoxy)phenyl]-8-fluoro-7-(4-methylsulfonylphenyl)-3,4-dihydro-1H-[1,4]oxazino[4,3-a]benzimidazole 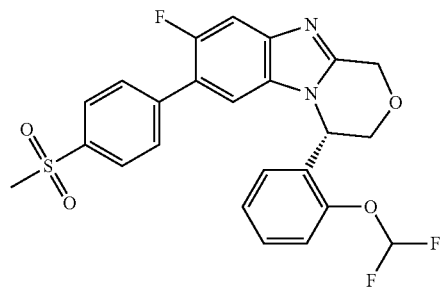 | LCMS (ES+) RT 1.39 min, 489.0 (M + H)+. |
| 45 | Ex 133 | enantiomer 2: (4R or S)-4-[2-(difluoromethoxy)phenyl]-8-fluoro-7-(6-methylsulfonyl-3-pyridyl)-3,4-dihydro-1H-[1,4]oxazino[4,3-a]benzimidazole 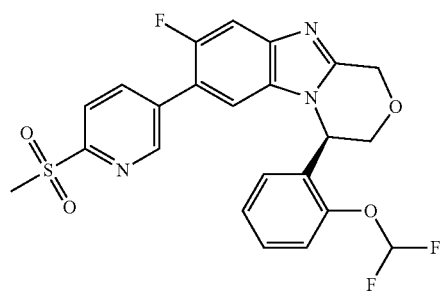 | LCMS (ES+) RT 1.37 min, 490.0 (M + H)+. |

-continued

| Example No. | Precursor | Compound Name | LCMS |
|---|---|---|---|
| 46 | Ex 132 | enantiomer 1: (4S or R)-4-[2-(difluoromethoxy)phenyl]-8-fluoro-7-(6-methylsulfonyl-3-pyridyl)-3,4-dihydro-1H-[1,4]oxazino[4,3-a]benzimidazole | LCMS (ES+) RT 1.37 min, 490.0 (M + H)+. |
| 47 | Ex 133 | enantiomer 2: tert-butyl 4-[5-[(4R or S)-4-[2-(difluoromethoxy)phenyl]-8-fluoro-3,4-dihydro-1H-[1,4]oxazino[4,3-a]benzimidazol-7-yl]-2-pyridyl]piperazine-1-carboxylate | LCMS (ES+) RT 1.50 min, 596.0 (M + H)+. |
| 48 | Ex 132 | enantiomer 1: tert-butyl 4-[5-[(4S or R)-4-[2-(difluoromethoxy)phenyl]-8-fluoro-3,4-dihydro-1H-[1,4]oxazino[4,3-a]benzimidazol-7-yl]-2-pyridyl]piperazine-1-carboxyalte | LCMS (ES+) RT 1.50 min, 596.0 (M + H)+. |

| Example No. | Precursor | Compound Name | LCMS |
|---|---|---|---|
| 49 | Ex 132 | enantiomer 1: (4S or R)-4-[2-(difluoromethoxy)phenyl]-8-fluoro-7-[4-(methylsulfonylmethyl)phenyl]-3,4-dihydro-1H-[1,4]oxazino[4,3-a]benzimidazole | LCMS (ES+) RT 1.34 min, 503.0 (M + H)+. |
| 50 | Ex 145 | enantiomer 1: tert-butyl (4S or R)-4-[2-(difluoromethoxy)phenyl]-8-fluoro-7-(4-methylsulfonylphenyl)-3,4-dihydro-1H-pyrazino[1,2-a]benzimidazole-2-carboxylate | LCMS (ES+) RT 1.53 min, 588.0 (M + H)+. |
| 51 | Ex 145 | enantiomer 1: tert-butyl (4S or R)-4-[2-(difluoromethoxy)phenyl]-8-fluoro-7-(3-methylsulfonylphenyl)-3,4-dihydro-1H-pyrazino[1,2-a]benzimidazole-2-carboxylate | LCMS (ES+) RT 1.53 min, 588.0 (M + H)+. |

| Example No. | Precursor | Compound Name | LCMS |
|---|---|---|---|
| 52 | Ex 145 | enantiomer 1: tert-btuyl (4S or R)-4-[2-(difluoromethoxy)phenyl]-8-fluoro-7-(2-methylsulfonyl-4-pyridyl)-3,4-dihydro-1H-pyrazino[1,2-a]benzimidazole-2-carboxylate | LCMS (ES⁺) RT 1.50 min, 589.0 (M + H)⁺. |
| 53 | Ex 145 | enantiomer 1: tert-butyl (4S or R)-4-[2-(difluoromethoxy)phenyl]-8-fluoro-7-(6-methylsulfonyl-3-pyridyl)-3,4-dihydro-1H-pyrazino[1,2-a]benzimidazole-2-carboxylate | LCMS (ES⁺) RT 1.50 min, 589.0 (M + H)⁺. |
| 54 | Ex 146 | enantiomer 2: tert-butyl (4R or S)-4-[2-(difluoromethoxy)phenyl]-8-fluoro-7-(6-methylsulfonyl-3-pyridyl)-3,4-dihydro-1H-pyrazino[1,2-a]benzimidazole-2-carboxylate | LCMS (ES⁺) RT 1.50 min, 589.0 (M + H)⁺. |

| Example No. | Precursor | Compound Name | LCMS |
|---|---|---|---|
| 55 | Ex 13 | tert-butyl 4-[2-(difluoromethoxy)phenyl]-7-(4-methylsulfonylphenyl)-3,4-dihydro-1H-pyrazino[1,2-a]benzimidazole-2-carboxylate | LCMS (ES+) RT 1.53 min, 570.0 (M + H)+. |
| | | 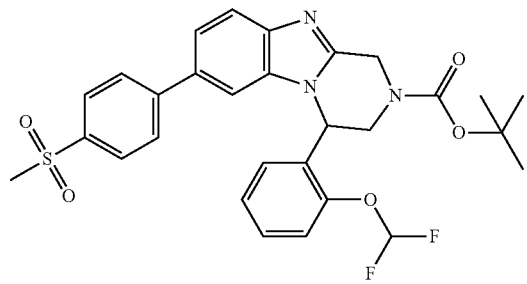 | |
| 56 | Ex 148 | Enantiomer 2: tert-butyl (4R or S)-4-[2-(difluoromethoxy)phenyl]-7-(6-methylsulfonyl-3-pyridyl)-3,4-dihydro-1H-pyrazino[1,2-a]benzimidazole-2-carboxylate | LCMS (ES+) RT 1.41 min, 571.0 (M + H)+. |
| | | 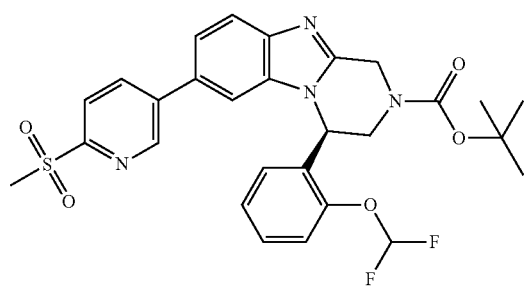 | |
| 57 | Ex 147 | Enantiomer 1: tert-butyl (4S or R)-4-[2-(difluoromethoxy)phenyl]-7-(6-methyslulfonyl-3-pyridyl)-3,4-dihydro-1H-pyrazino[1,2-a]benzimidazole-2-carboxylate | LCMS (ES+) RT 1.41 min, 571.0 (M + H)+. |
| | | 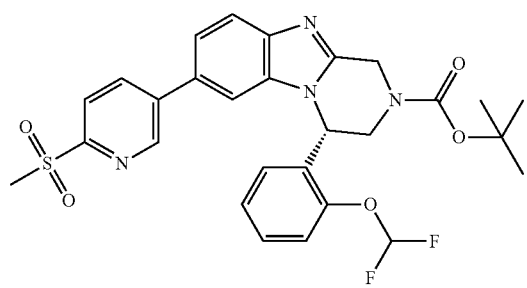 | |

| Example No. | Precursor | Compound Name | LCMS |
|---|---|---|---|
| 58 | Ex 147 | Enantiomer 1: tert-butyl (4S or R)-4-[2-(difluoromethoxy)phenyl]-7-(2-methylsulfonyl-4-pyridyl)-3,4-dihydro-1H-pyrazino[1,2-a]benzimidazole-2-carboxylate 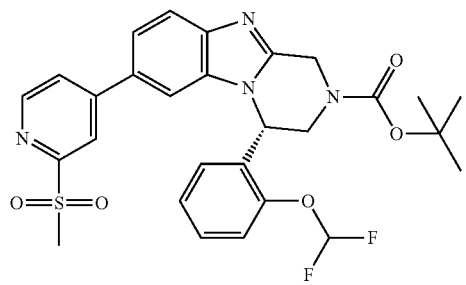 | LCMS (ES+) RT 1.41 min, 571.0 (M + H)+. |
| 59 | Ex 145 | Enantiomer 1: tert-butyl (S or R)-4-[2-(difluoromethoxy)phenyl]-8-fluoro-7-(3-methylsulfonylphenyl)-3,4-dihydro-1H-pyrazino[1,2-a]benzimidazole-2-carboxylate 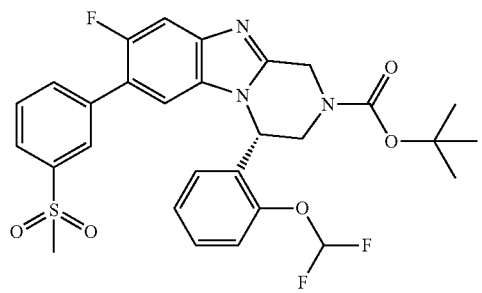 | LCMS (ES+) RT 1.45 min, 588.0 (M + H)+. |
| 60 | Ex 128 | 6-fluoro-7-(6-methylsulfonyl-3-pyridyl)-1-phenyl-2,3-dihydro-1H-pyrrolo[1,2-a]benzimidazol-3-ol 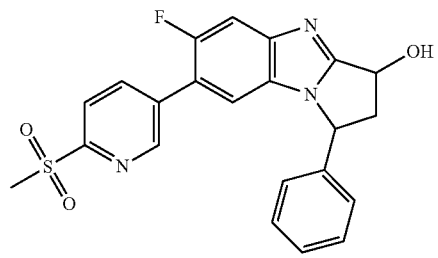 | LCMS (ES+) RT 1.24 min, 424.0 (M + H)+. |

-continued

| Example No. | Precursor | Compound Name | LCMS |
|---|---|---|---|
| 61 | Int 66 | Enantiomer 1: (1S or R)-6-fluoro-1-(4-fluorophenyl)-7-[2-(morpholin-4-yl)pyrimidin-5-yl]-2,3-dihydro-1H-pyrrolo[1,2-a]benzimidazole 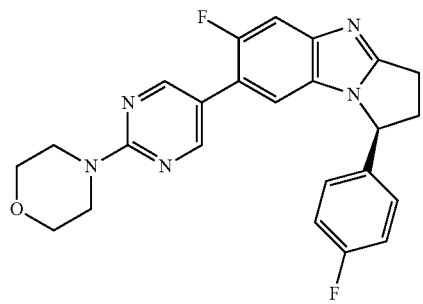 | LCMS (ES+) RT 1.47 min, 434.0 (M + H)+. |
| 62 | Int 67 | Enantiomer 2: (1R or S)-6-fluoro-1-(4-fluorophenyl)-7-[2-(morpholin-4-yl)pyrimidin-5-yl]-2,3-dihydro-1H-pyrrolo[1,2-a]benzimidazole 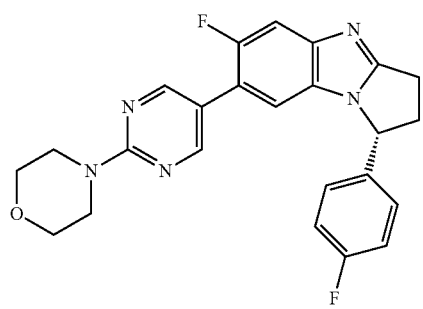 | LCMS (ES+) RT 1.47 min, 434.0 (M + H)+. |
| 63 | Int 55 | Enantiomer 1: (1R or S)-6-fluoro-1-(2-methoxyphenyl)-7-[2-(morpholin-4-yl)pyrimidin-5-yl]-2,3-dihydro-1H-pyrrolo[1,2-a]benzimidazole 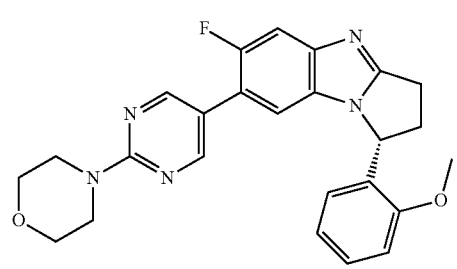 | LCMS (ES+) RT 1.51 min, 446.0 (M + H)+. |
| 64 | Int 56 | Enantiomer 2: (1S or R)-6-fluoro-1-(2-methoxyphenyl)-7-[2-(morpholin-4-yl)pyrimidin-5-yl]-2,3-dihydro-1H-pyrrolo[1,2-a]benzimidazole 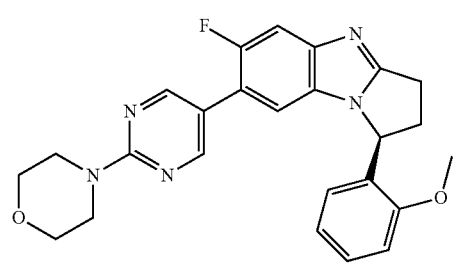 | LCMS (ES+) RT 1.51 min, 446.0 (M + H)+. |

| Example No. | Precursor | Compound Name | LCMS |
|---|---|---|---|
| 65 | Ex 162 | Enantiomer 1: 2-(5-{[1R or S,3R or S)-1-[2-(difluoromethoxy)phenyl]-6-fluoro-3-methoxy-2,3-dihydro-1H-pyrrolo[1,2-a]benzimidazol-7-yl}pyrimidin-2-yl)propan-2-ol | LCMS (ES+) RT 1.46 min, 485.0 (M + H)+. |
| 66 | Int 78 | Enantiomer 1: (1R or S)-6-fluoro-7-[2-(morpholin-4-yl)pyrimidin-5-yl]-1-[2-(trifluoromethyl)phenyl]-2,3-dihydro-1H-pyrrolo[1,2-a]benzimidazole | LCMS (ES+) RT 1.59 min, 484.0 (M + H)+. |
| 67 | Int 79 | Enantiomer 2: (1S or R)-6-fluoro-7-[2-(morpholin-4-yl)pyrimidin-5-yl]-1-[2-(trifluoromethyl)phenyl]-2,3-dihydro-1H-pyrrolo[1,2-a]benzimidazole | LCMS (ES+) RT 1.59 min, 484.0 (M + H)+. |
| 68 | Int 73 | Enantiomer 1: (1S or R)-6-fluoro-1-[2-(methylsulfonyl)phenyl]-7-[2-(morpholin-4-yl)pyrimidin-5-yl]-2,3-dihydro-1H-pyrrolo[1,2-a]benzimidazole | LCMS (ES+) RT 1.37 min, 494.0 (M + H)+. |

| Example No. | Precursor | Compound Name | LCMS |
|---|---|---|---|
| 69 | Ex 165 | Enantiomer 2: 2-(5-{(1S or R,3S or R)-1-[2-(difluoromethoxy)phenyl]-6-fluoro-3-methoxy-2,3-dihydro-1H-pyrrolo[1,2-a]benzimidazol-7-yl}pyrimidin-2-yl)propan-2-ol | LCMS (ES+) RT 1.46 min, 485.0 (M + H)+. |
| 70 | Ex 165 | Enantiomer 2: [1-[5-[(1S or R,3S or R)-1-[2-(difluoromethoxy)phenyl]-6-fluoro-3-methoxy-2,3-dihydro-1H-pyrrolo[1,2-a]benzimidazol-7-yl]-2-pyridyl]-1-methyl-ethoxy]-trimethyl-silane | LCMS (ES+) RT 1.60 min, 556.0 (M + H)+. |
| 71 | Ex 162 | Enantiomer 1: [1-[5-[(1R or S,3R or S)-1-[2-(difluoromethoxy)phenyl]-6-fluoro-3-methoxy-2,3-dihydro-1H-pyrrolo[1,2-a]benzimidazol-7-yl]-2-pyridyl]-1-methyl-ethoxy]-trimethyl-silane | LCMS (ES+) RT 1.60 min, 556.0 (M + H)+. |

| Example No. | Precursor | Compound Name | LCMS |
|---|---|---|---|
| 72 | Int 74 | Enantiomer 2: (1R or S)-6-fluoro-1-[2-(methylsulfonyl)phenyl]-7-[2-(morpholin-4-yl)pyrimidin-5-yl]-2,3-dihydro-1H-pyrrolo[1,2-a]benzimidazole | LCMS (ES⁺) RT 1.38 min, 494.0 (M + H)⁺. |
| 73 | Ex 162 | Enantiomer 1: (1R or S,3R or S)-1-[2-(difluoromethoxy)phenyl]-6-fluoro-3-methoxy-7-[6-(tetrahydro-2H-pyran-4-yl)pyridin-3-yl]-2,3-dihydro-1H-pyrrolo[1,2-a]benzimidazole | LCMS (ES⁺) RT 1.38 min, 510.0 (M + H)⁺. |
| 74 | Ex 161 | Enantiomer 1: (1R or S,3R or S)-1-[2-(difluoromethoxy)phenyl]-6-fluoro-7-[6-(tetrahydro-2H-pyran-4-yl)pyridin-3-yl]-2,3-dihydro-1H-pyrrolo[1,2-a]benzimidazol-3-ol | LCMS (ES⁺) RT 1.38 min, 496.0 (M + H)⁺. |
| 75 | Int 61 | Enantiomer 1: (1R or S)-1-(2-chlorophenyl)-6-fluoro-7-[2-(morpholin-4-yl)pyrimidin-5-yl]-2,3-dihydro-1H-pyrrolo[1,2-a]benzimidazole | LCMS (ES⁺) RT 1.55 min, 450.0 (M + H)⁺. |

| Example No. | Precursor | Compound Name | LCMS |
|---|---|---|---|
| 76 | Int 62 | Enantiomer 2: (1S or R)-1-(2-chlorophenyl)-6-fluoro-7-[2-(morpholin-4-yl)pyrimidin-5-yl]-2,3-dihydro-1H-pyrrolo[1,2-a]benzimidazole 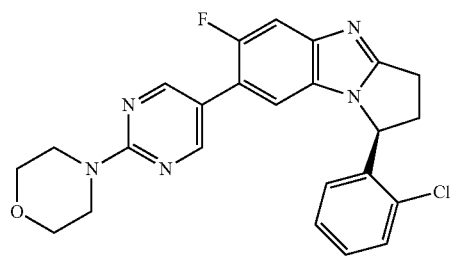 | LCMS (ES+) RT 1.55 min, 450.0 (M + H)+. |
| 77 | Ex 161 | Enantiomer 1: (1R or S,3R or S)-7-(6-cyclopropylpyridin-3-yl)-1-[2-(difluoromethoxy)phenyl]-6-fluoro-2,3-dihydro-1H-pyrrolo[1,2-a]benzimidazol-3-ol 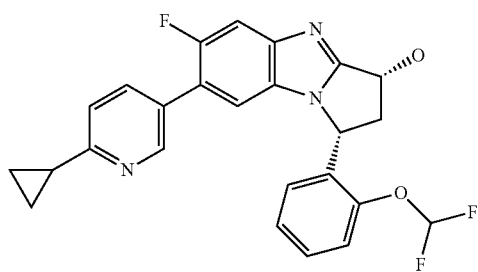 | LCMS (ES+) RT 1.50 min, 452.0 (M + H)+. |
| 78 | Ex 6 | Enantiomer 2 [1-[5-[(1R or S)-1-[2-(difluoromethoxy)phenyl]-6-fluoro-2,3-dihydro-1H-pyrrolo[1,2-a]benzimidazol-7-yl]-2-pyridyl]-1-methyl-ethoxy]-trimethyl-silane 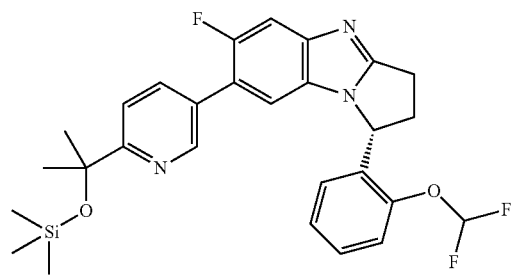 | LCMS (ES+) RT 1.60 min, 526.0 (M + H)+. |

| Example No. | Precursor | Compound Name | LCMS |
|---|---|---|---|
| 79 | Ex 6 | Enantiomer 2: 2-(5-{(1R or S)-1-[2-(difluoromethoxy)phenyl]-6-fluoro-2,3-dihydro-1H-pyrrolo[1,2-a]benzimidazol-7-yl}pyrimidin-2-yl)propan-2-ol | LCMS (ES$^+$) RT 1.42 min, 455.0 (M + H)$^+$. |
| 80 | Ex 6 | Enantiomer 2: (1R or S)-7-(6-cyclopropylpyridin-3-yl)-1-[2-(difluoromethoxy)phenyl]-6-fluoro-2,3-dihydro-1H-pyrrolo[1,2-a]benzimidazole | LCMS (ES$^+$) RT 1.60 min, 436.0 (M + H)$^+$. |
| 81 | Int 74 | Enantiomer 2: (1R or S)-7-(6-cyclopropylpyridin-3-yl)-6-fluoro-1-[2-(methylsulfonyl)phenyl]-2,3-dihydro-1H-pyrrolo[1,2-a]benzimidazole | LCMS (ES$^+$) RT 1.45 min, 448.0 (M + H)$^+$. |
| 82 | Ex 168 | (1R or S)-7-(6-cyclopropylpyridin-3-yl)-1-[2-(difluoromethoxy)phenyl]-3,6-difluoro-2,3-dihydro-1H-pyrrolo[1,2-a]benzimidazole | LCMS (ES$^+$) RT 1.62 min, 454.0 (M + H)$^+$. |

-continued

| Example No. | Precursor | Compound Name | LCMS |
|---|---|---|---|
| 83 | Ex 168 | 2-(5-{(1R or S)-1-[2-(difluoromethoxy)phenyl]-3,6-difluoro-2,3-dihydro-1H-pyrrolo[1,2-a]benzimidazol-7-yl}pyrimidin-2-yl)propan-2-ol | LCMS (ES$^+$) RT 1.45 min, 473.0 (M + H)$^+$. |
| 84 | Ex 161 | Enantiomer 2 (1R or S,3R or S)-1-[2-(difluoromethoxy)phenyl]-6-fluoro-7-[2-(2-hydroxypropan-2-yl)pyrimidin-5-yl]-2,3-dihydro-1H-pyrrolo[1,2-a]benzimidazol-3-ol | LCMS (ES$^+$) RT 1.34 min, 471.0 (M + H)$^+$. |
| 85 | Ex 171 | Diasteroisomer 2: (1R or S,3S or R)-1-[2-(difluoromethoxy)phenyl]-3,6-difluoro-7-[2-(morpholin-4-yl)pyrimidin-5-yl]-2,3-dihydro-1H-pyrrolo[1,2-a]benzimidazole | LCMS (ES$^+$) RT 1.62 min, 500.0 (M + H)$^+$. |

| Example No. | Precursor | Compound Name | LCMS |
|---|---|---|---|
| 86 | Ex 170 | Diasteroisomer 1: (1R or S,3R or S)-1-[2-(difluoromethoxy)phenyl]-3,6-difluoro-7-[2-(morpholin-4-yl)pyrimidin-5-yl]-2,3-dihydro-1H-pyrrolo[1,2-a]benzimidazole | LCMS (ES+) RT 1.62 min, 500.0 (M + H)+. |
| 87 | Ex 171 | Diasteroisomer 2: 2-(5-{(1R or S,3S or R)-1-[2-(difluoromethoxy)phenyl]-3,6-difluoro-2,3-dihydro-1H-pyrrolo[1,2-a]benzimidazol-7-yl}pyrimidin-2-yl)propan-2-ol | LCMS (ES+) RT 1.45 min, 473.0 (M + H)+. |
| 88 | Ex 170 | Diasteroisomer 1: 2-(5-{(1R or S,3R or S)-1-[2-(difluoromethoxy)phenyl]-3,6-difluoro-2,3-dihydro-1H-pyrrolo[1,2-a]benzimidazol-7-yl}pyrimidin-2-yl)propan-2-ol | LCMS (ES+) RT 1.45 min, 473.0 (M + H)+. |
| 89 | Ex 161 | Enantiomer 2: (1R or S,3R or S)-1-[2-(difluoromethoxy)phenyl]-6-fluoro-7-{6-[(methylsulfonyl)methyl]pyridin-3-yl}-2,3-dihydro-1H-pyrrolo[1,2-a]benzimidazol-3-ol | LCMS (ES+) RT 1.26 min, 504.0 (M + H)+. |

-continued

| Example No. | Precursor | Compound Name | LCMS |
|---|---|---|---|
| 90 | Ex 161 | Enantiomer 2: (1R or S,3R or S)-1-[2-(difluoromethoxy)phenyl]-6-fluoro-7-[1-(2-methylpropyl)-1H-pyrazol-4-yl]-2,3-dihydro-1H-pyrrolo[1,2-a]benzimidazol-3-ol 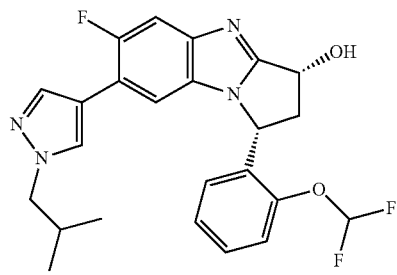 | LCMS (ES+) RT 1.46 min, 457.0 (M + H)+. |
| 91 | Ex 161 | Enantiomer 2: (1R or S,3R or S)-1-[2-(difluoromethoxy)phenyl]-6-fluoro-7-[2-(propan-2-yl)pyrimidin-5-yl]-2,3-dihydro-1H-pyrrolo[1,2-a]benzimidazol-3-ol 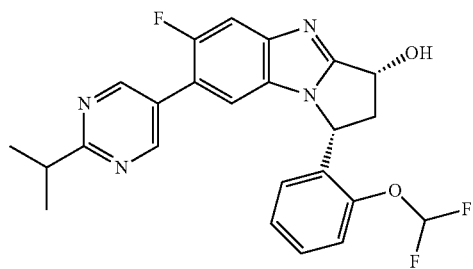 | LCMS (ES+) RT 1.48 min, 455.0 (M + H)+. |
| 92 | Ex 161 | Enantiomer 2: (1R or S,3R or S)-1-[2-(difluoromethoxy)phenyl]-6-fluoro-7-[2-(tetrahydro-2H-pyran-4-yl)pyrimidin-5-yl]-2,3-dihydro-1H-pyrrolo[1,2-a]benzimidazol-3-ol 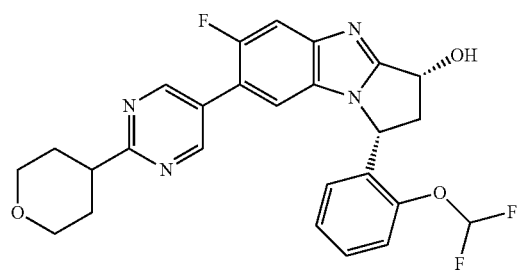 | LCMS (ES+) RT 1.37 min, 497.0 (M + H)+. |

| Example No. | Precursor | Compound Name | LCMS |
|---|---|---|---|
| 93 | Ex 173 | (1R or S,3R or S)-1-[2-(difluoromethoxy)phenyl]-6-fluoro-7-[6-(tetrahydro-2H-pyran-4-yl)pyridin-3-yl]-2,3-dihydro-1H-pyrrolo[1,2-a]benzimidazol-3-amine | LCMS (ES+) RT 1.34 min, 495.0 (M + H)+. |
| 94 | Ex 11 | Ethyl 1-[5-{1-[2-(difluoromethoxy)phenyl]-6-fluoro-2,3-dihydro-1H-pyrrolo[1,2-a]benzimidazol-7-yl}pyrimidin-2-yl]-4-methyl-piperidine-4-carboxylate | LCMS (ES+) RT 1.57 min, 566.0 (M + H)+. |
| 95 | Ex 3 | 1-(5-{1-[2-(difluoromethoxy)phenyl]2,3-dihydro-1H-pyrrolo[1,2-a]benzimidazol-7-yl}pyrimidin-2-yl)-1,4-diazepan-5-one | LCMS (ES+) RT 1.30 min, 491.0 (M + H)+. |

-continued

| Example No. | Precursor | Compound Name | LCMS |
|---|---|---|---|
| 96 | Ex 3 | 1-[2-(difluoromethoxy)phenyl]-7-[4-(methylsulfonyl)phenyl]-2,3-dihydro-1H-pyrrolo[1,2-a]benzimidazole | LCMS (ES+) RT 1.43 min, 455.0 (M + H)+. |
| 97 | Ex 4 | Enantiomer 1: 1-[5-[(1S or R)-1-[2-(difluoromethoxy)phenyl]-2,3-dihydro-1H-pyrrolo[1,2-a]benzimidazol-7-yl]pyrimidin-2-yl]-1,4-diazepan-5-one | LCMS (ES+) RT 1.32 min, 491.0 (M + H)+. |
| 98 | Ex 5 | Enantiomer 2: 1-[5-[(1R or S)-1-[2-(difluoromethoxy)phenyl]-2,3-dihydro-1H-pyrrolo[1,2-a]benzimidazol-7-yl]pyrimidin-2-yl]-1,4-diazepan-5-one | LCMS (ES+) RT 1.32 min, 491.0 (M + H)+. |

-continued

| Example No. | Precursor | Compound Name | LCMS |
|---|---|---|---|
| 99 | Ex 145 | Enantiomer 1: tert-butyl (4S or R)-4-[2-(Difluoromethoxy)phenyl]-8-fluoro-7-[2-[(1S,5R)-8-methoxycarbonyl-3-azabicyclo[3.2.1]octan-3-yl]pyrimidin-5-yl]-3,4-dihydro-1H-pyrazino[1,2-a]benzimidazole-2-carboxylate | LCMS (ES+) RT 1.60 min, 579.0 (M + H − tBu)+. |

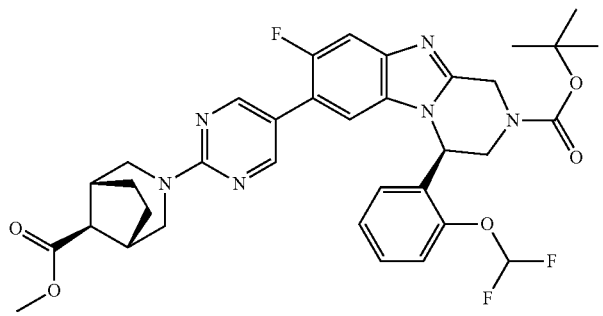

| 100 | Int 31 | Ethyl 1-[5-[1-[2-(difluoromethoxy)phenyl]-6-fluoro-2,3-dihydro-1H-imidazo[1,2-a]benzimidazol-7-yl]pyrimidin-2-yl]-4-methyl-piperidine-4-carboxylate | LCMS (ES+) RT 1.59 min, 567.2 (M + H)+. |

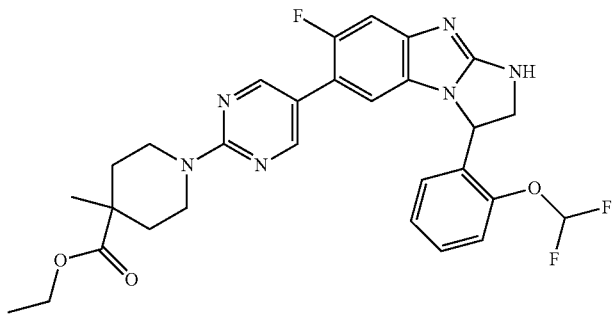

| 101 | Int 34 | methyl (1S,5R)-3-[5-[1-1-[2-(difluoromethoxy)phenyl]-2,3-dihydro-1H-imidazo[1,2-a]benzimidazol-7-yl]pyrimidin-2-yl]-3-azabicyclo[3.2.1]octane-8-carboxylate | LCMS (ES+) RT 1.53 min, 547.0 (M + H)+. |

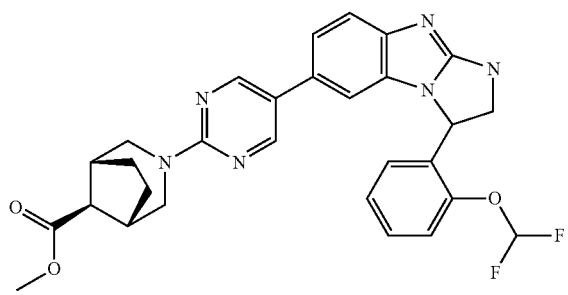

| Example No. | Precursor | Compound Name | LCMS |
|---|---|---|---|
| 102 | Ex 5 | Enantiomer 2: methyl (1S,5R)-3-[5-[(1R or S)-1-[2-(difluoromethoxy)phenyl]-2,3-dihydro-1H-pyrrolo[1,2-a]benzimidazol-7-yl]pyrimidin-2-yl]-3-azabicyclo[3.2.1]octane-8-carboxylate | LCMS (ES+) RT 2.52 min, 546.8 (M + H)+. |

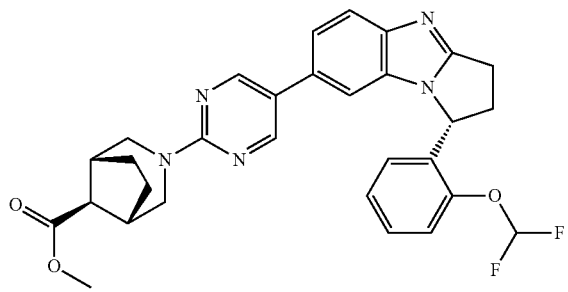

Example 103 Method D

5-[1-(2-methylphenyl)-2,3-dihydro-1H-pyrrolo[1,2-a]benzimidazol-7-yl]pyridin-2(1H)-one

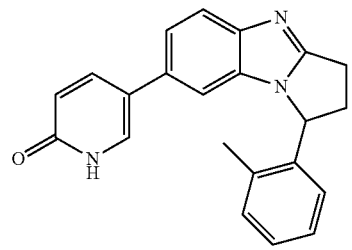 [SMILES: Cc1ccccc1C1CCc2nc3ccc(-c4ccc(=O)[nH]c4)cc3n21]

To a solution of Example 18 (0.10 g, 0.28 mmol) in EtOH (2 mL) was added aq. HBr (2 mL). The reaction was heated at 95° C. for 18 h. The reaction mixture concentrated in vacuo and the residue was diluted with EtOAc (10 mL), washed with sat. aq. NaHCO₃ solution (10 mL), water (10 mL), brine (10 mL) and the organic layer was separated, dried (Na₂SO₄) and concentrated in vacuo. The residue was purified by preparative TLC yielding the title compound (0.06 g, 62%). ¹H NMR (400 MHz, CDCl₃) δ 12.85 (s, 1H), 7.77 (d, J 8.4 Hz, 1H), 7.73-7.63 (m, 1H), 7.44 (d, J 2.7 Hz, 1H), 7.32-7.01 (m, 4H), 6.85 (d, J 1.8 Hz, 1H), 6.63 (dd, J 16.2, 8.6 Hz, 2H), 5.70 (dd, J 7.5, 4.9 Hz, 1H), 3.29-3.03 (m, 3H), 2.61-2.36 (m, 4H). LCMS (ES+) RT 1.35 min, 342.1 (M+H)+.

Example 104

5-(1-phenyl-2,3-dihydro-1H-pyrrolo[1,2-a]benzimidazol-7-yl)pyridin-2(1H)-one

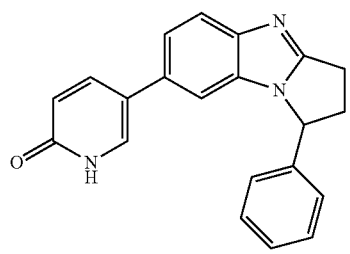 [SMILES: O=c1ccc(-c2ccc3nc4n(c3c2)C(c2ccccc2)CC4)c[nH]1]

The title compound was prepared from Example 20 (0.10 g, 0.02 mmol) and aq. HBr by the Method D, (0.07 g, 71%). ¹H NMR (400 MHz, DMSO-d₆) δ 7.75 (d, J 8.4 Hz, 1H), 7.64 (dd, J 9.5, 2.6 Hz, 1H), 7.51-7.28 (m, 4H), 7.33-7.06 (m, 3H), 6.82 (d, J 1.8 Hz, 1H), 6.61 (d, J 9.4 Hz, 1H), 5.48 (t, J 6.7 Hz, 1H), 3.30-3.06 (m, 3H), 2.70-2.51 (m, 1H). LCMS (ES+) RT 1.21 min, 328.1 (M+H)+.

Example 105

Enantiomer 1: (1S or R)-1-[2-(difluoromethoxy)phenyl]-6-fluoro-7-(4-methylsulfonylphenyl)-2,3-dihydro-1H-imidazo[1,2-a]benzimidazole

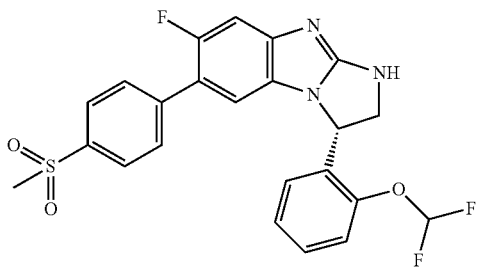 [SMILES: CS(=O)(=O)c1ccc(-c2cc3c(cc2F)nc2n3[C@@H](c3ccccc3OC(F)F)CN2)cc1]

The title compound was isolated from Example 22 by chiral purification under SFC conditions on Chiralpak IA (50*266 mm*mm, flow 360 mL/min, 25° C., CO2+20% MeOH, injection of 5 mL solution at a concentration of 8 g/L). First eluting enantiomer (6.88 min).

Example 106

Enantiomer 2: (1R or S)-1-[2-(difluoromethoxy)phenyl]-6-fluoro-7-(4-methylsulfonylphenyl)-2,3-dihydro-1H-imidazo[1,2-a]benzimidazole

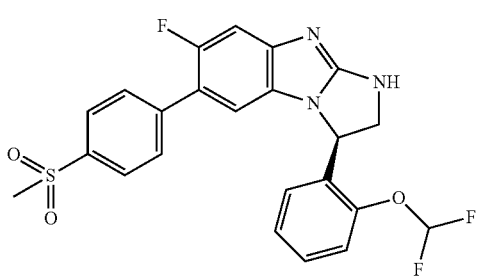 [SMILES: CS(=O)(=O)c1ccc(-c2cc3c(cc2F)nc2n3[C@H](c3ccccc3OC(F)F)CN2)cc1]

The title compound was isolated from Example 22 by chiral purification under SFC conditions on Chiralpak IA (50*266 mm*mm, flow 360 mL/min, 25° C., CO$_2$+20% MeOH, injection of 5 mL solution at a concentration of 8 g/L). Second eluting enantiomer (9.06 min).

Example 107

Enantiomer 1: (1S or R)-1-[2-(difluoromethoxy)phenyl]-7-(4-methylsulfonylphenyl)-2,3-dihydro-1H-imidazo[1,2-a]benzimidazole

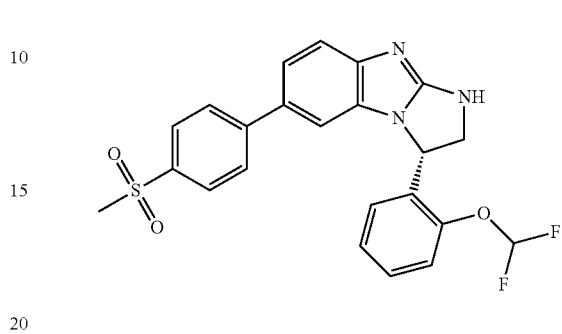

The title compound was prepared from Example 23 by chiral purification under LC conditions on Lux-Cell-2 (76*370 mm*mm, flow 200 mL/min, 30° C., EtOH 100%, injection of 10 mL solution at a concentration of 1.8 g/L) yielding the title compound (9 mg, 50%, first eluting enantiomer, RT 15 min) and the second eluting enantiomer (RT 24 min). LCMS (ES$^+$) RT 3.4 min, 456.3 (M+H)$^+$.

Example 108 (Method F)

Enantiomer 2: (1R or S)-1-[2-(difluoromethoxy)phenyl]-6-fluoro-7-(6-piperazin-1-yl-3-pyridyl)-2,3-dihydro-1H-pyrrolo[1,2-a]benzimidazole

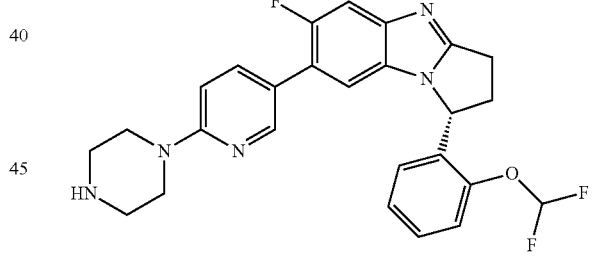

Example 24 (1.0 g, 1.73 mmol, 1 eq.) was dissolved in 1,4-dioxane (25 mL/mmol and HCl/1,4-dioxane 4 M (0.436 mL, 1 eq.) was added, followed by water (2 mL). The mixture was stirred 4 h at r.t. The reaction was concentrated in vacuo and the residue was dissolved in DCM (100 mL) and water (50 mL). The organic layer was discarded and the aq. layer was basified with Na$_2$CO$_3$ and extracted with DCM (2×100 mL). The organic layer was separated, dried (MgSO$_4$) and concentrated in vacuo to afford the title compound as a foam (650 mg, 79%). $^1$H NMR (400 MHz, CDCl$_3$) δ 8.19 (s, 1H), 7.64 (dt, J 8.8 Hz, J 2.1 Hz, 1H), 7.49 (d, J 11.2 Hz, 1H), 7.35 (td, J 7.7 Hz, J 1.2 Hz, 1H), 7.21 (d, J 8.1 Hz, 1H), 7.13 (t, J 7.3 Hz, 1H), 6.84 (d, J 7.6 Hz, 1H), 6.80 (d, J 6.7 Hz, 1H), 6.66 (d, J 8.8 Hz, 1H), 6.61 (t, J 73.2 Hz, 1H), 5.84 (dd, J 7.5 Hz, J 4.8 Hz, 1H), 3.54 (m, 4H), 3.19 (m, 3H), 3.00 (m, 4H), 2.55 (m, 1H). LCMS (ES$^+$) RT 2.99 min, 480 (M+H)$^+$.

Example 109

Enantiomer 2: 5-[(1R or S)-1-[2-(difluoromethoxy)phenyl]-6-fluoro-2,3-dihydro-1H-pyrrolo[1,2-a]benzimidazol-7-yl]-1H-pyridin-2-one

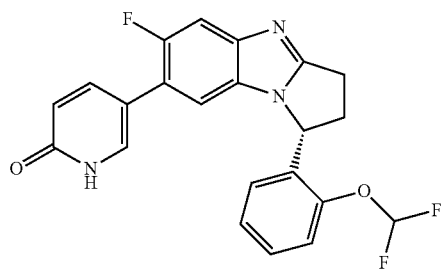 [SMILES: O=c1ccc(-c2cc3c(cc2F)nc2n3[C@@H](c3ccccc3OC(F)F)CC2)c[nH]1]

The title compound was prepared from Example 25 (26 mg, 0.064 mmol, 1.0 eq) by the Method D, yielding the title compound as a colorless glassy solid (17 mg, 65%). $^1$H NMR (400 MHz, CDCl$_3$) δ 7.61 (d, J 9.4 Hz, 1H), 7.49 (d, J 11.3 Hz, 1H), 7.45 (d, J 1.6 Hz, 1H), 7.37 (t, J 7.4 Hz, 1H), 7.24 (t, J 8.6 Hz, 1H), 7.14 (t, J 7.6 Hz, 1H), 6.78 (d, J 7.7 Hz, 1H), 6.75 (d, J 6.8 Hz, 1H), 6.65 (t, J 73.4 Hz, 1H), 6.60 (d, J 9.4 Hz, 1H), 5.84 (m, 1H), 3.21 (m, 3H), 2.56 (m, 1H). LCMS (condition #AC, ES$^+$) RT 3.13 min, 412.3 (M+H)$^+$, 96.3% purity. LCMS (ES$^+$) RT 3.71 min, 412.1 (M+H)$^+$.

Example 110

Enantiomer 2: 1-[4-[5-[(1R or S)-1-[2-(difluoromethoxy)phenyl]-6-fluoro-2,3-dihydro-1H-pyrrolo[1,2-a]benzimidazol-7-yl]-2-pyridyl]piperazin-1-yl]ethanone

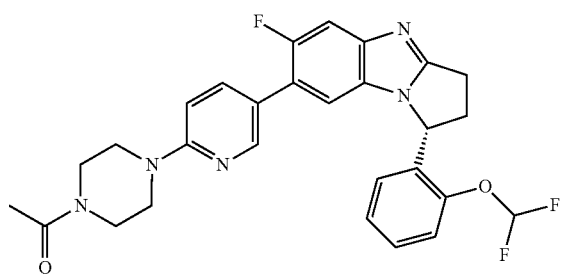 [SMILES: CC(=O)N1CCN(c2ccc(-c3cc4c(cc3F)nc3n4[C@@H](c4ccccc4OC(F)F)CC3)cn2)CC1]

To a solution of Example 108 (0.03 g, 0.067 mmol) and PS-DIPEA (Argonaut No 800280, 3.53 mmol/g, 0.035 g, 0.125 mmol) in DCM (5 mL/g) was added a solution of acetyl chloride (5.4 mg, 0.068 mmol, 1.1 eq.) in DCM (0.1 mL). The reaction was stirred for 2 h at r.t. The reaction mixture was filtered off and the filtrate was concentrated in vacuo. The residue was purified by column chromatography (SiO$_2$, 0-3% methanolic ammonia/DCM), yielding the title compound (12 mg, 36%). $^1$H NMR (400 MHz, CDCl$_3$) δ 8.21 (s, 1H), 7.66 (m, 1H), 7.50 (d, J 11.2 Hz, 1H), 7.35 (m, 1H), 7.21 (d, J 8.0 Hz, 1H), 7.13 (t, J 7.5 Hz, 1H), 6.64 (m, 4H), 5.85 (m, 1H), 3.74 (m, 2H), 3.65 (m, 2H), 3.58 (m, 2H), 3.53 (m, 2H), 3.20 (m, 3H), 2.55 (m, 1H), 2.15 (s, 3H). LCMS (ES$^+$) RT 3.4 min, 522.2 (M+H)$^+$.

Example 111

Enantiomer 2: (1R or S)-1-[2-(difluoromethoxy)phenyl]-6-fluoro-7-[6-(4-methylpiperazin-1-yl)-3-pyridyl]-2,3-dihydro-1H-pyrrolo[1,2-a]benzimidazole

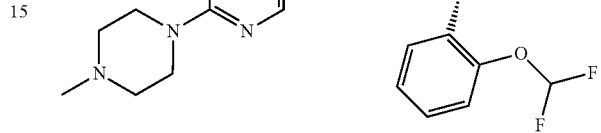

A solution of Example 108 (0.03 g, 0.067 mmol) and formaldehyde (33 μL, 0.43 mmol, 7 eq.) in MeOH (5 mL/g) was stirred for 4 h. MP-CNBH$_3$ (Biotage, ref 800406, loading 2.49 mmol/g, 70.5 mg, 0.173 mmol, 2.7 eq.) was added. The reaction was stirred at r.t. for 20 h. Formaldehyde (0.1 mL, 1.23 mmol, 18 eq.) was added, followed by NaBH$_3$CN (10 mg, 1.6 mmol, 23 eq.). The reaction was heated at 60° C. for 2 h. The mixture was filtered off and the filtrate was concentrated in vacuo. The residue was purified by column chromatography (SiO$_2$, 0-5% methanolic ammonia/DCM), yielding the title compound (20 mg, 78%). $^1$H NMR (400 MHz, CDCl$_3$) δ 8.19 (s, 1H), 7.63 (dt, J 8.7, 2.0 Hz, 1H), 7.48 (d, J 11.2 Hz, 1H), 7.34 (m, 1H), 7.21 (d, J 8.2 Hz, 1H), 7.12 (t, J 7.6 Hz, 1H), 6.64 (m, 4H), 5.84 (m, 1H), 3.59 (m, 4H), 3.19 (m, 3H), 2.55 (m, 5H), 2.35 (s, 3H). LCMS (ES$^+$) RT 2.9 min, 494.3 (M+H)$^+$.

Example 112

Enantiomer 2: (1R or S)-1-[2-(difluoromethoxy)phenyl]-6-fluoro-7-[6-(4-methylsulfonylpiperazin-1-yl)-3-pyridyl]-2,3-dihydro-1H-pyrrolo[1,2-a]benzimidazole To a solution of Example 108 (0.03 g, 0.067 mmol) and PS-DIEA (Argonaut Technologies, No 800280, loading 3.53 mmol/g, 70 mg, 0.250 mmol, 4 eq.) in DCM (5 mL/g) was added a solution of methanesulfonyl chloride (16.2 mg, 0.125 mmol, 2.2 eq.) in DCM (0.1 mL). The reaction was stirred at r.t. for 2 h. The reaction was filtered off and the filtrate was concentrated in vacuo. The residue was purified by column chromatography (SiO$_2$, 0-5% methanolic ammonia/DCM), yielding the title compound (20 mg, 57%). $^1$H NMR (400 MHz, CDCl₃) δ 8.21 (d, J 0.5 Hz, 1H), 7.67 (d, J 9.1 Hz, 1H), 7.49 (m, 1H), 7.35 (m, 1H), 7.22 (d, J 8.3 Hz, 1H), 7.13 (t, J 7.4 Hz, 1H), 6.66 (m, 4H), 5.90 (m, 1H), 3.70 (m, 4H), 3.26 (m, 7H), 2.80 (s, 3H), 2.55 (m, 1H). LCMS (ES⁺) RT 3.8 min, 558.3 (M+H)⁺.

Example 113

Enantiomer 1: (1R or S)-7-[6-(chloromethyl)-3-pyridyl]-1-phenyl-2,3-dihydro-1H-pyrrolo[1,2-a]benzimidazole

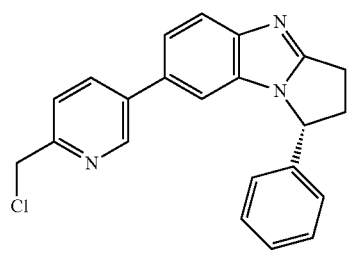 [SMILES: ClCc1ccc(-c2ccc3nc4n(c3c2)[C@@H](c2ccccc2)CC4)cn1]

To a solution of Example 33 (20 mg, 0.059 mmol) in CHCl₃ (0.2 mL) was added at 0° C. SOCl₂ (0.021 mL, 35 mg, 0.29 mmol, 5.0 eq.). The mixture was then heated at 60° C. for 3 h. A sat. aq. solution of NaHCO₃ was added, the mixture was extracted with DCM, dried (MgSO₄) and concentrated in vacuo to yield to the title compound (12 mg) used in the next step without further purification. LCMS (ES⁺) RT 4.58 min, 360.2/362.1 (M+H)⁺.

Example 114

Enantiomer 1: (1R or S)-7-[6-(methylsulfonylmethyl)-3-pyridyl]-1-phenyl-2,3-dihydro-1H-pyrrolo[1,2-a]benzimidazole

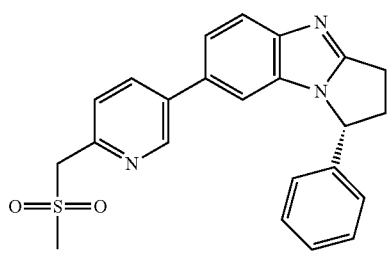 [SMILES: CS(=O)(=O)Cc1ccc(-c2ccc3nc4n(c3c2)[C@@H](c2ccccc2)CC4)cn1]

Example 113 (22 mg, 0.06 mmol, 1.0 eq.), sodium methanesulfinate (26 mg, 0.25 mmol, 4 eq.), NaI (1 mg, 0.07 mmol, 0.1 eq.) were heated at 100° C. in EtOH (0.75 mL) under microwave irradiation (300 Watt) for 15 min. The reaction mixture was diluted with water and extracted with DCM. The organics were dried (Na₂SO₄) and concentrated in vacuo. The residue was purified by column chromatography (SiO₂, 2-5% methanolic ammonia/DCM), yielding the title compound as a white solid (14 mg, 56%). ¹H NMR (400 MHz, CDCl₃) δ 8.67 (d, J 1.9 Hz, 1H), 7.82 (d, J 8.3 Hz, 1H), 7.80 (dd, J 7.9 Hz, J 1.9 Hz, 1H), 7.48 (d, J 8.0 Hz, 1H), 7.35-7.44 (m, 4H), 7.21 (d, J 2.0 Hz, 1H), 7.19 (t, J 1.4 Hz, 1H), 6.98 (s, 1H), 5.51 (t, J 6.4 Hz, 1H), 4.42 (s, 2H), 3.29 (ddd, J 14.3 Hz, J 8.1 Hz, 1H), 3.12-3.24 (m, 2H), 2.92 (s, 3H), 2.63 (m, 1H). LCMS (ES⁺) RT 3.7 min, 404.3 (M+H)⁺.

Example 115

(1R or S,3R or S)-1-[2-(difluoromethoxy)phenyl]-6-fluoro-7-(6-methylsulfonyl-3-pyridyl)-2,3-dihydro-1H-pyrrolo[1,2-a]benzimidazol-3-ol

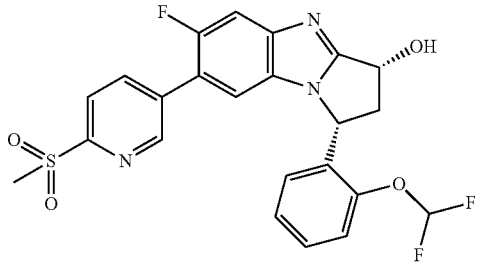 [SMILES: CS(=O)(=O)c1ccc(-c2cc3c(cc2F)nc2n3[C@@H](c3ccccc3OC(F)F)C[C@H]2O)cn1]

A solution A was prepared with Example 32 (1.07 mg, 0.00226 mmol, 1 eq) in 400 μL of MeCN and was diluted with 1.6 mL of water to reach a 0.5 mg/mL. A solution B was prepared from a solution of D-Glucose 6-phosphate disodium salt hydrate (2.113 g, 100 mM), B-nicotinamide adenine dinucleotide phosphate (533.5 mg, 10 mM) and 700 μL of MgCl₂.6H₂O (1 M) in 69 mL of phosphate buffer (100 mM, pH=7.4). In a glassware tube, 5.5 mL of phosphate buffer, 1 mL of mouse microsome (20 mg/mL Male CD1 pool of 1042, M1000), 1 mL of solution A, 2.5 mL of solution B, 12 μL of glucose-6-phosphate dehydrogenase was incubated at 37° C. under swelling for 30 minutes. The incubation was stopped by addition of MeCN (5 mL) and the tube was centrifuged for 15 minutes at 3000 rpm. The title compound was purified from the supernatant by preparative 2D LCMS yielding the title compound as a white solid (116 μg, 20%). ¹H NMR (400 MHz, DMSO-d₆) δ. 8.81 (s, 1H), 8.19 (d, J 8.3 Hz, 1H), 8.09 (d, J 8.1 Hz, 1H), 7.72 (d, J 11.7 Hz, 1H), 7.40 (d, J 7.3 Hz, 1H), 7.36 (t, J 74.0 Hz, 1H), 7.30 (d, J 7.9 Hz, 1H), 7.19 (m, 2H), 6.96 (d, J 7.6 Hz, 1H), 6.21 (bs, 1H), 5.87 (dd, J 7.9 Hz, J 4.8 Hz, 1H), 5.27 (m, 1H), 3.49 (dt, J 13.6 Hz, J 7.8 Hz, 1H), 3.30 (s, 3H), 2.30 (dt, J 13.3 Hz, J₂ 4.3 Hz, 1H). LCMS (ES+) RT 3.83 min, 490.2 (M+H)⁺.

Example 116

[7-bromo-1-[2-(difluoromethoxy)phenyl]-6-fluoro-2,3-dihydro-1H-pyrrolo[1,2-a]benzimidazol-3-yl]acetate

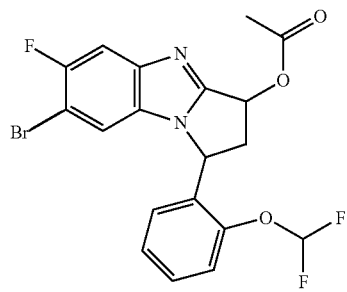

Intermediate 99 (37 g, 85.8 mmol) was dissolved in acetic anhydride (160 mL). ZnCl₂ (11.7 g, 85.8 mmol, 1.0 eq.) was added and the mixture was stirred at r.t. for 2 min then heated at 90° C. for 45 min. The mixture was chilled to 0° C., then water (200 mL) and EtOAc (200 mL) were added. The mixture decanted slowly after the addition of 50 mL water. The aq. layer was extracted with EtOAc (50 mL 2×). The combined organic layers were washed with an aq. solution of NaOH (1 N, 2×100 mL), then brine and then dried (MgSO$_4$), concentrated in vacuo to yield a black oil as a residue (52 g) which was purified by column chromatography (SiO$_2$, 0-1% methanolic ammonia/DCM). The combined fractions containing the desired compounds were purified by column chromatography (SiO$_2$, 0-35% EtOAc/heptane), to yield of the title compound (8.3 g, 21%, as a mixture of 4 isomers). LCMS (ES$^+$) RT 4.9 min, 455.1/457.1.1 (M+H)$^+$.

Example 117

1-[2-(difluoromethoxy)phenyl]-6-fluoro-7-(4-methylsulfonylphenyl)-2,3-dihydro-1H-pyrrolo[1,2-a]benzimidazol-3-ol

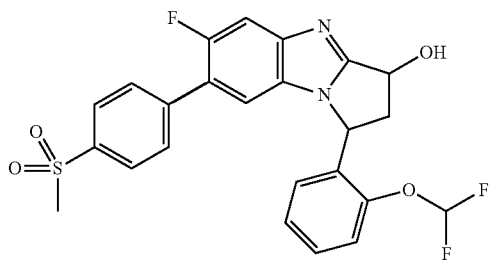

Example 34 (900 mg, 1.70 mmol) and K$_2$CO$_3$ (355 mg, 2.5 mmol, 1.5 eq.) were poured in MeOH (3.4 mL) and the mixture was stirred 2 h at r.t. The reaction mixture was concentrated in vacuo. Water (2 mL) and EtOAc (10 mL) were added. The mixture was decanted and the aq. layer was extracted with EtOAc. The combined organic layers were dried (MgSO$_4$), concentrated in vacuo, to yield the title compound as a colorless oil (886 mg, 89%) used in the next step without any further purification. LCMS (ES$^+$) RT 3.9 min, 489.2 (M+H)$^+$.

Examples 118, 119, 120 and 121

(1R or S,3R or S)(diastereoisomer 1)-1-[2-(difluoromethoxy)phenyl]-6-fluoro-7-(4-methylsulfonylphenyl)-2,3-dihydro-1H-pyrrolo[1,2-a]benzimidazol-3-ol, (1R or S,3S or R) (diastereoisomer 2)-1-[2-(difluoromethoxy)phenyl]-6-fluoro-7-(4-methylsulfonylphenyl)-2,3-dihydro-1H-pyrrolo[1,2-a]benzimidazol-3-ol, (1R or S,3S or R) (diastereoisomer 3)-1-[2-(difluoromethoxy) phenyl]-6-fluoro-7-(4-methylsulfonylphenyl)-2,3-dihydro-H-pyrrolo[1,2-a]benzimidazol-3-ol and (1S or R, 3S or R) (diastereoisomer 4)-1-[2-(difluoromethoxy) phenyl]-6-fluoro-7-(4-methylsulfonylphenyl)-2,3-dihydro-H-pyrrolo[1,2-a]benzimidazol-3-ol

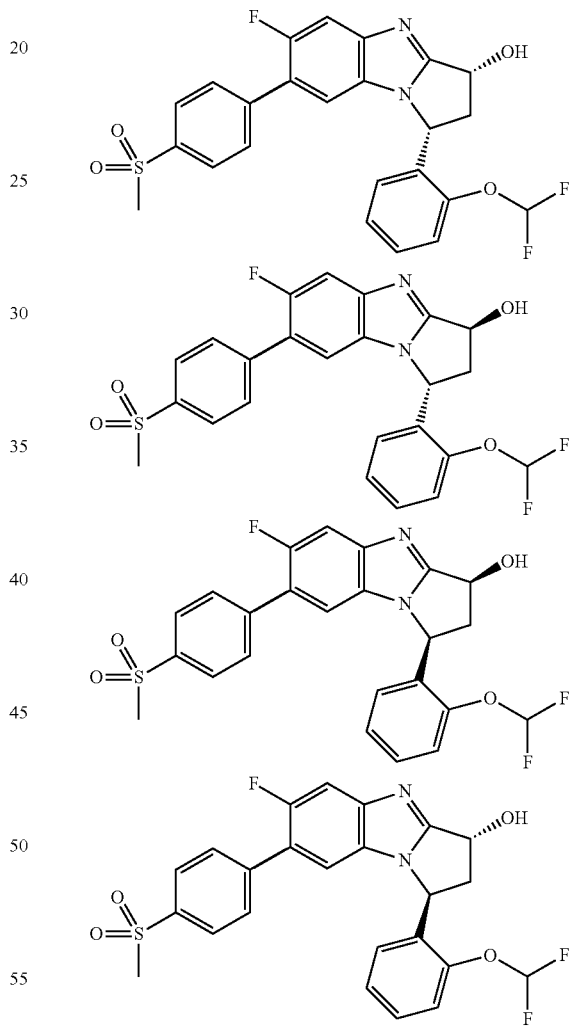

The title compounds were isolated by purification of Example 117 under LC conditions on Lux-Cell-4 (76*265 mm*mm, flow 200 mL/min, 30° C., EtOH/heptane 1/1, injection of 83 mL solution at a concentration of 1.8 g/L).
The first eluting enantiomer (RT 12.89 min) was collected and the fractions were evaporated to yield (diastereoisomer 1) (1R or S,3R or S)-1-[2-(difluoromethoxy)phenyl]-6-fluoro-7-(4-methylsulfonylphenyl)-2,3-dihydro-1H-pyrrolo[1,2-a]benzimidazol-3-ol (115 mg, 14%, Example 118). $^1$H NMR δ: 7.97 (d, J 8.4 Hz, 2H), 7.67 (m, 3H), 7.40 (m, 1H), 7.31 (m, 1H), 7.19 (m, 1H), 7.07 (d, J 6.9 Hz, 1H), 6.99 (d, J 7.7 Hz, 1H), 6.14 (d, J 4.8 Hz, 1H), 5.87 (dd, J 8.0 Hz, J 4.8 Hz, 1H), 5.27 (m, 1H), 3.49 (m, 1H), 3.24 (s, 3H), 2.30 (dt, J 13.5 Hz, J 4.4 Hz, 1H). LCMS (ES$^+$) RT 3.9 min, 489.2 (M+H)$^+$.

The second eluting enantiomer (RT 14.95 min) was collected and the fractions were evaporated to yield (diastereoisomer 2) (1R or S,3S or R)-1-[2-(difluoromethoxy)phenyl]-6-fluoro-7-(4-methylsulfonylphenyl)-2,3-dihydro-1H-pyrrolo[1,2-a]benzimidazol-3-ol (110 mg, 13%, Example 119). LCMS (ES$^+$) RT 3.9 min, 489.2 (M+H)$^+$.

The third eluting enantiomer (RT 21.61 min) was collected and the fractions were evaporated to yield (diastereoisomer 3) (1S or R,3S or S)-1-[2-(difluoromethoxy)phenyl]-6-fluoro-7-(4-methylsulfonylphenyl)-2,3-dihydro-1H-pyrrolo[1,2-a]benzimidazol-3-ol (135 mg, 16%, Example 120). LCMS (ES$^+$) RT 3.9 min, 489.2 (M+H)$^+$.

The fourth eluting enantiomer (RT 29.56 min) was collected and the fractions were evaporated to yield (diastereoisomer 4) (1S or R,3R or S)-1-[2-(difluoromethoxy)phenyl]-6-fluoro-7-(4-methylsulfonylphenyl)-2,3-dihydro-1H-pyrrolo[1,2-a]benzimidazol-3-ol (135 mg, 16%, Example 121). LCMS (ES$^+$) RT 3.9 min, 489.2 (M+H)$^+$.

Example 122

Enantiomer 1: (1R or S)-7-bromo-1-[2-(difluoromethoxy)phenyl]-1,3-dihydrothiazolo[3,4-a]benzimidazole

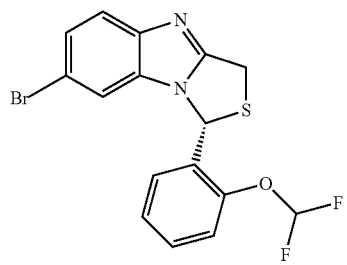 [SMILES: Br ; Cc1ccc2nc3n(c2c1)[C@@H](c1ccccc1OC(F)F)SC3]

The title compound was prepared following the methods described for Intermediate 48 and 49, starting from the Intermediate 46 (5 g) to yield the title compound (1.9 g, 43%). $^1$H NMR (400 MHz, CDCl$_3$) δ 7.49 (d, 1H, J 8.6 Hz), 7.28 (m, 2H), 7.13 (d, J 8.1 Hz, 1H), 7.06 (t, J 7.5 Hz, 1H), 6.91 (s, 1H), 6.85 (d, J 7.5 Hz, 1 H), 6.53 (m, 2H), 4.37 (m, 1H), 4.20 (m, 1H). LCMS (ES$^+$) RT 4.8 min, 397.0/399.0 (M+H)$^+$.

Example 123

Enantiomer 2: (1S or R)-7-bromo-1-[2-(difluoromethoxy)phenyl]-1,3-dihydrothiazolo[3,4-a]benzimidazole

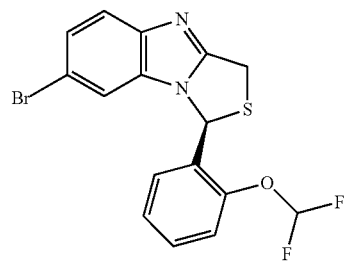 [SMILES: Br ; Cc1ccc2nc3n(c2c1)[C@H](c1ccccc1OC(F)F)SC3]

The title compound was prepared following the methods described for Intermediate 48 and 49, starting from the Intermediate 47 (5 g) to yield the title compound (1.7 g, 38%). $^1$H NMR (400 MHz, CDCl$_3$) δ 7.58 (d, J 8.6 Hz, 1H), 7.36 (m, 2H), 7.22 (d, J 8.1 Hz, 1H), 7.15 (t, J 7.6 Hz, 1H), 7.00 (d, J 1.4 Hz, 1H), 6.93 (d, J 7.6 Hz, 1H), 6.62 (m, 2H), 4.45 (m, 1H), 4.29 (m, 1H). LCMS (ES$^+$) RT 4.8 min, 397 (M+H)$^+$.

Example 124

Enantiomer 2: (1R or S)-1-[2-(difluoromethoxy)phenyl]-7-(6-piperazin-1-yl-3-pyridyl)-2,3-dihydro-1H-pyrrolo[1,2-a]benzimidazole

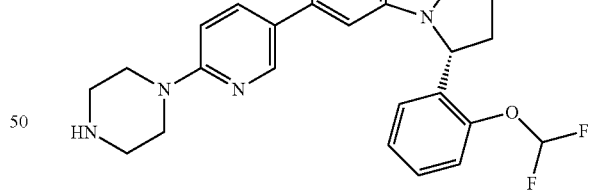

The title compound was prepared from Example 35 (0.3 g, 36.2 mmol 1 eq.) and TFA (2 mL) by the Method F. (0.085 g, 34%). $^1$H NMR (400 MHz, CDCl$_3$) δ 8.31 (d, J 2.2 Hz, 1H), 7.76 (m, 1H), 7.63 (m, 1H), 7.35 (m, 2H), 7.22 (d, J 7.9 Hz, 1H), 7.12 (t, J 7.7 Hz, 1H), 6.98 (m, 1H), 6.86 (m, 1H), 6.63 (m, 2H), 5.86 (m, 1H), 3.51 (m, 4H), 3.20 (m, 3H), 3.00 (m, 4H), 2.55 (m, 1H). LCMS (ES$^+$) RT 2.7 min, 462 (M+H)$^+$.

Example 125

Enantiomer 1: (1R or S)-7-bromo-1-[2-(difluoromethoxy)phenyl]-3H-[1,3]thiazolo[3,4-a]benzimidazole 2-oxide

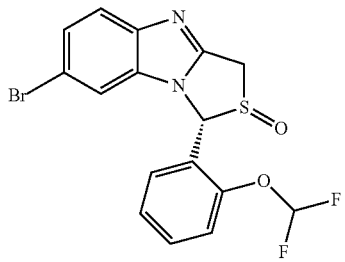 [SMILES: Br ; Cc1ccc2nc3n(c2c1)[C@@H](c1ccccc1OC(F)F)S(=O)C3]

Example 122 (1.0 g, 1.0 eq) was dissolved in AcOH (10 mL). Hydrogen peroxide (0.56 mL, 2.2 eq, 30-37% in water) was added and the mixture was stirred at r.t. for 18 h. The reaction mixture was concentrated in vacuo, and the mixture was diluted with DCM (10 mL) washed with water, dried (MgSO$_4$) and concentrated in vacuo. The residue was purified by column chromatography (SiO$_2$, 0-2% methanolic ammonia/DCM), yielding the title compound as a beige solid (6 mg, 0.6%). $^1$H NMR (400 MHz, CDCl$_3$) δ 7.70 (m, 1H), 7.55 (m, 1H), 7.44 (m, 1H), 7.33 (m, 1H), 7.10 (m, 1H), 6.88 (m, 1H), 6.82 (m, 1H), 6.55 (m, 1H), 4.70 (m, 1H), 4.11 (m, 1H), 4.10 (m, 1H). LCMS (ES$^+$) RT 5.85 min, 413.0/415.0 (M+H)$^+$.

Example 126

Enantiomer 2: (1S or R)-7-bromo-1-[2-(difluoromethoxy)phenyl]-3H-[1,3]thiazolo[3,4-a]benzimidazole 2-oxide

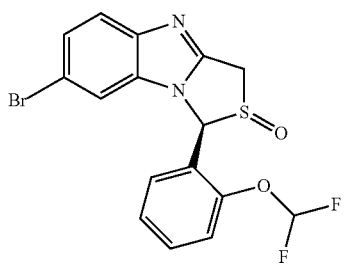 [SMILES: Br ; Cc1ccc2nc3n(c2c1)[C@H](c1ccccc1OC(F)F)S(=O)C3]

The title compound was prepared from Example 123 (1.50 g, 1.0 eq) following the procedure described for Example 125. The title compound was obtained as a brown oil (21 mg, 1.4%). $^1$H NMR (400 MHz, CDCl$_3$) δ 0.70 (m, 1H), 7.55 (m, 1H), 7.44 (m, 1H), 7.33 (m, 1H), 7.10 (m, 1H), 6.88 (m, 1H), 6.82 (m, 1H), 6.55 (m, 1H), 4.70 (m, 1H), 4.11 (m, 1H), 4.10 (m, 1H). LCMS (ES$^+$) RT 5.85 min, 413.0/415.0 (M+H)$^+$.

Example 127

7-bromo-1-phenyl-2,3-dihydro-1H-pyrrolo[1,2-a]benzimidazol-3-yl) acetate

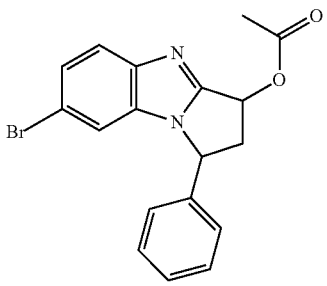 [SMILES: Br ; CC(=O)OC1CC(c2ccccc2)n2c1nc1ccc(C)cc12]

The title compound (as a mixture of 2 diastereoisomers) was prepared from Intermediate 100 following the method described for Example 116. LCMS (ES$^+$) RT 4.82 and 4.77 min, 371.1/373.1 (M+H)+(ratio: 49/51).

Example 128

7-bromo-1-phenyl-2,3-dihydro-1H-pyrrolo[1,2-a]benzimidazol-3-ol

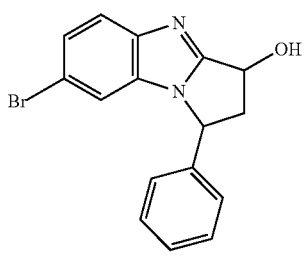 [SMILES: Br ; Cc1ccc2nc3n(c2c1)C(c1ccccc1)CC3O]

The title compound (as a mixture of 2 diastereoisomers) was prepared from Example 127 following the method described for Example 117. LCMS (ES$^+$) RT 4.06 and 4.12 min, 329.1/331.1 (M+H)$^+$ (ratio 27/72).

Example 129

7-bromo-1-phenyl-1,2-dihydro-3H-pyrrolo[1,2-a]benzimidazol-3-one

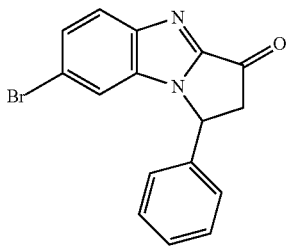 [SMILES: Br ; Cc1ccc2nc3n(c2c1)C(c1ccccc1)CC3=O]

A solution of Example 128 (1.85 g, 5.62 mmol) in CHCl$_3$ (25 mL) was heated at 60° C. in the presence of manganese dioxide (10 eq., 56.2 mmol) for 1 h. The reaction mixture was cooled, and filtered on a bed of celite, and the solid was washed with DCM (3×50 mL), then MeCN (2×25 mL). The filtrates were concentrated in vacuo, to yield brown oil (1.44 g). The residue was purified by column chromatography (SiO$_2$, 25-100% DCM/hexanes), yielding the title compound (390 mg, 21%). $^1$H NMR (400 MHz, DMSO-d$_6$) δ 7.87 (d, J 8.8 Hz, 1H), 7.50 (dd, J 8.8 Hz, J 1.8 Hz, 1H), 7.41 (m, 5H), 7.26 (d, J 1.5 Hz, 1H), 6.02 (dd, J 7.3 Hz, J 3.6 Hz, 1H), 3.84 (dd, J 18.9 Hz, J 7.4 Hz, 1H), 3.19 (dd, J 18.9 Hz, J 3.6 Hz, 1H). LCMS (ES$^+$) RT 4.62 min, 327.1/329.1 (M+H)$^+$.

Example 130

(3Z)-7-bromo-N-hydroxy-1-phenyl-1,2-dihydro-3H-pyrrolo[1,2-a]benzimidazol-3-imine

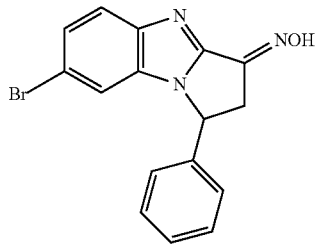

Hydroxylamine hydrochloride (0.198 g, 2.85 mmol) was added to a solution Example 129 (600 mg, 1.84 mmol) in EtOH (25 mL) and pyridine (2 mL). The resulting suspension was heated for 1 h at 65° C. The mixture was then cooled to r.t. and EtOAc (200 mL) was added and the mixture was washed with water (3×30 mL), then brine (2×50 mL), dried (Na$_2$SO$_4$) and concentrated in vacuo. The residue was triturated with a solution of Et$_2$O/EtOAc (15:5) and the solid was filtered and dried in vacuo to yield an off white powder (220 mg, 35%). $^1$H NMR (400 MHz, DMSO-d$_6$) δ 7.67 (d, J 8.7 Hz, 1H), 7.39 (m, 6H), 7.24 (m, 3H), 7.16 (d, J 1.4 Hz, 1H), 5.86 (dd, J 8.3 Hz, J 3.5 Hz, 1H), 3.96 (dd, J 18.5 Hz, J 8.4 Hz, 1H), 3.16 (dd, J 18.6 Hz, J 3.6 Hz, 1H). LCMS (ES$^+$) RT 4.45 min, 342.0/344.0 (M+H)$^+$.

Example 131

Enantiomer 1: (1R or S)-1-phenyl-7-[6-(piperazin-1-yl)pyridin-3-yl]-2,3-dihydro-1H-pyrrolo[1,2-a]benzimidazole

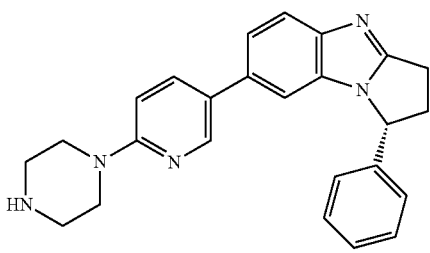 [SMILES: c1ccc([C@H]2CCc3nc4ccc(-c5ccc(N6CCNCC6)nc5)cc4n32)cc1]

The title compound was prepared from Example 42 (250 mg, 1.0 eq.), and (1:1) mixture of DCM-TFA (2 mL) by the Method F (157 mg, 39.7%). LCMS (ES$^+$) RT 2.5 min, 396 (M+H)$^+$.

Examples 132 and 133

Enantiomer 1: (4S or R)-7-bromo-4-[2-(difluoromethoxy)phenyl]-8-fluoro-3,4-dihydro-1 H-[1,4] oxazino[4,3-a]benzimidazole; enantiomer 2: (4R or S)-7-bromo-4-[2-(difluoromethoxy)phenyl]-8-fluoro-3,4-dihydro-1H-[1,4]oxazino[4,3-a]benzimidazole

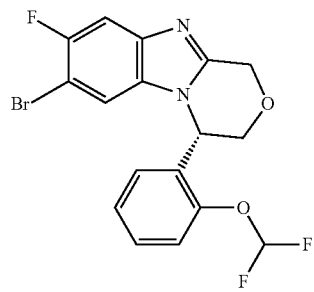

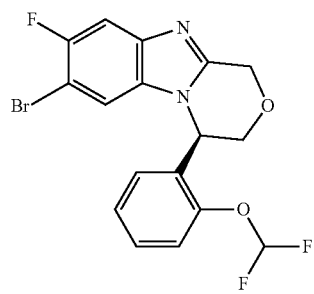

The title compounds were isolated by chiral separation Example 10 under SFC conditions on Chiralpak AD (50*216 mm*mm, flow 360 mL/min, 25° C., CO$_2$+20% MeOH for 2.1 min then 40% MeOH for 3.3 min, injection of 16 mL solution at a concentration of 15 g/L). The first eluting enantiomer (RT 2.1 min) was collected and the fractions were evaporated to yield (enantiomer 1) (4S or R)-7-bromo-4-[2-(difluoromethoxy)phenyl]-8-fluoro-3, 4-dihydro-1H-[1, 4]oxazino[4,3-a]benzimidazole (Example 132). The second eluting enantiomer (RT 3.4 min) was collected and the fractions were evaporated to yield (enantiomer 2) (4R or S)-7-bromo-4-[2-(difluoromethoxy) phenyl]-8-fluoro-3, 4-dihydro-1H-[1, 4]oxazino[4,3-a]benzimidazole (Example 133) $^1$H NMR (400 MHz, CDCl$_3$) δ 7.42 (d, J 8.9 Hz, 1H), 7.32 (m, 1H), 7.17 (m, 2H), 7.05 (t, J 7.6 Hz, 1H), 6.91 (d, J 5.8 Hz, 1H), 6.61 (m, 1H), 5.71 (t, J 3.9 Hz, 1H), 5.02 (m, 2H), 4.16 (m, 2H). LCMS (ES$^+$) RT 4.76 min, 413.0/415.0 (M+H)$^+$.

Examples 134-144

The following Examples were prepared from the assigned precursor by the Method F.

| Example No. | Precursor | Compound Name | LCMS |
|---|---|---|---|
| 134 | Ex 47 | Enantiomer 2: (4R or S)-4-[2-(difluoromethoxy)phenyl]-8-fluoro-7-(6-piperazin-1-yl-3-pyridyl)-3,4-dihydro-1H-[1,4]oxazino[4,3-a]benzimidazole | LCMS (ES+) RT 1.32 min, 496.0 (M + H)+. |
| 135 | Ex 48 | Enantiomer 1: (4S or R)-4-[2-(difluoromethoxy)phenyl]-8-fluoro-7-(6-piperazin-1-yl-3-pyridyl)-3,4-dihydro-1H-[1,4]oxazino[4,3-a]benzimidazole | LCMS (ES+) RT 1.32 min, 496.0 (M + H)+. |
| 136 | Ex 50 | Enantiomer 1: (4S or R)-4-[2-(difluoromethoxy)phenyl]-8-fluoro-7-(4-methylsulfonylphenyl)-1,2,3,4-tetrahydropyrazino[1,2-a]benzimidazole | LCMS (ES+) RT 1.31 min, 488.0 (M + H)+. |
| 137 | Ex 52 | Enantiomer 1: (4S or R)-4-[2-(difluoromethoxy)phenyl)-8-fluoro-7-(2-methylsulfonyl-4-pyridyl)-1,2,3,4-tetrahydropyrazino[1,2-a]benzimidazole | LCMS (ES+) RT 1.30 min, 489.0 (M + H)+. |

| Example No. | Precursor | Compound Name | LCMS |
|---|---|---|---|
| 138 | Ex 53 | Enantiomer 1: (4S or R)-4-[2-(difluoromethoxy)phenyl)-8-fluoro-7-(6-methylsulfonyl-3-pyridyl)-1,2,3,4-tetrahydropyrazino[1,2-a]benzimidazole | LCMS (ES+) RT 1.29 min, 489.0 (M + H)+. |
| 139 | Ex 54 | Enantiomer 2: (4R or S)-4-[2-(difluoromethoxy)phenyl)-8-fluoro-7-(6-methylsulfonyl-3-pyridyl)-1,2,3,4-tetrahydropyrazino[1,2-a]benzimidazole | LCMS (ES+) RT 1.29 min, 489.0 (M + H)+. |
| 140 | Ex 55 | 4[2-(difluoromethoxy)phenyl]-7-(4-methylsulfonylphenyl)-1,2,3,4-tetrahydropyrazino[1,2-a]benzimidazole | LCMS (ES+) RT 1.30 min, 470.0 (M + H)+. |
| 141 | Ex 56 | Enantiomer 2: (4R or S)-4-[2-(difluoromethoxy)phenyl]-7-(6-methylsulfonyl-3-pyridyl)-1,2,3,4-tetrahydropyrazino[1,2-a]benzimidazole | LCMS (ES+) RT 1.26 min, 471.0 (M + H)+. |

-continued

| Example No. | Precursor | Compound Name | LCMS |
|---|---|---|---|
| 142 | Ex 57 | Enantiomer 1: (4S or R)-4-[2-(difluoromethoxy)phenyl]-7-(6-methylsulfonyl-3-pyridyl)-1,2,3,4-tetrahydropyrazino[1,2-a]benzimidazole | LCMS (ES+) RT 1.26 min, 471.0 (M + H)+. |
| 143 | Ex 58 | Enantiomer 1: (4S or R)-4-[2-(difluoromethoxy)phenyl]-7-(2-methylsulfonyl-4-pyridyl)-1,2,3,4-tetrahydropyrazino[1,2-a]benzimidazole | LCMS (ES+) RT 1.26 min, 471.0 (M + H)+. |
| 144 | Ex 59 | Enantiomer 1: (4S or R)-4-[2-(difluoromethoxy)phenyl]-8-fluoro-7-[3-(methylsulfonyl)phenyl]-1,2,3,4-tetrahydropyrazino[1,2-a]benzimidazole | LCMS (ES+) RT 1.31 min, 488.0 (M + H)+. |

Examples 145 and 146

Enantiomer 1: tert-butyl (4S or R)-7-bromo-4-[2-(difluoromethoxy)phenyl]-8-fluoro-3,4-dihydro-1H-pyrazino[1,2-a]benzimidazole-2-carboxylate; enantiomer 2: tert-butyl (4R or S)-7-bromo-4-[2-(difluoromethoxy)phenyl]-8-fluoro-3,4-dihydro-1H-pyrazino[1,2-a]benzimidazole-2-carboxylate

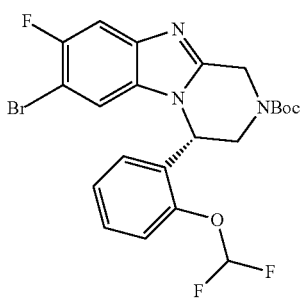

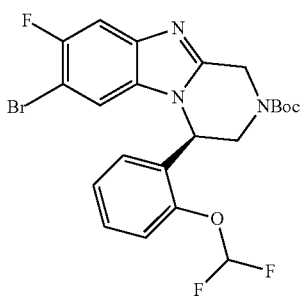

The title compounds were isolated by chiral purification of Example 12 under SFC conditions on Chiralpak AD (50*216 mm*mm, flow 360 mL/min, 15° C., CO$_2$+20% i-PrOH, injection of 5 mL solution at a concentration of 20 g/L). The first eluting enantiomer (RT 3.9 min) was collected and the fractions were evaporated to yield Enantiomer 1: tert-butyl (4S or R)-7-bromo-4-[2-(difluoromethoxy)phenyl]-8-fluoro-3,4-dihydro-1H-pyrazino[1,2-a]benzimidazole-2-carboxylate (Example 145). The second eluting enantiomer (RT 5.9 min) was collected and the fractions were evaporated to yield enantiomer 2: tert-butyl (4R or S)-7-bromo-4-[2-(difluoromethoxy)phenyl]-8-fluoro-3,4-dihydro-1H-pyrazino[1,2-a]benzimidazole-2-carboxylate (Example 146).

Examples 147 and 148

Enantiomer 1: tert-butyl 7-bromo-(4S or R)-(2-(difluoromethoxy)phenyl)-3,4-dihydrobenzo[4,5]imidazo[1,2-a]pyrazine-2(1H)-carboxylate; enantiomer 2: tert-butyl 7-bromo-(4R)-(2-(difluoromethoxy)phenyl)-3,4-dihydrobenzo[4,5]imidazo[1,2-a]pyrazine-2(1H)-carboxylate

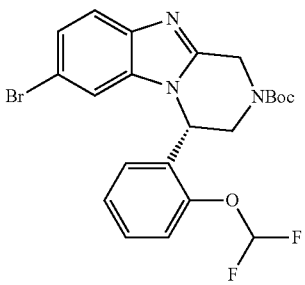

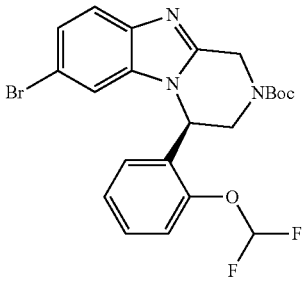

The title compounds were isolated by chiral purification of Example 13 under SFC conditions on Chiralpak IC (50*264 mm*mm, flow 360 mL/min, 25° C., CO$_2$+20% i-PrOH, injection of 15.5 mL solution at a concentration of 20 g/L). The first eluting enantiomer (RT 6.6 min) was collected and the fractions were evaporated to yield enantiomer 1: tert-butyl 7-bromo-(4R or S)-(2-(difluoromethoxy)phenyl)-3,4-dihydrobenzo[4,5]imidazo[1,2-a]pyrazine-2(1H)-carboxylate (Example 147). The second eluting enantiomer (RT 11.3 min) was collected and the fractions were evaporated to yield enantiomer 2: tert-butyl 7-bromo-(4S)-(2-(difluoromethoxy)phenyl)-3,4-dihydrobenzo[4,5]imidazo[1,2-a]pyrazine-2(1H)-carboxylate (Example 148).

Example 149

Enantiomer 1: 1-[(4S or R)-4-[2-(difluoromethoxy)phenyl]-8-fluoro-7-(4-methylsulfonylphenyl)-3,4-dihydro-1H-pyrazino[1,2-a]benzimidazol-2-yl]ethanone

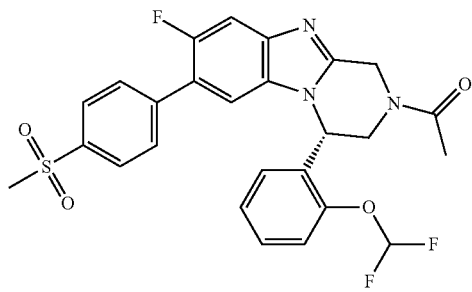 [SMILES: CC(=O)N1Cc2nc3cc(F)c(-c4ccc(S(C)(=O)=O)cc4)cc3n2[C@@H](c2ccccc2OC(F)F)C1]

To a solution of Example 136 (0.150 g, 1 eq.) in DCM (10 mL/g) were added sequentially PS-DIEA (Argonaut No 800280, 261 mg, 3.0 eq., 3.53 mmol/g), acetyl chloride (1.2 eq.) and N,N-diisopropylethylamine (0.1 eq.) and the mixture was stirred at r.t. After 20 h, DIPEA (2 drops) and acetyl chloride (0.5 eq.) were added to the mixture which was stirred at r.t. for an additional 3 h until disappearance of the starting material. Then the mixture was filtered, the filtrate was washed with sat. aq. NH$_4$Cl, dried (MgSO$_4$), concentrated in-vacuo, purified by column chromatography (SiO$_2$, 0-100% EtOAc/hexanes), yielding the title compound as an off white solid (94 mg, 58%). LCMS (ES$^+$) RT 3.9 min, 530.3 (M+H)$^+$.

Example 150

Enantiomer 1: (4S or R)-4-[2-(difluoromethoxy)phenyl]-8-fluoro-2-methylsulfonyl-7-(4-methylsulfonylphenyl)-3,4-dihydro-1H-pyrazino[1,2-a]benzimidazole

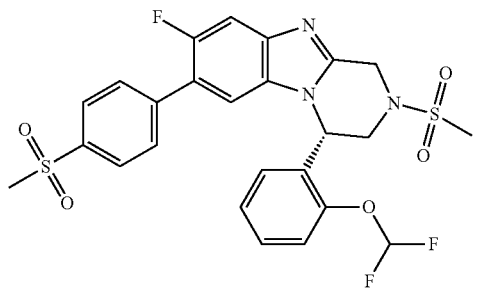

To a solution of Example 136 (0.150 g, 1 eq.) in DCM (10 mL/g) were added sequentially PS-DIEA (Argonaut No 800280, 261 mg, 3.0 eq., 3.53 mmol/g), methanesulfonyl chloride (43 mg, 1.2 eq.) and N,N-diisopropylethylamine (4 mg, 0.1 eq.). The mixture was stirred at r.t. After 20 h DIPEA (2 drops) and methanesulfonyl chloride (0.5 eq.) were added to the mixture which was stirred at r.t. for 3 h until the disappearance of starting material. Then the mixture was filtered, the filtrate was washed with sat. aq. NH$_4$Cl, dried (MgSO$_4$), concentrated in-vacuo, purified by column chromatography (SiO$_2$, 0-100% EtOAc/hexanes), yielding the title compound as an off white solid (51 mg, 29% yield). $^1$H NMR (400 MHz, CDCl$_3$) δ 7.94 (d, J 8.3 Hz, 2H), 7.56 (m, 3H), 7.41 (t, J 8.1 Hz, 1H), 7.26 (d, J 6.7 Hz, 1H), 7.13 (t, J 7.5 Hz, 1H), 6.85 (d, J 8.4 Hz, 1H), 6.67 (t, J 68.2 Hz, 1H), 6.66 (d, J 18.7 Hz, 1H), 5.97 (t, J 4.1 Hz, 1H), 5.03 (d, J 16.8 Hz, 1H), 4.78 (d, J 16.6 Hz, 1H), 4.06 (dd, J 13.5 Hz, J 4.2 Hz, 1H), 3.98 (dd, J 13.7 Hz, J 4.3 Hz, 1H), 2.78 (s, 3H), 3.07 (s, 3H). LCMS (ES$^+$) RT 4.2 min, 566.3 (M+H)$^+$.

Example 151

Enantiomer 1: (4S or R)-4-[2-(difluoromethoxy)phenyl]-8-fluoro-2-methyl-7-(4-methylsulfonylphenyl)-3,4-dihydro-1H-pyrazino[1,2-a]benzimidazole

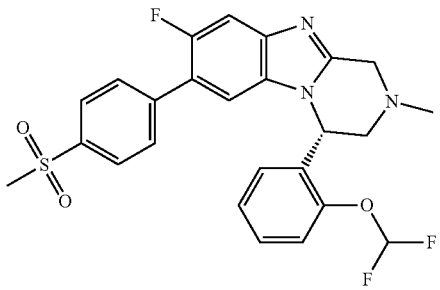

To a solution of Example 136 (0.150 g, 0.308 mmol) in MeOH (0.673 g, 21.0 mmol) were added Et$_3$N (0.029 g, 0.28 mmol), formaldehyde (0.0244 g, 0.301 mmol) and sodium cyanoborohydride (0.02 g, 0.317 mmol). The reaction mixture was stirred at r.t. for 14 h. The reaction mixture was taken up in EtOAc, washed with water and brine, dried (MgSO$_4$), and concentrated in vacuo. The residue was purified by prep TLC (Eluent: 90 DCM/10 methanolic ammonia) yielding the title compound (12 mg, 8%). LCMS (ES$^+$) RT 4 min, 502 (M+H)$^+$.

Examples 152 and 153

Enantiomer 1: ((4S or R)-4-[2-(difluoromethoxy)phenyl]-7-(4-methylsulfonylphenyl)-1,2,3,4-tetrahydropyrazino[1,2-a]benzimidazole; enantiomer 2 (4R or S)-4-[2-(difluoromethoxy)phenyl]-7-(4-methylsulfonylphenyl)-1,2,3,4-tetrahydropyrazino[1,2-a]benzimidazole

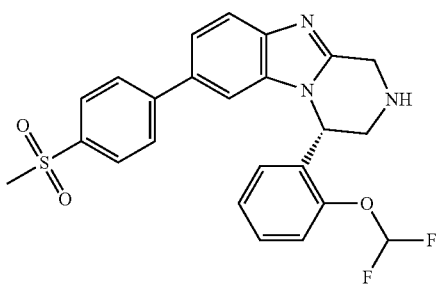

-continued

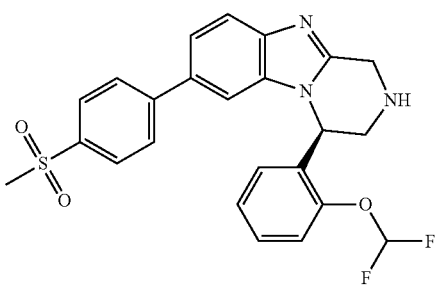

The title compounds were isolated by chiral purification of Example 140 under LC conditions on Lux-Cell-4 (76*265 mm*mm, flow 200 mL/min, 30° C., EtOH 100%, injection of 10 mL solution at a concentration of 5.7 g/L). The first eluting enantiomer (RT 13 min) was collected and the fractions were evaporated to yield the enantiomer 1 (Example 152). $^1$H NMR (400 MHz, CDCl$_3$) δ 7.92 (d, J 8.4 Hz, 2H), 7.81 (d, J 8.4 Hz, 1H), 7.60 (d, J 8.4 Hz, 2H), 7.48 (dd, J 8.4 Hz, J 1.4 Hz, 1H), 7.36 (td, J 7.9 Hz, J 1.2 Hz, 1H), 7.25 (d, J 6.3 Hz, 1H), 7.09 (t, J 7.6 Hz, 1H), 7.00 (d, J 1.0 Hz, 1H), 6.72 (t, J 72.9 Hz, 1H), 6.66 (d, J 8.1 Hz, 1H), 5.88 (t, J 4.0 Hz, 1H), 4.44 (q, J 17.4 Hz, 2H), 3.68 (dd, J 13.9 Hz, J 4.6 Hz, 1H), 3.38 (dd, J 13.4 Hz, J 3.6 Hz, 1H), 3.06 (s, 3H). LCMS (ES$^+$) RT 1.30 min, 470.0 (M+H)$^+$.

The second eluting enantiomer (RT 18 min) was collected and the fractions were evaporated to yield enantiomer 2 (Example 153). $^1$H NMR (400 MHz, CDCl$_3$) δ 7.92 (d, J 8.4 Hz, 2H), 7.82 (d, J 8.2 Hz, 1H), 7.60 (d, J 8.4 Hz, 2H), 7.48 (dd, J 8.5 Hz, J 1.2 Hz, 1H), 7.36 (t, J 7.0 Hz, 1H), 7.25 (d, J 5.9 Hz, 1H), 7.09 (t, J 6.9 Hz, 1H), 7.01 (d, J 0.3 Hz, 1H), 6.71 (t, J 73.0 Hz, 1H), 6.66 (d, J 7.2 Hz, 1H), 5.88 (t, J 4.0 Hz, 1H), 4.44 (q, J 17.0 Hz, 2H), 3.68 (dd, J 13.7 Hz, J 4.6 Hz, 1H), 3.38 (dd, J 13.7 Hz, J 3.6 Hz, 1H), 3.06 (s, 3H). LCMS (ES$^+$) RT 1.30 min, 470.0 (M+H)$^+$.

Example 154

(7-bromo-6-fluoro-1-phenyl-2,3-dihydro-1H-pyrrolo[1,2-a]benzimidazol-3-yl) acetate

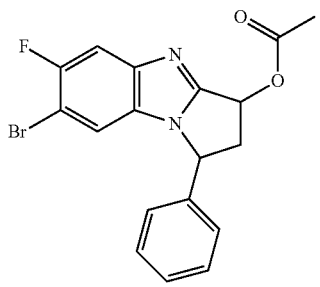 [SMILES: CC(=O)OC1CC(c2ccccc2)n2c1nc1cc(F)c(Br)cc12]

The title compound (as a mixture of 2 diastereoisomers) was prepared from 1-(5-bromo-4-fluoro-2-nitro-phenyl)-2-phenyl-pyrrolidine following the method described for Example 116. LCMS (ES$^+$) RT 4.85 and 4.90 min, 389.1/391.1 (M+H)$^+$.

Example 155

7-bromo-6-fluoro-1-phenyl-2,3-dihydro-1H-pyrrolo[1,2-a]benzimidazol-3-ol

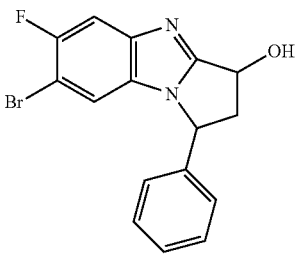 [SMILES: OC1CC(c2ccccc2)n2c1nc1cc(F)c(Br)cc12]

The title compound (as a mixture of 2 diastereoisomers 67/33 trans/cis) was prepared from Example 154 following the method described for Example 117 as a colorless oil (89%). The compound is used in the next step without further purification. $^1$H NMR (400 MHz, CDCl$_3$) δ 7.51 (m, 1H), 7.40 (m, 4H), 7.18 (m, 2H), 7.00 (m, 1H), 5.69 (t, J 6.8 Hz, 1H), 5.53 (m, 1H), 3.19 (m, 1H), 2.91 (m, 1H), LCMS (ES+) RT 4.82 and 4.76 min, 347.1/349.1 (M+H)$^+$.

Example 156

7-bromo-6-fluoro-1-phenyl-1,2-dihydropyrrolo[1,2-a]benzimidazol-3-one

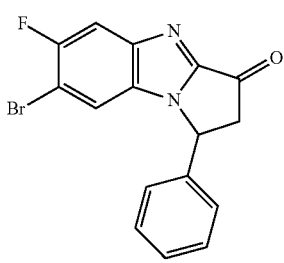

MnO$_2$ (1.06 g, 12.2 mmol) was added to a solution of Example 155 (0.507 g, 1.46 mmol) in CHCl$_3$ (20 mL) and the mixture was heated at 60° C. for 5 h. MnO$_2$ (405 mg) and CHCl$_3$ (20 mL) were added and the mixture heated for another 2 h. The residue is cooled to r.t., filtered on a bed of celite, and the solid is washed with DCM. The filtrates were washed with water (2×50 mL), a sat. aq. NaHCO$_3$ (2×50 mL), a sat. solution of NH$_4$Cl (2×50 mL), dried (MgSO$_4$), concentrated in vacuo, to yield the title compound used in the next step without any purification (370 mg, 74%). LCMS (ES$^+$) RT 4.67 min, 345/347 (M+H)$^+$.

Example 157

7-bromo-6-fluoro-1-phenyl-2,3-dihydro-1H-pyrrolo[1,2-a]benzimidazol-3-ol

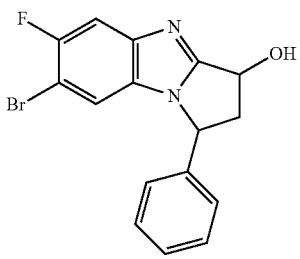 [SMILES: OC1CC(c2ccccc2)n2c1nc1cc(F)c(Br)cc12]

Lithium tri-sec-butylborohydride (1M, 1.7 mL, 1.5 eq.) was added drop wise to a cold (−78° C.) solution of Example 156 (307 mg, 1.1 mmol) in THF (10 mL). The resulting mixture was stirred 2 h, then the solution was allowed to reach 0° C. After 0.5 h at 0° C., MeOH (2 mL) was added. After 20 min, an aq. solution of NaOH (3 mL), followed by water (50 mL) were added and the resulting mixture was extracted with EtOAc (100 mL). The combined organic layers were washed with water (50 mL), with brine (2×50 mL), dried (MgSO$_4$) and concentrated in vacuo. The residue was purified by column chromatography (SiO$_2$, 0-10% methanolic ammonia/EtOAc) to yield the tile compound as a mixture of 2 cis diastereoisomers (270 mg, 72%). LCMS (ES$^+$) RT 4.27 min, 347.08/349.07 (M+H)$^+$.

Examples 158 and 159

Diasteroisomer 1 (1S or R,3S or R)-6-fluoro-7-[6-(methylsulfonyl)pyridin-3-yl]-1-phenyl-2,3-dihydro-1H-pyrrolo[1,2-a]benzimidazol-3-ol; diastereoisomer 2 (1R or S,3R or S)-6-fluoro-7-[6-(methylsulfonyl)pyridin-3-yl]-1-phenyl-2,3-dihydro-1H-pyrrolo[1,2-a]benzimidazol-3-ol

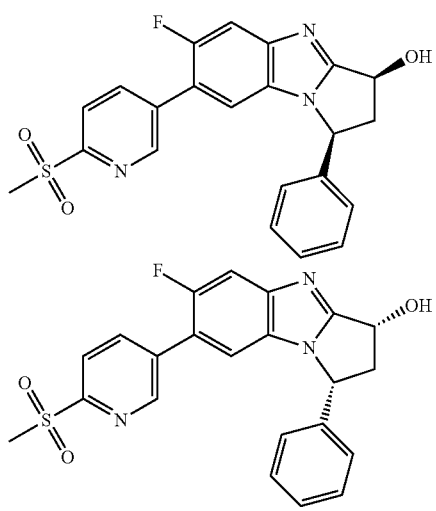

The title compounds were isolated by chiral purification under SFC conditions on Chiralcel OD (50*266 mm*mm, flow 360 mL/min, 25° C., CO$_2$+20% MeOH, injection of 17 mL solution at a concentration of 3.6 g/L). The first eluting enantiomer (RT 8.9 min) was collected and the fractions were evaporated to yield the title compound, diastereoisomer 1 (Example 158) as an off white solid (36 mg, 11%). $^1$H NMR (400 MHz, CDCl$_3$) δ 8.68 (s, 1H), 8.10 (m, 1H), 7.99 (m, 1H), 7.62 (m, 1H), 7.39 (m, 6H), 6.85 (s, 1H), 5.59 (m, 1H), 5.46 (m, 1H), 3.61 (m, 1H), 3.24 (s, 3H), 2.75 (m, 1H). LCMS (ES$^+$) RT 1.24 min, 424.0 (M+H)$^+$. The second eluting enantiomer (RT 12.9 min) was collected to yield the second enantiomer diastereoisomer 2 (Example 159) as a white solid (6 mg, 11%). $^1$H NMR (400 MHz, CDCl$_3$) δ 8.68 (d, J 0.5 Hz, 1H), 8.10 (d, J 8.6 Hz, 1H), 7.99 (m, 1H), 7.40 (m, 7H), 6.87 (m, 1H), 5.58 (m, 1H), 5.46 (m, 1H), 3.61 (m, 1H), 3.24 (s, 3H), 2.75 (m, 1H). LCMS (ES$^+$) RT 1.24 min, 424.0 (M+H)$^+$.

Example 160

Diastereoisomer 1 [(1R or S,3R or S)-7-bromo-1-[2-(difluoromethoxy)phenyl]-6-fluoro-2,3-dihydro-1H-pyrrolo[1,2-a]benzimidazol-3-yl]acetate

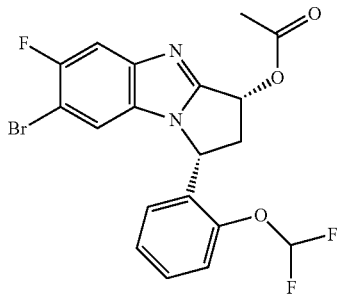 [SMILES: CC(=O)O[C@@H]1C[C@H](c2ccccc2OC(F)F)n2c1nc1cc(F)c(Br)cc12]

The title intermediate was isolated by purification of the 4 diastereoisomers Example 116 by chiral purification under LC conditions on Chiralpak AD (100*500 mm*mm, flow 300 mL/min, 30° C., heptane-i-PrOH (1:1), injection of 10 mL solution at a concentration of 25 g/L). The first eluting peak (RT 13 min) contained 2 diastereoisomers (1R or S,3R or S) and (1S or R, 3R or S). The second peak (RT 22 min) contained the third diastereoisomer (1R or S, 3S or R) and the third pic (RT 30 min) contained the fourth diastereoisomer (1S or R, 3S or R).

The mixture of the 2 diastereoisomers (1R or S,3R or S) and (1S or R, 3R or S) were separated by chiral purification under LC conditions on Lux-Cell-4 (78*265 mm*mm, flow 200 mL/min, 30° C., heptane-i-PrOH (7:3), injection of 2.5 mL solution at a concentration of 100 g/L). The first eluting enantiomer (RT 9 min) was collected and the fractions were evaporated to yield the title compound as colorless foam. The second eluting enantiomer (RT 12 min) was collected and the fractions were concentrated in-vacuo to yield the diastereoisomer (1S or R, 1R or S). $^1$H NMR δ: 7.75 (d, J 9.6 Hz, 1H), 7.45 (m, 1H), 7.33 (m, 3H), 7.21 (t, J 7.6 Hz, 1H), 6.86 (d, J 7.0 Hz, 1H), 6.23 (dd, J 7.6 Hz, 1H), 5.92 (dd, J 8.2 Hz, J 4.3 Hz, 1H), 3.66 (m, 1H), 2.41 (dt, J 14.3 Hz, J 4.0 Hz, 1H), 2.03 (s, 3H).

Example 161

Diastereoisomer 1: (1R or S,3R or S)-7-bromo-1-[2-(difluoromethoxy)phenyl]-6-fluoro-2,3-dihydro-1H-pyrrolo[1,2-a]benzimidazol-3-ol

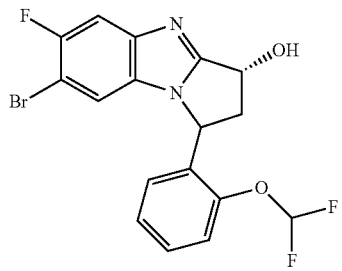 [SMILES: O[C@@H]1CC(c2ccccc2OC(F)F)n2c1nc1cc(F)c(Br)cc12]

K$_2$CO$_3$ (172 mg, 1 eq.) was added to a solution of Example 160 (743 mg, 1.72 mmol) in MeOH (5.2 mL). The resulting mixture was stirred at r.t. for 4 h. The mixture was filtered, evaporated and the resulting residue was taken up in EtOAc, washed with brine (1×), dried (MgSO$_4$) and concentrated in vacuo to yield the title intermediate as an off white solid (710 mg, 89%). LCMS (ES+) RT 1.50 min, 413.0/415.0 (M+H)$^+$.

Example 162

Diastereoisomer 1: (1R or S,3R or S)-7-bromo-1-[2-(difluoromethoxy)phenyl]-6-fluoro-3-methoxy-2,3-dihydro-1H-pyrrolo[1,2-a]benzimidazole

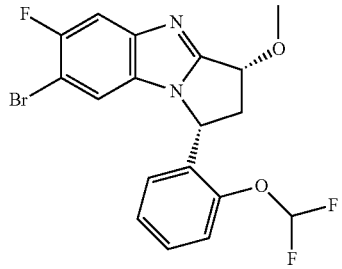 [SMILES: CO[C@@H]1C[C@H](c2ccccc2OC(F)F)n2c1nc1cc(F)c(Br)cc12]

Sodium Hydride (50 mg, dispersed in mineral oil, 1.25 mmol, 80% w/w) was added portion wise to a solution of Example 161 (413 mg, 1.0 mmol) in anhydrous THF (5 mL). The mixture was sonicated 5 min, then stirred at r.t. for 30 min. Iodomethane (287 mg, 2 mmol) was added and the reaction mixture was stirred 2 h at 0° C., then at r.t. for 18 h. Purification by column chromatography (SiO$_2$, 0-45% EtOAc/heptane), gave the title intermediate as a colorless oil (350 mg, 82%). LCMS (ES$^+$) RT 5.24 min, 427.0/429.0 (M+H)$^+$.

Example 163

Diastereoisomer 4 [(1S or R,3S or R)-7-bromo-1-[2-(difluoromethoxy)phenyl]-6-fluoro-2,3-dihydro-1H-pyrrolo[1,2-a]benzimidazol-3-yl]acetate

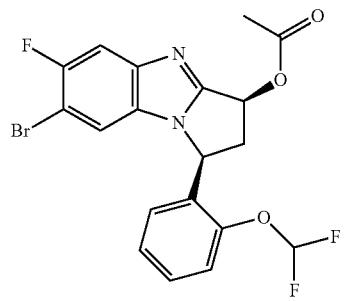 [SMILES: CC(=O)O[C@H]1C[C@@H](c2ccccc2OC(F)F)n2c1nc1cc(F)c(Br)cc12]

The title intermediate was isolated by the purification of a mixture of the 4 diastereoisomers of Example 116 described in Example 160 as the fourth diastereoisomer (RT 30 min). $^1$H NMR (DMSO-d6) δ: 7.75 (d, J 9.6 Hz, 1H), 7.45 (m, 1H), 7.33 (m, 3H), 7.21 (t, J 7.6 Hz, 1H), 6.86 (d, J 7.6 Hz, 1H), 6.23 (dd, J 7.9 Hz, J 3.6 Hz, 1H), 5.92 (dd, J 8.3 Hz, J 4.3 Hz, 1H), 3.66 (m, 1H), 2.41 (dt, J 14.3 Hz, J 3.9 Hz, 1H), 2.03 (s, 3H).

Example 164

Distereoisomer 4: (1S or R, 3S or R)-7-bromo-1-[2-(difluoromethoxy)phenyl]-6-fluoro-2,3-dihydro-1H-pyrrolo[1,2-a]benzimidazol-3-ol

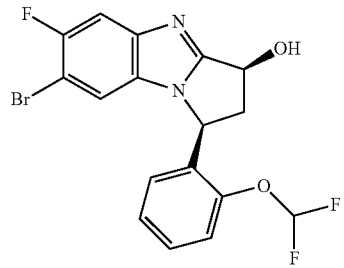 [SMILES: O[C@H]1C[C@@H](c2ccccc2OC(F)F)n2c1nc1cc(F)c(Br)cc12]

K$_2$CO$_3$ (172 mg, 1 eq.) was added to a solution of Example 163 (430 mg, 0.95 mmol) in MeOH (3.0 mL). The resulting mixture was stirred at r.t. for 4 h. The mixture was filtered, concentrated in vacuo, and the resulting residue was taken up in EtOAc, washed with brine (1×), dried (MgSO$_4$) and concentrated in vacuo to yield the title compound as an off white solid (346 mg, 88%). LCMS (ES$^+$) RT 4.62 min, 413.1/415.1 (M+H)$^+$.

Example 165

Diastereoisomer 4: (1S or R, 3S or R)-7-bromo-1-[2-(difluoromethoxy)phenyl]-6-fluoro-3-methoxy-2,3-dihydro-1H-pyrrolo[1,2-a]benzimidazole

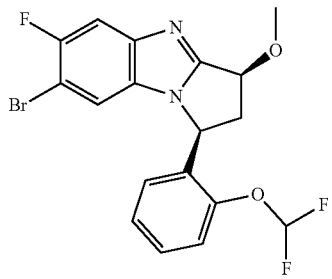 [SMILES: CO[C@H]1C[C@@H](c2ccccc2OC(F)F)n2c1nc1cc(F)c(Br)cc12]

Sodium hydride (50 mg, dispersed in mineral oil, 1.25 mmol, 80% w/w was added portion wise to a solution of Example 164 (348 mg, 0.84 mmol) in anhydrous THF (4.2 mL). The mixture was sonicated 5 min, then stirred at r.t. for 30 min. Iodomethane (241 mg, 1.68 mmol) was added and the reaction mixture was stirred 2 h at 0° C., then at r.t. for 18 h. Purification by column chromatography (SiO$_2$, 0-40% EtOAc/heptane), gave the title intermediate as a colorless oil (290 mg, 80%). LCMS (ES$^+$) RT 5.24 min, 427.1/429.1 (M+H)$^+$.

Example 166

Diastereoisomer 4: 2-(5-{(1S or R,3S or R)-1-[2-(difluoromethoxy)phenyl]-6-fluoro-3-methoxy-2,3-dihydro-1H-pyrrolo[1,2-a]benzimidazol-7-yl}pyridin-2-yl)propan-2-ol

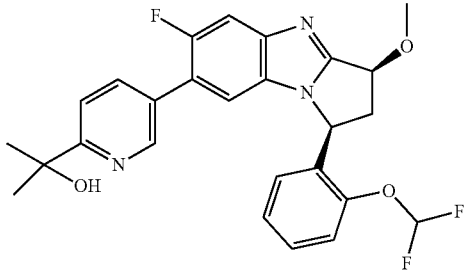 [SMILES: CO[C@H]1C[C@@H](c2ccccc2OC(F)F)n2c1nc1cc(F)c(-c3ccc(C(C)(C)O)nc3)cc12]

HCl (4 N in 1,4-dioxane, 0.2 mL) was added onto a solution of Example 78 (25 mg, 0.045 mmol) in DCM (0.5 mL) and the mixture was stirred at r.t. for 1 h. The solvent was concentrated in vacuo and the residue triturated in Et$_2$O. The resulting powder was collected by filtration and concentrated in vacuo to yield the title compound as a pale orange powder (5 mg, 23%). $^1$H NMR (400 MHz, DMSO-d$_6$) δ 8.69 (s, 1H), 8.48 (d, J 8.1 Hz, 1H), 8.12 (d, J 8.4 Hz, 1H), 7.84 (d, J 11.4 Hz, 1H), 7.36 (m, 6H), 6.82 (d, J 7.5 Hz, 1H), 5.96 (dd, J 8.3 Hz, J 3.4 Hz, 1H), 5.04 (dd, J 7.4 Hz, J$_2$ 2.6 Hz, 1H), 3.58 (m, 4H), 2.42 (m, 1H), 1.59 (s, 6H). LCMS (ES$^+$) RT 1.45 min, 484.0 (M+H)$^+$.

Example 167

Diastereoisomer 1: 2-(5-{(1R or S,3R or S)-1-[2-(difluoromethoxy)phenyl]-6-fluoro-3-methoxy-2,3-dihydro-1H-pyrrolo[1,2-a]benzimidazol-7-yl}pyridin-2-yl)propan-2-ol

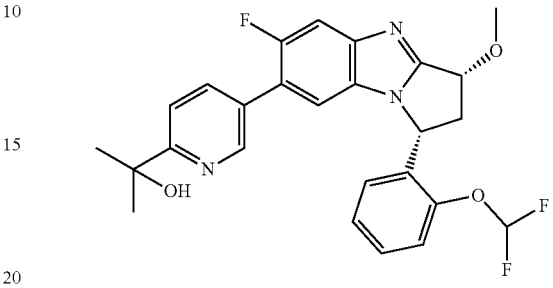

HCl (4 N in 1,4-dioxane, 0.5 mL) was added onto a solution of Example 79 (168 mg) in DCM (0.5 mL) and the mixture was stirred at 0° C. for 3 h. The solvent was concentrated in vacuo and the residue triturated in Et$_2$O, then in EtOAc. The resulting powder was collected by filtration and concentrated in vacuo to yield the title compound as an off white powder (135 mg, 100%). $^1$H NMR (400 MHz, DMSO-d$_6$) δ 8.69 (s, 1H), 8.48 (d, J 8.1 Hz, 1H), 8.12 (d, J 8.4 Hz, 1H), 7.84 (d, J 11.4 Hz, 1H), 7.36 (m, 6H), 6.82 (d, J 7.5 Hz, 1H), 5.96 (dd, J 8.3 Hz, J 3.4 Hz, 1H), 5.04 (dd, J 7.4 Hz, J$_2$ 2.6 Hz, 1H), 3.58 (m, 4H), 2.42 (m, 1H), 1.59 (s, 6H). LCMS (ES$^+$) RT 1.45 min, 484.0 (M+H)$^+$.

Example 168

(1R or S)-7-bromo-1-[2-(difluoromethoxy)phenyl]-3,6-difluoro-2,3-dihydro-1H-pyrrolo[1,2-a]benzimidazole

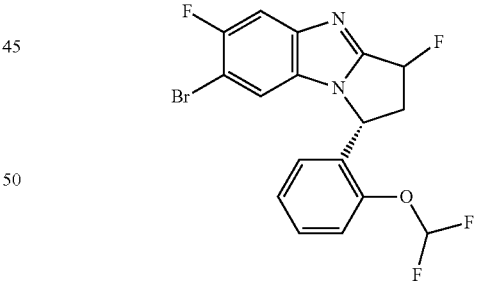

The title compound was prepared from a solution of Intermediate 161 (200 mg, 1.0 eq.), dissolved in DCM (2.5 mL). At 0° C., a solution of diethylaminosulfur trifluoride (1.2 eq.) in 0.5 mL of DCM was added. The mixture was stirred at 0° C. for 30 min. The reaction mixture was quenched with sat. aq. NaHCO$_3$, extracted with DCM, dried (MgSO$_4$) and concentrated in vacuo. The residue was purified by column chromatography (SiO$_2$, 0-6% MeOH/DCM), followed by purification by UV directed preparative reverse chromatography, yielding the title compound as a beige solid glass (102 mg, 51%). LCMS (ES+) RT1.60 min, 415.0/417.0 (M+H)$^+$.

Example 169

Enantiomer 2: 2-(5-{(1R or S)-1-[2-(difluoromethoxy)phenyl]-6-fluoro-2,3-dihydro-1H-pyrrolo[1,2-a]benzimidazol-7-yl}pyridin-2-yl)propan-2-ol hydrochloride

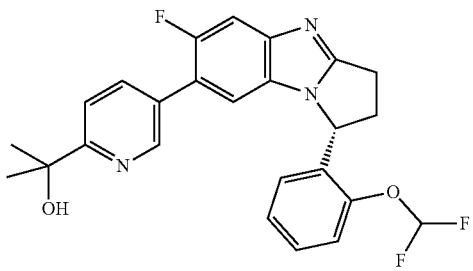 [SMILES: CC(C)(O)c1ccc(-c2cc3c(cc2F)nc2n3[C@@H](c3ccccc3OC(F)F)CC2)cn1]

4N HCl (0.5 mL) was added to a solution of Example 78 (0.38 g, 0.75 mmol) in DCM (5 mL) at 0° C. The reaction was stirred at r.t. for 30 min. The reaction mixture was concentrated in vacuo and triturated with EtOAc/iPr$_2$O (1:1, 2 mL), yielding the title compound as a beige powder (355 mg, 96%). LCMS (ES$^+$) RT 1.45 min, 454.0 (M+H)$^+$.

Examples 170 and 171

Diastereoisomer 1: (1R or S,3R or S)-7-bromo-1-[2-(difluoromethoxy)phenyl]-3,6-difluoro-2,3-dihydro-1H-pyrrolo[1,2-a]benzimidazole; diastereoisomer 2: (1R or S,3S or R)-7-bromo-1-[2-(difluoromethoxy)phenyl]-3,6-difluoro-2,3-dihydro-1H-pyrrolo[1,2-a]benzimidazole

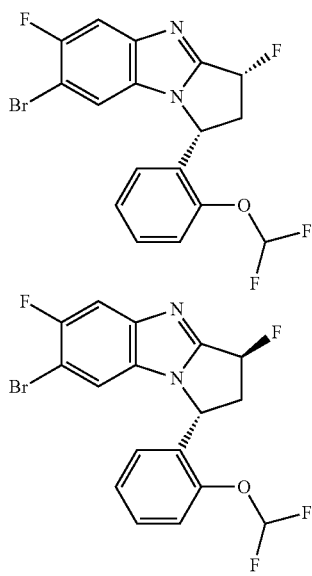

The title compounds were obtained by chiral purification Example 168 (diastereomeric ratio 60/40) by chiral purification under SFC conditions on Whelko-O1 (R,R) (50*227 mm*mm, flow 360 mL/min, 25° C., CO$_2$+20% i-PrOH, injection of 22.5 mL solution at a concentration of 11.6 g/L). The first eluting diastereoisomer (RT 4.9 min) was collected and the fractions were evaporated to yield the title compound, diastereoisomer 1 (Example 170) (96 mg, 19%). The second eluting diastereoisomer (RT 7.9 min) was collected and the fractions were evaporated to yield the other diastereoisomer, diastereoisomer 2 (Example 171) (154 mg, 31%).

Example 172

(1R or S,3R or S)-3-azido-7-bromo-1-[2-(difluoromethoxy)phenyl]-6-fluoro-2,3-dihydro-1H-pyrrolo[1,2-a]benzimidazole

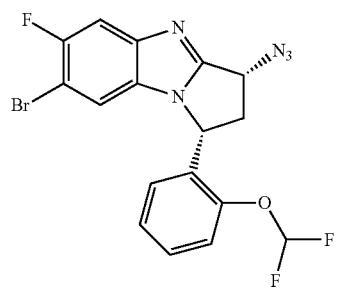 [SMILES: [N-]=[N+]=N[C@@H]1C[C@H](c2ccccc2OC(F)F)n2c1nc1cc(F)c(Br)cc12]

To a solution of Intermediate 108 (0.1 g, 1.0 eq.) in toluene (0.5 mL), diphenylphosphorylazide (1.3 eq.) is added drop wise at 0° C., followed by 1,8-diazabicyclo[5.4.0]undec-7-ene (1.4 eq.). The reaction mixture was stirred at 0° C. for 1 h and at r.t. for 16 h. The reaction mixture was taken up by EtOAc and washed with water. The organic phase is dried (Na$_2$SO$_4$) and concentrated in vacuo to afford 110 mg (100%) of orange oil which was used in the next step without further purification. LCMS (ES$^+$) RT 5.20 min, 438.0/440.0 (M+H)$^+$.

Example 173

(1R or S,3R or S)-7-bromo-1-[2-(difluoromethoxy)phenyl]-6-fluoro-2,3-dihydro-1H-pyrrolo[1,2-a]benzimidazol-3-amine

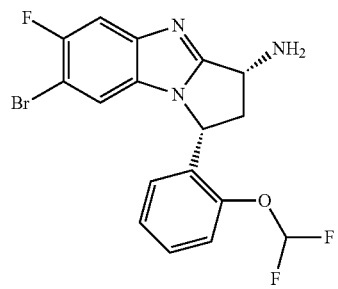 [SMILES: N[C@@H]1C[C@H](c2ccccc2OC(F)F)n2c1nc1cc(F)c(Br)cc12]

Example 172 (0.110 g, 1.1 eq.) was dissolved in 1 mL of toluene. Triphenylphosphine (3 eq.) and 0.5 mL of water were added and the reaction mixture was stirred at r.t. for 16 h. The mixture was concentrated in vacuo and dissolved in EtOAc and extracted with HCl 1N. The aq. phase was neutralized with NaHCO$_3$, extracted with DCM, dried (Na$_2$SO$_4$) and concentrated in vacuo to afford the title compound (87, 84%). LCMS (ES$^+$) RT 3.51 min, 412.0/414.0 (M+H)$^+$.

Example 174 (Method G)

1-(5-{1-[2-(difluoromethoxy)phenyl]-6-fluoro-2,3-dihydro-1H-pyrrolo[1,2-a]benzimidazol-7-yl}pyrimidin-2-yl)-4-methylpiperidine-4-carboxylic acid

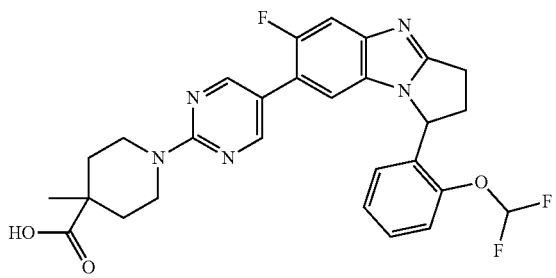 [SMILES: CC1(C(=O)O)CCN(c2ncc(-c3cc4c(cc3F)nc3n4C(c4ccccc4OC(F)F)CC3)cn2)CC1]

Example 94 (0.384 g, 0.679 mmol) was dissolved in THF (8 mL) and 2 mL water. Lithium hydroxide monohydrate (0.102 g, 1.36 mmol) was added and the reaction was heated to 70° C. for 18 h. The reaction was concentrated in vacuo and the residue dissolved in a minimal amount of THF and diluted with water. The mixture was treated with EtOAc, and the organic layer extracted. The aq. was treated with AcOH, drop wise, to pH7, and the solution was stirred. The precipitate was filtered off and dried in vacuo. The solid was purified by prep-HPLC yielding the title compound as a cream solid (0.084 g, 23%). $^1$H NMR (300 MHz, DMSO-$d_6$) δ: 8.38 (d, J 1.7 Hz, 2H), 7.55 (m, 1H), 7.41 (m, 1H), 7.31 (m, 2H), 7.18 (td, J 7.6 Hz, J 0.9 Hz, 1H), 6.98 (d, J 7.1 Hz, 1H), 6.85 (dd, J 7.7 Hz, J 1.4 Hz, 1H), 5.88 (m, 1H), 4.24 (m, 2H), 3.15 (m, 6H), 1.97 (m, 2H), 1.34 (m, 2H), 1.16 (s, 3H). LCMS (ES$^+$) RT 1.57 min, 538.0 (M+H)$^+$.

Example 175

1-(5-{3-[2-(difluoromethoxy)phenyl]-7-fluoro-2,3-dihydro-1H-imidazo[1,2-a]benzimidazol-6-yl}pyrimidin-2-yl)-4-methylpiperidine-4-carboxylic acid

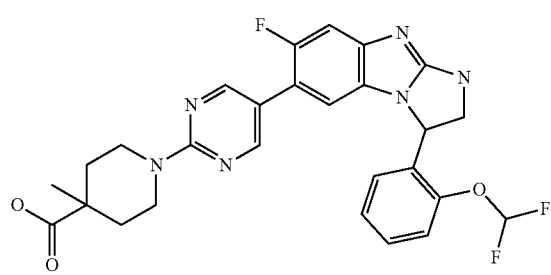 [SMILES: CC1(C(=O)O)CCN(c2ncc(-c3cc4c(cc3F)nc3n4C(c4ccccc4OC(F)F)CN3)cn2)CC1]

The title compound was prepared from Example 100 (0.21 g, 0.36 mmol) was and lithium hydroxide monohydrate (0.055 g, 0.74 mmol) by the Method G (0.041 g, 21%). 1H NMR (DMSO-$d_6$, 300 MHz) δ: 8.36 (d, J 1.6 Hz, 2H), 7.42 (m, 2H), 7.31 (m, 2H), 7.21 (td, J 7.7 Hz, J 1.0 Hz, 1H), 7.14 (d, J 11.8 Hz, 1H), 6.96 (dd, J 7.8 Hz, J 1.5 Hz, 1H), 6.78 (d, J 7.1 Hz, 1H), 5.89 (dd, J 8.8 Hz, J 4.8 Hz, 1H), 4.47 (t, J 9.6 Hz, 1H), 4.22 (m, 1H), 3.76 (dd, J 9.8 Hz, $_2$5.2 Hz, 1H), 3.26 (m, 4H), 1.98 (m, 2H), 1.27 (m, 2H), 1.11 (s, 2H). LCMS (ES$^+$) RT 1.96 min, 539.8 (M+H)$^+$.

Example 176

(1S,5R)-3-[5-[1-1-[2-(difluoromethoxy)phenyl]-2,3-dihydro-1H-imidazo[1,2-a]benzimidazol-7-yl]pyrimidin-2-yl]-3-azabicyclo[3.2.1]octane-8-carboxylic acid

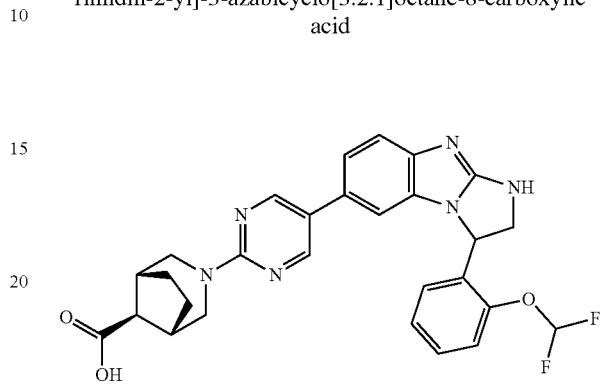

The title compound was prepared from Example 101 (0.197 g, 0.36 mmol) and lithium hydroxide monohydrate (0.108 g, 1.44 mmol) by the Method G (0.077 g, 40%). 1H NMR (DMSO-d6) δ: 8.48 (s, 2H), 7.39 (m, 2H), 7.29 (m, 3H), 7.19 (m, 2H), 6.95 (m, 2H), 5.90 (dd, $J_1$ 8.8 Hz, $J_2$ 4.7 Hz, 1H), 4.47 (t, J 9.3 Hz, 1H), 4.37 (d, J 12.3 Hz, 2H), 3.75 (dd, $J_1$ 9.7 Hz, $J_2$ 4.9 Hz, 1H), 2.96 (d, J 12.0 Hz, 2H), 2.57 (s, 3H), 1.67 (m, 2H), 1.35 (d, J 7.5 Hz, 2H). LCMS (ES$^+$) RT 1.55 min, 533.8 (M+H)$^+$.

Example 177

Enantiomer 2: (1S,5R)-3-[5-[(1R or S)-1-[2-(difluoromethoxy)phenyl]-2,3-dihydro-1H-pyrrolo[1,2-a]benzimidazol-7-yl]pyrimidin-2-yl]-3-azabicyclo[3.2.1]octane-8-carboxylic acid

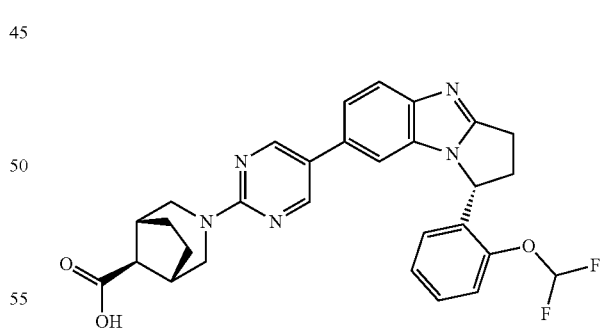

The title compound was prepared from Example 102 (0.163 g, 0.30 mmol) and lithium hydroxide monohydrate (0.089 g, 1.19 mmol) by the Method G (0.083 g, 52%). $^1$H NMR (DMSO-$d_6$) δ: 12.29 (m, 1H), 8.50 (s, 2H), 7.65 (d, J 8.4 Hz, 1H), 7.40 (m, 3H), 7.31 (m, 1H), 7.18 (m, 1H), 7.10 (s, 1H), 6.85 (d, J 7.6 Hz, 1H), 5.89 (m, 1H), 4.40 (d, J 12.4 Hz, 2H), 3.14 (m, 3H), 2.99 (m, 2H), 2.62 (d, J 25.7 Hz, 3H), 1.68 (m, 2H), 1.37 (d, J 8.2 Hz, 2H). LCMS (ES+) RT 1.20 min, 532.2 (M+H)$^+$.

Example 178

Enantiomer 1: (1S,5R)-3-[5-[(4S or R)-2-tert-butoxycarbonyl-4-[2-(difluoromethoxy)phenyl]-8-fluoro-3,4-dihydro-1H-pyrazino[1,2-a]benzimidazol-7-yl]pyrimidin-2-yl]-3-azabicyclo[3.2.1]octane-8-carboxylic acid

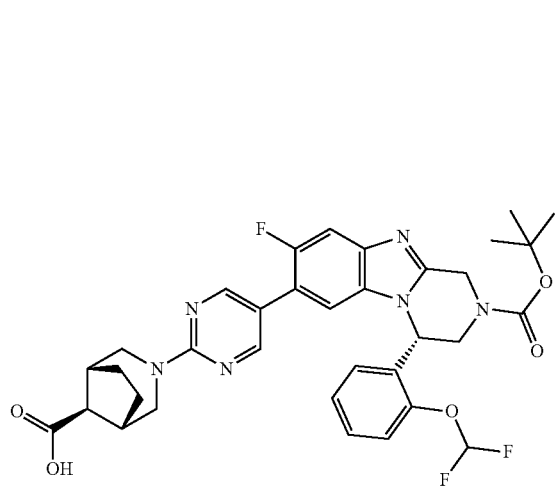 [SMILES: CC(C)(C)OC(=O)N1Cc2nc3cc(F)c(-c4cnc(N5C[C@H]6CC[C@@H](C5)[C@@H]6C(=O)O)nc4)cc3n2[C@@H](c2ccccc2OC(F)F)C1]

Example 99 (100 mg, 0.15 mmol) in THF (3 mL) was treated with NaOH (10% w/v aq. solution, 286 uL) and water (1 mL), and heated to 70° C. for 9 h then allowed to cool to r.t. The reaction mixture was diluted with EtOAc (25 mL), acidified by the addition of AcOH (2 mL) and washed with water (25 mL). The aq. layer was extracted with EtOAc (25 mL) and the combined organic extracts were washed with water (25 mL) and brine (25 mL) and dried (MgSO$_4$) and concentrated in vacuo, yielding colourless gum. LCMS (ES+) RT 1.30 min, 665.0 (M+H)$^+$.

Example 179

Enantiomer 1: (1S,5R)-3-[5-[(4S or R)-4-[2-(Difluoromethoxy)phenyl]-8-fluoro-1,2,3,4-tetrahydropyrazino[1,2-a]benzimidazol-7-yl]pyrimidin-2-yl]-3-azabicyclo[3.2.1]octane-8-carboxylic acid dihydrochloride

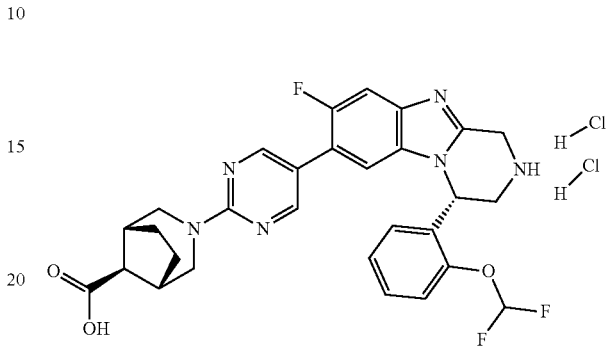

Example 178 (200 mg, 0.30 mmol) was dissolved in 4 M HCl in 1,4-dioxane (4 mL) and stirred at rt for 1.5 h. The reaction mixture was diluted with 1,4-dioxane (10 mL), concentrated in vacuo, suspended in 1,4-dioxane (25 mL) and concentrated in vacuo. The crude residue was triturated in i-Pr$_2$O to give the title compound (94 mg) as yellow solid (100%). δ$_H$ (400 MHz, DMSO-d$_6$) 10.2 (brs, 1H), 8.20 (s, 2H), 7.63 (d, J 11.2 Hz, 1H), 7.56 (m, 1H), 7.40 (d, 1H), 7.38 (tr, J 74.4 Hz, 1H), 7.27 (m, 2H), 6.49 (d, J 6.9 Hz, 1H), 6.12 (dd, J 9.6, 4.9 Hz, 1H), 4.75 (s, 2H), 4.37 (dd, J 12.9, 3.3 Hz, 2H), 4.03 (m, 1H), 3.70-3.57 (m, 2H), 3.00 (d, J 11.9 Hz, 2H), 2.65 (s, 1H), 2.58 (s, 2H), 1.68 (m, 2H), 1.37 (d, J 7.8 Hz, 2H), 1.04 (d, J 6.1 Hz, 2H). LCMS (ES+) RT 0.90 min, 565.0 (M+H)$^+$.

Examples 180-186

The following Examples were prepared using Method C from the assigned precursor using the appropriate boronate ester or boronic acid, either commercially available or prepared in the Intermediates above.

| Example No. | Precursor | Compound Name | LCMS |
|---|---|---|---|
| 180 | Int 109 | 3-[2-(difluoromethoxy)phenyl]-7-fluoro-1-methyl-6-12-(tetrahydro-2H-pyran-4-yl)pyrimidin-5-yl]-2,3-dihydro-1H-imidazo[1,2-a]benzimidazole | LCMS (ES+) RT 4.35 min, 496.3 (M + H)$^+$ |

-continued

| Example No. | Precursor | Compound Name | LCMS |
|---|---|---|---|
| 181 | Int 130 | (1R,3R or S)-1-[2-chloro-6-(difluoromethoxy)phenyl]-7-[2-(1-hydroxy-1-methyl-ethyl)pyrimidin-5-yl]-2,3-dihydro-1H-pyrrolo[1,2-a]benzimidazol-3-ol | LCMS (ES+) RT 1.99 min. 487.0 (M + H)+. |
| 182 | Int 131 | (1R,3S or R)-1-[2-chloro-6-(difluoromethoxy)phenyl]-7-[2-(1-hydroxy-1-methyl-ethyp)pyrimidin-5-yl]-2,3-dihydro-1H-pyrrolo[1,2-a]benzimidazol-3-ol | LCMS (ES+) RT 2.00 min. 487.0 (M + H)+. |
| 183 | Int 111 | (1R,3R)-1-[2-(difluoromethoxy)phenyl]-3-fluoro-7-[2-(2-oxa-7-azaspiro[3.5]non-7-yl)pyrimidin-5-yl]-2,3-dihydro-1H-pyrrolo[1,2-a]benzimidazole | LCMS (ES+) RT 1.52 min. 522.0 (M + H)+. |
| 184 | Int 111 | 2-(5-{(1R,3R)-1-[2-(difluoromethoxy)phenyl]-3-fluoro-2,3-dihydro-1H-pyrrolo[1,2-a]benzimidazol-7-yl}pyrimidin-2-yl)propan-2-ol | LCMS (ES+) RT 1.41 min. 455.0 (M + H)+. |

| Example No. | Precursor | Compound Name | LCMS |
|---|---|---|---|
| 185 | Int 112 | 2-(5-{(1R,3S)-1-[2-(difluoromethoxy)phenyl]-3-fluoro-2,3-dihydro-1H-pyrrolo[1,2-a]benzimidazol-7-yl}pyrimidin-2-yl)propan-2-ol | LCMS (ES+) RT 1.41 min. 455.0 (M + H)+. |
| 186 | Int 137 | 2-(5-{(1R)-[2-(difluoromethoxy)phenyl]-3,8-difluoro-2,3-dihydro-1H-pyrrolo[1,2-a]benzimidazol-7-yl}pyrimidin-2-yl)propan-2-ol | LCMS (ES+) RT 1.45 min. 473.0 (M + H)+. |

Example 187 Method H 2-(5-{(1R)-1-[2-(difluoromethoxy)phenyl]-8-fluoro-3-hydroxy-2,3-dihydro-1H-pyrrolo[1,2-a]benzimidazol-7-yl}pyrimidin-2-yl)-2-methylpropanenitrile

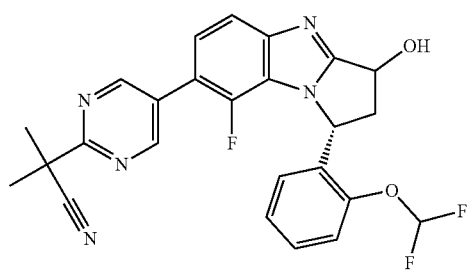 [SMILES: CC(C)(C#N)c1ncc(-c2ccc3nc4n(c3c2F)[C@@H](c2ccccc2OC(F)F)CC4O)cn1]

2-(5-bromopyrimidin-2-yl)-2-methyl-propanenitrile (170 mg, 0.75 mmol), bis(pinacolato)diboron (0.235 g, 0.927 mmol), potassium acetate (0.153 g, 1.545 mmol) were suspended in 5 mL of degassed anhydrous dioxane before addition of [1,1'-bis(diphenylphosphino)ferrocene]dichloropalladium(II) (0.028 g, 0.039 mmol). The reaction mixture was degassed for further 5 minutes and heated at 105° C. for 1 hour. The reaction was cooled to r.t. and Intermediate 110 (0.200 g, 0.484 mmol), cesium carbonate (0.187 g, 0.968 mmol), water (0.315 mL) were added and the mixture was heated at 100° C. for 18 h. The reaction mixture was filtered over Na$_2$SO$_4$ and 45 μM filter washing with EtOAc, and concentrated in vacuo. The residue was purified by chromatography (SiO$_2$, 80% EtOAc/5% MeOH in hexane) to afford the title compound as a brown solid (175 mg, 75%). LCMS (ES+) RT 4.39 min, 480.2 (M+H)+

Example 188

(1R)-1-[2-(difluoromethoxy)phenyl]-8-fluoro-7-[2-(4-fluorotetrahydro-2H-pyran-4-yl)pyrimidin-5-yl]-2,3-dihydro-1H-pyrrolo[1,2-a]benzimidazol-3-ol

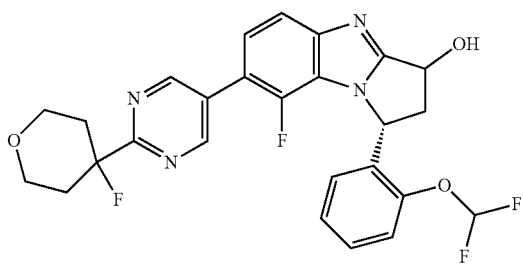 [SMILES: OC1C[C@H](c2ccccc2OC(F)F)n2c1nc1ccc(-c3cnc(C4(F)CCOCC4)nc3)c(F)c12]

The title compound was prepared following the Method H using the Intermediate 114 (200 mg, 0.766 mmol) and Intermediate 110 affording the compound as a brown solid (108 mg, 43%). LCMS (ES+) RT 4.15 min, 515.3 (M+H)+.

Example 189

(1R)-1-[2-(difluoromethoxy)phenyl]-8-fluoro-7-[2-(3-fluorooxetan-3-yl)pyrimidin-5-yl]-2,3-dihydro-1H-pyrrolo[1,2-a]benzimidazol-3-ol

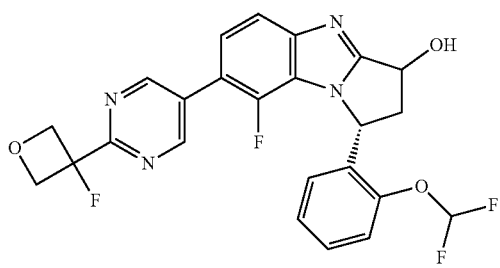 [SMILES: OC1C[C@H](c2ccccc2OC(F)F)n2c1nc1ccc(-c3cnc(C4(F)COC4)nc3)c(F)c12]

The title compound was prepared following the Method H, using Intermediate 135 (180 mg, 0.77 mmol) and Intermediate 110. LCMS (ES+) RT 1.32 min, 487.2 (M+H)+.

Example 191

Butyl 3-(difluoromethoxy)-2-[(1R,3S)-6-fluoro-3-hydroxy-7-[2-(1-hydroxy-1-methyl-ethyl)pyrimidin-5-yl]-2,3-dihydro-1H-pyrrolo[1,2-a]benzimidazol-1-yl]benzoate

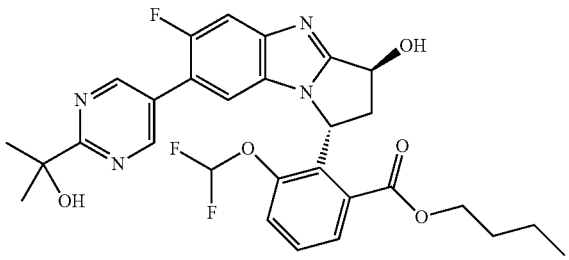 [SMILES: CCCCOC(=O)c1cccc(OC(F)F)c1[C@H]1C[C@H](O)c2nc3cc(F)c(-c4cnc(C(C)(C)O)nc4)cc3n21]

A solution of Example 182 (900 mg, 1.783 mmoL), sodium carbonate (944 mg, 8.913 mmoL), dichloro[bis(dicyclohexylphosphino)propane]palladium(II) (54.7 mg, 0.08913 mmol) in 10 mL of 1-butanol was heated for 16 h at 150° C. under 4 atm of CO gas. The reaction mixture was concentrated in vacuo, the residue was taken up in 50 mL of EtOAc and washed with 3×20 mL of NaOH 0.1 M. The organic layer was dried over anhydrous sodium sulphate and concentrated in vacuo. The crude material was purified by chromatography (SiO2, 80% EtOAc in hexane), to afford the title compound (490 mg, 48.2%). LCMS (ES+) RT 2.66 min. 571.25 (M+H)+.

Example 192

(1R,3R)-1-[2-(difluoromethoxy)phenyl]-6-fluoro-7-[2-(4-fluorotetrahydropyran-4-yl)pyrimidin-5-yl]-2,3-dihydro-1H-pyrrolo[1,2-a]benzimidazol-3-ol

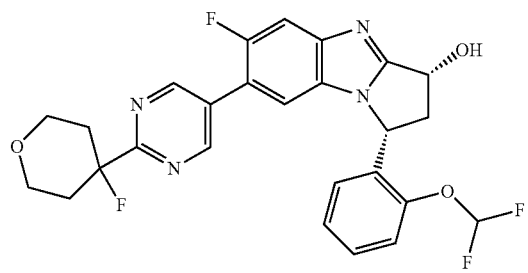 [SMILES: O[C@@H]1C[C@H](c2ccccc2OC(F)F)n2c1nc1cc(F)c(-c3cnc(C4(F)CCOCC4)nc3)cc12]

The title compound was prepared following the Method H using the Intermediate 114 (0.50 g, 1.92 mmol) and Example 161 (0.300 g, 0.75 mmol), affording the compound (195 mg, 52%). LCMS (ES+) RT 1.39 min, 515.0 (M+H)+.

Example 193

(1R)-1-[2-(difluoromethoxy)phenyl]-3,6-difluoro-7-[2-(4-fluorotetrahydro-2H-pyran-4-yl)pyrimidin-5-yl]-2,3-dihydro-1H-pyrrolo[1,2-a]benzimidazole

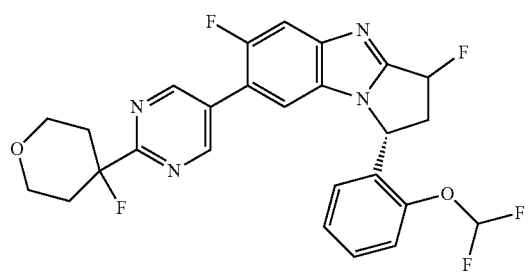 [SMILES: Fc1cc2nc3n(c2cc1-c1cnc(C2(F)CCOCC2)nc1)[C@@H](c1ccccc1OC(F)F)CC3F]

The title compound was prepared following the Method I using the Example 192 (0.050 g, 0.097 mmol) and DAST (0.017 mL, 0.117 mmol) yielding the title compound as a white solid (20 mg, 42%). LCMS (ES+) RT 1.45 min. 517.0 (M+H)+.

Example 194

(1R,3R)-1-[2-(difluoromethoxy)phenyl]-6-fluoro-7-[2-(3-fluorooxetan-3-yl)pyrimidin-5-yl]-2,3-dihydro-1H-pyrrolo[1,2-a]benzimidazol-3-ol

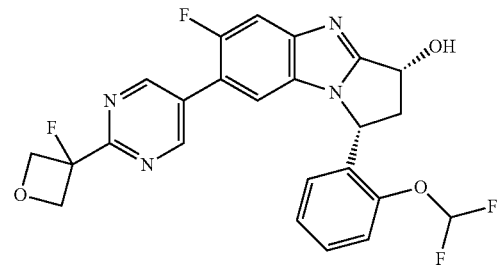 [SMILES: O[C@@H]1C[C@H](c2ccccc2OC(F)F)n2c1nc1cc(F)c(-c3cnc(C4(F)COC4)nc3)cc12]

The title compound was prepared from Example 161 and Intermediate 135 by the Method H. LCMS (ES+) RT 1.36 min, 487.0 (M+H)+.

Example 195

(1R)-1-[2-(difluoromethoxy)phenyl]-3,6-difluoro-7-[2-(3-fluorooxetan-3-yl)pyrimidin-5-yl]-2,3-dihydro-1H-pyrrolo[1,2-a]benzimidazole

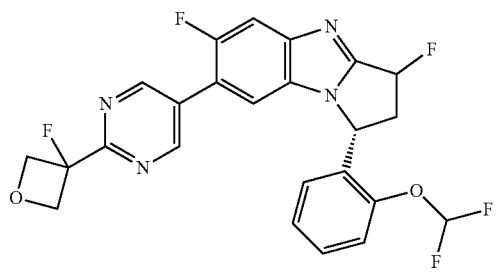 [SMILES: Fc1cc2nc3n(c2cc1-c1cnc(C2(F)COC2)nc1)[C@@H](c1ccccc1OC(F)F)CC3F]

The title compound was prepared following the Method I using the Example 194 (0.170 g, 0.350 mmol) and DAST (0.061 mL, 0.419 mmol) yielding the title compound as a white solid (102 mg, 62%). LCMS (ES+) RT 1.46 min, 489.0 (M+H)+.

Examples 196 and 197

(1R,3R or S)-1-[2-(difluoromethoxy)phenyl]-3,6-difluoro-7-[2-(3-fluorooxetan-3-yl)pyrimidin-5-yl]-2,3-dihydro-1H-pyrrolo[1,2-a]benzimidazole and (1R,3S or R)-1-[2-(difluoromethoxy)phenyl]-3,6-difluoro-7-[2-(3-fluorooxetan-3-yl)pyrimidin-5-yl]-2,3-dihydro-1H-pyrrolo[1,2-a]benzimidazole

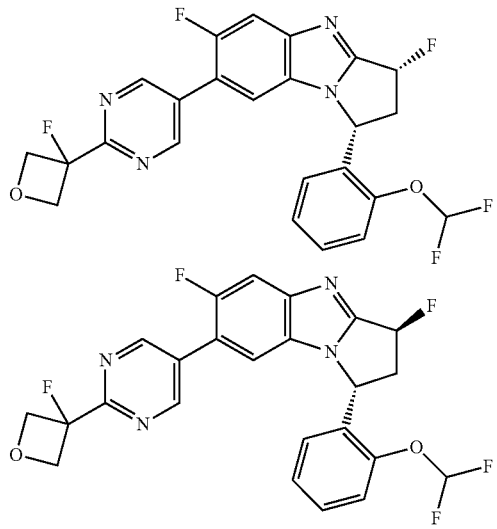

The title compounds were prepared from Example 170 and Example 171 respectively with Intermediate 135 by the Method H. LCMS (ES+) RT 1.46 min, 489.0 (M+H)+.

Example 198

(1R,3R)-1-[2-(difluoromethoxy)phenyl]-7-[2-(3-fluorooxetan-3-yl)pyrimidin-5-yl]-2,3-dihydro-1H-pyrrolo[1,2-a]benzimidazol-3-ol

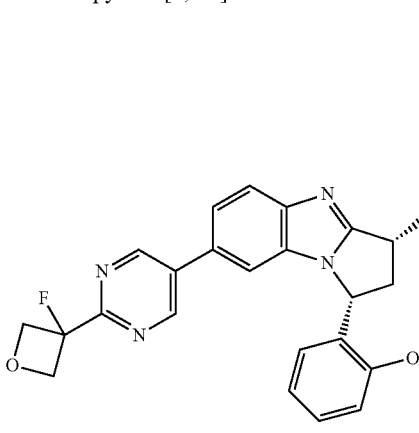

The title compound was prepared from Intermediate 148 and Intermediate 135 by the Method H. LCMS (ES+) RT 1.33 min, 469.0 (M+H)+.

Example 199

(1R)-1-[2-(difluoromethoxy)phenyl]-3-fluoro-7-[2-(3-fluorooxetan-3-yl)pyrimidin-5-yl]-2,3-dihydro-1H-pyrrolo[1,2-a]benzimidazole

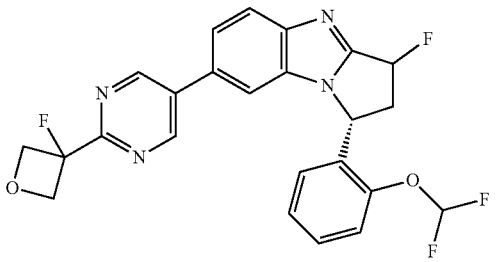 [SMILES: FC(F)Oc1ccccc1[C@H]1CC(F)c2nc3ccc(-c4cnc(C5(F)COC5)nc4)cc3n21]

The title compound was prepared following the Method I using the Example 198 (00.170 g, 0.363 mmol) and DAST (0.06 mL, 0.43 mmol) yielding the title compound as a white solid (50 mg, 29%). LCMS (ES+) RT 1.39 min, 471.0 (M+H)+.

Examples 200 and 201

(1R,3R or S)-1-[2-(difluoromethoxy)phenyl]-3-fluoro-7-[2-(3-fluorooxetan-3-yl)pyrimidin-5-yl]-2,3-dihydro-1H-pyrrolo[1,2-a]benzimidazole and (1R,3S or R)-1-[2-(difluoromethoxy)phenyl]-3-fluoro-7-[2-(3-fluorooxetan-3-yl)pyrimidin-5-yl]-2,3-dihydro-1H-pyrrolo[1,2-a]benzimidazole

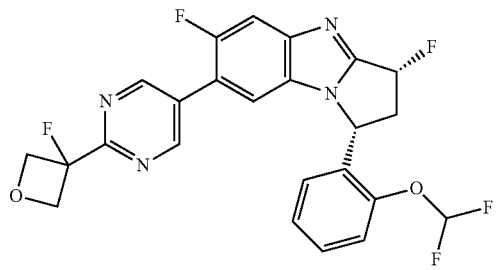

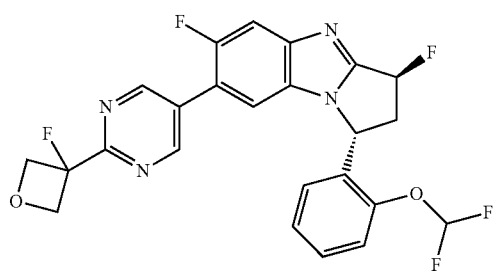

The title compounds were prepared from Intermediates 111 and 112 respectively with Intermediate 135 by the Method H. LCMS (ES+) RT 1.40 min, 471.0 (M+H)+.

Example 202

2-(5-{(1R,3R)-1-[2-(difluoromethoxy)phenyl]-3-fluoro-2,3-dihydro-1H-pyrrolo[1,2-a]benzimidazol-7-yl}pyrimidin-2-yl)-2-methylpropanenitrile

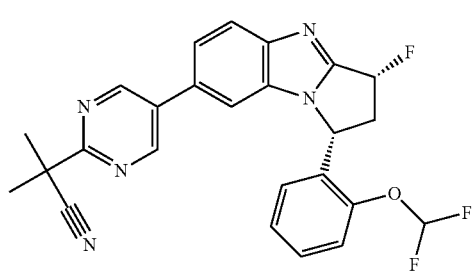 [SMILES: CC(C)(CN)c1ncc(-c2ccc3nc4n(c3c2)[C@@H](c2ccccc2OC(F)F)C[C@H]4F)cn1]

The title compound was prepared following the Method H using the Intermediate 111 (0.068 g, 0.30216 mmol) and 2-(5-bromopyrimidin-2-yl)-2-methyl-propanenitrile (0.108 g, 92%). LCMS (ES+) RT 1.55 min, 464.0 (M+H)+.

Example 203

(1R,3R)-1-[2-(difluoromethoxy)phenyl]-3-fluoro-7-[2-(4-fluorotetrahydropyran-4-yl)pyrimidin-5-yl]-2,3-dihydro-1H-pyrrolo[1,2-a]benzimidazole

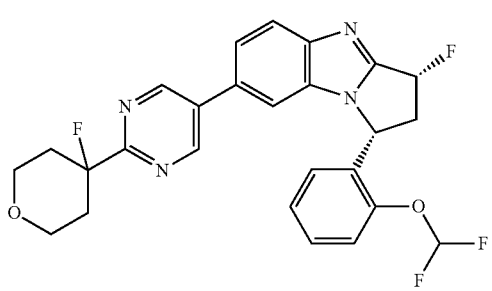 [SMILES: FC(F)Oc1ccccc1[C@H]1C[C@@H](F)c2nc3ccc(-c4cnc(C5(F)CCOCC5)nc4)cc3n21]

The title compound was prepared following the Method H using the Intermediate 111 (122 mg, 0.30 mmol) and Intermediate 114 (100 mg, 0.38 mmol), (0.025 g, 13%). LCMS (ES+) RT 1.47 min, 499.0 (M+H)+.

Example 204

3-[5-[(1R,3R)-1-[2-(difluoromethoxy)phenyl]-3-fluoro-2,3-dihydro-1H-pyrrolo[1,2-a]benzimidazol-7-yl]pyrimidin-2-yl]oxetan-3-ol

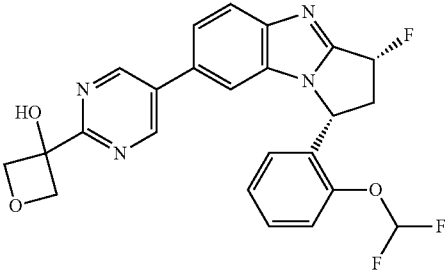 [SMILES: OC1(c2ncc(-c3ccc4nc5n(c4c3)[C@@H](c3ccccc3OC(F)F)C[C@H]5F)cn2)COC1]

The title compound was prepared following the Method H using the Intermediate 111 (100 mg, 0.25 mmol) and Intermediate 133 (116 mg, 0.50 mmol) yielding a brown solid (0.072 g, 61%). LCMS (ES+) RT 1.32 min, 469.0 (M+H)+.

Example 205

(1R)-1-[2-(difluoromethoxy)phenyl]-6-fluoro-7-[6-(1-fluoro-1-methyl-ethyl)-3-pyridyl]-2,3-dihydro-1H-pyrrolo[1,2-a]benzimidazole

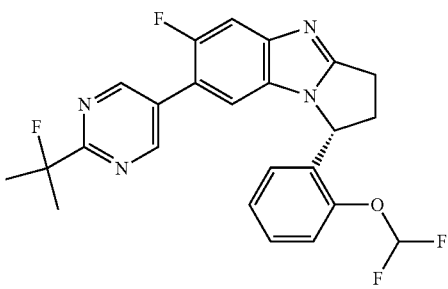 [SMILES: CC(C)(F)c1ncc(-c2cc3c(cc2F)nc2n3[C@@H](c3ccccc3OC(F)F)CC2)cn1]

The title compound was prepared following the Method I from Example 169 (0.315 g, 0.695 mmol) and DAST (1.39 mmol) yielding a white solid (0.220 g, 66%). LCMS (ES+) RT 1.64 min, 456.0 (M+H)+.

Example 206

9-[5-[(1R,3R)-1-[2-(difluoromethoxy)phenyl]-3-fluoro-2,3-dihydro-1H-pyrrolo[1,2-a]benzimidazol-7-yl]pyrimidin-2-yl]-3,7-dioxa-9-azabicyclo[3.3.1]nonane

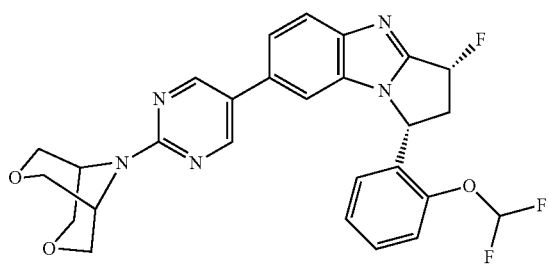 [SMILES: FC(F)Oc1ccccc1[C@H]1C[C@@H](F)c2nc3ccc(-c4cnc(N5C6COCC5COC6)nc4)cc3n21]

The title compound was prepared following the Method H using the Intermediate 111 (216 mg, 0.54 mmol) and Intermediate 140 (195 mg, 0.68 mmol) yielding a brown solid (0.206 g, 58%). LCMS (ES+) RT 1.43 min, 524.0 (M+H)+.

Example 207

3-(difluoromethoxy)-2-{(1R,3R)-3-hydroxy-7-[2-(2-hydroxypropan-2-yl)pyrimidin-5-yl]-2,3-dihydro-1H-pyrrolo[1,2-a]benzimidazol-1-yl}benzonitrile

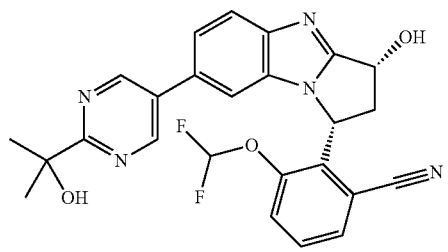 [SMILES: CC(C)(O)c1ncc(-c2ccc3nc4n(c3c2)[C@@H](c2c(C#N)cccc2OC(F)F)C[C@H]4O)cn1]

Example 181 (180 mg, 0.37 mmol) and zinc cyanide (87 mg, 0.74 mmol) were dissolved in anhydrous DMF (3 mL). Tetrakis(triphenylphosphine)palladium (0) (43.2 mg, 0.037 mmol) was added and the mixture was heated at 180° C. for 30 minutes under microwave irradiation. The reaction mixture was poured on ice, a saturated solution of NaHCO$_3$ was added and the reaction mixture was extracted with EtOAc (3×10 mL) and a mixture of DCM/MeOH (9:1) (3×10 mL). The combined organic layers were dried over MgSO$_4$ and concentrated in vacuo. The crude compound was purified by chromatography (SiO$_2$, 0.5-1% MeOH in DCM) and recrystallized in Et$_2$O to afford the title compound as a white solid (76 mg, 43%). LCMS (ES+) RT 1.22 min, 478.0 (M+H)+.

Example 208

3-(difluoromethoxy)-2-{(1R,3S)-3-hydroxy-7-[2-(2-hydroxypropan-2-yl)pyrimidin-5-yl]-2,3-dihydro-1H-pyrrolo[1,2-a]benzimidazol-1-yl}benzonitrile

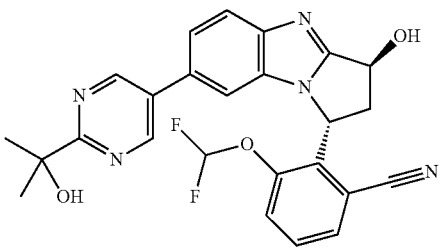

The title compound was prepared from Example 182 (150 mg, 0.308 mmol), zinc cyanide (73 mg, 0.62 mmol), DMF (2 mL) and tetrakis(triphenylphosphine)palladium (0) (36 mg, 0.031 mmol) by the analogous procedure to the preparation of Example 210 (14 mg, 9.5%). LCMS (ES+) RT 1.76 min, 478.0 (M+H)+.

Examples 209 and 210—Method J (1R,3R)-1-(5-chloro-2-(difluoromethoxy)phenyl)-7-(4-((R or S)—S methylsulfonimidoyl)phenyl)-2,3-dihydro-1H-benzo[d]pyrrolo[1,2-a]imidazol-3-ol and (1R,3R)-1-(5-chloro-2-(difluoromethoxy)phenyl)-7-(4-((S or R)—S-methylsulfonimidoyl)phenyl)-2,3-dihydro-1H-benzo[d]pyrrolo[1,2-a]imidazol-3-ol

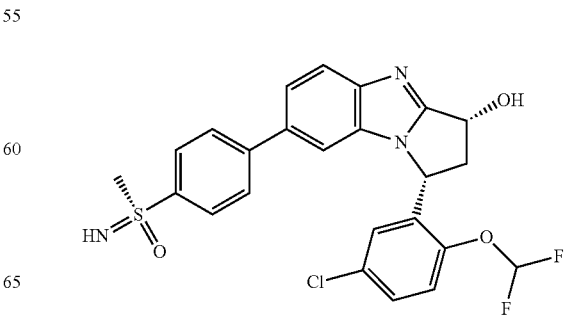

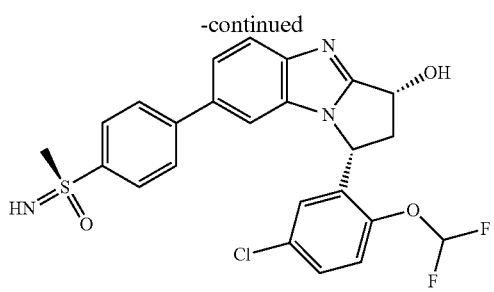

To a mixture of Intermediate 161 (250 mg, 0.58 mmol) in degassed dioxane (4 mL), Intermediate 143 (164 mg, 0.58 mmol), Na₂CO₃ (123 mg, 1.16 mmol) and water (1 mL) was added and the mixture was flushed with Argon. Pd₂(dba)₃ (11 mg, 0.12 mmol) and phosphonium tetrafluoroborate (17 mg, 0.58 mmol) was added and the mixture was stirred in a microwave apparatus (Biotage Initiator) at 100° C. for 15 minutes. The reaction mixture was distributed between NaCl solution (3 mL) and EtOAc (4 mL). The organic phase was separated, dried over Na₂SO₄ and concentrated in vacuo. The residue was purified by chromatography (SiO₂, 5% MeOH in DCM) and by preparative HPLC on SiO₂ (Prep-C18) with water/MeCN as eluent (gradient 30/70 up to 70/30). After concentration in vacuo and lyophilisation (147 mg, 50%) of the desired product was obtained as a mixture of 2 diastereoisomers which were separated by chiral chromatography (Chiracel OJ-H, 250×30 mm, 5 μM, eluent: heptane/EtOH/MeOH, 2/1/1, flow=30 ml/min). The first eluting isomer (8.4 min) was collected and the fractions evaporated to yield Example 209 (57 mg, 19.4%). $^1$H NMR (400 MHz, DMSO-d6) δ ppm 7.95 (d, J 8.4 Hz, 2H), 7.80 (d, J 8.4 Hz, 1H), 7.77 (d, J 8.4 Hz, 2H), 7.60 (dd, J 8.4, 1.77 Hz, 1H), 7.48 (dd, J 8.8, 2.7 Hz, 1H), 7.44 (t, J 73.4 Hz, 1H), 7.38 (m, 2H), 7.01 (d, J 2.6 Hz, 1H), 6.13 (d, J 5.5 Hz, 1H), 5.88 (dd, J 8.4, 4.0 Hz, 1H), 5.23 (m, 1H), 4.19 (s, 1H), 3.50 (m, 1H), 3.07 (s, 3H), 2.34 (m, 1H). LCMS (ES⁺) RT 1.39 min, 504.14 (M+H)⁺

The second eluting isomer (13.9 min) was collected and the fractions evaporated to yield Example 210 (56 mg, 19%). LCMS (ES⁺) RT 1.39 min, 504.14 (M+H)⁺.

The absolute configuration at the sulfoximine residue was not assigned.

Examples 211 and 212

(1R,3R)-1-(2-(difluoromethoxy)phenyl)-7-(4-((R or S)—S-methylsulfonimidoyl)phenyl)-2,3-dihydro-1-H-benzo[d]pyrrolo[1,2-a]imidazol-3-ol and (1R, 3R)-1-(2-(difluoromethoxy)phenyl)-7-(4-((S or R)—S-methylsulfonimidoyl)phenyl)-2,3-dihydro-1-H-benzo[d]pyrrolo[1,2-a]imidazol-3-ol

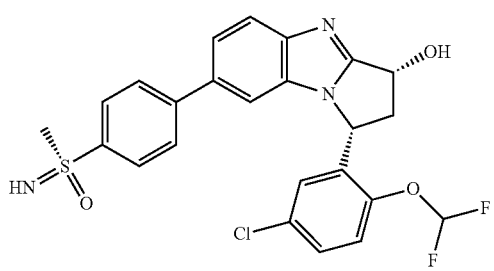

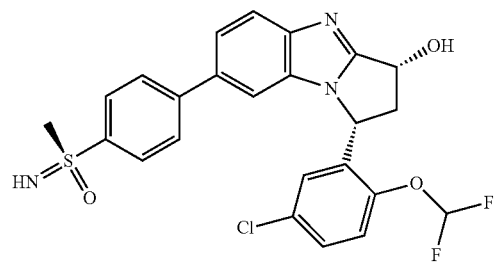

The title compounds were prepared as described in examples 212 and 213 from Intermediate 148 (500 mg, 1.27 mmol) and 4,4,5,5-tetramethyl-2-(4-(S-methylsulfonimidoyl)phenyl)-1,3,2-dioxaborolane (356 mg, 1.27 mmol) to yield 330 mg (55.6%) as a mixture of 2 diastereoisomers which were separated by chromatography 5 (Chiralpak AY, 230×100 mm, 20 μm, eluent: heptane/ethanol 1/1, flow=400 ml/min). The first eluting isomer (9.6 min) was collected and the fractions evaporated to yield Example 211 (146 mg, 24%). $^1$H NMR (400 MHz, DMSO-d6) δ ppm 7.93 (d, J 8.4 Hz, 2H), 7.78 (d, J 8.4 Hz, 1H), 7.72 (d, J 8.4 Hz, 2H), 7.56 (dd, J 8.4, 1.7 Hz, 1H), 7.41 (t, J 73.7 Hz, 1H), 7.40 (m, 1H), 7.33 (d, J 7.8 Hz, 1H), 7.24 (m, 1H), 7.18 (dd, J 7.8, 1.0 Hz, 1H), 7.00 (dd, J 7.8, 1.3 Hz, 1H), 6.09 (d, J 5.5 Hz, 1H), 5.88 (dd, J 8.2, 4.8 Hz, 1H), 5.25 (m, 1H), 4.18 (s, 1H), 3.49 (m, 1H), 3.07 (s, 3H), 2.31 (m, 1H). LCMS (ES⁺) RT 1.28 min, 470.22 (M+H)⁺.

The second eluting isomer (12.9 min) was collected, the fractions evaporated and the residue further purified by chromatography (SiO₂, 5% MeOH in DCM) to yield Example 212 (115 mg, 19%). LCMS (ES+) RT 1.28 min, 470.17 (M+H)⁺.

The absolute configuration at the sulfoximine residue was not assigned.

Examples 213-235

The following Examples were prepared using Method J from the assigned precursor using the appropriate boronate ester or boronic acid, either available commercially or prepared as set out in the Intermediates above.

| Example No. | Precursor | Compound Name | LCMS |
|---|---|---|---|
| 213 | Int 148 | 5-[(1R,3R)-1-(2-Difluoromethoxy-phenyl)-3-hydroxy-2,3-dihydro-1H-benzo[d]pyrrolo[1,2-a]imidazol-7-yl]-1H-pyridin-2-one | LCMS (ES+) RT 1.15 min, 410.13 (M + H)+. |
| 214 | Int 150 | 5-[(1R,3R)-1-(2-Difluoromethoxy-phenyl)-3-(2-hydroxy-ethoxy)-2,3-dihydro-1H-benzo[d]pyrrolo[1,2-a]imidazol-7-yl]-1H-pyridin-2-one | LCMS (ES+) RT 1.25 min, 454.17 (M + H)+. |
| 215 | Int 151 | 5-[(1R,3R)-1-(2-Difluoromethoxy-phenyl)-3-(3-hydroxy-propoxy)-2,3-dihydro-1H-benzo[d]pyrrolo[1,2-a]imidazol-7-yl]-1H-pyridin-2-one | LCMS (ES+) RT 1.37 min, 468.15 (M + H)+. |
| 216 | Int 148 | 5-[(1R,3R)-1-(2-Difluoromethoxy-phenyl)-3-hydroxy-2,3-dihydro-1H-benzo[d]pyrrolo[1,2-a]imidazol-7-yl]-3-methyl-1H-pyridin-2-one | LCMS (ES+) RT 1.25 min, 424.15 (M + H)+. |

-continued

| Example No. | Precursor | Compound Name | LCMS |
|---|---|---|---|
| 217 | Int 153 | 5-{(1R,3R)-1-(2-Difluoromethoxy-phenyl)-3-[2-(2-oxo-pyrrolidin-1-yl)-ethoxy]-2,3-dihydro-1H-benzo[d]pyrrolo[1,2-a]imidazol-7-yl}-1H-pyridin-2-one 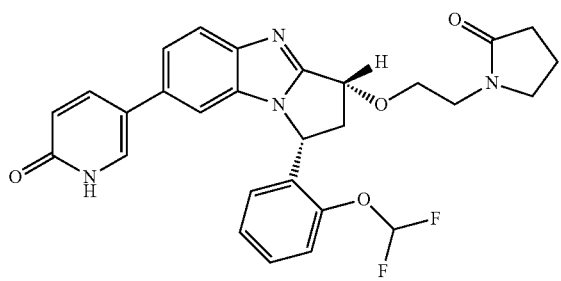 [SMILES: O=C1CCCN1CCO[C@@H]1C[C@H](c2ccccc2OC(F)F)n2c1nc1ccc(-c3ccc(=O)[nH]c3)cc12] | LCMS (ES+) RT 1.35 min, 521.22 (M + H)+. |
| 218 | Int 161 | 5-[(1R,3R)-1-(5-Chloro-2-difluoromethoxy-phenyl)-3-hydroxy-2,3-dihydro-1H-benzo[d]pyrrolo[1,2-a]imidazol-7-yl]-3-methyl-1H-pyridin-2-one 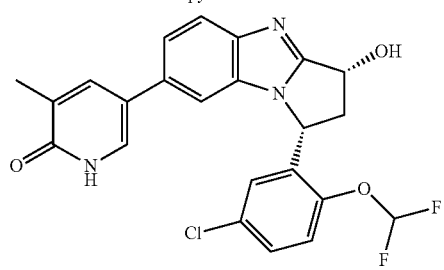 | LCMS (ES+) RT 1.35 min, 458.15 (M + H)+. |
| 219 | Int 148 | 5-[(1R,3R)-1-(2-Difluoromethoxy-phenyl)-3-hydroxy-2,3-dihydro-1H-benzo[d]pyrrolo[1,2-a]imidazol-7-yl]-6-methyl-1H-pyridin-2-one 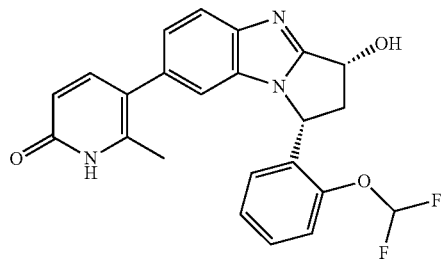 [SMILES: Cc1[nH]c(=O)ccc1-c1ccc2nc3n(c2c1)[C@@H](c1ccccc1OC(F)F)C[C@H]3O] | LCMS (ES+) RT 1.16 min, 424.2 (M + H)+. |
| 220 | Int 148 | 5-[(1R,3R)-1-(2-Difluoromethoxy-phenyl)-3-hydroxy-2,3-dihydro-1H-benzo[d]pyrrolo[1,2-a]imidazol-7-yl]-4-methyl-1H-pyridin-2-one 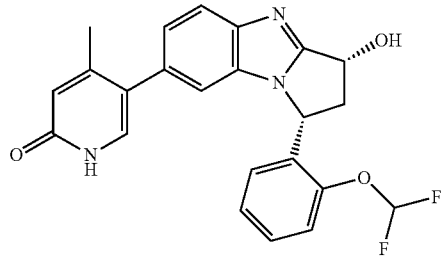 [SMILES: Cc1cc(=O)[nH]cc1-c1ccc2nc3n(c2c1)[C@@H](c1ccccc1OC(F)F)C[C@H]3O] | LCMS (ES+) RT 1.19 min, 424.16 (M + H)+. |

| Example No. | Precursor | Compound Name | LCMS |
|---|---|---|---|
| 221 | Int 150 | 2-[(1R,3R)-1-(2-Difluoromethoxy-phenyl)-7-(4-methylsulfonimidoyl-phenyl)-2,3-dihydro-1H-benzo[d]pyrrolo[1,2-a]imidazol-3-yloxy]-ethanol | LCMS (ES+) RT 1.36 min, 514.2 (M + H)+. |
| 222 | Int 150 | 2-[(1R,3R)-1-(2-Difluoromethoxy-phenyl)-7-(4 methanesulfonyl-phenyl)-2,3-dihydro-1H-benzo[d]pyrrolo[1,2-a]imidazol-3-yloxy]-ethanol | LCMS (ES+) RT 1.53 min, 515.19 (M + H)+. |
| 223 | Int 148 | (1R,3R)-1-(2-Difluoromethoxy-phenyl)-7-(4 methanesulfonyl-phenyl)-2,3-dihydro-1H-benzo[d]pyrrolo[1,2-a]imidazol-3-ol | LCMS (ES+) RT 1.47 min, 471.17 (M + H)+. |
| 224 | Int 148 | (1R,3R)-7-(4-Cyclopropanesulfonyl-phenyl)-1-(2-difluoromethoxy-phenyl)-2,3-dihydro-1H-benzo[d]pyrrolo[1,2-a]imidazol-3-ol | LCMS (ES+) RT 1.57 min, 497.22 (M + H)+. |

| Example No. | Precursor | Compound Name | LCMS |
|---|---|---|---|
| 225 | Int 161 | (1R,3R)-1-(5-Chloro-2-difluoromethoxy-phenyl)-7-(4-methanesulfonyl-phenyl)-2,3-dihydro-1H-benzo[d]pyrrolo[1,2-a]imidazol-3-ol | LCMS (ES$^+$) RT 1.56 min, 505.14 (M + H)$^+$. |
| 226 | Int 161 | (1R,3R)-1-(5-Chloro-2-difluoromethoxy-phenyl)-7-(4-cyclopropanesulfonyl-phenyl)-2,3-dihydro-1H-benzo[d]pyrrolo[1,2-a]imidazol-3-ol | LCMS (ES$^+$) RT 1.65 min, 531.14 (M + H)$^+$. |
| 227 | Int 150 | 2-[(1R,3R)-7-(4-Cyclopropanesulfonyl-phenyl)-1-(2-difluoromethoxy-phenyl)-2,3-dihydro-1H-benzo[d]pyrrolo[1,2-a]imidazol-3-yloxy]-ethanol | LCMS (ES$^+$) RT 1.63 min, 541.22 (M + H)$^+$. |
| 228 | Int 148 | 5-[(1R,3R)-1-(2-Difluoromethoxy-phenyl)-3-hydroxy-2,3-dihydro-1H-benzo[d]pyrrolo[1,2-a]imidazol-7-yl]-1-methyl-1H-pyridin-2-one | LCMS (ES$^+$) RT 1.24 min, 424.2 (M + H)$^+$. |

| Example No. | Precursor | Compound Name | LCMS |
|---|---|---|---|
| 229 | Int 148 | 4-[(1R,3R)-1-(2-Difluoromethoxy-phenyl)-3-hydroxy-2,3-dihydro-1H-benzo[d]pyrrolo[1,2-a]imidazol-7-yl]-benzenesulfonamide | LCMS (ES+) RT 1.35 min, 472.13 (M + H)+. |
| 230 | Int 152 | 2-[(1R,3R)-1-(5-Chloro-2-difluoromethoxy-phenyl)-7-(4-methanesulfonyl-phenyl)-2,3-dihydro-1H-benzo[d]pyrrolo[1,2-a]imidazol-3-yloxyl-ethanol | LCMS (ES+) RT 1.6 min, 549.09 (M + H)+. |
| 231 | Int 152 | 2-[(1R,3R)-1-(5-Chloro-2-difluoromethoxy-phenyl)-7-(4-cyclopropanesulfonyl-phenyl)-2,3-dihydro-1H-benzo[d]pyrrolo[1,2-a]imidazol-3-yloxy]-ethanol | LCMS (ES+) RT 1.68 min, 575.09 (M + H)+. |
| 232 | Int 148 | (1R,3R)-1-(2-Difluoromethoxy-phenyl)-7-[4-(propane-2-sulfonyl)-phenyl]-2,3-dihydro-1H-benzo[d]pyrrolo[1,2a]imidazol-3-ol | LCMS (ES+) RT 1.6 min, 499.18 (M + H)+. |

| Example No. | Precursor | Compound Name | LCMS |
|---|---|---|---|
| 233 | Int 148 | 4-[(1R,3R)-1-(2-Difluoromethoxy-phenyl)-3-hydroxy-2,3-dihydro-1H-benzo[d]pyrrolo[1,2-a]imidazol-7-yl]-N-(2-hydroxy-ethyl)-benzenesulfonamide 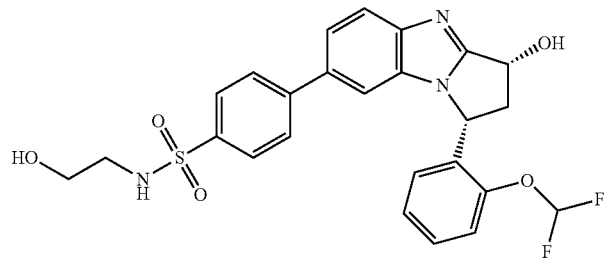 [SMILES: O=S(=O)(NCCO)c1ccc(-c2ccc3nc4n(c3c2)[C@@H](c2ccccc2OC(F)F)C[C@H]4O)cc1] | LCMS (ES⁺) RT 1.36 min, 516.14 (M + H)⁺. |
| 234 | Int 148 | 5-[(1R,3R)-1-(2-Difluoromethoxy-phenyl)-3-hydroxy-2,3-dihydro-1H-benzo[d]pyrrolo[1,2-a]imidazol-7-yl]-1,3-dimethyl-1H-pyridin-2-one 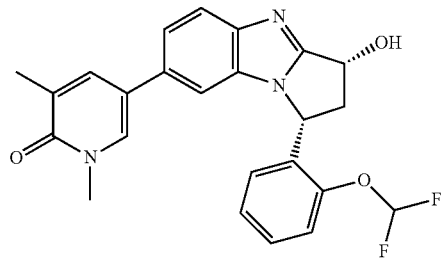 [SMILES: Cc1cc(-c2ccc3nc4n(c3c2)[C@@H](c2ccccc2OC(F)F)C[C@H]4O)cn(C)c1=O] | LCMS (ES⁺) RT 1.33 min, 438.19 (M + H)⁺. |
| 235 | Int 148 | 3-Cyclopropyl-5-[(1R,3R)-1-(2-difluoromethoxy-phenyl)-3-hydroxy-2,3-dihydro-1H-benzo[d]pyrrolo[1,2-a]imidazol-7-yl]-1H-pyridin-2-one 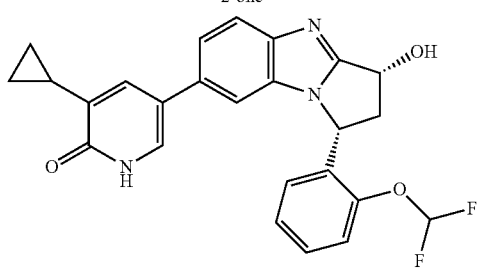 | LCMS (ES⁺) RT 1.34 min, 450.18 (M + H)⁺. |

Example 236

(8-anti)-3-(5-{(1R,3R)-1-[2-(difluoromethoxy)phenyl]-6-fluoro-3-hydroxy-2,3-dihydro-1H-pyrrolo[1,2-a]benzimidazol-7-yl}pyrimidin-2-yl)-3-azabicyclo[3.2.1]octane-8-carboxylic acid

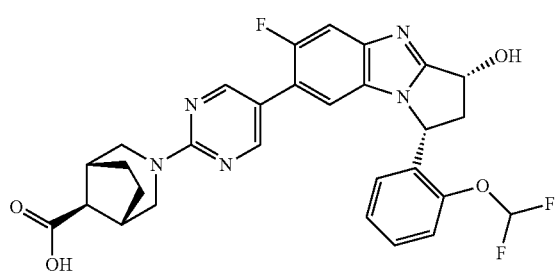 [SMILES: O=C(O)[C@@H]1[C@@H]2CC[C@H]1CN(c1ncc(-c3cc4c(cc3F)nc3n4[C@@H](c4ccccc4OC(F)F)C[C@H]3O)cn1)C2]

The title compound was prepared from Intermediate 163 (501 mg, 0.86 mmol), by the Method G (418 mg, 85%). LCMS (ES+) RT 1.08 min, 566.0 (M+H)+.

Example 237 Method L (1R,3R or S)-1-[2-(difluoromethoxy)phenyl]-8-fluoro-7-[4-(methylsulfonyl)phenyl]-2,3-dihydro-1H-pyrrolo[1,2-a]benzimidazol-3-ol

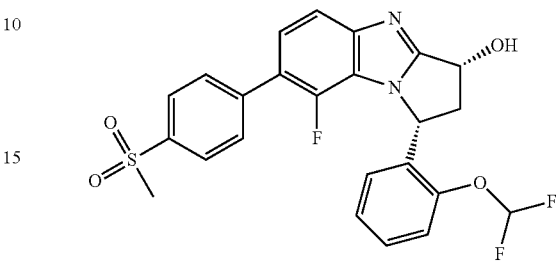

In a microwave vessel (20 ml), Intermediate 164 (50 mg, 121 μmol), sodium carbonate (52 mg, 484 μmol), 4-(methylsulphonyl)phenylboronic acid (49 mg, 242 μmol), and 1,1'-bis(diphenylphosphino)ferrocene-palladium(II)dichloride dichloromethane complex (20 mg, 24 μmol) were mixed with DME (4 mL) and water (1 mL). After heating for 15 minutes at 100° C. and cooling to r.t. water was added and the aqueous phase was extracted with DCM (×3). The combined organic phases were dried over sodium sulphate, filtered and concentrated in vacuo. The residue was purified by chromatography (SiO$_2$, 0-10% EtOH in DCM). The residue was further purified by preparative HPLC (M2b) yielding the title compound (42 mg, 71%). LCMS [M 1b](ES+) RT 1.57 min, 489.1 (M+H)+.

Examples 238-239

The following Examples were prepared from the given starting material using the appropriate boronate ester or boronic acid by the Method L.

| Example No. | Precursor | Compound Name | LCMS |
|---|---|---|---|
| 238 | Int 164 | (1R,3R or S)-[2-(difluoromethoxy)phenyl]-8-fluoro-7-[2-(2-hydroxypropan-2-yl)pyrimidin-5-yl]-2,3-dihydro-1H-pyrrolo[1,2-a]benzimidazol-3-ol 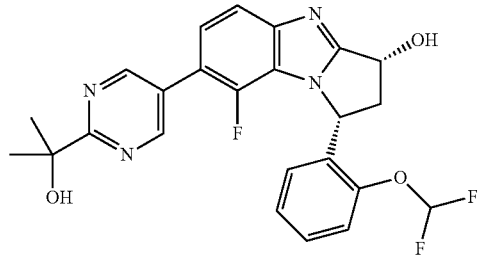 [SMILES: CC(C)(O)c1ncc(-c2ccc3nc4n(c3c2F)[C@@H](c2ccccc2OC(F)F)C[C@H]4O)cn1] | LCMS [M 1b] (ES+) RT 1.56 min, 471.2 (M + H)+ |

| Example No. | Precursor | Compound Name | LCMS |
|---|---|---|---|
| 239 | Int 164 | (1R,3R or S)-7-[4-(cyclopropylsulfonyl)phenyl]-1-[2-(difluoromethoxy)phenyl]-8-fluoro-2,3-dihydro-1H-pyrrolo[1,2-a]benzimidazol-3-ol 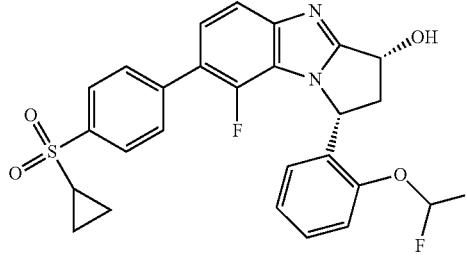 | LCMS [M 1b] (ES+) RT 1.66 min, 515.1 (M + H)+ |

Example 240

Example 40 was prepared from the given starting material using the appropriate boronate ester or boronic acid by the Method L

| Example No. | Precursor | Compound Name | LCMS |
|---|---|---|---|
| 240 | Int 164 | (1R,3R or S)-1-[2-(difluoromethoxy)phenyl]-8-fluoro-7-(6-methoxy-3-pyridyl)-2,3-dihydro-1H-pyrrolo[1,2-a]benzimidazol-3-ol 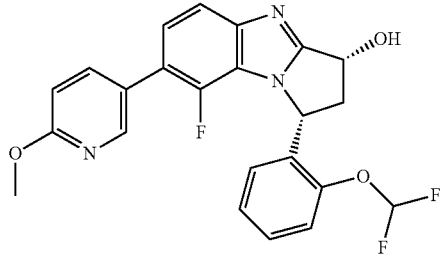 [SMILES: COc1ccc(-c2ccc3nc4n(c3c2F)[C@@H](c2ccccc2OC(F)F)C[C@H]4O)cn1] | LCMS [M 1b] (ES+) RT 1.70 min; 442.1 (M + H)+. |

Example 241

2-(5-{4-[2-(difluoromethoxy)phenyl]-8-fluoro-1,2,3,4-tetrahydropyrazino[1,2-a]benzimidazol-7-yl}pyrimidin-2-yl)propan-2-ol

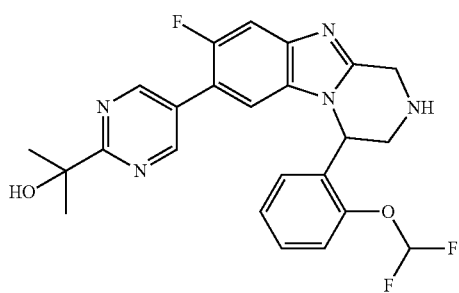 [SMILES: CC(C)(O)c1ncc(-c2cc3c(cc2F)nc2n3C(c3ccccc3OC(F)F)CNC2)cn1]

Intermediate 165 (210 mg, 369 μmol) was dissolved in dioxane (5 mL) and hydrogen chloride solution (1 mL) followed by TFA (0.5 mL) were added at r.t. After stirring for 1 h the mixture stood for 18 h and was heated to 60° C. for 1.5 h. An additional amount of TFA (0.5 mL) was added and after 1.25 h, the mixture was cooled to r.t. and EtOAc and saturated sodium bicarbonate solution were added. After phase separation the aqueous phase was extracted twice with EtOAc. The combined organic phases were washed with brine, dried over sodium sulphate, filtered and concentrated in vacuo. The residue was purified by preparative HPLC (M2d) yielding the title compound (105 mg, 61%). LCMS [M 1b](ES+) RT 1.31 min, 470.3 (M+H)+.

The invention claimed is:
1. A compound of formula (I), or a pharmaceutically acceptable thereof,

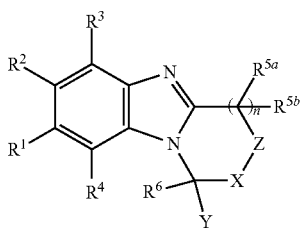

(I)

wherein n represents an integer equal to 0 or 1;

X and Z independently represent a covalent bond; an heteroatom; S(O)—, —S(O)$_2$—, —S(O)(N—R$^d$), —NC(O)—R$^d$, —N(CO)—OR$^d$, —NS(O)$_2$R$^d$, —N(R$^d$); or a straight or branched C$_{1-4}$ alkylene chain;

Y represents aryl or heteroaryl, either of which groups may be optionally substituted by one, two or three substituents selected from halogen, cyano, C$_{1-6}$ alkyl, trifluoromethyl, C$_{1-6}$ alkoxy, difluoromethoxy, trifluoromethoxy, and C$_{1-6}$ alkylsulfonyl;

R$^1$ represents aryl, (C$_{3-7}$)heterocycloalkenyl-, heteroaryl, (C$_{3-7}$)heterocycloalkyl-heteroaryl-, (C$_{4-9}$)heterobicycloalkyl-heteroaryl- or (C$_{4-9}$)spiroheterocycloalkyl-heteroaryl, any of which groups may be optionally substituted by one or more substituents selected from halogen, hydroxy, C$_{1-6}$ alkyl, C$_{1-6}$ alkoxy, C$_{1-6}$ alkylcarbonyl, (hydroxy)C$_{1-6}$ alkyl, (C$_{3-7}$)cycloalkyl, C$_{1-6}$ alkylsulphonyl, (C$_{1-6}$)alkylsulphonyl(C$_{1-6}$)alkyl, (C$_{1-6}$) alkylsulphoximinyl, heteroaryl, oxo, carboxy, (cyano) C$_{1-6}$ alkyl, (halo)C$_{1-6}$ alkyl, aminosulphonyl, (C$_{3-7}$) cycloalkylsulphonyl and hydroxy(C$_{1-6}$) alkylaminosulphonyl;

R$^2$ represents hydrogen, halogen, cyano, trifluoromethyl; or a C$_{1-6}$ alkyl which group may be optionally substituted by alkoxycarbonyl;

R$^3$ and R$^4$ independently represents hydrogen, halogen, or C$_{1-6}$ alkyl;

R$^{5a}$ and R$^{5b}$ independently represent hydrogen, hydroxy, halogen, or trifluoromethyl; or —NR$^b$R$^c$, S(O)$_2$R$^a$, —OR$^a$, —O—(CO)—R$^d$ or C$_{1-6}$ alkyl;

R$^6$ represents hydrogen, hydroxy, halogen or trifluoromethyl; and

R$^a$ represents C$_{1-6}$ alkyl which group may be optionally substituted by one or more substituents selected from hydroxy, methoxy, oxo, and 2-oxo-1-pyrrolidinyl;

R$^b$ represents hydrogen or C$_{1-6}$ alkyl;

R$^c$ represents hydrogen, C$_{1-6}$ alkyl or C$_{3-7}$ cycloalkyl; and

R$^d$ represents hydrogen or C$_{1-6}$ alkyl.

2. The compound as claimed in claim 1 wherein R$^1$ represents aryl, heteroaryl, or (C$_{3-7}$)heterocycloalkyl-heteroaryl-, either of which groups may be optionally substituted by one or more substituents selected from halogen, hydroxy, C$_{1-6}$ alkyl, C$_{1-6}$ alkoxy, C$_{1-6}$ alkylcarbonyl, (hydroxy)C$_{1-6}$ alkyl, (C$_{3-7}$)cycloalkyl, C$_{1-6}$ alkylsulphonyl, (C$_{1-6}$)alkylsulphonyl(C$_{1-6}$)alkyl, (C$_{1-6}$)alkylsulphoximinyl, heteroaryl, oxo, carboxy, (cyano)C$_{1-6}$ alkyl, (halo)C$_{1-6}$ alkyl, aminosulphonyl, (C$_{3-7}$)cycloalkylsulphonyl and hydroxy(C$_{1-6}$)alkylaminosulphonyl.

3. The compound as claimed in claim 1 wherein Y represents phenyl optionally substituted by one or more substituents selected from chloro, fluoro, cyano, methoxy, methylsulphonyl, trifluoromethoxy and difluoromethoxy.

4. The compound as claimed in claim 1 represented by formula (IIC), or a pharmaceutically acceptable salt, wherein V represents C—R$^{12}$ or N;

R$^9$ represents hydrogen, hydroxy, oxo or carboxy; C$_{1-6}$ alkyl, (hydroxy)C$_{1-6}$ alkyl, C$_{1-6}$ alkoxy, C$_{2-6}$ alkylcarbonyl, C$_{1-6}$ alkylsulphonyl, (C$_{1-6}$)alkylsulphonyl(C$_{1-6}$) alkyl, (C$_{1-6}$)alkylsulphoximinyl, (C$_{3-7}$)cycloalkyl, (C$_{3-7}$)heterocycloalkyl, (C$_{4-9}$)heterobicycloalkyl, cyano(C$_{1-6}$)alkyl, (C$_{3-7}$)cycloalkylsulphonyl or (C$_{1-6}$) alkylaminosulphonyl, any of which groups may be optionally substituted by one or more substitutents independently selected from halogen, C$_{1-6}$ alkyl, C$_{1-6}$ alkylsulphonyl, C$_{1-6}$ alkylcarbonyl, oxo and carboxy;

R$^{10}$ and R$^{11}$ independently represents hydrogen, halogen, cyano, trifluoromethyl, hydroxyl, —NR$^b$R$^c$, —OR$^a$, C$_{1-6}$ alkyl, or C$_{1-6}$ alkylsulphonyl;

R$^{12}$ represents hydrogen, halogen or C$_{1-6}$ alkyl;

X is methylene, —S(O), oxygen atom or sulphur atom;

Y represents phenyl optionally substituted by one or more substituents selected from chloro, fluoro, cyano, methoxy, methylsulphonyl, trifluoromethoxy and difluoromethoxy;

R$^2$ represents hydrogen, halogen, cyano, trifluoromethyl; or a C$_{1-6}$ alkyl which group may be optionally substituted by alkoxycarbonyl;

R$^{5a}$ and R$^{5b}$ independently represent hydrogen, hydroxy, halogen, or trifluoromethyl; or —NR$^b$R$^c$, S(O)$_2$R$^a$, —OR$^a$, —O—(CO)—R$^d$ or C$_{1-6}$ alkyl;

R$^a$ represents C$_{1-6}$ alkyl which group may be optionally substituted by one or more substituents selected from hydroxy, methoxy, oxo, and 2-oxo-1-pyrrolidinyl;

R$^b$ represents hydrogen or C$_{1-6}$ alkyl;

R$^c$ represents hydrogen, C$_{1-6}$ alkyl or C$_{3-7}$ cycloalkyl; and

R$^d$ represents hydrogen or C$_{1-6}$ alkyl.

5. The compound as claimed in claim 2, wherein X represents methylene.

6. The compound as claimed in claim 1, wherein R$^{5a}$ represents hydrogen or hydroxy.

7. The compound as claimed in claim 1, wherein R$^{5b}$ represents hydrogen or methyl.

8. The compound as claimed in claim 1, wherein Y represents (difluoromethoxy)phenyl, (difluoromethoxy) (fluoro)phenyl, (chloro)(difluoromethoxy)phenyl or (difluoromethoxy)(cyano)phenyl.

9. The compound as claimed in claim 2, wherein R$^9$ represents fluorotetrahydropyranyl, fluorooxetanyl, tetrahydropyranyl, isopropyl, methylsulphonyl, hydroxyisopropyl, morpholinyl, cyclopropyl, carboxy-3-azabicyclo[3.2.1]octanyl, piperazinyl, methylpiperazinyl, acetylpiperazinyl, oxodiazepanyl, and (methyl)(carboxy)piperidinyl, hydroxyoxetanyl, methylsulphoximinyl, 2-oxa-7-aza-spiro[3,5] nonanyl, 3,7-dioxa-9-azabicyclo[3.3.1]nonanyl, 3,7-dioxa-9-azabicyclo[3.3.1]nonanyl, -azabicyclo[3.2.1]octanyl, cyanoisopropyl, fluoroisopropyl, methylsulphoximinyl, cyclopropylsulphonyl, aminosulphonyl, isopropylsulphonyl, and (hydroxy)ethylaminosulphonyl.

10. The compound as claimed in claim 1 represented by formula (IIP) or a pharmaceutically acceptable salt thereof,

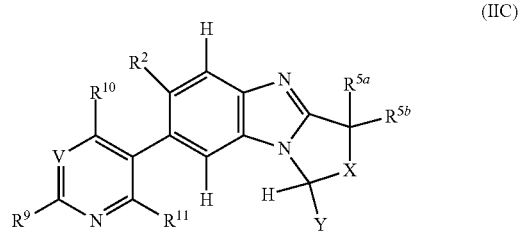

(IIC)

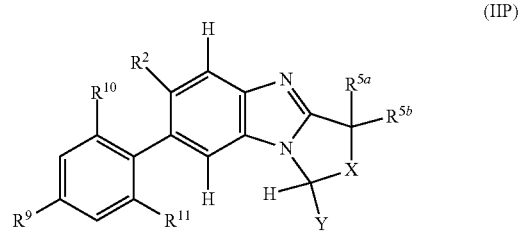

(IIP)

wherein

X is methylene, —S(O), oxygen atom or sulphur atom;

Y represents phenyl optionally substituted by one or more substituents selected from chloro, fluoro, cyano, methoxy, methylsulphonyl, trifluoromethoxy and difluoromethoxy;

$R^2$ represents hydrogen, halogen, cyano, trifluoromethyl; or a $C_{1-6}$ alkyl which group may be optionally substituted by alkoxycarbonyl;

$R^{5a}$ and $R^{5b}$ independently represent hydrogen, hydroxy, halogen, or trifluoromethyl; or —$NR^bR^c$, $S(O)_2R^a$, —$OR^a$, —O—(CO)—$R^d$ or $C_{1-6}$ alkyl;

$R^9$ represents hydrogen, hydroxy, oxo or carboxy; $C_{1-6}$ alkyl, (hydroxy)$C_{1-6}$ alkyl, $C_{1-6}$ alkoxy, $C_{2-6}$ alkylcarbonyl, $C_{1-6}$ alkylsulphonyl, $(C_{1-6})$alkylsulphonyl$(C_{1-6})$alkyl, $(C_{1-6})$alkylsulphoximinyl, $(C_{3-7})$cycloalkyl, $(C_{3-7})$heterocycloalkyl, $(C_{4-9})$heterobicycloalkyl, cyano$(C_{1-6})$alkyl, $(C_{3-7})$cycloalkylsulphonyl or $(C_{1-6})$alkylaminosulphonyl, any of which groups may be optionally substituted by one or more substituents independently selected from halogen, $C_{1-6}$ alkyl, $C_{1-6}$ alkylsulphonyl, $C_{1-6}$ alkylcarbonyl, oxo and carboxy; and $R^{10}$ and $R^{11}$ independently represents hydrogen, halogen, cyano, trifluoromethyl, hydroxy, —$NR^bR^c$, —$OR^a$, $C_{1-6}$ alkyl, or $C_{1-6}$ alkylsulphonyl.

11. The compound as claimed in claim 1 represented by formula (IIR) or a pharmaceutically acceptable salt thereof,

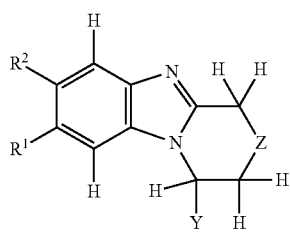

(IIR)

wherein

Z represents an heteroatom; —$NC(O)R^d$, —$N(CO)$—$OR^d$, —$NS(O)_2R^d$, or —$N(R^d)$;

$R^1$ represents aryl, $(C_{3-7})$heterocycloalkenyl-, heteroaryl, $(C_{3-7})$heterocycloalkyl-heteroaryl-, $(C_{4-9})$heterobicycloalkyl-heteroaryl- or $(C_{4-9})$spiroheterocycloalkyl-heteroaryl, any of which groups may be optionally substituted by one or more substituents selected from halogen, hydroxy, $C_{1-6}$ alkyl, $C_{1-6}$ alkoxy, $C_{-6}$ alkylcarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, $(C_{1-6})$alkylsulphoximinyl, heteroaryl, oxo, carboxy (cyano) $C_{1-6}$ alkyl, (halo)$C_{1-6}$ alkyl, aminosulphonyl, $(C_{3-7})$cycloalkylsulphonyl and hydroxy$(C_{1-6})$alkylaminosulphonyl;

$R^2$ represents hydrogen, halogen, cyano, trifluoromethyl; or a $C_{1-6}$ alkyl which group may be optionally substituted by alkoxycarbonyl; and Y represents phenyl optionally substituted by one or more substituents selected from chloro, fluoro, cyano, methoxy, methylsulphonyl, trifluoromethoxy and difluoromethoxy.

12. The compound as claimed in claim 1 represented by formula (IIS) or a pharmaceutically acceptable salt thereof

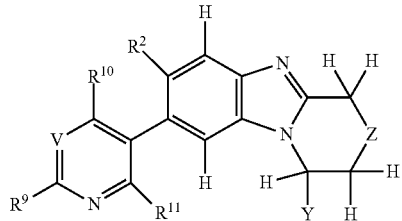

(IIS)

wherein

Z represents an heteroatom; —$NC(O)R^d$, —$N(CO)$—$OR^d$, —$NS(O)_2R^d$, or —$N(R^d)$;

Y represents phenyl optionally substituted by one or more substituents selected from chloro, fluoro, cyano, methoxy, methylsulphonyl, trifluoromethoxy and difluoromethoxy;

$R^2$ represents hydrogen, halogen, cyano, trifluoromethyl; or a $C_{1-6}$ alkyl which group may be optionally substituted by alkoxycarbonyl;

V represents C—$R^{12}$ or N;

$R^9$ represents hydrogen, hydroxy, oxo or carboxy; $C_{1-6}$ alkyl, (hydroxy)$C_{1-6}$ alkyl, $C_{1-6}$ alkoxy, $C_{2-6}$ alkylcarbonyl, $C_{1-6}$ alkylsulphonyl, $(C_{1-6})$alkylsulphonyl$(C_{1-6})$alkyl, $(C_{1-6})$alkylsulphoximinyl, $(C_{3-7})$cycloalkyl, $(C_{3-7})$heterocycloalkyl, $(C_{4-9})$heterobicycloalkyl, cyano$(C_{1-6})$alkyl, $(C_{3-7})$cycloalkylsulphonyl or $(C_{1-6})$alkylaminosulphonyl, any of which groups may be optionally substituted by one or more substituents independently selected from halogen, $C_{1-6}$ alkyl, $C_{1-6}$ alkylsulphonyl, $C_{1-6}$ alkylcarbonyl, oxo and carboxy;

$R^{10}$ and $R^{11}$ independently represents hydrogen, halogen, cyano, trifluoromethyl, hydroxyl, —$NR^bR^c$, —$OR^a$, $C_{1-6}$ alkyl, or $C_{1-6}$ alkylsulphonyl; and $R^{12}$ represents hydrogen, halogen or $C_{1-6}$ alkyl.

13. The compound as claimed in claim 1 represented by formula (IIQ), or a pharmaceutically acceptable salt thereof,

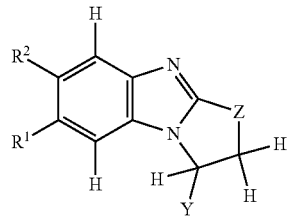

(IIQ)

wherein

Z represents N—$R^d$;

$R^d$ represents hydrogen;

Y represents phenyl optionally substituted by one or more substituents selected from chloro, fluoro, cyano, methoxy, methylsulphonyl, trifluoromethoxy and difluoromethoxy;

$R^1$ represents aryl, $(C_{3-7})$heterocycloalkenyl-, heteroaryl, $(C_{3-7})$heterocycloalkyl-heteroaryl-, $(C_{4-9})$heterobicycloalkyl-heteroaryl- or $(C_{4-9})$spiroheterocycloalkyl-heteroaryl, any of which groups may be optionally substituted by one or more substituents selected from halogen, hydroxy, $C_{1-6}$ alkyl, $C_{1-6}$ alkoxy, $C_{-6}$ alkylcarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, $(C_{1-6})$alkylsulphoximinyl, heteroaryl, oxo, carboxy, (cyano)

$C_{1-6}$ alkyl, (halo)$C_{1-6}$ alkyl, aminosulphonyl, $(C_{3-7})$ cycloalkylsulfonyl and hydroxy($C_{1-6}$) alkylaminosulphonyl; and $R^2$ represents hydrogen, halogen, cyano, trifluoromethyl; or a $C_{1-6}$ alkyl which group may be optionally substituted by alkoxycarbonyl.

14. A compound selected from the group consisting of
1-(2,5-dimethylphenyl)-7-(6-methoxy-3-pyridyl)-2,3-dihydro-1H-pyrrolo[1,2-a]benzimidazole;
(1R or S)-1-[2-(difluoromethoxy)phenyl]-7-(6-methoxy-3-pyridyl)-2,3-dihydro-1H-pyrrolo[1,2-a]benzimidazole;
4-[5-[(1S or R)-1-[2-(difluoromethoxy)phenyl]-2,3-dihydro-1H-pyrrolo[1,2-a]benzimidazol-7-yl]pyrimidin-2-yl]morpholine;
7-(6-methoxypyridin-3-yl)-1-(2-methylphenyl)-2,3-dihydro-1H-pyrrolo[1,2-a]benzimidazole;
1-(2-methylphenyl)-7-[2-(morpholin-4-yl)pyrimidin-5-yl]-2,3-dihydro-1H-pyrrolo[1,2-a]benzimidazole;
7-(6-methoxypyridin-3-yl)-1-phenyl-2,3-dihydro-1H-pyrrolo[1,2-a]benzimidazole;
7-[2-(morpholin-4-yl)pyrimidin-5-yl]-1-phenyl-2,3-dihydro-1H-pyrrolo[1,2-a]benzimidazole;
1-[2-(difluoromethoxy)phenyl]-7-(4-methylsulfonylphenyl)-2,3-dihydro-1H-imidazo[1,2-a]benzimidazole;
(1R or S)-1-[2-(difluoromethoxy)phenyl]-6-fluoro-7-(6-methoxy-3-pyridyl)-2,3-dihydro-1H-pyrrolo[1,2-a]benzimidazole;
(1R or S)-1-[2-(difluoromethoxy)phenyl]-6-fluoro-7-(3-pyridyl)-2,3-dihydro-1H-pyrrolo[1,2-a]benzimidazole;
(1R or S)-1-[2-(difluoromethoxy)phenyl]-6-fluoro-7-(3-methylsulfonylphenyl)-2,3-dihydro-1H-pyrrolo[1,2-a]benzimidazole;
(1R or S)-1-[2-(difluoromethoxy)phenyl]-6-fluoro-7-(2-methylsulfonyl-4-pyridyl)-2,3-dihydro-1H-pyrrolo[1,2-a]benzimidazole;
(1R or S)-1-[2-(difluoromethoxy)phenyl]-6-fluoro-7-(6-methylsulfonyl-3-pyridyl)-2,3-dihydro-1H-pyrrolo[1,2-a]benzimidazole;
(1R or S)-1-[2-(difluoromethoxy)phenyl]-7-(2,5-dimethyl-3-pyridyl)-6-fluoro-2,3-dihydro-1H-pyrrolo[1,2-a]benzimidazole;
(1R or S)-1-[2-(difluoromethoxy)phenyl]-6-fluoro-7-(5-methylsulfonyl-3-pyridyl)-2,3-dihydro-1H-pyrrolo[1,2-a]benzimidazole;
(1R or S)-7-(6-methylsulfonyl-3-pyridyl)-1-phenyl-2,3-dihydro-1H-pyrrolo[1,2-a]benzimidazole;
(1R or S)-7-(6-cyclopropyl-3-pyridyl)-1-[2-(difluoromethoxy)phenyl]-2,3-dihydro-1H-pyrrolo[1,2-a]benzimidazole;
(1R or S)-1-[2-(difluoromethoxy)phenyl]-7-(3-pyridyl)-2,3-dihydro-1H-pyrrolo[1,2-a]benzimidazole;
(1R or S)-1-[2-(difluoromethoxy)phenyl]-7-(6-methylsulfonyl-3-pyridyl)-2,3-dihydro-1H-pyrrolo[1,2-a]benzimidazole;
(1R or S)-1-[2-(difluoromethoxy)phenyl]-7-(1-methylpyrazol-4-yl)-2,3-dihydro-1H-pyrrolo[1,2-a]benzimidazole;
(4R or S)-4-[2-(difluoromethoxy)phenyl]-8-fluoro-7-(4-methylsulfonylphenyl)-3,4-dihydro-1H-[1,4]oxazino[4,3-a]benzimidazole;
(4R or S)-4-[2-(difluoromethoxy)phenyl]-8-fluoro-7-(6-methylsulfonyl-3-pyridyl)-3,4-dihydro-1H-[1,4]oxazino[4,3-a]benzimidazole;
(4S or R)-4-[2-(difluoromethoxy)phenyl]-8-fluoro-7-[4-(methylsulfonylmethyl)phenyl]-3,4-dihydro-1H-[1,4]oxazino[4,3-a]benzimidazole;
tert-butyl (4 S or R)-4-[2-(difluoromethoxy)phenyl]-8-fluoro-7-(3-methylsulfonylphenyl)-3,4-dihydro-1H-pyrazino[1,2-a]benzimidazole-2-carboxylate;
(1S or R)-6-fluoro-1-(4-fluorophenyl)-7-[2-morpholin-4-yl)pyrimidin-5-yl]-2,3-dihydro-1H-pyrrolo[1,2-a]benzimidazole;
(1R or S)-6-fluoro-1-(2-methoxyphenyl)-7-[2-(morpholin-4-yl)pyrimidin-5-yl]-2,3-dihydro-1H-pyrrolo[1,2-a]benzimidazole;
2-(5-1{(1R or S,3R or S)-1-[2-(difluoromethoxy)phenyl]-6-fluoro-3-methoxy-2,3-dihydro-1H-pyrrolo[1,2-a]benzimidazol-7-yl}pyrimidin-2-yl)propan-2-ol,
(1R or S)-6-fluoro-7-[2-(morpholin-4-yl)pyrimidin-5-yl]-1-[2-(trifluoromethyl)phenyl]-2,3-dihydro-1H-pyrrolo[1,2-a]benzimidazole;
(1S or R)-6-fluoro-1-[2-(methylsulfonyl)phenyl]-7-[2-(morpholin-4-yl)pyrimidin-5-yl]-2,3-dihydro-1H-pyrrolo[1,2-a]benzimidazole;
(1R or S,3R or S)-1-[2-(difluoromethoxy)phenyl]-6-fluoro-3-methoxy-7-[6-(tetrahydro-2H-pyran-4-yl)pyridin-3-yl]-2,3-dihydro-1H-pyrrolo[1,2-a]benzimidazole;
(1R or S,3R or S)-1-[2-(difluoromethoxy)phenyl]-6-fluoro-7-[6-(tetrahydro-2H-pyran-4-yl)pyridin-3-yl]-2,3-dihydro-1H-pyrrolo[1,2-a]benzimidazol-3-ol;
(1R or S)-1-(2-chlorophenyl)-6-fluoro-7-[2-(morpholin-4-yl)pyrimidin-5-yl]-2,3-dihydro-1H-pyrrolo[1,2-a]benzimidazole;
(1R or S,3R or S)-7-(6-cyclopropylpyridin-3-yl)-1-[2-(difluoromethoxy)phenyl]-6-fluoro-2,3-dihydro-1H-pyrrolo[1,2-a]benzimidazol-3-ol;
2-(5-1{(1R or S)-1-[2-(difluoromethoxy)phenyl]-6-fluoro-2,3-dihydro-1H-pyrrolo[1,2-a]benzimidazol-7-yl}pyrimidin-2-yl)propan-2-ol;
(1R or S)-7-(6-cyclopropylpyridin-3-yl)-1-[2-(difluoromethoxy)phenyl]-6-fluoro-2,3-dihydro-1H-pyrrolo[1,2-a]benzimidazole;
(1R or S)-7-(6-cyclopropylpyridin-3-yl)-6-fluoro-1-[2-(methylsulfonyl)phenyl]-2,3-dihydro-1H-pyrrolo[1,2-a]benzimidazole;
(1R or S)-7-(6-cyclopropylpyridin-3-yl)-1-[2-(difluoromethoxy)phenyl]-3,6-difluoro-2,3-dihydro-1H-pyrrolo[1,2-a]benzimidazole;
2-(5-1{(1R or S)-1-[2-(difluoromethoxy)phenyl]-3,6-difluoro-2,3-dihydro-1H-pyrrolo[1,2-a]benzimidazol-7-yl}pyrimidin-2-yl)propan-2-ol;
(1R or S,3R or S)-1-[2-(difluoromethoxy)phenyl]-6-fluoro-7-[2-(2-hydroxypropan-2-yl)pyrimidin-5-yl-2,3-dihydro-1H-pyrrolo[1,2-a]benzimidazol-3-ol;
(1R or S,3S or R)-1-2-(difluoromethoxy)phenyl]-3,6-difluoro-7-[2-(morpholin-4-yl)pyrimidin-5-yl]-2,3-dihydro-1H-pyrrolo[1,2-a]benzimidazole;
(1R or S,3R or S)-1-[2-(difluoromethoxy)phenyl]-3,6-difluoro-7-[2-(morpholin-4-yl)pyrimidin-5-yl-2,3-dihydro-1H-pyrrolo[1,2-a]benzimidazole;
2-(5-{(1R or S,3S or R)-1-[2-(difluoromethoxy)phenyl]-3,6-difluoro-2,3-dihydro-1H-pyrrolo[1,2-a]benzimidazol-7-yl}pyrimidin-2-yl)propan-2-ol;
2(5-{(1R or S,3R or S)-1-2-(difluoromethoxy)phenyl]-3,6-difluoro-2,3-dihydro-1H-pyrrolo[1,2-a]benzimidazol-7-yl}pyrimidin-2-yl)propan-2-ol;
(1R or S,3R or S)-1-[2-(difluoromethoxy)phenyl]-6-fluoro-7-{6-[(methylsulfonyl)methyl]pyridin-3-yl}-2,3-dihydro-1H-pyrrolo[1,2-a]benzimidazol-3-ol;
(1R or S,3R or S)-1-[2-(difluoromethoxy)phenyl]-6-fluoro-7-[1-(2-methylpropyl)-1H-pyrazol-4-yl]-2,3-dihydro-1H-pyrrolo[1,2-a]benzimidazol-3-ol;

(1R or S,3R or S)-1-[2-(difluoromethoxy)phenyl]-6-fluoro-7-[2-(propan-2-yl)pyrimidin-5-yl]-2,3-dihydro-1H-pyrrolo[1,2-a]benzimidazol-3-ol, (1R or S,3R or S)-1-[2(difluoromethoxy)phenyl]-6-fluoro-7-[2-(tetrahydro-2H-pyran-4-yl)pyrimidin-5-yl]-2,3-dihydro-1H-pyrrolo[1,2-a]benzimidazol-3-ol;

(1R or S,3R or S)-1-[2-(difluoromethoxy)phenyl]-6-fluoro-7-[6-(tetrahydro-2H-pyran-4-yl)pyridin-3-yl]-2,3-dihydro-1H-pyrrolo[1,2-a]benzimidazol-3-amine, 1-(5-{1-[2-(difluoromethoxy)phenyl]-2,3-dihydro-1H-pyrrolo[1,2-a]benzimidazol-7-yl}pyrimidin-2-yl)-1,4-diazepan-5-one;

1-[2-(difluoromethoxy)phenyl]-7-[4-(methyl sulfonyl)phenyl]-2,3-dihydro-1H-pyrrolo[1,2-a]benzimidazole;

1-[5-[(1S or R)-1-[2-(difluoromethoxy)phenyl]-2,3-dihydro-1H-pyrrolo[1,2-a]benzimidazol-7-yl]pyrimidin-2-yl]-1,4-diazepan-5-one;

5-[1-(2-methylphenyl)-2,3-dihydro-1H-pyrrolo[1,2-a]benzimidazol-7-yl]pyridin-2(1H)-one;

5-(1-phenyl-2,3-dihydro-1H-pyrrolo[1,2-a]benzimidazol-7-yl)pyridin-2(1H)-one;

(1S or R)-1-[2-(difluoromethoxy)phenyl]-6-fluoro-7-(4-methylsulfonylphenyl)-2,3-dihydro-1H-imidazo[1,2-a]benzimidazole;

(1S or R)-1-[2-(difluoromethoxy)phenyl]-7-(4-methylsulfonylphenyl)-2,3-dihydro-1H-imidazo[1,2-a]benzimidazole;

(1R or S)-1-[2-(difluoromethoxy)phenyl]-6-fluoro-7-(6-piperazin-1-yl-3-pyridyl)-2,3-dihydro-1H-pyrrolo[1,2-a]benzimidazole;

5-[(1R or S)-1-[2-(difluoromethoxy)phenyl]-6-fluoro-2,3-dihydro-1H-pyrrolo[1,2-a]benzimidazol-7-yl]-1H-pyridin-2-one;

1-[4-[5-[(1R or S)-1-[2-(difluoromethoxy)phenyl]-6-fluoro-2,3-dihydro-1H-pyrrolo[1,2-a]benzimidazol-7-yl]-2-pyridyl]piperazin-1-yl]ethenone;

(1R or S)-1-[2-(difluoromethoxy)phenyl]-6-fluoro-7-[6-(4-methylpiperazin-1-yl)-3-pyridyl]-2,3-dihydro-1H-pyrrolo[1,2-a]benzimidazole;

(1R or S)-1-[2-(difluoromethoxy)phenyl]-6-fluoro-7-[6-(4-methylsulfonylpiperazin-1-yl)-3-pyridyl]-2,3-dihydro-1H-pyrrolo[1,2-a]benzimidazole;

(1R or S)-7-[6-(methyl sulfonylmethyl)-3-pyridyl]-1-phenyl-2,3-dihydro-1H-pyrrolo[1,2-a]benzimidazole;

(1R or S, 3R or S)-1-[2-(difluoromethoxy)phenyl]-6-fluoro-7-(4-methyl sulfonylphenyl)-2,3-dihydro-1H-pyrrolo[1,2-a]benzimidazol-3-ol;

(1R or S,3S or R)-1-[2-(difluoromethoxy)phenyl]-6-fluoro-7-(4-methyl sulfonylphenyl)-2,3-dihydro-1H-pyrrolo[1,2-a]benzimidazol-3-ol, (1R or S,3S or R)-1-[2-(difluoromethoxy)phenyl]-6-fluoro-7-(4-methylsulfonylphenyl)-2,3-dihydro-1H-pyrrolo[1,2-a]benzimidazol-3-ol;

(1R or S)-1-[2-(difluoromethoxy)phenyl]-7-(6-piperazin-1-yl-3-pyridyl)-2,3-dihydro-1H-pyrrolo[1,2-a]benzimidazole;

(4R or S)-4-[2-(difluoromethoxy)phenyl]-8-fluoro-7-(6-piperazin-1-yl-3-pyridyl)-3,4-dihydro-1H-[1,4]oxazino[4,3-a]benzimidazole;

(4S or R)-4-[2-(difluoromethoxy)phenyl]-8-fluoro-7-(4-methylsulfonylphenyl)-1,2,3,4-tetrahydropyrazino[1,2-a]benzimidazole;

(4S or R)-4-[2-(difluoromethoxy)phenyl]-8-fluoro-7-(2-methylsulfonyl-4-pyridyl)-1,2,3,4-tetrahydropyrazino[1,2-a]benzimidazole;

(4S or R)-4-[2-(difluoromethoxy)phenyl]-8-fluoro-7-(6-methylsulfonyl-3-pyridyl)-1,2,3,4-tetrahydropyrazino[1,2-a]benzimidazole;

4-[2-(difluoromethoxy)phenyl]-7-(4-methylsulfonylphenyl)-1,2,3,4-tetrahydropyrazino[1,2-a]benzimidazole;

(4R or S)-4-[2-(difluoromethoxy)phenyl]-7-(6-methylsulfonyl-3-pyridyl)-1,2,3,4-tetrahydropyrazino[1,2-a]benzimidazole;

(4S or R)-4-[2-(difluoromethoxy)phenyl]-7-(2-methylsulfonyl-4-pyridyl)-1,2,3,4-tetrahydropyrazino[1,2-a]benzimidazole;

(4S or R)-4-[2-(difluoromethoxy)phenyl]-8-fluoro-7-[3-(methylsulfonyl)phenyl]-1,2,3,4-tetrahydropyrazino[1,2-a]benzimidazole;

1-[(4S or R)-4-[2-(difluoromethoxy)phenyl]-8-fluoro-7-(4-methyl sulfonylphenyl)-3,4-dihydro-1H-pyrazino[1,2-a]benzimidazol-2-yl]ethenone;

(4S or R)-4-[2-(difluoromethoxy)phenyl]-8-fluoro-2-methylsulfonyl-7-(4-methylsulfonylphenyl)-3,4-dihydro-1H-pyrazino[1,2-a]benzimidazole;

(4S or R)-4-[2-(difluoromethoxy)phenyl]-8-fluoro-2-methyl-7-(4-methylsulfonylphenyl)-3,4-dihydro-1H-pyrazino[1,2-a]benzimidazole;

(4S or R)-4-[2-(difluoromethoxy)phenyl]-7-(4-methylsulfonylphenyl)-1,2,3,4-tetrahydropyrazino[1,2-a]benzimidazole;

(1R or S,3R or S)-6-fluoro-7-[6-(methylsulfonyl)pyridin-3-yl]-1-phenyl-2,3-dihydro-1H-pyrrolo[1,2-a]benzimidazol-3-ol;

2-(5-{(1S or R,3S or R)-1-[2-(difluoromethoxy)phenyl]-6-fluoro-3-methoxy-2,3-dihydro-1H-pyrrolo[1,2-a]benzimidazol-7-yl}pyridin-2-yl)propan-2-ol;

2-(5-{(1R or S,3R or S)-1-[2-(difluoromethoxy)phenyl]-6-fluoro-3-methoxy-2,3-dihydro-1H-pyrrolo[1,2-a]benzimidazol-7-yl}pyridin-2-yl)propan-2-ol;

(1R or S)-7-bromo-1-[2-(difluoromethoxy)phenyl]-3,6-difluoro-2,3-dihydro-1H-pyrrolo[1,2-a]benzimidazole;

2-(5-{(1R or S)-1-[2-(difluoromethoxy)phenyl]-6-fluoro-2,3-dihydro-1H-pyrrolo[1,2-a]benzimidazol-7-yl}pyridin-2-yl)propan-2-ol hydrochloride;

1-(5-{1-[2-(difluoromethoxy)phenyl]-6-fluoro-2,3-dihydro-1H-pyrrolo[1,2-a]benzimidazol-7-yl}pyrimidin-2-yl)-4-methylpiperidine-4-carboxylic acid;

1-(5-{3-[2-(difluoromethoxy)phenyl]-7-fluoro-2,3-dihydro-1H-imidazo[1,2-a]benzimidazol-6-yl}pyrimidin-2-yl)-4-methylpiperidine-4-carboxylic acid;

(1S,5R)-3-[5-[1-1-[2-(difluoromethoxy)phenyl]-2,3-dihydro-1H-imidazo[1,2-a]benzimidazol-7-yl]pyrimidin-2-yl]-3-azabicyclo[3.2.1]octane-8-carboxylic acid;

(1S,5R)-3-[5-[(1R or S)-1-[2-(difluoromethoxy)phenyl]-2,3-dihydro-1H-pyrrolo[1,2-a]benzimidazol-7-yl]pyrimidin-2-yl]-3-azabicyclo[3.2.1]octane-8-carboxylic acid;

(1S,5R)-3-[5-[(4S or R)-4-[2-(Difluoromethoxy)phenyl]-8-fluoro-1,2,3,4-tetrahydropyrazino[1,2-a]benzimidazol-7-yl]pyrimidin-2-yl]-3-azabicyclo[3.2.1]octane-8-carboxylic acid dihydrochloride;

3-[2-(difluoromethoxy)phenyl]-7-fluoro-1-methyl-6-[2-(tetrahydro-2H-pyran-4-yl)pyrimidin-5-yl]-2,3-dihydro-1H-imidazo[1,2-a]benzimidazole;

(1R,3R)-1-[2-chloro-6-(difluoromethoxy)phenyl]-7-[2-(1-hydroxy-1-methyl-ethyl)pyrimidin-5-yl]-2,3-dihydro-1H-pyrrolo[1,2-a]benzimidazol-3-ol;

(1R,3S)-1-[2-chloro-6-(difluoromethoxy)phenyl]-7-[2-(1-hydroxy-1-methyl-ethyl)pyrimidin-5-yl]-2,3-dihydro-1H-pyrrolo[1,2-a]benzimidazol-3-ol;

(1R,3R)-1-[2-(difluoromethoxy)phenyl]-3-fluoro-7-[2-(2-oxa-7-azaspiro[3.5]non-7-yl)pyrimidin-5-yl]-2,3-dihydro-1H-pyrrolo[1,2-a]benzimidazole;

2-(5-{(1R,3R)-1-[2-(difluoromethoxy)phenyl]-3-fluoro-2,3-dihydro-1H-pyrrolo[1,2-a]benzimidazol-7-yl}pyrimidin-2-yl)propan-2-ol;

2-(5-{(1R,3S)-1-[2-(difluoromethoxy)phenyl]-3-fluoro-2,3-dihydro-1H-pyrrolo[1,2-a]benzimidazol-7-yl}pyrimidin-2-yl)propan-2-ol;

2-(5-{(1R)-1-[2-(difluoromethoxy)phenyl]-3,8-difluoro-2,3-dihydro-1H-pyrrolo[1,2-a]benzimidazol-7-yl}pyrimidin-2-yl)propan-2-ol;

2-(5-{(1R)-1-[2-(difluoromethoxy)phenyl]-8-fluoro-3-hydroxy-2,3-dihydro-1H-pyrrolo[1,2-a]benzimidazol-7-yl}pyrimidin-2-yl)-2-methylpropanenitrile;

(1R)-1-[2-(difluoromethoxy)phenyl]-8-fluoro-7-[2-(4-fluorotetrahydro-2H-pyran-4-yl)pyrimidin-5-yl]-2,3-dihydro-1H-pyrrolo[1,2-a]benzimidazol-3-ol;

(1R)-1-[2-(difluoromethoxy)phenyl]-8-fluoro-7-[2-(3-fluorooxetan-3-yl)pyrimidin-5-yl]-2,3-dihydro-1H-pyrrolo[1,2-a]benzimidazol-3-ol;

(1R,3R)-1-[2-(difluoromethoxy)phenyl]-6-fluoro-7-[2-(4-fluorotetrahydropyran-4-yl)pyrimidin-5-yl]-2,3-dihydro-1H-pyrrolo[1,2-a]benzimidazol-3-ol;

(1R)-1-[2-(difluoromethoxy)phenyl]-3,6-difluoro-7-[2-(4-fluorotetrahydro-2H-pyran-4-yl)pyrimidin-5-yl]-2,3-dihydro-1H-pyrrolo[1,2-a]benzimidazole;

(1R,3R)-1-[2-(difluoromethoxy)phenyl]-6-fluoro-7-[2-(3-fluorooxetan-3-yl)pyrimidin-5-yl]-2,3-dihydro-1H-pyrrolo[1,2-a]benzimidazol-3-ol;

(1R)-1-[2-(difluoromethoxy)phenyl]-3,6-difluoro-7-[2-(3-fluorooxetan-3-yl)pyrimidin-5-yl]-2,3-dihydro-1H-pyrrolo[1,2-a]benzimidazole;

(1R,3R)-1-[2-(difluoromethoxy)phenyl]-3,6-difluoro-7-[2-(3-fluorooxetan-3-yl)pyrimidin-5-yl]-2,3-dihydro-1H-pyrrolo[1,2-a]benzimidazole;

(1R,3S)-1-[2-(difluoromethoxy)phenyl]-3,6-difluoro-7-[2-(3-fluorooxetan-3-yl)pyrimidin-5-yl]-2,3-dihydro-1H-pyrrolo[1,2-a]benzimidazole;

(1R,3R)-1-[2-(difluoromethoxy)phenyl]-7-[2-(3-fluorooxetan-3-yl)pyrimidin-5-yl]-2,3-dihydro-1H-pyrrolo[1,2-a]benzimidazol-3-ol;

(1R)-1-[2-(difluoromethoxy)phenyl]-3-fluoro-7-[2-(3-fluorooxetan-3-yl)pyrimidin-5-yl]-2,3-dihydro-1H-pyrrolo[1,2-a]benzimidazole;

(1R,3R)-1-[2-(difluoromethoxy)phenyl]-3-fluoro-7-[2-(3-fluorooxetan-3-yl)pyrimidin-5-yl]-2,3-dihydro-1H-pyrrolo[1,2-a]benzimidazole;

(1R,3S)-1-[2-(difluoromethoxy)phenyl]-3-fluoro-7-[2-(3-fluorooxetan-3-yl)pyrimidin-5-yl]-2,3-dihydro-1H-pyrrolo[1,2-a]benzimidazole;

2-(5-{(1R,3R)-1-[2-(difluoromethoxy)phenyl]-3-fluoro-2,3-dihydro-1H-pyrrolo[1,2-a]benzimidazol-7-yl}pyrimidin-2-yl)-2-methylpropanenitrile;

(1R,3R)-1-[2-(difluoromethoxy)phenyl]-3-fluoro-7-[2-(4-fluorotetrahydropyran-4-yl)pyrimidin-5-yl]-2,3-dihydro-1H-pyrrolo[1,2-a]benzimidazole;

3-[5-[(1R,3R)-1-[2-(difluoromethoxy)phenyl]-3-fluoro-2,3-dihydro-1H-pyrrolo[1,2-a]benzimidazol-7-yl]pyrimidin-2-yl]oxetan-3-ol;

(1R)-1-[2-(difluoromethoxy)phenyl]-6-fluoro-7-[6-(1-fluoro-1-methyl-ethyl)-3-pyridyl]-2,3-dihydro-1H-pyrrolo[1,2-a]benzimidazole;

9-[5-[(1R,3R)-1-[2-(difluoromethoxy)phenyl]-3-fluoro-2,3-dihydro-1H-pyrrolo[1,2-a]benzimidazol-7-yl]pyrimidin-2-yl]-3,7-dioxa-9-azabicyclo[3.3.1]nonane;

3-(difluoromethoxy)-2-{(1R,3R)-3-hydroxy-7-[2-(2-hydroxypropan-2-yl)pyrimidin-5-yl]-2,3-dihydro-1H-pyrrolo[1,2-a]benzimidazol-1-yl}benzonitrile;

3-(difluoromethoxy)-2-{(1R,3S)-3-hydroxy-7-[2-(2-hydroxypropan-2-yl)pyrimidin-5-yl]-2,3-dihydro-1H-pyrrolo[1,2-a]benzimidazol-1-yl}benzonitrile;

(1R,3R)-1-(5-chloro-2-(difluoromethoxy)phenyl)-7-(4-((R)—S-methylsulfonimidoyl)phenyl)-2,3-dihydro-1H-benzo[d]pyrrolo[1,2-a]imidazol-3-ol, (1R,3R)-1-(5-chloro-2-(difluoromethoxy)phenyl)-7-(4-((S)—S-methylsulfonimidoyl)phenyl)-2,3-dihydro-1H-benzo[d]pyrrolo[1,2-a]imidazol-3-ol;

(1R,3R)-1-(2-(difluoromethoxy)phenyl)-7-(4-((R)—S-methylsulfonimidoyl)phenyl)-2,3-dihydro-1-H-benzo[d]pyrrolo[1,2-a]imidazol-3-ol;

(1R,3R)-1-(2-(difluoromethoxy)phenyl)-7-(4-((S)—S-methylsulfonimidoyl)phenyl)-2,3-dihydro-1-H-benzo[d]pyrrolo[1,2-a]imidazol-3-ol;

5-[(1R,3R)-1-(2-Difluoromethoxy-phenyl)-3-hydroxy-2,3-dihydro-1H-benzo[d]pyrrolo[1,2-a]imidazol-7-yl]-1H-pyridin-2-one;

5-[(1R,3R)-1-(2-Difluoromethoxy-phenyl)-3-(2-hydroxy-ethoxy)-2,3-dihydro-1H-benzo[d]pyrrolo[1,2-a]imidazol-7-yl]-1H-pyridin-2-one;

5-[(1R,3R)-1-(2-Difluoromethoxy-phenyl)-3-(3-hydroxy-propoxy)-2,3-dihydro-1H-benzo[d]pyrrolo[1,2-a]imidazol-7-yl]-1H-pyridin-2-one;

5-[(1R,3R)-1-(2-Difluoromethoxy-phenyl)-3-hydroxy-2,3-dihydro-1H-benzo[d]pyrrolo[1,2-a]imidazol-7-yl]-3-methyl-1H-pyridin-2-one;

5-{(1R,3R)-1-(2-Difluoromethoxy-phenyl)-3-[2-(2-oxo-pyrrolidin-1-yl)-ethoxy]-2,3-dihydro-1H-benzo[d]pyrrolo[1,2-a]imidazol-7-yl}-1H-pyridin-2-one;

5-[(1R,3R)-1-(5-Chloro-2-difluoromethoxy-phenyl)-3-hydroxy-2,3-dihydro-1H-benzo[d]pyrrolo[1,2-a]imidazol-7-yl]-3-methyl-1H-pyridin-2-one;

5-[(1R,3R)-1-(2-Difluoromethoxy-phenyl)-3-hydroxy-2,3-dihydro-1H-benzo[d]pyrrolo[1,2-a]imidazol-7-yl]-6-methyl-1H-pyridin-2-one;

5-[(1R,3R)-1-(2-Difluoromethoxy-phenyl)-3-hydroxy-2,3-dihydro-1H-benzo[d]pyrrolo[1,2-a]imidazol-7-yl]-4-methyl-1H-pyridin-2-one;

2-[(1R,3R)-1-(2-Difluoromethoxy-phenyl)-7-(4-methylsulfonimidoyl-phenyl)-2,3-dihydro-1H-benzo[d]pyrrolo[1,2-a]imidazol-3-yloxy]-ethanol;

2-[(1R,3R)-1-(2-Difluoromethoxy-phenyl)-7-(4 methanesulfonyl-phenyl)-2,3-dihydro-1H-benzo[d]pyrrolo[1,2-a]imidazol-3-yloxy]-ethanol;

(1R,3R)-1-(2-Difluoromethoxy-phenyl)-7-(4 methanesulfonyl-phenyl)-2,3-dihydro-1H-benzo[d]pyrrolo[1,2-a]imidazol-3-ol;

(1R,3R)-7-(4-Cyclopropanesulfonyl-phenyl)-1-(2-difluoromethoxy-phenyl)-2,3-dihydro-1H-benzo[d]pyrrolo[1,2-a]imidazol-3-ol;

(1R,3R)-1-(5-Chloro-2-difluoromethoxy-phenyl)-7-(4-methanesulfonyl-phenyl)-2,3-dihydro-1H-benzo[d]pyrrolo[1,2-a]imidazol-3-ol;

(1R,3R)-1-(5-Chloro-2-difluoromethoxy-phenyl)-7-(4-cyclopropanesulfonyl-phenyl)-2,3-dihydro-1H-benzo[d]pyrrolo[1,2-a]imidazol-3-ol;

2-[(1R,3R)-7-(4-Cyclopropanesulfonyl-phenyl)-1-(2-difluoromethoxy-phenyl)-2,3-dihydro-1H-benzo[d]pyrrolo[1,2-a]imidazol-3-yloxy]-ethanol;

5-[(1R,3R)-1-(2-Difluoromethoxy-phenyl)-3-hydroxy-2,3-dihydro-1H-benzo[d]pyrrolo[1,2-a]imidazol-7-yl]-1-methyl-1H-pyridin-2-one;

4-[(1R,3R)-1-(2-Difluoromethoxy-phenyl)-3-hydroxy-2,3-dihydro-1H-benzo[d]pyrrolo[1,2-a]imidazol-7-yl]-benzenesulfonamide;

2-[(1R,3R)-1-(5-Chloro-2-difluoromethoxy-phenyl)-7-(4-methanesulfonyl-phenyl)-2,3-dihydro-1H-benzo[d]pyrrolo[1,2-a]imidazol-3-yloxy]-ethanol;

2-[(1R,3R)-1-(5-Chloro-2-difluoromethoxy-phenyl)-7-(4-cyclopropanesulfonyl-phenyl)-2,3-dihydro-1H-benzo[d]pyrrolo[1,2-a]imidazol-3-yloxy]-ethanol;

(1R,3R)-1-(2-Difluoromethoxy-phenyl)-7-[4-(propane-2-sulfonyl)-phenyl]-2,3-dihydro-1H-benzo[d]pyrrolo[1,2a]imidazol-3-ol;

4-[(1R,3R)-1-(2-Difluoromethoxy-phenyl)-3-hydroxy-2,3-dihydro-1H-benzo[d]pyrrolo[1,2-a]imidazol-7-yl]-N-(2-hydroxy-ethyl)-benzenesulfonamide;

5-[(1R,3R)-1-(2-Difluoromethoxy-phenyl)-3-hydroxy-2,3-dihydro-1H-benzo[d]pyrrolo[1,2-a]imidazol-7-yl]-1,3-dimethyl-1H-pyridin-2-one;

3-Cyclopropyl-5-[(1R,3R)-1-(2-difluoromethoxy-phenyl)-3-hydroxy-2,3-dihydro-1H-benzo[d]pyrrolo[1,2-a]imidazol-7-yl]-1H-pyridin-2-one;

(8-anti)-3-(5-{(1R,3R)-1-[2-(difluoromethoxy)phenyl]-6-fluoro-3-hydroxy-2,3-dihydro-1H-pyrrolo[1,2-a]benzimidazol-7-yl}pyrimidin-2-yl)-3-azabicyclo[3.2.1]octane-8-carboxylic acid;

(1R,3R or S)-1-[2-(difluoromethoxy)phenyl]-8-fluoro-7-[4-(methyl sulfonyl)phenyl]-2,3-dihydro-1H-pyrrolo[1,2-a]benzimidazol-3-ol;

(1R,3R or S)-1-[2-(difluoromethoxy)phenyl]-8-fluoro-7-[2-(2-hydroxypropan-2-yl)pyrimidin-5-yl]-2,3-dihydro-1H-pyrrolo[1,2-a]benzimidazol-3-ol;

(1R,3R or S)-7-[4-(cyclopropylsulfonyl)phenyl]-1-[2-(difluoromethoxy)phenyl]-8-fluoro-2,3-dihydro-1H-pyrrolo[1,2-a]benzimidazol-3-ol; and (1R,3R or S)-1-[2-(difluoromethoxy)phenyl]-8-fluoro-7-(6-methoxy-3-pyridyl)-2,3-dihydro-1H-pyrrolo[1,2-a]benzimidazol-3-ol.

15. A pharmaceutical composition comprising a compound of formula (I) as defined in claim 1, or a pharmaceutically acceptable salt thereof, in association with a pharmaceutically acceptable carrier.

16. A method of treating an inflammatory or autoimmune disorder, which method comprises administering to a patient in need of such a treatment an effective amount of a compound of formula (I) as defined in claim 1, or a pharmaceutically acceptable salt thereof.

\* \* \* \* \*